US011866441B2

(12) United States Patent
Comer et al.

(10) Patent No.: US 11,866,441 B2
(45) Date of Patent: *Jan. 9, 2024

(54) COMPOUNDS AND METHODS FOR THE TREATMENT OF PARASITIC DISEASES

(71) Applicants: THE BROAD INSTITUTE, INC., Cambridge, MA (US); PRESIDENT AND FELLOWS OF HARVARD COLLEGE, Cambridge, MA (US)

(72) Inventors: Eamon Comer, Cambridge, MA (US); Nobutaka Kato, Cambridge, MA (US); Marshall Morningstar, Cambridge, MA (US); Bruno Melillo, Cambridge, MA (US)

(73) Assignees: THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/387,639

(22) Filed: Jul. 28, 2021

(65) Prior Publication Data

US 2022/0162211 A1 May 26, 2022

Related U.S. Application Data

(63) Continuation of application No. 16/495,357, filed as application No. PCT/US2018/023270 on Mar. 20, 2018, now Pat. No. 11,174,260.

(60) Provisional application No. 62/473,771, filed on Mar. 20, 2017.

(51) Int. Cl.
| | |
|---|---|
| *C07D 487/04* | (2006.01) |
| *A61K 31/397* | (2006.01) |
| *A61K 31/44* | (2006.01) |
| *A61K 31/4406* | (2006.01) |
| *A61P 33/00* | (2006.01) |
| *A61P 33/02* | (2006.01) |
| *A61P 33/06* | (2006.01) |

(52) U.S. Cl.
CPC .......... *C07D 487/04* (2013.01); *A61P 33/06* (2018.01)

(58) Field of Classification Search
CPC ........ C07D 487/04; A61P 33/00; A61P 33/02; A61P 33/06; A61K 31/397; A61K 31/44; A61K 31/4406; Y02A 50/30
See application file for complete search history.

(56) References Cited

U.S. PATENT DOCUMENTS

| | | |
|---|---|---|
| 3,176,017 A | 3/1965 | Freed |
| 3,531,485 A | 9/1970 | Freed |
| 3,542,780 A | 11/1970 | Freed et al. |
| 10,059,711 B2 | 8/2018 | Comer et al. |
| 10,738,055 B2 | 8/2020 | Comer et al. |
| 11,174,260 B2 | 11/2021 | Comer et al. |
| 11,325,913 B2 | 5/2022 | Comer et al. |
| 2007/0135402 A1 | 6/2007 | Habashita et al. |
| 2016/0289235 A1 | 10/2016 | Comer et al. |
| 2020/0095253 A1 | 3/2020 | Comer et al. |
| 2022/0033404 A1 | 2/2022 | Sibley et al. |
| 2022/0193034 A1 | 6/2022 | Sibley et al. |

FOREIGN PATENT DOCUMENTS

| | | |
|---|---|---|
| CN | 105008360 A | 10/2015 |
| CN | 105164124 A | 12/2015 |
| JP | 2017502080 A | 1/2017 |
| JP | 6172288 B2 | 8/2017 |
| RU | 2236413 C2 | 9/2004 |
| RU | 2310656 C2 | 11/2007 |
| WO | 2015055535 A1 | 4/2015 |
| WO | 2015070204 A1 | 5/2015 |
| WO | 2015103583 A1 | 7/2015 |
| WO | 2016063933 A1 | 4/2016 |
| WO | 2016172631 A2 | 10/2016 |

OTHER PUBLICATIONS

Office Action dated Aug. 30, 2022 in corresponding Brazilian Patent Application No. BR112019019494-0 (4 pages).
English translation of the Office Action dated Aug. 30, 2022 in corresponding Brazilian Patent Application No. BR112019019494-0 (2 pages).
Office Action dated Aug. 31, 2022 in corresponding Vietnamese Patent Application No. 1-2019-05677 (2 pages).
English translation of the Office Action dated Aug. 31, 2022 in corresponding Vietnamese Patent Application No. 1-2019-05677 (2 pages).
Belikov, V.G., "Pharmaceutical Chemistry," Moscow MEDpress-inform, 2007, pp. 27-29.
English translation of Belikov, V.G., "Pharmaceutical Chemistry," Moscow MEDpress-inform, 2007, pp. 27-29.
Cowell et al., "Mapping the malaria parasite druggable genome by using in vitro evolution and chemogenomics," Science, Jan. 12, 2018, vol. 359, No. 6372, pp. 191-199.
Kato et al., "Diversity-oriented synthesis yields novel multistage antimalarial inhibitors," Nature, Oct. 2016, vol. 538, No. 7625, pp. 344-349.
Patani et al., "Bioisosterism: A Rational Approach in Drug Design," Chemical Reviews, 1996, vol. 96, No. 8, pp. 3147-3176.
International Search Report and Written Opinion dated Jun. 18, 2018 in corresponding PCT Patent Application No. PCT/US18/23270 (15 pages).
Office Action dated Jan. 6, 2020 in corresponding Vietnamese Patent Application No. 1-2019-05677 (3 pages).

(Continued)

*Primary Examiner* — Brenda L Coleman
(74) *Attorney, Agent, or Firm* — Melissa Hunter-Ensor; Scott Goncher; Greenberg Traurig, LLP

(57) ABSTRACT

Provided herein are compounds useful for the treatment of various parasitic diseases. These compounds, as well as pharmaceutically acceptable salts thereof may be formulated in pharmaceutical compostions, veterinary compositions and may be used in methods of treatment and/or prophylaxis of diseases spread by parasites, including malaria and cryptosporidiosis.

19 Claims, No Drawings

(56) References Cited

OTHER PUBLICATIONS

English translation of the Office Action dated Jan. 6, 2020 in corresponding Vietnamese Patent Application No. 1-2019-05677 (3 pages).
Office Action dated Jul. 16, 2020 in corresponding Mexican Patent Application No. MX/a/2019/011271 (3 pages).
English translation of the Office Action dated Jul. 16, 2020 in corresponding Mexican Patent Application No. MX/a/2019/011271 (3 pages).
Partial Supplementary European Search Report dated Jul. 27, 2020 in corresponding European Patent Application No. 18771869.7 (12 pages).
Extended European Search Report dated Oct. 30, 2020 in corresponding European Patent Application No. 18771869.7 (10 pages).
Office Action dated Mar. 4, 2021 in corresponding Mexican Patent Application No. MX/a/2019/011271 (5 pages).
English translation of the Office Action dated Mar. 4, 2021 in corresponding Mexican Patent Application No. MX/a/2019/011271 (5 pages).
Examination and Search Report dated May 18, 2021 in corresponding ARIPO Patent Application No. AP/P/2019/011878 (5 pages).
Office Action dated Jun. 29, 2021 in corresponding Russian Patent Application No. 2019132950 (12 pages).
English translation of the Office Action dated Jun. 29, 2021 in corresponding Russian Patent Application No. 2019132950 (5 pages).
Search Report dated Jun. 29, 2021 in corresponding Russian Patent Application No. 2019132950 (2 pages).
English translation of Search Report dated Jun. 29, 2021 in corresponding Russian Patent Application No. 2019132950 (2 pages).
Office Action dated Aug. 9, 2021 in corresponding Mexican Patent Application No. MX/a/2019/011271 (6 pages).
English translation of the Office Action dated Aug. 9, 2021 in corresponding Mexican Application No. MX/a/2019/011271 (5 pages).
Office Action dated Aug. 23, 2021 in corresponding Israeli Patent Application No. 269390 (4 pages).
English translation of the Office Action dated Aug. 23, 2021 in corresponding Israeli Patent Application No. 269390 (4 pages).
Office Action dated Aug. 24, 2021 in corresponding Columbian Patent Application No. NC2019/0011546 (5 pages).
Examination Report dated Oct. 22, 2021 in corresponding Indian Patent Application No. 201917042235 (8 pages).
Examination Report dated Aug. 4, 2022 in corresponding Philippines Patent Application No. 1/2019/502150 (3 pages).
Office Action dated Sep. 13, 2022 in corresponding Colombian Patent Application No. NC2019/0011546 (8 pages).
English translation of the Office Action dated Sep. 13, 2022 in corresponding Colombian Patent Application No. NC2019/0011546 (6 pages).
Examination and Search Report dated Nov. 8, 2022 in corresponding Malaysian Patent Application No. PI2019005496 (3 pages).
Office Action dated Oct. 31, 2022 in corresponding Japanese Patent Application No. 2019-551706 (3 pages).
English translation of the Office Action dated Oct. 31, 2022 in corresponding Japanese Patent Application No. 2019-551706 (2 pages).
Cramer et al., "Hydroxyl Groups in Synthetic and Natural-Product-Derived Therapeutics: A Perspective on a Common Functional Group," Journal of Medical Chemistry, 2019, pp. 8915-8930; A-P.
Office Action dated Feb. 16, 2022 in corresponding Japanese Patent Application No. 2019-551706 (3 pages).
English translation of the Office Action dated Feb. 16, 2022 in corresponding Japanese Patent Application No. 2019-551706 (3 pages).
Office Action dated Mar. 22, 2022 in corresponding Thai Patent Application No. 1901005814 (3 pages).
English translation of the Office Action dated Mar. 22, 2022 in corresponding Thai Patent Application No. 1901005814 (2 pages).
Office Action dated Mar. 30, 2022 in corresponding European Patent Application No. 18771869.7 (7 pages).
Office Action dated Mar. 17, 2023 in corresponding Indonesian Patent Application No. P00201909317 (4 pages).
English translation of the Office Action dated Mar. 17, 2023 in corresponding Indonesian Patent Application No. P00201909317 (3 pages).
Kummerer, Klaus, "Pharmaceuticals in the Environment," Annual Review of Environment and Resources, 2010, vol. 35, pp. 57-75.
Office Action dated Apr. 22, 2022 in corresponding Australian Patent Application No. 2018240031 (3 pages).
Office Action dated Apr. 22, 2022 in corresponding Russian Patent Application No. 2019132950 (14 pages).
English translation of the Office Action dated Apr. 22, 2022 in corresponding Russian Patent Application No. 2019132950 (11 pages).
Office Action dated May 12, 2022 in corresponding Columbian Patent Application No. NC2019/0011546 (10 pages).
English translation of the Office Action dated May 12, 2022 in corresponding Columbian Patent Application No. NC2019/0011546 (6 pages).
Office Action dated Jul. 6, 2022 in corresponding Chinese Patent Application No. 201880033124.6 (9 pages).
English translation of the Office Action dated Jul. 6, 2022 in corresponding Chinese Patent Application No. 201880033124.6 (9 pages).
Office Action dated Apr. 3, 2023 in corresponding Korean Patent Application No. 10-2019-7030814 (6 pages).
English translation of the Office Action dated Apr. 3, 2023 in corresponding Korean Patent Application No. 10-2019-7030814 (5 pages).

COMPOUNDS AND METHODS FOR THE TREATMENT OF PARASITIC DISEASES

CROSS REFERENCE TO RELATED APPLICATIONS

The present application is a continuation of U.S. patent application Ser. No. 16/495,357, filed Sep. 18, 2019, which is the U.S. national phase application, pursuant to 35 U.S.C. § 371, of PCT International Application No.: PCT/US2018/023270, filed Mar. 20, 2018, designating the United States and published in English, which claims priority to U.S. Provisional Application No. 62/473,771, filed Mar. 20, 2017, the contents of which are hereby incorporated by reference in their entirety.

BACKGROUND

Malaria is a vector-borne infectious disease caused by protozoan parasites and is widespread in tropical and subtropical regions, including parts of the Americas, Asia and Africa. Of the five *Plasmodium* parasite species that can infect humans (*P. falciparum, P. vivax, P. ovale, P. malariae*, and *P. knowlesi*), the most serious forms of the disease are caused by *P. falciparum* and *P. vivax*. Additionally, several *Plasmodium* parasite species infect mammals other than humans. For example, *P. berghei, P. chabaudi, P. vinckei*, and *P. yoelii*, may cause malaria in certain rodents.

Approximately 515 million people are stricken with malaria each year, and between one and three million of these people die from the disease. The majority of the current antimalarial drugs target the replicating asexual blood stage, where the parasites live inside erythrocytes. Even though liver- and transmission-stage parasites do not cause malaria symptoms, prophylaxis and transmission-blocking drugs are essential to proactively prevent epidemics of the disease and protect vulnerable populations. The current armament of approved anti-malarial drugs, such as chloroquine, atovaquone, pyrimethamine, and sulfadoxine, is limited to only a few targets within the human malaria parasite, and growing widespread resistance to current drugs is prompting the development of new antimalarial agents that have new biological targets.

Cryptosporidiosis is another parasitic disease and is caused by *Cryptosporidium*, a genus of protozoan parasites in the phylum Apicomplexa. Cryptosporidiosis is most commonly caused by the intracellular apicomplexan parasistes *C. parvum* and *C. hominis*. It may also be caused by *C. canis, C. felis, C. meleagridis*, and *C. muris*. Cryptosporidiosis affects the distal small intestine and can affect the respiratory tract in both immunocompetent and immunocompromised individuals. Cryptosporidiosis is one of the most common waterborne diseases and is found worldwide. It can also be transmitted to other animals, including cattle, sheep, pigs, horses, goats, and geckos. Nitazoxanide is the current standard of care for cryptosporidiosis, but the drug only exhibits partial efficacy in children and is no more effective than placebo in patients with AIDS.

SUMMARY

Disclosed herein are compounds, pharmaceutical compositions, and methods of treating or preventing parasitic diseases including malaria and *cryptosporidium* including/using a compound as described above or elsewhere herein.

In some embodiments, these pharmaceutical compositions are formulated as veterinary compositions for use with subjects other than human.

The compounds may have the structure of formula (I):

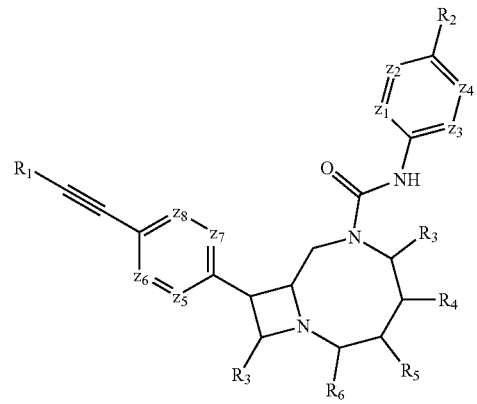

wherein the "dashed" bond may be a single or double bond;
$R_1$ is optionally substituted aryl or heteroaryl;
$R_2$ is optionally substituted alkoxy, cycloalkoxy or heterocyclyl;
$R_3$ is hydrogen, or —$CH_2$—X;
$R_4$ and $R_5$ are independently hydrogen, —X, or —$CH_2$—X, $R_4$ and $R_5$ may together form a five- or six-membered fused ring, and at least one of $R_4$ and $R_5$ is not hydrogen;
$R_6$ and $R_7$ are independently hydrogen or R; and
$z_1$-$z_8$ are independently selected at each occurrence from CH or N; where
—X is independently selected at each occurrence from —OH, —OR, —S(O)R, —S(O)$_2$R, —N(R)—S(O)$_2$R, —S(O)$_2$—N(R)(R), —S(O)$_2$—NHR, —N(R)—C(O)—R or —N(R)(R); and
R is independently at each occurrence an optionally substituted $C_1$-$C_{12}$ alkyl; or a pharmaceutically acceptable salt thereof —X may be independently selected at each occurrence from —OH—NH$_2$ or —N(R)(R). In some embodiments —X groups in $R_4$ and/or $R_5$ (including —X groups when $R_4$ and/or $R_5$ is —$CH_2$—X) may be selected from —OH, NH$_2$, or —N(R)(R). Also, R may be independently selected at each occurrence a $C_{1-4}$ linear or branched hydrocarbon.

In some embodiments, $R_6$ and $R_7$ are each hydrogen In some embodiments, $R_4$ and $R_5$ may be the same functional group selected from —X or —$CH_2$—X (e.g., $R_4$ is —OH and $R_5$ is —OH, $R_4$ is —NH$_2$ and $R_5$ is —NH$_2$, $R_4$ is —OCH$_3$ and $R_5$ is —OCH$_3$, etc.). In other embodiments, $R_5$ is hydrogen and $R_4$ is —X, or —(CH$_2$)—X. In other embodiments, $R_4$ is hydrogen and $R_5$ is —X, or —(CH$_2$)—X. In some embodiments, $R_4$ and $R_5$ are independently selected from —OH and —OR and $R_4$ and $R_5$ together form a 6-membered fused ring. In some embodiments, $R_6$ is a $C_{1-4}$ linear or branched hydrocarbon. In other embodiments, $R_6$ is hydrogen. $R_1$ may be an optionally substituted $C_6$ aryl or heteroaryl (e.g., phenyl, fluorophenyl, difluorophenyl, pyridyl, etc.). In some embodiments, $R_2$ is $C_{1-4}$ linear or branched alkoxy (e.g., methoxy, ethoxy, propoxy, isopropoxy, etc.). In some embodiments, $R_2$ is $C_{1-4}$ linear or branched alkoxy substituted with one or more F (e.g., —OCF$_3$, —OCHF$_2$, or —OCH$_2$F). In other embodiments, $R_2$ is $C_{3-6}$ heterocyclyl (e.g., aziridinyl, oxiranyl, thiiranyl, oxetanyl, azetidnyl, thietanyl, diazetidinyl, dioxetanyl, dithietanyl, pyrrolidinyl, tetrahydrofuranyl, imidazolyl, pyrazolyl, oxazolyl, etc.). In preferred embodiments, $R_2$ is oxetanyl or azetidinyl. In other embodiments, $R_2$ is $C_{3-6}$ cycloalkoxy (e.g., cyclopropoxy). In some embodiments, $R_3$ is —$CH_2$—X and —X is N(R)(R).

Each of $z_1$-$z_8$ may be CH. In some embodiments, one of $z_1$-$z_4$ is N and the rest are CH. In some embodiments, one of $z_5$-$z_8$ is N and the rest are CH. In some embodiments, $z_1$ and $z_4$ are each N and $z_3$ and $z_2$ are each CH. In some embodiments, $z_5$ and $z_7$ are each N and $z_6$ and $z_8$ are each CH.

Any stereocenters in the structure of formula (I) may be in either configuration, or be present as a racemic mixture of each stereocenter (e.g., stereoisomers, diastereomers, etc.). In some embodiments, the compounds have the structure of formula (II):

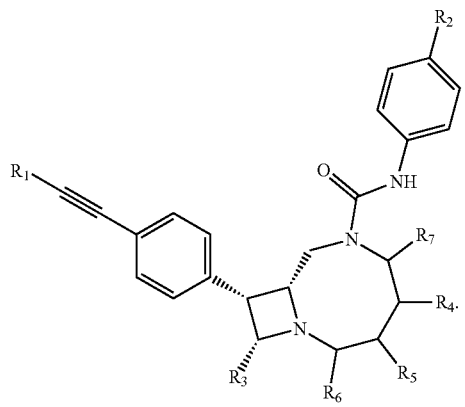

(II)

In some embodiments, the compounds have the structure of formula (IIb):

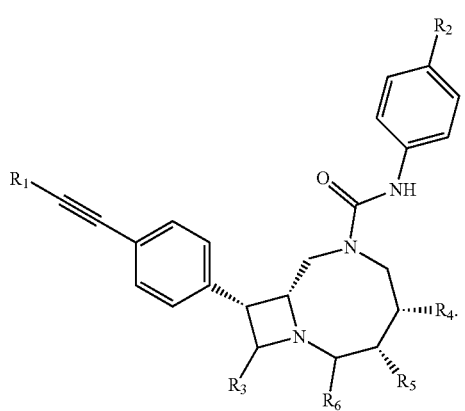

(IIIb)

In other embodiments, the compounds have the structure of formula (IIa):

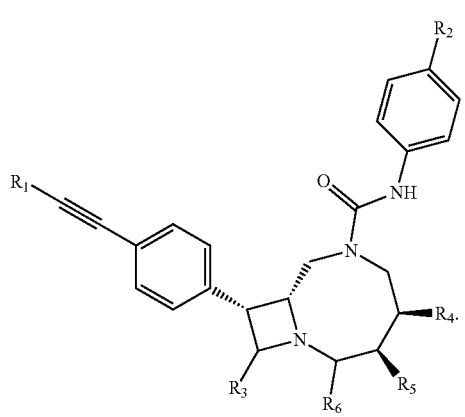

(IIIa)

The compound may also have the structure of formula (III):

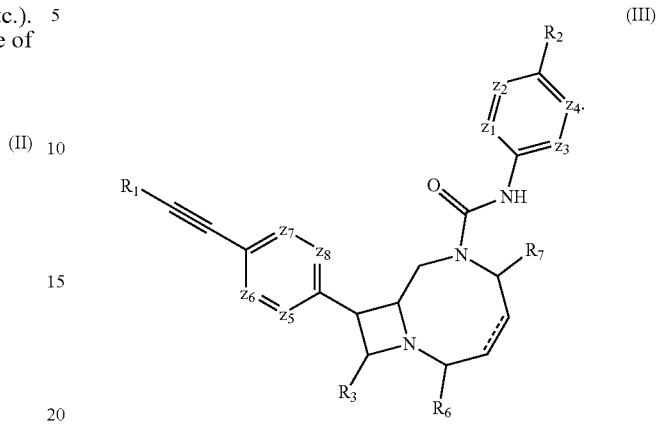

(III)

wherein the "dashed" bond may be a single or double bond;

$R_1$ is optionally substituted aryl or heteroaryl;

$R_2$ is optionally substituted alkoxy, cycloalkoxy or heterocyclyl;

$R_3$ is hydrogen or —$CH_2$—X;

$R_6$ and $R_7$ are independently hydrogen or R; and $z_1$-$z_8$ are independently selected at each occurrence from CH or N; where —X is independently selected at each occurrence from —OH, —OR, —S(O)R, —S(O)$_2$R, —N(R)—S(O)$_2$R, —S(O)$_2$—N(R)(R), —S(O)$_2$—NHR, —N(R)—C(O)—R or —N(R)(R); and R is independently at each occurrence a $C_1$-$C_{12}$ alkyl;

with the proviso that in the case where $R_6$ is hydrogen, $R_3$ is —$CH_2$—N(R)(R) and said "dashed" bond is a double bond. In some embodiments, the "dashed bond is a double bond. In other embodiments, the "dashed" bond is a single bond. —X may be independently selected at each occurrence from —OH—$NH_2$ or —N(R)(R). Also, R may be independently selected at each occurrence a $C_{1-4}$ linear or branched hydrocarbon.

Each of $z_1$-$z_8$ may be CH. In some embodiments, one of $z_1$-$z_4$ is N and the rest are CH. In some embodiments, one of $z_5$-$z_8$ is N and the rest are CH. In some embodiments, $z_1$ and $z_4$ are each N and $z_3$ and $z_2$ are each CH. In some embodiments, $z_5$ and $z_7$ are each N and $z_6$ and $z_8$ are each CH.

In some embodiments, $R_6$ and $R_7$ are each hydrogen. In some embodiments, $R_6$ is lower alkyl (e.g, methyl, ethyl, etc.). In some embodiments, $R_6$ is a $C_{1-4}$ linear or branched hydrocarbon. In other embodiments, $R_6$ is hydrogen. $R_1$ may be an optionally substituted $C_6$ aryl or heteroaryl (e.g., phenyl, fluorophenyl, difluorophenyl, pyridyl, etc.). In some embodiments, $R_2$ is $C_{1-4}$ linear or branched alkoxy (e.g., methoxy, ethoxy, propoxy, isopropoxy, etc.). In some embodiments, $R_2$ is $C_{1-4}$ linear or branched alkoxy substituted with one or more F (e.g., —$OCF_3$, —$OCHF_2$, or —$OCH_2F$). In other embodiments, $R_2$ is $C_{3-6}$ heterocyclyl (e.g., aziridinyl, oxiranyl, thiiranyl, oxetanyl, azetidnyl, thietanyl, diazetidinyl, dioxetanyl, dithietanyl, pyrrolidinyl, tetrahydrofuranyl, imidazolyl, pyrazolyl, oxazolyl, etc.). In preferred embodiments, $R_2$ is oxetanyl or azetidinyl. In other embodiments, $R_2$ is $C_{3-6}$ cycloalkoxy (e.g., cyclopropoxy).

In some embodiments, the compound may have the structure of formula (IV):

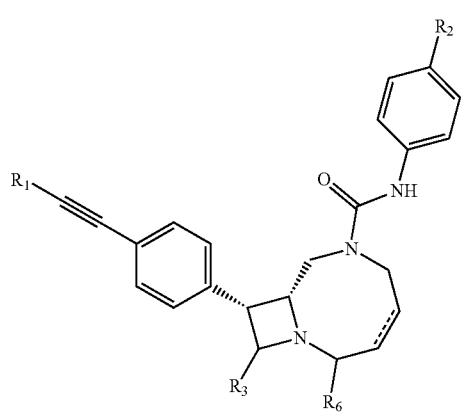

(IV)

In some embodiments, the compound is any of compounds E1-E38 of pharmaceutically acceptable salts thereof.

Any of the compounds described above may be used in pharmaceutical compositions. In some embodiments, the pharmaceutical composition may comprise a pharmaceutically acceptable excipient and a compound having the structure of formula (I):

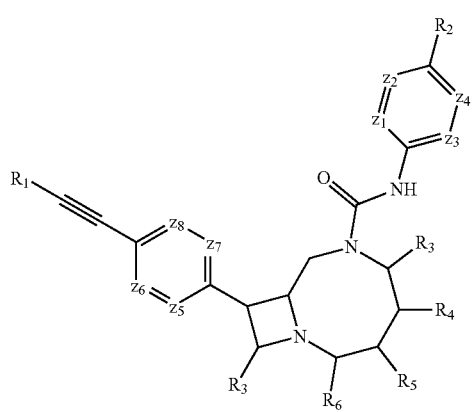

(I)

wherein the "dashed" bond may be a single or double bond;
$R_1$ is optionally substituted aryl or heteroaryl;
$R_2$ is optionally substituted alkoxy, cycloalkoxy or heterocyclyl;
$R_3$ is hydrogen, or —$CH_2$—X;
$R_4$ and $R_5$ are independently hydrogen, —X, or —$CH_2$—X, $R_4$ and $R_5$ may together form a five- or six-membered fused ring, and at least one of $R_4$ and $R_5$ is not hydrogen;
$R_6$ and $R_7$ are independently hydrogen or R; and
$z_1$-$z_8$ are independently selected at each occurrence from CH or N; where
—X is independently selected at each occurrence from —OH, —OR, —S(O)R, —S(O)$_2$R, —N(R)—S(O)$_2$R, —S(O)$_2$—N(R)(R), —S(O)$_2$—NHR, —N(R)—C(O)—R or —N(R)(R); and
R is independently at each occurrence an optionally substituted $C_1$-$C_{12}$ alkyl;
or a pharmaceutically acceptable salt thereof —X may be independently selected at each occurrence from —OH— $NH_2$ or —N(R)(R). In some embodiments —X groups in $R_4$ and/or $R_5$ (including —X groups when $R_4$ and/or $R_5$ is —$CH_2$—X) may be selected from —OH, $NH_2$, or —N(R)(R). Also, R may be independently selected at each occurrence a $C_{1-4}$ linear or branched hydrocarbon.

In some embodiments, the pharmaceutical composition may comprise a pharmaceutically acceptable excipient and a compound having the structure of formula (III):

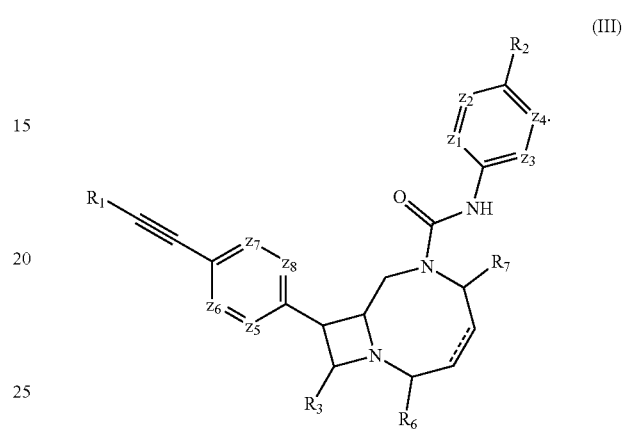

(III)

wherein the "dashed" bond may be a single or double bond;
$R_1$ is optionally substituted aryl or heteroaryl;
$R_2$ is optionally substituted alkoxy, cycloalkoxy or heterocyclyl;
$R_3$ is hydrogen or —$CH_2$—X;
$R_6$ and $R_7$ are independently hydrogen or R; and
$z_1$-$z_8$ are independently selected at each occurrence from CH or N; where
—X is independently selected at each occurrence from —OH, —OR, —S(O)R, —S(O)$_2$R, —N(R)—S(O)$_2$R, —S(O)$_2$—N(R)(R), —S(O)$_2$—NHR, —N(R)—C(O)—R or —N(R)(R); and
R is independently at each occurrence a $C_1$-$C_{12}$ alkyl;
with the proviso that in the case where $R_6$ is hydrogen, $R_3$ is —$CH_2$—N(R)(R) and said "dashed" bond is a double bond. In some embodiments, the "dashed bond is a double bond. In other embodiments, the "dashed" bond is a single bond. —X may be independently selected at each occurrence from —OH—$NH_2$ or —N(R)(R). Also, R may be independently selected at each occurrence a $C_{1-4}$ linear or branched hydrocarbon. In some embodiments, the compound is present the pharmaceutical composition in an effective amount. For example, the compound may be present in an effective amount for the treatment or prophylaxis of malaria. In some embodiments, the compound may be present in an effective amount for the treatment or prophylaxis of a disease caused by a parasite from the genus *Cryptosporidium* (e.g., cryptosporidiosis). In some embodiments, the pharmaceutical composition may be formulated for treatment of malaria and cryptosporidiosis.

Related methods of the treatment or prophylaxis of a disease in a subject are also disclosed. In some embodiments, the method of treatment or prophylaxis of a parasitic disease in a subject, comprises the step of administering to the subject an effective amount of any compound disclosed herein. In some embodiments, the effective amount of compound is formulated in a pharmaceutical composition (e.g., veterinary composition, etc.).

The parasitic disease may be malaria. In some embodiments, the malaria is drug resistant malaria (e.g., malaria resistant to chloroquine, quinine, prymethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof, etc.). In some embodiments, the malaria is blood stage malaria. In some embodiments, the malaria is transmission stage malaria. In some embodiments, the malaria is liver stage malaria. In some embodiments, the subject is infected with a malaria-causing parasite and said treatment prevents spread of said infection from their liver. In some embodiments, the malaria is carried in a mosquito species selected from *P. falciparum, P. vivax, P. ovale, P. malariae, P. knowlesi, P. berghei, P. chabaudi, P. vinckei,* or *P. yoelii*. In preferred embodiments, the mosquito species is *P. falciparum* (particularly when the subject is human).

The parasitic disease may be cryptosporidiosis. In some embodiments, the cryptosporidiosis is carried by *C. parvum*.

In some embodiments, the subject is human. In other embodiments, the subject is not human (e.g., the pharmaceutical composition is formulated as a veterinary composition). In some embodiments, the subject is a mouse, rat, rabbit, non-human primate, lizards, geckos, cow, calf, sheep, lamb, horse, foal, pig, or piglet.

These and other aspects of the invention will be apparent to those skilled in the art from the following detailed description, which is simply, by way of illustration, various modes contemplated for carrying out the invention. As will be realized, the invention is capable of additional, different obvious aspects, all without departing from the invention.

Accordingly, the specification is illustrative in nature and not restrictive.

DETAILED DESCRIPTION

Definitions

It is to be understood that the terminology employed herein is for the purpose of describing particular embodiments, and is not intended to be limiting. Further, although any methods and materials similar or equivalent to those described herein can be used in the practice or testing of the disclosure, the preferred methods and materials are now described.

The term "acyl," as used herein, represents a hydrogen or an alkyl group, as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons. In some embodiments, the alkyl group is further substituted with 1, 2, 3, or 4 substituents as described herein.

As used herein, the term "alkyl," alone or in combination with other groups, refers to a branched or straight-chain monovalent saturated aliphatic hydrocarbon radical of one to twenty carbon atoms (e.g., one to sixteen carbon atoms, one to twelve carbon atoms, one to ten carbon atoms, or one to six carbon atoms, etc.).

The term "alkylene" as used herein, represents a saturated divalent hydrocarbon group derived from a straight or branched chain saturated hydrocarbon by the removal of two hydrogen atoms, and is exemplified by methylene, ethylene, and isopropylene. In some embodiments, the alkylene can be further substituted with 1, 2, 3, or 4 substituent groups as defined herein for an alkyl group.

As used herein, the term "alkenyl," alone or in combination with other groups, refers to a straight-chain or branched hydrocarbon residue having an olefinic bond.

The term "amino," as used herein, represents —N(R$^{N1}$)$_2$, wherein each RN is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or heterocyclylalkyl (e.g., heteroarylalkyl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups can be an unsubstituted amino (i.e., —NH$_2$) or a substituted amino (i.e., —N(R$^{N1}$)$_2$). In a preferred embodiment, amino is —NH$_2$ or —NHR$^{N1}$, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, C$_{1-20}$ alkyl (e.g., C$_{1-6}$ alkyl), or C$_{6-10}$ aryl.

The term "aryl" refers to an aromatic mono- or polycyclic radical of 6 to 12 carbon atoms having at least one aromatic ring. Examples of such groups include, but are not limited to, phenyl, naphthyl, 1,2,3,4-tetrahydronaphthalyl, 1,2-dihydronaphthalyl, indanyl, and 1H-indenyl.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as C$_{6-10}$ aryl C$_{1-6}$ alkyl, C$_{6-10}$ aryl C$_{1-10}$ alkyl, or C$_{6-10}$ aryl C$_{1-20}$ alkyl). In some embodiments, the alkylene and the aryl each can be further substituted with 1, 2, 3, or 4 substituent groups as defined herein for the respective groups.

The alkyl, carbocyclic, and aryl groups may be substituted or unsubstituted. When substituted, there will generally be, for example, 1 to 4 substituents present. These substituents may optionally form a ring with the alkyl, carbocyclic, or aryl group with which they are connected. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, cylcoalkoxy, aryloxy, alkoxyalkyl, aryloxyalkyl, more preferably, for example, methoxy, ethoxy, propoxy, isopropoxy, cyclopropoxy, etc.), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); heterocyclyl heteroalkyl groups, and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "azido" represents an —$N_3$ group, which can also be represented as —N=N=N.

The terms "carbocyclic" and "carbocyclyl," as used herein, refer to an optionally substituted non-aromatic $C_{3-12}$ monocyclic, bicyclic, or tricyclic structure in which the rings are formed by carbon atoms. Carbocyclic structures include cycloalkyl, cycloalkenyl, and cycloalkynyl groups.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, and indanyl. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, and optionally substituted cycloheptyl, or those which are specifically exemplified herein.

The term "cyano," as used herein, represents a —CN group.

As used herein, the term "halo" or "halogen" means a fluorine (fluoro), chlorine (chloro), bromine (bromo) or iodine (iodo) radical.

The term "heteroalkyl," as used herein, refers to an alkyl group, as defined herein, in which one or more of the constituent carbon atoms have each been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O—; and "alkoyl" which, as used herein, refers to alkyl-CO—. Alkoxy substituent groups or alkoxy-containing substituent groups may be substituted by, for example, one or more alkyl groups.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, benzooxazolyl, benzoimidazolyl, and benzothiazolyl.

The term "heterocycle" or "heterocyclyl" denotes a mono- or polycyclic alkyl ring, wherein one, two or three of the carbon ring atoms is replaced by a heteroatom such as N, O or S. Examples of hetereocyclyl groups include, but are not limited to, oxetanyl, morpholinyl, thiomorpholinyl, piperazinyl, piperidinyl, pyrrolidinyl, tetrahydropyranyl, tetrahydrofuranyl, and 1,3-dioxanyl. The heterocyclyl groups may be unsubstituted or substituted, and attachment may be through their carbon frame or through their heteroatom(s) where appropriate.

The term "heterocyclyl heteroalkyl" refers to a heterocyclic group, as defined herein, attached to the parent molecular group through a heteroalkyl group (e.g., an ether or alkoxy group). An example of a heterocyclyl heteroalkyl group is —$OCH_2CH_2$(morpholino) group.

The heterocyclyl and heteroaryl groups described above may be substituted independently with one, two, three, or more substituents. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, aryloxy, alkoxyalkyl, aryloxyalkyl), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazolyl and carbolinyl).

The term "hydroxyl," as used herein, represents an —OH group. In some embodiments, the hydroxyl group can be substituted with a O-protecting group as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. The term "perfluoroalkyl," as used herein, represents alkyl group, as defined herein, where each hydrogen radical bound to the alkyl group has been replaced by a fluoride radical. For example, perfluoroalkyl groups are exemplified by trifluoromethyl and pentafluoroethyl.

The term "sulfonyl," as used herein, represents an —S(O)$_2$— group.

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In some embodiments, a heteroatom or group may substitute a carbon. In some embodiments, a heteratom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo", replacing a hydrogen in the backbone or chain, etc.).

The term "substituent" refers to a group "substituted" on, e.g., an alkyl, haloalkyl, cycloalkyl, heterocyclyl, heterocycloalkenyl, cycloalkenyl, aryl, or heteroaryl group) at any atom of that group, replacing one or more hydrogen atoms therein. In one aspect, the substituent(s) on a group are independently any, one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo, $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with an H) or substituted. As used herein, the term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable.

Compounds provided herein can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art. "Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms (e.g., to a carbon-carbon double bond, to a cycloalkyl ring, to a bridged bicyclic system, etc.). Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds disclosed herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9%) by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The disclosure embraces all of these forms.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an antimalarial agent, an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver, preventing systemic disease, preventing the symptomatic stage of malaria, preventing establishment of *Plasmodium* infection and/or preventing further spread of the disease by preventing transmission back to the mosquito, etc.); delay or slowing the progress of the disease, disorder, or condition; amelioration or palliation of the disease, disorder, or condition; and remission (whether partial or total), whether detectable or undetectable, as compared to the response obtained without administration of the agent.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, non-human primates, and humans, lizards, geckos, etc.). The subject may be domesticated animals (e.g., cows, calves, sheep, lambs, horses, foals, pigs, piglets, etc.), or animals in the family Muridae (e.g., rats, mice, etc.). A subject may seek or be in need of treatment, require treatment, be receiving treatment, may be receiving treatment in the future, or a human or animal that is under care by a trained professional for a particular disease or condition.

As used herein, and as well understood in the art, "to treat" a condition or "treatment" of the condition (e.g., the conditions described herein such as malaria) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver or preventing transmission back to the mosquito, preventing systemic disease, preventing the symptomatic stage of malaria, and/or preventing establishment of *Plasmodium* infection); delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup (also see below).

Other features and advantages of the disclosure are described in the following detailed description and the claims.

Compounds

The present disclosure provides for novel compounds and pharmaceutical compositions useful for the treatment of malaria. The disclosure also provides methods of using these compounds and compositions.

In some embodiments, the compounds may be any compound listed in Table 1.

TABLE 1

| Comp. | Structure | Name |
|---|---|---|
| E1 | 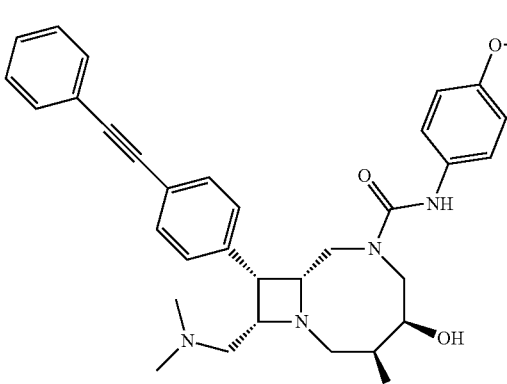 | (3S,4R,8R,9S,10S)-N-(4-cyclopropoxyphenyl)-10-((dimethylamino)methyl)-3,4-dihydroxy-9-(4-(phenylethynyl)phenyl)-1,6-diazabicyclo[6.2.0]decane-6-carboxamide |

TABLE 1-continued

| Comp. | Structure | Name |
|---|---|---|
| E2 | 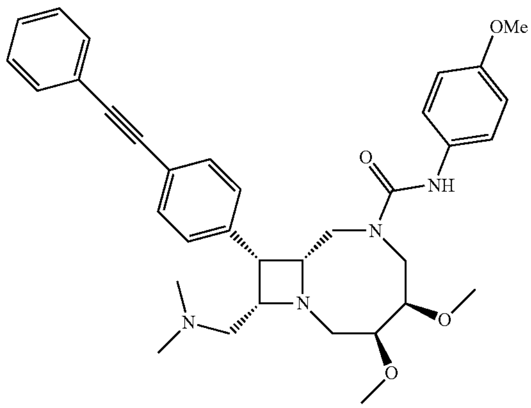 [SMILES: COc1ccc(NC(=O)N2C[C@@H](OC)[C@@H](OC)CN3[C@H](CN(C)C)[C@H](c4ccc(C#Cc5ccccc5)cc4)[C@@H]3C2)cc1] | (3S,4R,8R,9S,10S)-10-((dimethylamino)methyl)-3,4-dimethoxy-N-(4-methoxyphenyl)-9-(4-(phenylethynyl)phenyl)-1,6-diazabicyclo[6.2.0]decane-6-carboxamide |
| E3 | 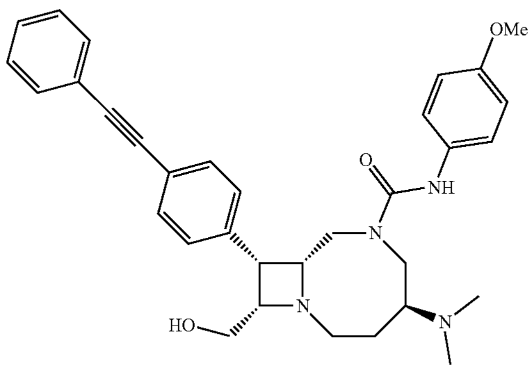 [SMILES: COc1ccc(NC(=O)N2C[C@@H](N(C)C)CCN3[C@H](CO)[C@H](c4ccc(C#Cc5ccccc5)cc4)[C@@H]3C2)cc1] | (4S,8R,9R,10S)-4-(dimethylamino)-10-(hydroxymethyl)-N-(4-methoxyphenyl)-9-(4-(phenylethynyl)phenyl)-1,6-diazabicyclo[6.2.0]decane-6-carboxamide |
| E4 | 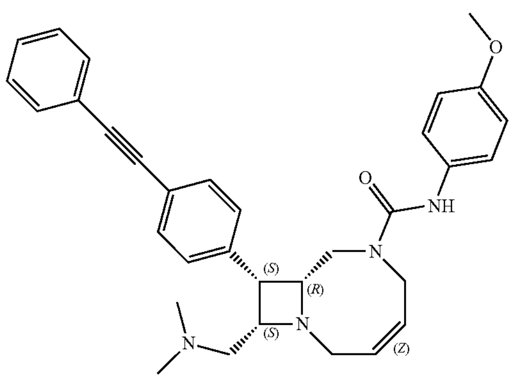 | (3Z,8R,9S,10S)-10-[(dimethylamino)methyl]-N-(4-methoxyphenyl)-9-[4-(2-phenylethynyl)phenyl]-1,6-diazabicyclo[6.2.0]dec-3-ene-6-carboxamide |
| E5 | 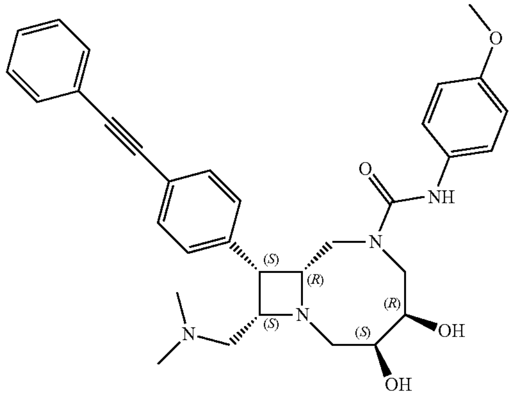 | (3S,4R,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide |

TABLE 1-continued

| Comp. | Structure | Name |
|---|---|---|
| E6 | 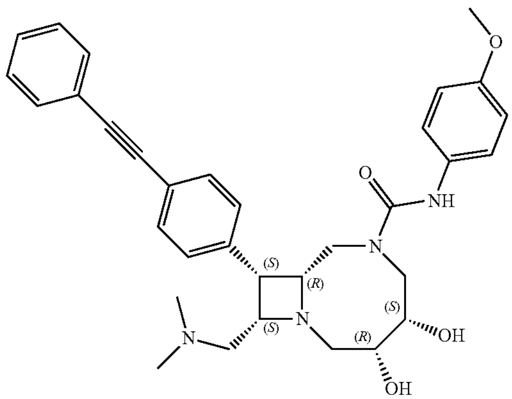 | (3R,4S,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide |
| E7 | 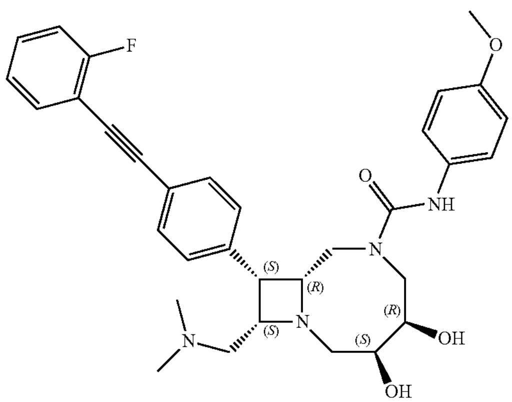 | (3S,4R,8R,9S,10S)-10-[(dimethylamino)methyl]-9-[4-[2-(2-fluorophenyl)ethynyl]phenyl]-3,4-dihydroxy-N-(4-methoxyphenyl)-1,6-diazabicyclo[6.2.0]decane-6-carboxamide |
| E8 | 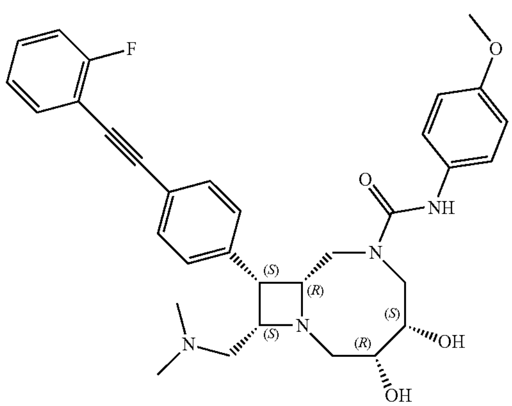 | (3R,4S,8R,9S,10S)-10-[(dimethylamino)methyl]-9-[4-[2-(2-fluorophenyl)ethynyl]phenyl]-3,4-dihydroxy-N-(4-methoxyphenyl)-1,6-diazabicyclo[6.2.0]decane-6-carboxamide |
| E9 | 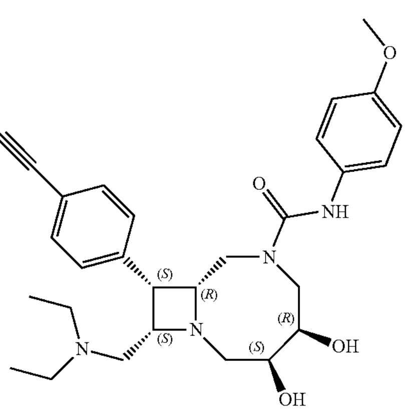 | (3S,4R,8R,9S,10S)-10-(diethylaminomethyl)-3,4-dihydroxy-N-(4-methoxyphenyl)-9-[4-(2-phenylethynyl)phenyl]-1,6-diazabicyclo[6.2.0]decane-6-carboxamide |

TABLE 1-continued

| Comp. | Structure | Name |
|---|---|---|
| E10 | 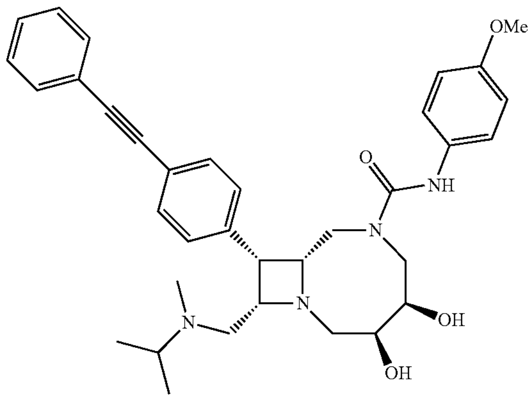 [SMILES: COc1ccc(NC(=O)N2C[C@@H](O)[C@@H](O)CN3[C@H](CN(C)C(C)C)[C@H](c4ccc(C#Cc5ccccc5)cc4)[C@@H]3C2)cc1] | (3S,4R,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide |
| E11 | 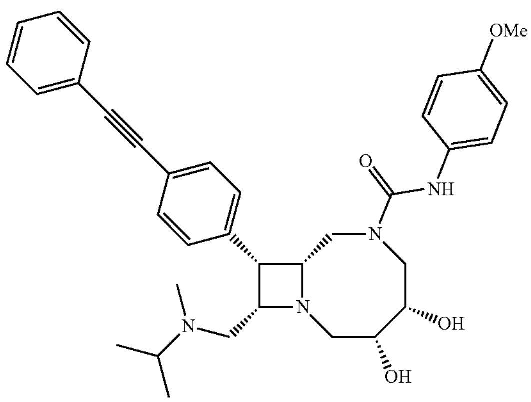 [SMILES: COc1ccc(NC(=O)N2C[C@H](O)[C@H](O)CN3[C@H](CN(C)C(C)C)[C@H](c4ccc(C#Cc5ccccc5)cc4)[C@@H]3C2)cc1] | (3R,4S,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide |
| E12 | 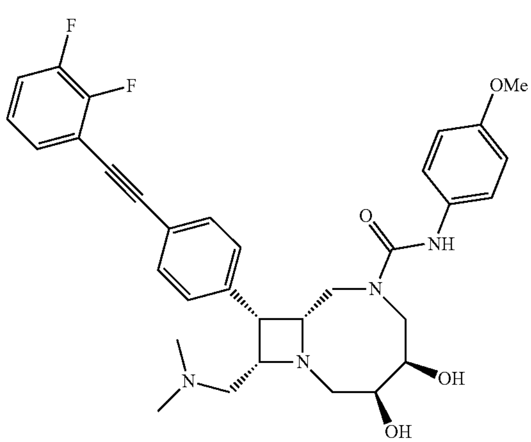 [SMILES: COc1ccc(NC(=O)N2C[C@@H](O)[C@@H](O)CN3[C@H](CN(C)C)[C@H](c4ccc(C#Cc5cccc(F)c5F)cc4)[C@@H]3C2)cc1] | (3S,4R,8R,9S,10S)-9-(4-((2,3-difluorophenyl)ethynyl)phenyl)-10-((dimethylamino)methyl)-3,4-dihydroxy-N-(4-methoxyphenyl)-1,6-diazabicyclo[6.2.0]decane-6-carboxamide |

TABLE 1-continued

| Comp. | Structure | Name |
|---|---|---|
| E13 | 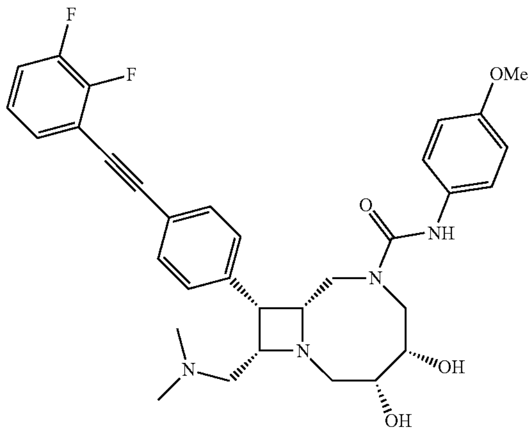 [SMILES: COc1ccc(NC(=O)N2C[C@H](O)[C@H](O)CN3[C@H](CN(C)C)[C@H](c4ccc(C#Cc5cccc(F)c5F)cc4)[C@@H]3C2)cc1] | (3R,4S,8R,9S,10S)-9-[4-[2-(2,3-difluorophenyl)ethynyl]phenyl]-10-[(dimethylamino)methyl]-3,4-dihydroxy-N-(4-methoxyphenyl)-1,6-diazabicyclo[6.2.0]decane-6-carboxamide |
| E14 | 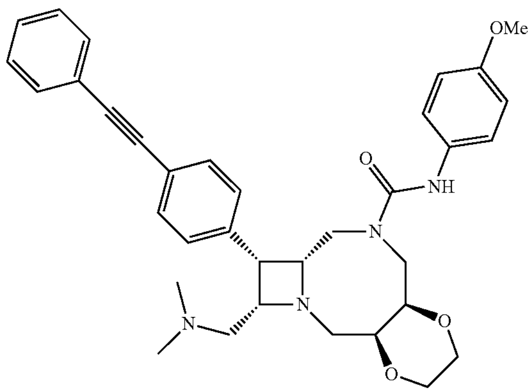 [SMILES: COc1ccc(NC(=O)N2C[C@H]3OCCO[C@H]3CN3[C@H](CN(C)C)[C@H](c4ccc(C#Cc5ccccc5)cc4)[C@@H]3C2)cc1] | (4aR,7aR,8S,9S,11aS)-9-((dimethylamino)methyl)-N-(4-methoxyphenyl)-8-(4-(phenylethynyl)phenyl)octahydro-2H-azeto[1,2-a][1,4]dioxino[2,3-f][1,4]diazocine-6(3H)-carboxamide |
| E15 | 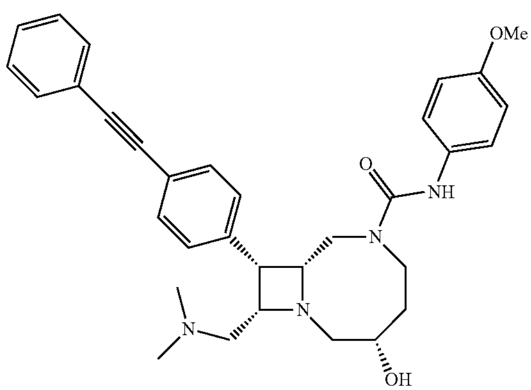 [SMILES: COc1ccc(NC(=O)N2CC[C@H](O)CN3[C@H](CN(C)C)[C@H](c4ccc(C#Cc5ccccc5)cc4)[C@@H]3C2)cc1] | (3S,8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide |
| E16 | 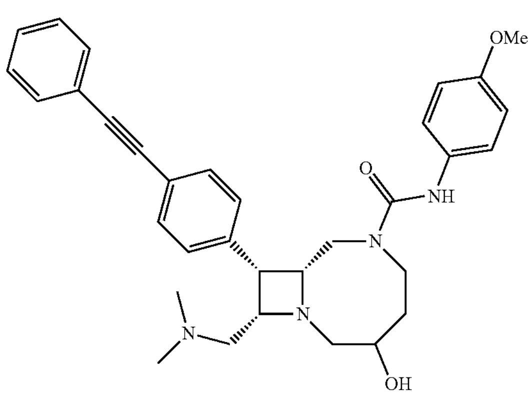 | (8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide, isomer 1* |

TABLE 1-continued

| Comp. | Structure | Name |
|---|---|---|
| E17 | 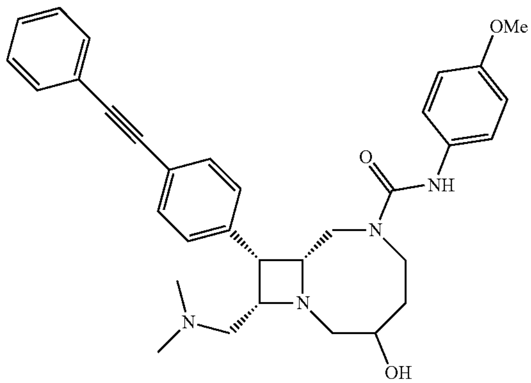 | (8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide, isomer 2* |
| E18 | 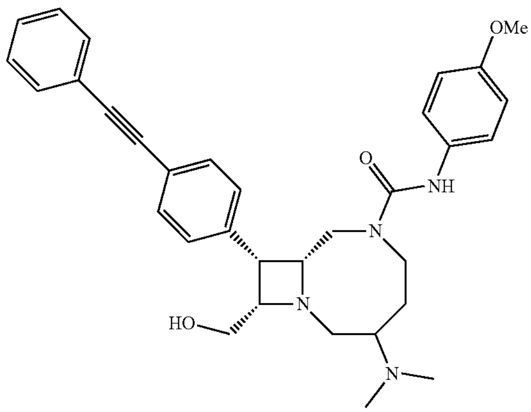 | (8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide, isomer 1* |
| E19 | 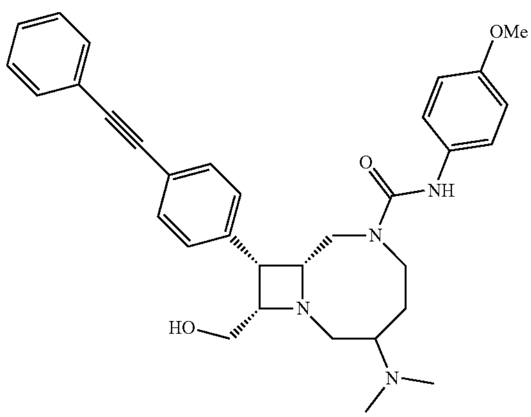 | (8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide, isomer 2* |
| E20 | 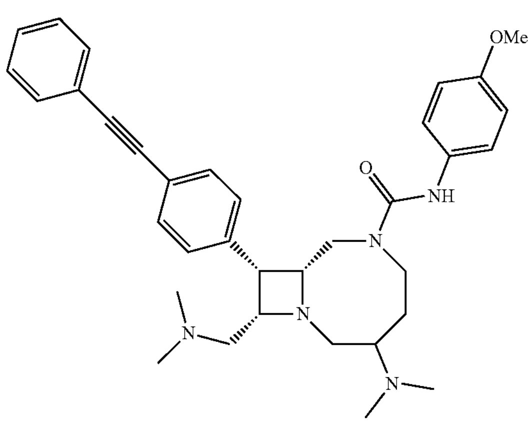 | (8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide, isomer 1* |

TABLE 1-continued

| Comp. | Structure | Name |
|---|---|---|
| E21 | 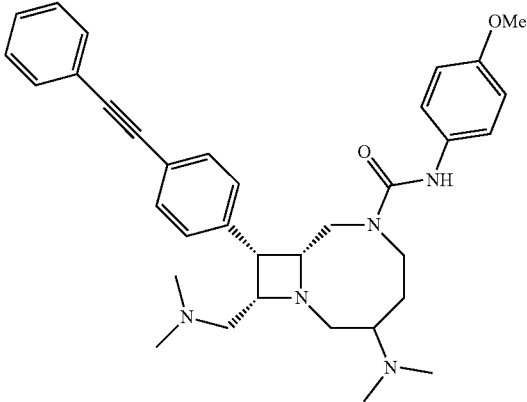 | (8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide, isomer 2* |
| E22 | 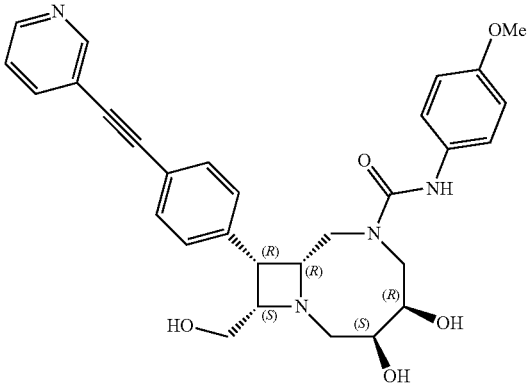 | (3S,4R,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide |
| E23 | 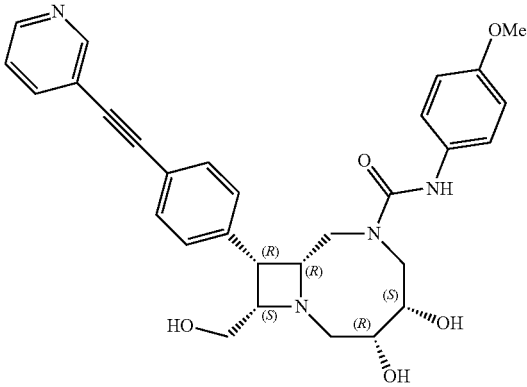 | (3R,4S,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide |
| E24 | 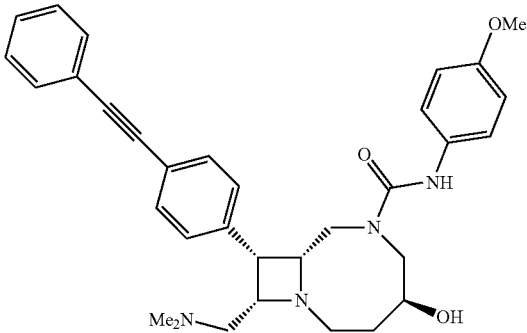 [SMILES: COc1ccc(NC(=O)N2C[C@@H](O)CCN3[C@H](CN(C)C)[C@H](c4ccc(C#Cc5ccccc5)cc4)[C@@H]3C2)cc1] | (4S,8R,9S,10S)-10-[(dimethylamino)methyl]-4-hydroxy-N-(4-methoxyphenyl)-9-[4-(2-phenylethynyl)phenyl]-1,6-diazabicyclo[6.2.0]decane-6-carboxamide |

TABLE 1-continued

| Comp. | Structure | Name |
|---|---|---|
| E25 | 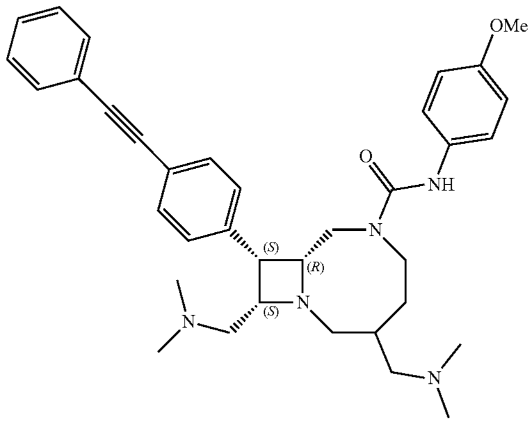 | (8R,9S,10S)-3,10-bis[(dimethylamino)methyl]-N-(4-methoxyphenyl)-9-[4-(2-phenylethynyl)phenyl]-1,6-diazabicyclo[6.2.0]decane-6-carboxamide |
| E26 | 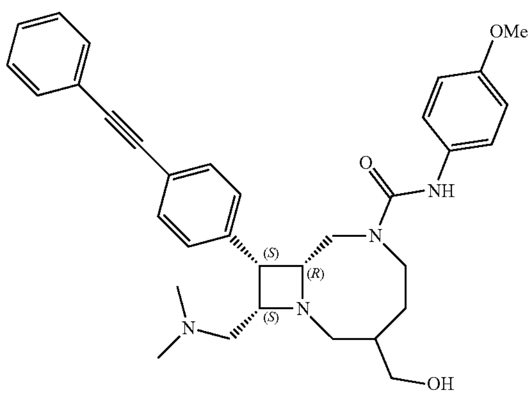 | (8R,9S,10S)-10-[(dimethylamino)methyl]-3-(hydroxymethyl)-N-(4-methoxyphenyl)-9-[4-(2-phenylethynyl)phenyl]-1,6-diazabicyclo[6.2.0]decane-6-carboxamide |
| E27 | 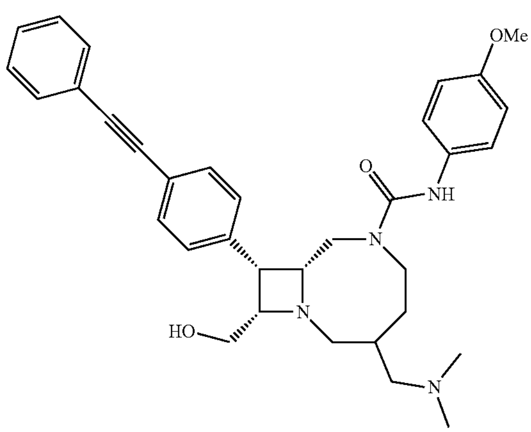 | (8R,9R,10S)-3-[(dimethylamino)methyl]-10-(hydroxymethyl)-N-(4-methoxyphenyl)-9-[4-(2-phenylethynyl)phenyl]-1,6-diazabicyclo[6.2.0]decane-6-carboxamide |

TABLE 1-continued

| Comp. | Structure | Name |
|---|---|---|
| E28 | 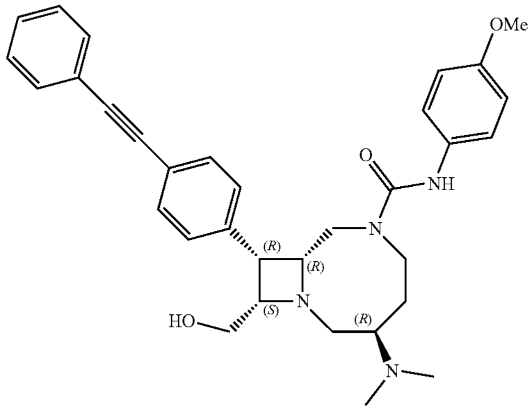 | (3R,8R,9R,10S)-3-(dimethylamino)-10-(hydroxymethyl)-N-(4-methoxyphenyl)-9-[4-(2-phenylethynyl)phenyl]-1,6-diazabicyclo[6.2.0]decane-6-carboxamide |
| E29 | 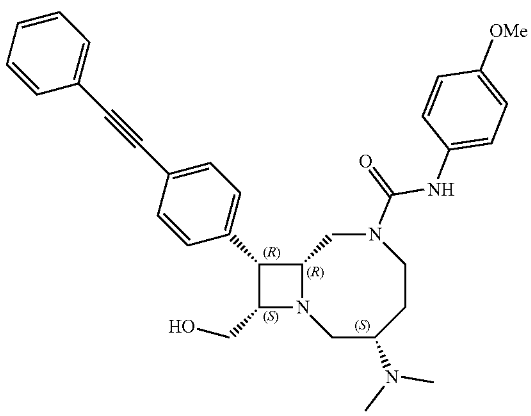 | (3S,8R,9R,10S)-3-(dimethylamino)-10-(hydroxymethyl)-N-(4-methoxyphenyl)-9-(4-(phenylethynyl)phenyl)-1,6-diazabicyclo[6.2.0]decane-6-carboxamide |
| E30 | 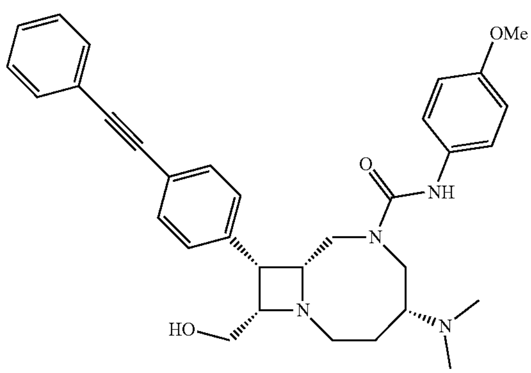 [SMILES: COc1ccc(NC(=O)N2C[C@H](N(C)C)CCN3[C@H](CO)[C@H](c4ccc(C#Cc5ccccc5)cc4)[C@@H]3C2)cc1] | (4R,8R,9R,10S)-4-(dimethylamino)-10-(hydroxymethyl)-N-(4-methoxyphenyl)-9-(4-(phenylethynyl)phenyl)-1,6-diazabicyclo[6.2.0]decane-6-carboxamide |
| E31 | 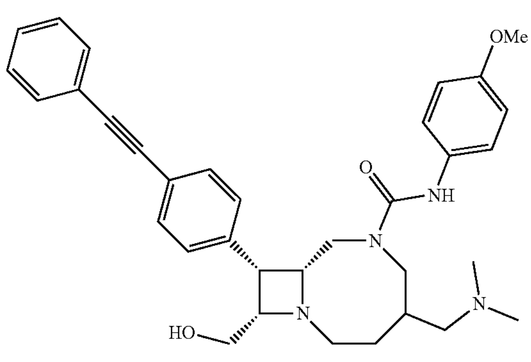 | (8R,9R,10S)-4-((dimethylamino)methyl)-10-(hydroxymethyl)-N-(4-methoxyphenyl)-9-(4-(phenylethynyl)phenyl)-1,6-diazabicyclo[6.2.0]decane-6-carboxamide |

TABLE 1-continued

| Comp. | Structure | Name |
|---|---|---|
| E32 | 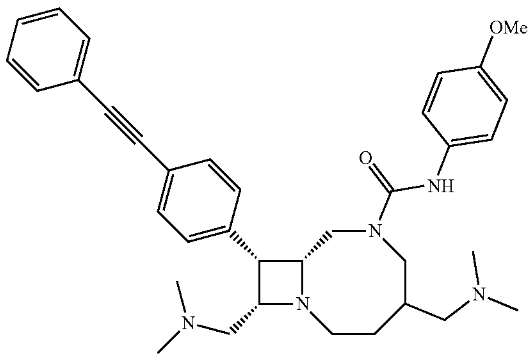 | (8R,9S,10S)-4,10-bis[(dimethylamino)methyl]-N-(4-methoxyphenyl)-9-[4-(2-phenylethynyl)phenyl]-1,6-diazabicyclo[6.2.0]decane-6-carboxamide |
| E33 | 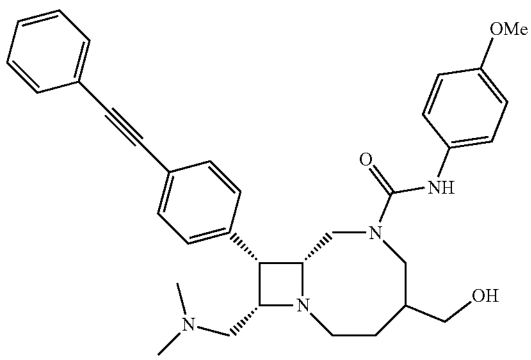 | (8R,9S,10S)-10-[(dimethylamino)methyl]-4-(hydroxymethyl)-N-(4-methoxyphenyl)-9-[4-(2-phenylethynyl)phenyl]-1,6-diazabicyclo[6.2.0]decane-6-carboxamide |
| E34 | 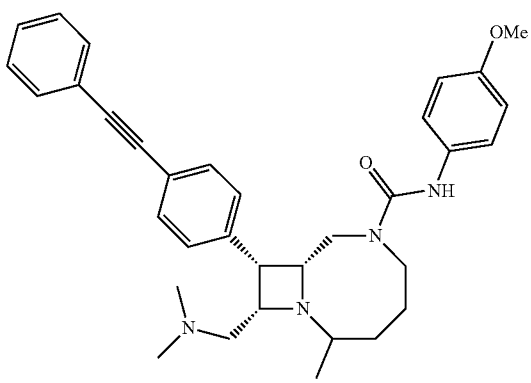 | (8R,9S,10S)-10-((dimethylamino)methyl)-N-(4-methoxyphenyl)-2-methyl-9-(4-(phenylethynyl)phenyl)-1,6-diazabicyclo[6.2.0]decane-6-carboxamide |
| E35 | 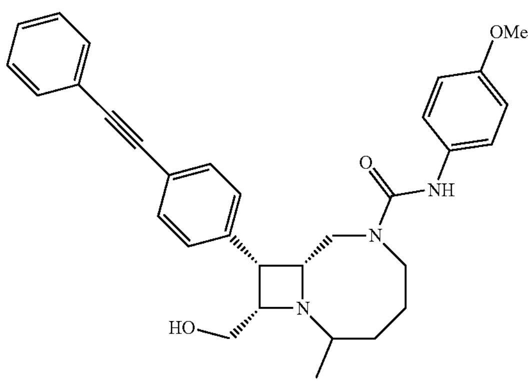 | (8R,9R,10S)-10-(hydroxymethyl)-N-(4-methoxyphenyl)-2-methyl-9-[4-(2-phenylethynyl)phenyl]-1,6-diazabicyclo[6.2.0]decane-6-carboxamide |

TABLE 1-continued

| Comp. | Structure | Name |
|---|---|---|
| E36 | 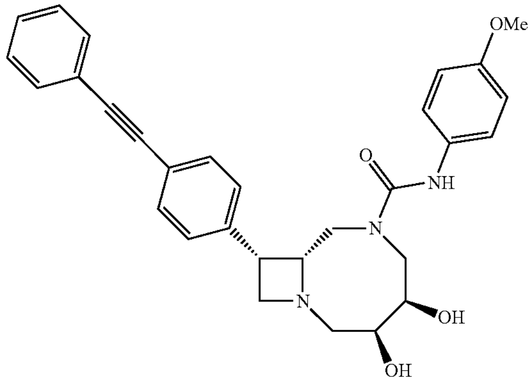 [SMILES: COc1ccc(NC(=O)N2C[C@@H](O)[C@@H](O)CN3C[C@H](c4ccc(C#Cc5ccccc5)cc4)[C@@H]3C2)cc1] | (3S,4R,8R,9S)-3,4-dihydroxy-N-(4-methoxyphenyl)-9-[4-(2-phenylethynyl)phenyl]-1,6-diazabicyclo[6.2.0]decane-6-carboxamide |
| E37 | 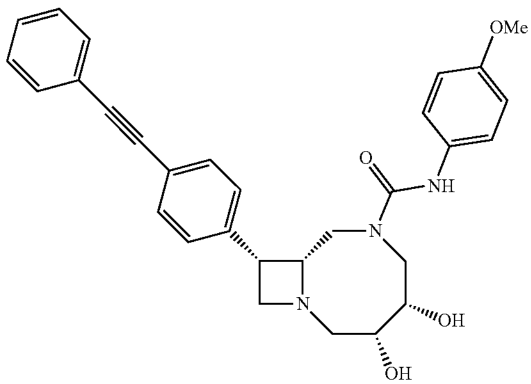 [SMILES: COc1ccc(NC(=O)N2C[C@H](O)[C@H](O)CN3C[C@H](c4ccc(C#Cc5ccccc5)cc4)[C@@H]3C2)cc1] | (3R,4S,8R,9S)-3,4-dihydroxy-N-(4-methoxyphenyl)-9-[4-(2-phenylethynyl)phenyl]-1,6-diazabicyclo[6.2.0]decane-6-carboxamide |
| E38 | 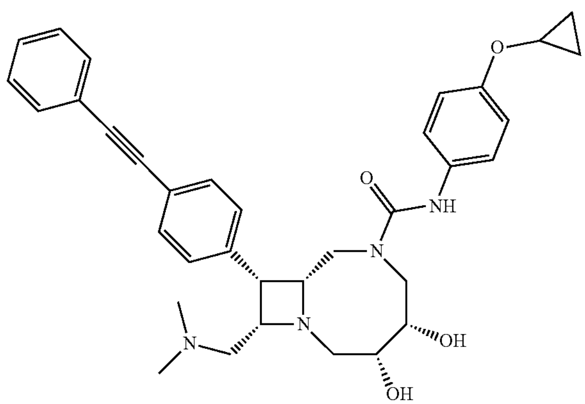 [SMILES: CN(C)C[C@@H]1[C@H](c2ccc(C#Cc3ccccc3)cc2)[C@@H]2CN(C(=O)Nc3ccc(OC4CC4)cc3)C[C@H](O)[C@H](O)CN12] | (3R,4S,8R,9S, 10S)-N-(4-cyclopropoxyphenyl)-10-((dimethylamino)methyl)-3,4-dihydroxy-9-(4-(phenylethynyl)phenyl)-1,6-diazabicyclo[6.2.0]decane-6-carboxamide |

*Each stereoisomer was isolated as described in the exemplary synthesis and used in any biological experiments as described below. However, stereochemistry at the C3 or C4 position could not be determined - although each diastereomer (i.e., isomer 1 or isomer 2) was isolated as described and not present as a mixture.

It will be understood that in the event of any inconsistency between a chemical name and formula, both compounds with the indicated chemical name and compounds with the indicated chemical structure will be considered as embraced by the invention.

The compounds of the present invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Methods

The compounds described herein are useful in the methods provided herein and, while not bound by any particular theory, are believed to exert their desirable effects through their ability to inhibit the growth of or kill a parasitic protozoan that causes malaria (e.g., *P. falciparum, P. vivax, P. ovale, P. malariae*, and/or *P. knowlesi*) and/or cryptosporidiosis (e.g. *C. parvum, C. hominis, C. canis, C. felis, C. meleagridis*, and *C. muris*). In some embodiments, the treatment includes causative prophylaxis, such as preventing the spread of *Plasmodium* and/or *Cryptosporidium* infection beyond the liver, preventing systemic disease, preventing the symptomatic stage of malaria, preventing the establishment of the infection, and/or preventing further transmission (e.g., to a mosquito). In some embodiments, the treatment of malaria refers to treatment intended to achieve cure (e.g., of *P. vivax* or *P. malariae*), e.g., treatment for radical cure (i.e., clearing hypnozoites from the liver). In various examples, the methods include preventing spread of infection of a malaria-causing parasite from the liver. In some embodiments, the treatment of cryptosporidiosis includes causative prophylaxis, such as preventing the spread of *Cryptosporidium* beyond infected portions of a subject (e.g. liver, intestines, respiratory tract, etc.).

The compounds may be useful in the treatment of drug resistant malaria, such as malaria resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, and any combination thereof.

Pharmaceutical Compositions

1. Formulations

For use in the methods described herein, the compounds can be formulated as pharmaceutical or veterinary compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy*, 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference. Exemplary routes of administration and formulations are described as follows.

In the practice of the disclosed methods, the compounds (or pharmaceutically acceptable salts thereof) or compositions can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface)), parenterally (e.g., by intramuscular, intravenous, subcutaneous, intraarticular, intravesicular, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions, in general, include an effective amount of a compound described herein and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 1-95% by weight of the total weight of the composition.

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, camauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The pharmaceutical composition may also be formulated as a veterinary composition, intended for use with subjects other than humans. The veterinary compositions according to the present invention can be in any appropriate forms to suit the requested administration modes, for instance nasal, oral, intradermic, cutaneous or parenteral. In a preferred embodiment, the composition is in a form intended for an oral administration and, for instance when the domestic animal eating, either mixed to the food ration, or directly into the mouth after meal. The veterinary compositions of the invention are in the form of a nasal, oral or injectable liquid suspension or solution, or in solid or semi-solid form, powders, pellets, capsules, granules, sugar-coated pills, gelules, sprays, cachets, pills, tablets, pastes, implants or gels. In a particular embodiment, the compositions are in the form of an oral solid form, preferably tablets. In some embodiments, the veterinary compositions may have an effective amount of the compound for a specific species of animal (e.g., cow, lamb, goat, horse, etc.).

In a preferred embodiment, the compositions of the invention are formulated in pellets or tablets for an oral administration. According to this type of formulation, they comprise lactose monohydrate, cellulose microcrystalline, crospovidone/povidone, aroma, compressible sugar and magnesium stearate as excipients. When the compositions are in the form of pellets or tablets, they are for instance 1 mg, 2 mg, or 4 mg torasemide pellets or tablets. Such pellets or tablets are divisible so that they can be cut to suit the posology according to the invention in one or two daily takes. In a further preferred embodiment, the compositions of the invention are formulated in injectable solutions or suspensions for a parenteral administration. The injectable compositions are produced by mixing therapeutically efficient quantity of torasemide with a pH regulator, a buffer agent, a suspension agent, a solubilisation agent, a stabilizer, a tonicity agent and/or a preservative, and by transformation of the mixture into an intravenous, sub-cutaneous, intramuscular injection or perfusion according to a conventional method. Possibly, the injectable compositions may be lyophilized according to a conventional method. Examples of suspension agents include methylcellulose, polysorbate 80, hydroxyethylcellulose, xanthan gum, sodic carboxymethylcellulose and polyethoxylated sorbitan monolaurate. Examples of solubilisation agent include polyoxy ethylenesolidified castor oil, polysorbate 80, nicotinamide, polyethoxylated sorbitan monolaurate, macrogol and ethyl ester of caste oil fatty acid. Moreover, the stabilizer includes sodium sulfite, sodium metalsulfite and ether, while the preservative includes methyl p-hydroxybenzoate, ethyl p-hydroxybenzoate, sorbic acid, phenol, cresol and chlorocresol. An example of tonicity agent is mannitol. When preparing injectable suspensions or solutions, it is desirable to make sure that they are blood isotonic.

2. Kits

The compounds and compositions can be packaged in a kit, optionally with one or more other pharmaceutical agents (see below). Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects ("bulk packaging"). The kit components can be assembled in cartons, blister packs, bottles, and tubes.

3. Dosage

The dose of a compound depends on a number of factors, such as the manner of administration, the age and the body weight of the subject, and the condition of the subject to be treated, and ultimately will be decided by the attending physician or veterinarian. Such an amount of the compound, as determined by the attending physician or veterinarian, is referred to herein, and in the claims, as a "therapeutically effective amount." For example, the dose of a compound disclosed herein is typically in the range of about 1 to about 1000 mg per day. Preferably, the therapeutically effective amount is in an amount of from about 1 mg to about 500 mg per day.

Administration of each drug, as described herein, can, independently, be one to four times daily for one day to one year, and may even be for the life of the subject. Chronic, long-term administration may be indicated.

4. Combination Therapies

The compounds and pharmaceutical compositions can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

Examples of other drugs to combine with the compounds described herein include pharmaceuticals for the treatment of malaria (e.g., chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, any other therapeutic approved for the treatment of malaria, and any combination thereof) and/or pharmaceuticals for the treatment of cryptosporidiosis (e.g., nitazoxanide). Other examples of drugs to combine with the compounds described herein include pharmaceuticals for the treatment of different, yet associated or related symptoms or indications. Combination methods can involve the use of the two (or more) agents formulated together or separately, as determined to be appropriate by those of skill in the art. In one example, two or more drugs are formulated together for the simultaneous or near simultaneous administration of the agents.

EXAMPLES

The following Examples illustrate the synthesis of a representative number of compounds and the use of these compounds in the treatment of malaria. Accordingly, the Examples are intended to illustrate but not to limit the disclosure. Additional compounds not specifically exemplified may be synthesized using conventional methods in combination with the methods described herein.

Synthesis of Compounds

Materials and Methods

All reactions were carried out under $N_2$ or argon atmosphere. All reagents and solvents were purchased from commercial vendors and used as received, or synthesized according to the footnoted references. NMR spectra were recorded on a Bruker 300 (300 MHz $^1H$, 75 MHz $^{13}C$) and Bruker 400 (400 MHz $^1H$, 100 MHz $^{13}C$) spectrometer. Proton chemical shifts are reported in ppm ($\delta$) referenced to the NMR solvent. Data are reported as follows: chemical shifts, multiplicity (br=broad, s=singlet, d=doublet, t=triplet, q=quartet, p=pentet, m=multiplet; coupling constant(s) in Hz; integration). Unless otherwise indicated NMR data were collected at 25° C. Flash chromatography was performed using 40-60 pirn Silica Gel (60 Å mesh) on a Teledyne Isco Combiflash Rf. For purity analysis, purity was measured by UV absorbance at 210 nm for all examples, and identity was determined on a SQ mass spectrometer by positive electrospray ionization. The following method was used: Tandem Liquid Chromatography/Mass Spectrometry (LCMS) was performed on a Waters 2795 separations module and 3100 mass detector. Mobile phase A consisted of 0.01% formic acid in water, while mobile phase B consisted of 0.01% formic acid in acetonitrile. The gradient ran from 5% to 95% mobile phase B over 2.5, 5 or 7.5 min at 1.75 mL/min. An Agilent Poroshell 120 EC-C18, 2.7 mM, 3.0×30 mm column was used with column temperature maintained at 40° C. 2.1 mL of sample solution were injected. Analytical TLC was performed on EM Reagent 0.25 mm silica gel 60-F plates. Visualization was accomplished with UV light and aqueous potassium permanganate ($KMnO_4$) stain followed by heating. Accurate mass measurements were obtained on an Agilent 6230 Time-of-Flight mass spectrometer as the $(M+H)^+$. Compound purity and identity were also determined by UPLC-MS. Purity was measured by UV absorbance at 210 nm. Identity was determined on a SQ mass spectrometer by positive and negative electrospray ionization. Mobile phase A consisted of either 0.1% ammonium hydroxide or 0.05% trifluoroacetic acid in water, while mobile phase B consisted of either 0.1% ammonium hydroxide or 0.06% trifluoroacetic acid in acetonitrile. The gradient ran from 5% to 95% mobile phase B over 2.65 min at 0.9 mL/min. An Acquity BEH C18, 1.7 um, 2.1×50 mm column was used with column temperature maintained at 65° C. Compounds were dissolved in DMSO at a nominal concentration of 1 mg/mL, and 1.0 μL of this solution was injected. Chiral separations were performed by SFC-MS. A Berger G600 supercritical fluid chromatograph was coupled with a Waters ZQ single quadrupole mass spectrometer operating in positive APCI mode. Using liquefied $CO_2$ modified with 20% isopropanol, an isocratic separation was performed for 5.0 minutes at 4.0 mL/min on a 4.6×100 mm Chiralpak AD-H column maintained at 40° C. Compounds were dissolved in methanol at a nominal concentration of 1 mg/mL, and 10 μL of this solution was injected. The synthetic examples below are not particularly limiting, and other methodologies to synthesize the compounds of the present invention are well known to persons of skill in the art.

Abbreviations

Throughout the synthetic examples below, various abbreviations are employed and are well known to persons of ordinary skill in the art. Table 2 illustrates various examples of abbreviations used throughout the examples and the corresponding reference.

TABLE 2

| Abbreviation | Reference |
|---|---|
| ACN | acetonitrile |
| DCM | dichlormethane |
| DMF | dimethylformamide |
| EtOAc | ethyl acetate |
| HPLC | High Performance Liquid Chromatography |
| MeOH | Methanol |
| PBS | Phosphate Buffered Saline |
| THF | Tetrahydrofuran |
| TFA | Trifluoroacetic Acid |
| TLD | Thin Layer Chromatography |
| UPLC | Ultra Performance Liquid Chromatography |
| DBU | 1,8-diazabicyclo[5.4.0]undec-7-ene |
| XPhos Pd G3 | XPhos Precatalyst (i.e., 2-dicyclohexylphosphino-2',4',6'-triisopropyl-1,1'-biphenyl)[2-(2'-amino-1,1'-biphenyl)]palladium(II) methanesulfonate, CAS Number 1445085-55-1) |
| TMSOTf | trimethylsilyl trifluoromethanesulfonate |
| DIAD | diisopropyl azodicarboxylate |
| NMO | N-methylmorpholine N-oxide |
| TsOH | p-toluenesulfonic acid |
| TBAB/F | tetra-N-butylammonium bromide/fluoride |
| DCE | dichloroethylene |
| TFAA | trifluoroacetic anhydride |
| DMP | 2,2-dimethoxypropane |
| Dess-Martin | Dess-Martin periodinane (i.e., 1,1,1-Tris(acetyloxy)-1,1-dihydro-1,2-benziodoxol-3-(1H)-one, CAS Number 87413-09-0) |
| Hoyveda-Grubbs $2^{nd}$ Generation Catalyst | Hoyveda-Grubbs 2nd Generation ruthenium based catalyst (i.e., (1,3-bis-(2,4,6-trimethylphenyl)-2-imidazolidinylidene)dichloro(o-isopropoxyphenyl-methylene)ruthenium, Dichloro[1,3-bis(2,4,6-trimethylphenyl)-2-imidazolidinylidene](2-isopropoxyphenylmethylene)ruthenium(II), CAS Number 301224-40-8). |
| Hoyveda-Grubbs $1^{st}$ Generation Catalyst | Hoyveda-Grubbs 1st Generation ruthenium based catalyst (i.e., ichloro(2-isopropoxyphenylmethylene)(tricyclohexylphosphine)ruthenium(II), Dichloro(o-isopropoxyphenylmethylene)(tricyclohexylphosphine)-ruthenium(II), CAS Number 203714-71-0). |
| NBSH | 2-nitrobenzenesulfonohydrazide |
| PhSH | Benzenethiol |
| DIBAL-H | Diisobutylaluminium Hydride |

Example 1: (3S,4R,8R,9S,10S)—N-(4-cyclopropoxyphenyl)-10-((dimethylamino)methyl)-3,4-dihydroxy-9-(4-(phenylethynyl)phenyl)-1,6-diazabi-cyclo[6.2.0]decane-6-carboxamide ("E1")

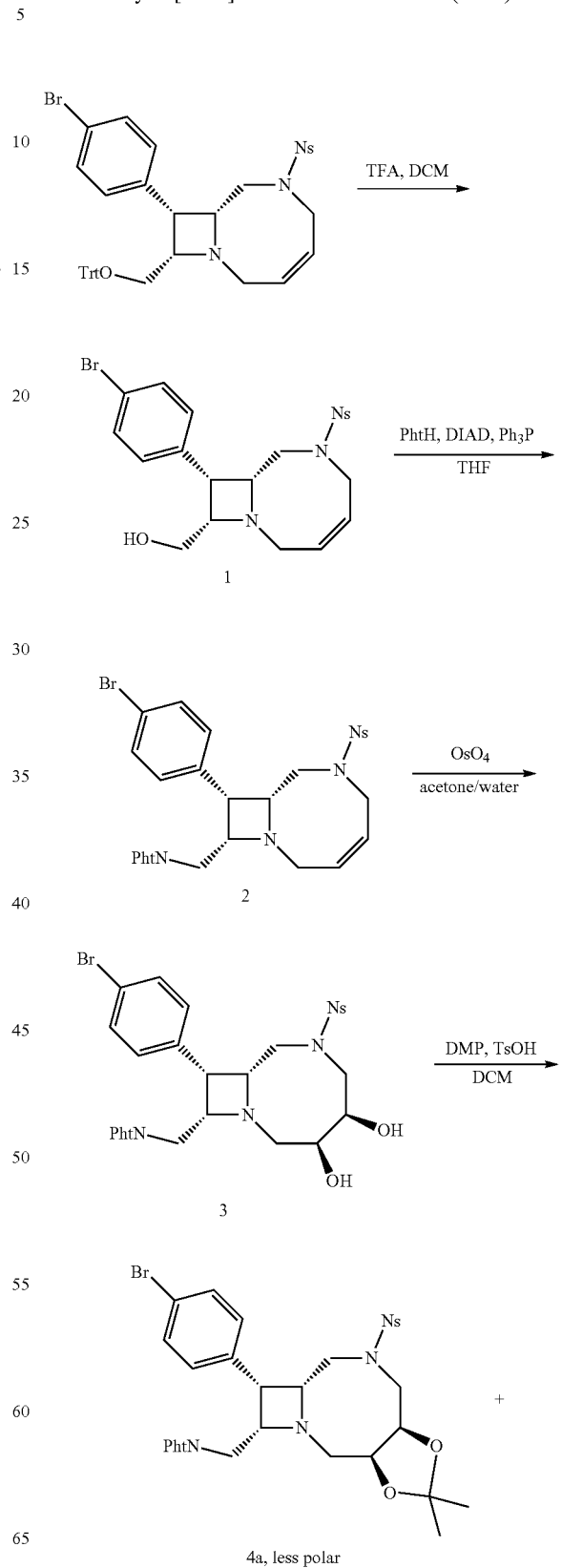

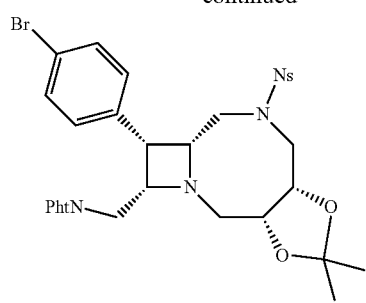

4b, more polar

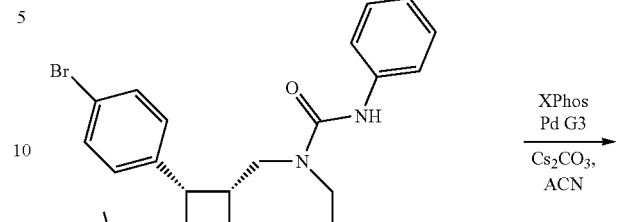

8

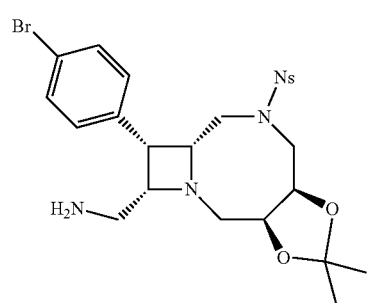

5

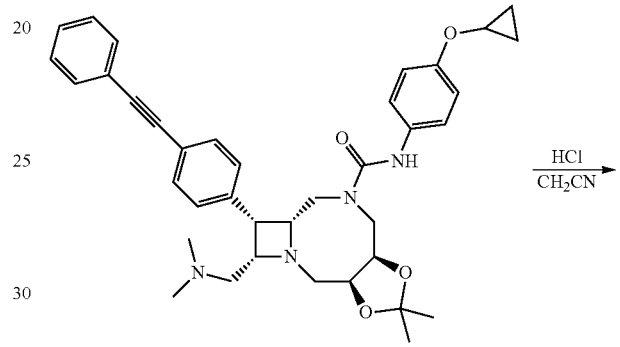

9

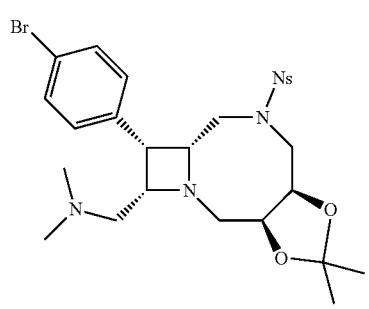

6

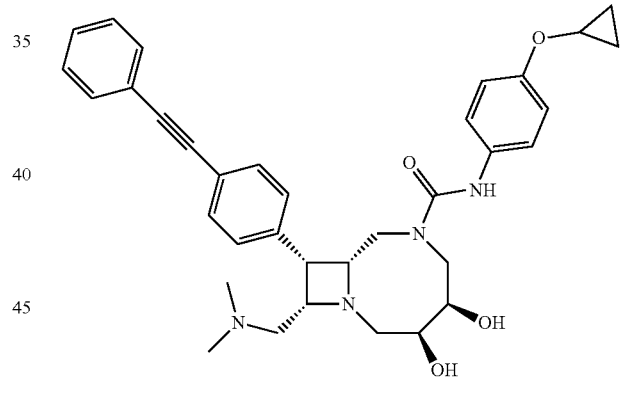

E1

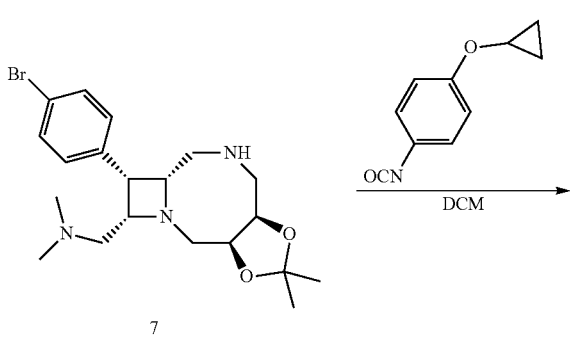

7

Intermediate 1: ((8R,9R,10S,Z)-9-(4-bromophenyl)-6-((2-nitrophenyl)sulfonyl)-1,6-diazabicyclo[6.2.0]dec-3-en-10-yl)methanol To a solution of (8R,9R,10S,Z)-10-((bis(4-methoxyphenyl)(phenyl)methoxy)methyl)-9-(4-bromophenyl)-6-((2-nitrophenyl)sulfonyl)-1,6-diazabicyclo[6.2.0]dec-3-ene (2.00 g, 2.66 mmol) (Journal of Organic Chemistry (2012), 77(17), 7187-7211; WO 2015070204) in DCM (27.00 mL) was added TFA (3.03 g, 26.60 mmol, 1.97 mL). The mixture was stirred at 15° C. for 20 hours. The reaction mixture was quenched by addition NaHCO₃ solution (100 mL), and then extracted with DCM 180 mL (3×60 mL). The combined organic layers were dried over [NaSO₄], filtered and concentrated under reduced pressure to give a residue. The residue was purified by column chromatography (SiO$_2$, petroleum ether:DCM=1:1 to DCM:MeOH=10:1 yielding Intermediate 1 (1.47 g, crude) as a black solid. Presence of the reaction product was confirmed by NMR and LCMS.

Intermediate 2: 2-(((8R,9S,10S,Z)-9-(4-bromophenyl)-6-((2-nitrophenyl)sulfonyl)-1,6-diazabicyclo[6.2.0]dec-3-en-10-yl)methyl)isoindoline-1,3-dione To a mixture of triphenylphosphine (1.52 g, 5.78 mmol) in THF (5 mL) degassed and purged with N$_2$ was added diisopropyl azodicarboxylate (1.17 g, 5.78 mmol, 1.12 mL). To this mixture stirred at 0° C. under N$_2$ atmosphere was added a mixture of Intermediate 1 (1.47 g, 2.89 mmol, 1.00 eq) and isoindoline-1,3-dione (637.81 mg, 4.34 mmol, 1.50 eq) in THF (5 mL) degassed and purged with N$_2$. The mixture was stirred at 16° C. for 18 hours under N$_2$ atmosphere. The reaction mixture was quenched by addition H$_2$O (20 mL), and then extracted with DCM (3×20 mL). The combined organic layers were dried over [Na$_2$SO$_4$], filtered and concentrated under reduced pressure to give a residue. The residue was purified by column chromatography (SiO$_2$, petroleum ether:ethylacetate=5:1 to 2:1) yielding Intermediate 2 (1.26 g, 1.98 mmol, 68.39% yield) as a brown solid as confirmed by NMR and LCMS.

Intermediate 3: 2-(((8R,9S,10S)-9-(4-bromophenyl)-3,4-dihydroxy-6-((2-nitrophenyl)sulfonyl)-1,6-diazabicyclo[6.2.0]decan-10-yl)methyl)isoindoline-1,3-dione To a solution of Intermediate 2 (1.26 g, 1.98 mmol) in acetone/water (15.00 mL) was added N-methylmorpholine N-oxide (463.09 mg, 3.95 mmol, 417.20 µL) and then OsO$_4$ (5.02 mg, 19.76 µmol, 1.03 µL). The mixture was stirred at 15° C. for 1.5 hour. The reaction mixture was dried over [Na$_2$SO$_4$], filtered and concentrated under reduced pressure. The residue was purified by column chromatography (SiO$_2$, petroleum ether/ethyl acetate=3/1 to 0:1) to yield Intermediate 3 (1.11 g, 1.65 mmol, 83.48% yield) as a white solid as confirmed by LCMS and NMR.

Intermediates 4a and 4b: 2-(((3aR,6aR,7S,8R,10aS)-7-(4-bromophenyl)-2,2-dimethyl-5-((2-nitrophenyl)sulfonyl)octahydro-3aH-azeto[1,2-a][1,3]dioxolo[4,5-f][1,4]diazocin-8-yl)methyl)isoindoline-1,3-dione (Intermediate 4a) and 2-(((3aS,6aS,7S,8R,10aS)-7-(4-bromophenyl)-2,2-dimethyl-5-((2-nitrophenyl)sulfonyl)octahydro-3aH-azeto[1,2-a][1,3]dioxolo[4,5-f][1,4]diazocin-8-yl)methyl)isoindoline-1,3-dione (Intermediate 4b)

To a solution of Intermediate 3 (880.00 mg, 1.31 mmol) and 2,2-dimethoxypropane (272.97 mg, 2.62 mmol, 321.14 µL) in DCM (10.00 mL) was added TsOH (225.66 mg, 1.31 mmol). The mixture was stirred at 15° C. After 20 hours, the reaction mixture was concentrated under reduced pressure to give a residue. The residue was purified by prep-TLC (SiO$_2$, petroleum ether/ethyl acetate=1:1) yielding each cis-diol, Intermediate 4a (less polar, 53.00 mg, 74.48 µmol, 5.68% yield) as a white solid and Intermediate 4b (more polar, 260.00 mg, 365.38 µmol, 27.88% yield) as a white solid as confirmed by NMR and LCMS.

Intermediate 5: ((3aR,6aR,7S,8S,10aS)-7-(4-bromophenyl)-2,2-dimethyl-5-((2-nitrophenyl)sulfonyl)octahydro-3aH-azeto[1,2-a][1,3]dioxolo[4,5-f][1,4]diazocin-8-yl)methanamine To a solution of Intermediate 4b (360.00 mg, 505.92 µmol) in ethanol (5.00 mL) was added hydrazine hydrate (37.99 mg, 758.88 µmol, 36.88 µL). After stirring at 70° C. for 1.5 hour, the reaction mixture was filtered through celite and concentrated under reduced pressure to yield Intermediate 5 (239.00 mg, 411.02 µmol, 81.24% yield) as a yellow solid as confirmed by NMR and LCMS.

Intermediate 6: 1-((3aR,6aR,7S,8S,10aS)-7-(4-bromophenyl)-2,2-dimethyl-5-((2-nitrophenyl)sulfonyl)octahydro-3aH-azeto[1,2-a][1,3]dioxolo[4,5-f][1,4]diazocin-8-yl)-N,N-dimethylmethanamine To a solution of Intermediate 5 (239.00 mg, 411.02 µmol) and formaldehyde (200.47 mg, 2.47 mmol, 183.92 µL) in DCM (500 µL) was added MgSO4 (494.74 mg, 4.11 mmol) and acetic acid (49.36 mg, 822.04 µmol, 47.01 µL). After 20 mins, sodium triacetoxyborohydride (60.32 mg, 1.23 mmol) was added and the mixture was stirred at 15° C. for 23 hour. The reaction mixture was filtered by celite and concentrated under reduced pressure to give a residue. The residue was purified by prep-TLC (SiO$_2$, DCM:MeOH=10:1) yielding Intermediate 6 (210.00 mg, 344.53 µmol, 83.82% yield) as a yellow oil as confirmed by LCMS.

Intermediate 7: 1-((3aR,6aR,7R,8S,10aS)-7-(4-bromophenyl)-2,2-dimethyloctahydro-3aH-azeto[1,2-a][1,3]dioxolo[4,5-f][1,4]diazocin-8-yl)-N,N-dimethylmethanamine To a solution of Intermediate 6 (210.00 mg, 344.53 µmol) in CH$_3$CN (2.00 mL) was added benzenethiol (17.08 mg, 155.04 µmol, 15.82 µL) and then added Cs$_2$CO$_3$ (224.51 mg, 689.06 µmol). The mixture was stirred at 40° C. for 1.5 hour under N$_2$ atmosphere. The reaction mixture was quenched by addition H$_2$O (5 mL), and extracted with DCM 15 mL (3×5 mL). The combined organic layers were dried over [Na$_2$SO$_4$], filtered and concentrated under reduced pressure to give a residue. The residue was purified by prep-TLC (SiO$_2$, DCM:MeOH=10:1) yielding Intermediate 7 (72.00 mg, 169.66 µmol, 49.24% yield) as a yellow oil as confirmed by NMR and LCMS.

Intermediate 8: (3aR,6aR,7S,8S,10aS)-7-(4-bromophenyl)-N-(4-cyclopropoxyphenyl)-8-((dimethylamino)methyl)-2,2-dimethylhexahydro-3aH-azeto[1,2-a][1,3]dioxolo[4,5-f][1,4]diazocine-5 (4H)-carboxamide To a solution of Intermediate 7 (48.00 mg, 113.11 µmol) in DCM (2.00 mL) was added TEA (5.72 mg, 56.55 µmol, 7.84 µL) and 1-(cyclopropoxy)-4-isocyanato-benzene (23.78 mg, 135.73 µmol) under N$_2$ atmosphere. After stirring at 15° C. for 22 hour, the reaction mixture was quenched by addition H$_2$O (5 mL), and then extracted with DCM 15 mL (3×5 mL). The combined organic layers were concentrated under reduced pressure to give a residue. The residue was purified by prep-TLC (SiO$_2$, DCM:MeOH=10:1) yielding Intermediate 8 (29.40 mg, 49.04 µmol, 43.35% yield) as a pale oil as confirmed by LCMS.

Intermediate 9: (3aR,6aR,7S,8S,10aS)—N-(4-cyclopropoxyphenyl)-8-((dimethylamino)methyl)-2,2-dimethyl-7-(4-(phenylethynyl)phenyl)hexahydro-3aH-azeto[1,2-a][1,3]dioxolo[4,5-f][1,4]diazocine-5 (4H)-carboxamide To a solution of Intermediate 8 (29.00 mg, 48.37 µmol) in CH$_3$CN (1.00 mL) under N$_2$ atmosphere mixture was added TEA (97.89 mg, 967.38 μmol, 134.09 μL) and ethynylbenzene (24.70 mg, 241.84 μmol, 26.56 μL) and XPhos Pd G3 (6.14 mg, 7.26 μmol). After stirring at 70° C. for 1 h, the reaction mixture was quenched by addition H₂O (4 mL), and then extracted with DCM 15 mL (3×5 mL). The combined organic layers were dried over Na₂SO₄, filtered and concentrated under reduced pressure to give Intermediate 9 (30.00 mg) as a pale oil as confirmed by LCMS.

Synthesis of E1: (3S,4R,8R,9S,10S)—N-(4-cyclopropoxyphenyl)-10-((dimethylamino)methyl)-3,4-dihydroxy-9-(4-(phenylethynyl)phenyl)-1,6-diazabicyclo[6.2.0]decane-6-carboxamide To a solution of Intermediate 9 (20.00 mg, 32.22 μmol) in CH₃CN (500.00 μL) was added 1 M HCl (500.00 μL). After stirring at 15° C. for 18 h, the reaction mixture was concentrated under reduced pressure to give a residue. The residue was purified by prep-HPLC (column: Waters Xbridge Prep OBD C18 150*30 5u; A: water (0.225% formic acid) B: acetonitrile) yielding compound E1 (8.20 mg, 14.12 μmol, 43.83% yield) as a yellow solid.

¹H NMR (400 MHz, CHLOROFORM-d) δ ppm 0.73 (d, J=4.52 Hz, 4H) 1.26 (s, 1H) 2.32 (s, 6H) 2.60-2.70 (m, 2H) 2.86-2.92 (m, 1H) 2.96-3.05 (m, 2H) 3.22 (br d, J=15.56 Hz, 1H) 3.52-3.65 (m, 3H) 3.65-3.75 (m, 2H) 3.86 (br s, 2H) 3.97-4.05 (m, 1H) 4.13 (br s, 1H) 4.31 (br d, J=9.54 Hz, 1H) 6.95 (d, J=9.03 Hz, 2H) 7.24 (d, J=9.03 Hz, 2H) 7.32-7.46 (m, 6H) 7.49-7.57 (m, 4H) 8.37 (br s, 1H) 8.56 (br s, 1H).

Example 2: (3S,4R,8R,9S,10S)-10-((dimethylamino)methyl)-3,4-dimethoxy-N-(4-methoxyphenyl)-9-(4-(phenylethynyl)phenyl)-1,6-diazabicyclo[6.2.0]decane-6-carboxamide ("E2")

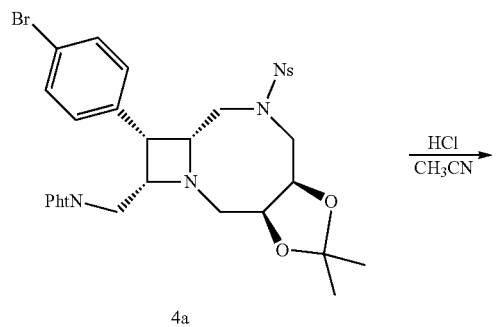

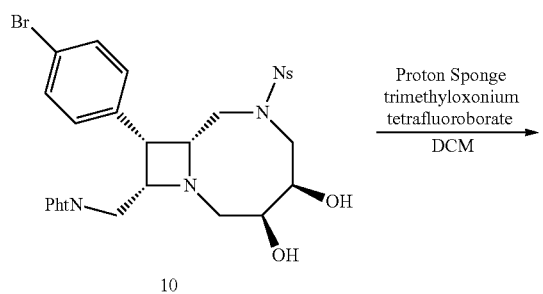

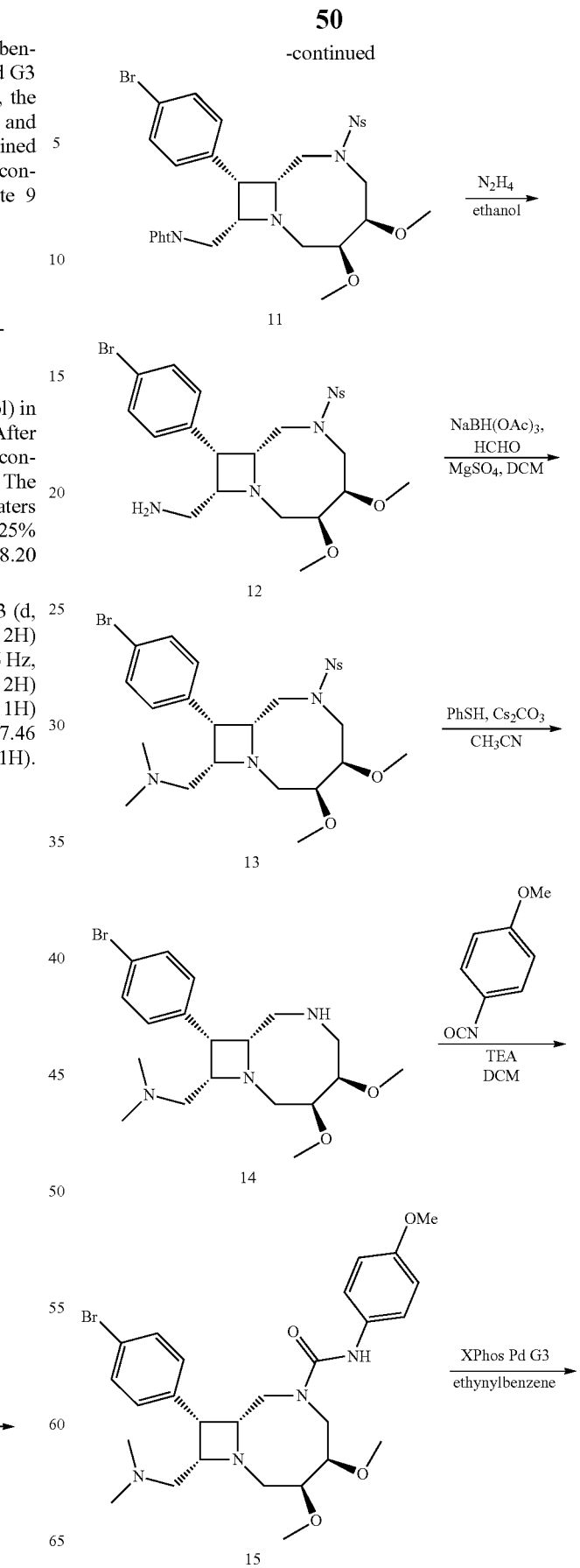

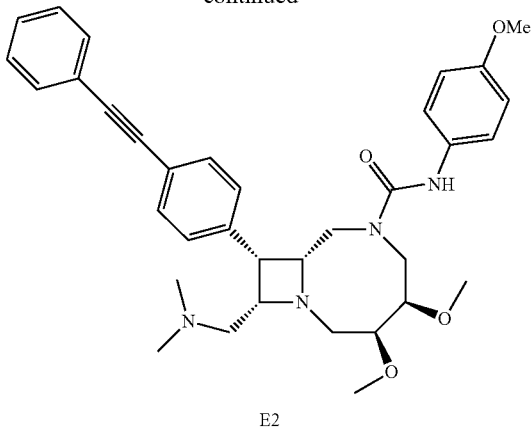

E2

Intermediate 10: 2-(((3S,4R,8R,9S,10S)-9-(4-bromophenyl)-3,4-dihydroxy-6-((2-nitrophenyl)sulfonyl)-1,6-diazabicyclo[6.2.0]decan-10-yl)methyl)isoindoline-1,3-dione A solution of Intermediate 4a (170.00 mg, 238.90 µmol) in CH$_3$CN (2.00 mL) and 1 M HCl (2.00 mL) was stirred at 20° C. for 18 hours. The reaction mixture was concentrated under reduced pressure to give a residue. The residue was purified by prep-TLC (SiO$_2$, DCM:MeOH=10:1) yielding Intermediate 10 (140.00 mg, 208.49 µmol, 87.27% yield) as a white solid as confirmed by NMR.

Intermediate 11: 2-(((3S,4R,8R,9S,10S)-9-(4-bromophenyl)-3,4-dimethoxy-6-((2-nitrophenyl)sulfonyl)-1,6-diazabicyclo[6.2.0]decan-10-yl)methyl)isoindoline-1,3-dione To a solution of Intermediate 10 (125.00 mg, 186.15 µmol) in DCM (4.00 mL) was added trimethyloxonium tetrafluoroborate (137.67 mg, 930.75 µmol) and N1,N1,N8,N8-tetramethylnaphthalene-1,8-diamine (239.36 mg, 1.12 mmol) at 0° C. under N$_2$ atmosphere. After stirring at RT (15° C.) for 18 h, the reaction mixture was concentrated under reduced pressure to give a residue. The residue was purified by prep-TLC (SiO$_2$, ethyl acetate) yielding Intermediate 11 (100.00 mg, 142.94 µmol, 76.79% yield) as a white solid as confirmed by NMR.

Intermediate 12: ((3S,4R,8R,9S,10S)-9-(4-bromophenyl)-3,4-dimethoxy-6-((2-nitrophenyl)sulfonyl)-1,6-diazabicyclo[6.2.0]decan-10-yl)methanamine To a solution of Intermediate 11 (100.00 mg, 142.94 µmol) in ethanol (3.00 mL) was added N$_2$H$_4$·H$_2$O (10.73 mg, 214.42 µmol, 10.42 µL). After stirring at 70° C. for 1 hour, the reaction mixture was filtered through celite and concentrated under reduced pressure to give crude Intermediate 12 (87.00 mg) as a yellow solid as confirmed by NMR.

Intermediate 13: 1-((3S,4R,8R,9S,10S)-9-(4-bromophenyl)-3,4-dimethoxy-6-((2-nitrophenyl)sulfonyl)-1,6-diazabicyclo[6.2.0]decan-10-yl)-N,N-dimethylmethanamine To a solution of Intermediate 12 (87.00 mg, 152.77 µmol) in DCM (2.00 mL) was added HCHO (27.53 mg, 916.64 µmol, 25.25 µL), MgSO$_4$ (183.89 mg, 1.53 mmol), NaBH(OAc)$_3$ (97.14 mg, 458.32 µmol) and AcOH (18.35 mg, 305.55 µmol, 17.47 µL). After stirring at 15° C. for 3 h, the reaction mixture was filtered through celite and concentrated under reduced pressure to give a residue. The residue was purified by prep-TLC (SiO$_2$, DCM:MeOH=10:1) to give Intermediate 13 (46.00 mg, 76.98 µmol, 50.39% yield) as a white oil.

Intermediate 14: ((3S,4R,8R,9S,10S)-9-(4-bromophenyl)-3,4-dimethoxy-1,6-diazabicyclo[6.2.0]decan-10-yl)methanamine To a solution of Intermediate 13 (46.00 mg, 76.98 µmol) in CH$_3$CN (2.00 mL) was added benzenethiol (12.72 mg, 115.48 µmol, 11.78 µL) and Cs$_2$CO$_3$ (50.17 mg, 153.97 µmol). After stirring at 40° C. for 1.5 hour under N$_2$ atmosphere, the reaction mixture was quenched by addition H$_2$O (2 mL), and extracted with DCM 15 mL (3×5 mL). The combined organic layers were dried over [Na$_2$SO$_4$], filtered and concentrated under reduced pressure to give a residue. The residue was purified by prep-TLC (SiO$_2$, DCM:MeOH=10:1) yielding Intermediate 14 (17.00 mg, 41.23 µmol, 53.55% yield) as a white oil as confirmed by LCMS.

Intermediate 15: (3S,4R,8R,9S,10S)-10-(aminomethyl)-9-(4-bromophenyl)-3,4-dimethoxy-N-(4-methoxyphenyl)-1,6-diazabicyclo[6.2.0]decane-6-carboxamide To a solution of Intermediate 14 (17.00 mg, 41.23 µmol) in DCM (2.00 mL) was added TEA (2.09 mg, 20.61 µmol, 2.86 µL) and 1-isocyanato-4-methoxy-benzene (6.15 mg, 41.23 µmol, 5.30 µL). After stirring under N$_2$ atmosphere mixture at 15° C. for 2.5 h, the reaction mixture was quenched by addition H$_2$O (5 mL), and then extracted with DCM 15 mL (3×5 mL). The combined organic layers were concentrated under reduced pressure to give a residue. The residue was purified by prep-TLC (DCM:MeOH=10:1) to give Intermediate 15 (33.00 mg, crude) as a clear oil as confirmed by LCMS.

Synthesis of E2: (3S,4R,8R,9S,10S)-10-((dimethylamino)methyl)-3,4-dimethoxy-N-(4-methoxyphenyl)-9-(4-(phenylethynyl)phenyl)-1,6-diazabicyclo[6.2.0]decane-6-carboxamide To a solution of Intermediate 15 (33.00 mg, 58.77 µmol) in acetonitrile (2.00 mL) was added TEA (118.94 mg, 1.18 mmol, 162.93 µL) and XPhos Pd G3 (7.46 mg, 8.82 µmol) under N$_2$ atmosphere. After stirring at 70° C. for 1 hour, the reaction mixture was quenched by addition H$_2$O (2 mL), and then extracted with DCM 15 mL (3×5 mL). The combined organic layers were dried over [Na$_2$SO$_4$], filtered and concentrated under reduced pressure to give a residue. The residue was purified by prep-TLC (SiO$_2$, DCM:MeOH=10:1) followed by prep-HPLC (Column: Waters Xbridge Prep OBD C18 150*30 5u; A: water (0.225% formic acid) B: acetonitrile) to give 4.4 mg, 7.55 µmol, 12.85% yield as a white solid. The structure was confirmed by LCMS and NMR.

$^1$H NMR (400 MHz, CHLOROFORM-d) δ ppm 2.06 (s, 6H) 2.39 (br s, 2H) 2.58 (br s, 2H) 3.03-3.14 (m, 1H) 3.30 (br s, 1H) 3.48 (s, 4H) 3.51-3.58 (m, 2H) 3.61-3.67 (m, 4H) 3.78 (s, 3H) 3.89-4.12 (m, 3H) 6.83 (d, J=8.91 Hz, 2H) 7.18

(d, J=8.78 Hz, 2H) 7.36 (br d, J=5.40 Hz, 3H) 7.43-7.47 (m, 2H) 7.48-7.51 (m, 2H) 7.52-7.56 (m, 2H) 7.99 (br s, 1H).
Example 3: (4S,8R,9R,10S)-4-(dimethylamino)-10-(hydroxymethyl)-N-(4-methoxyphenyl)-9-(4-(phenylethynyl)phenyl)-1,6-diazabicyclo[6.2.0]decane-6-carboxamide ("E3")
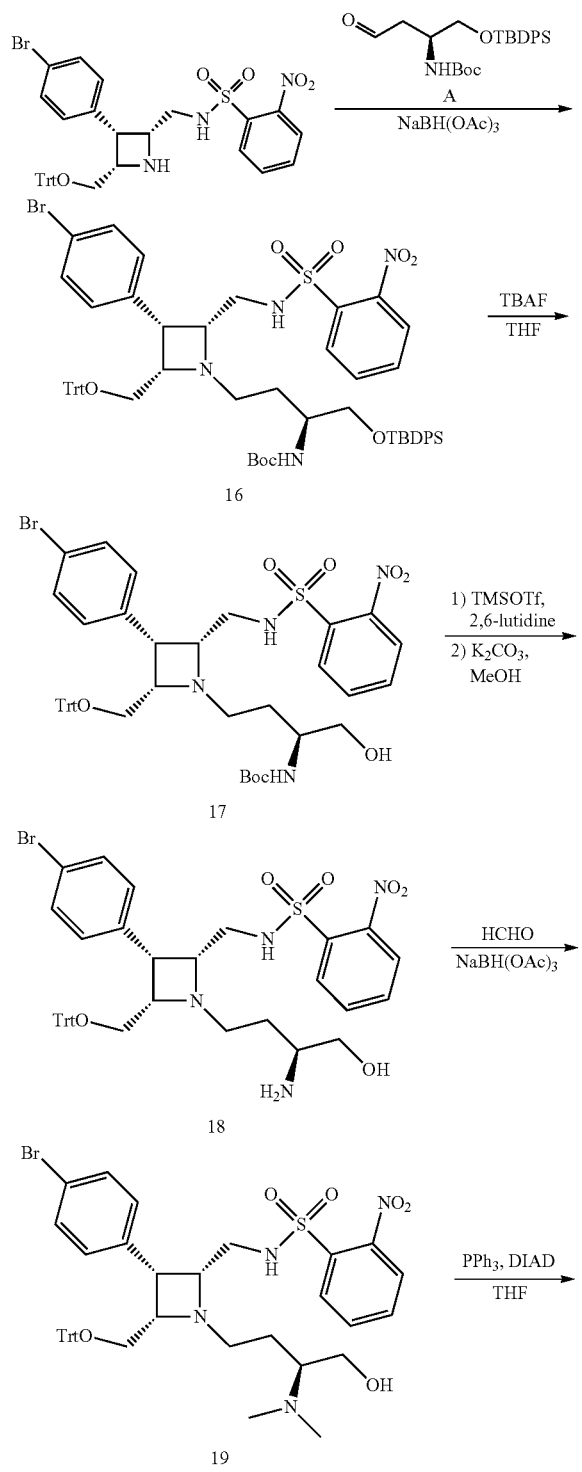
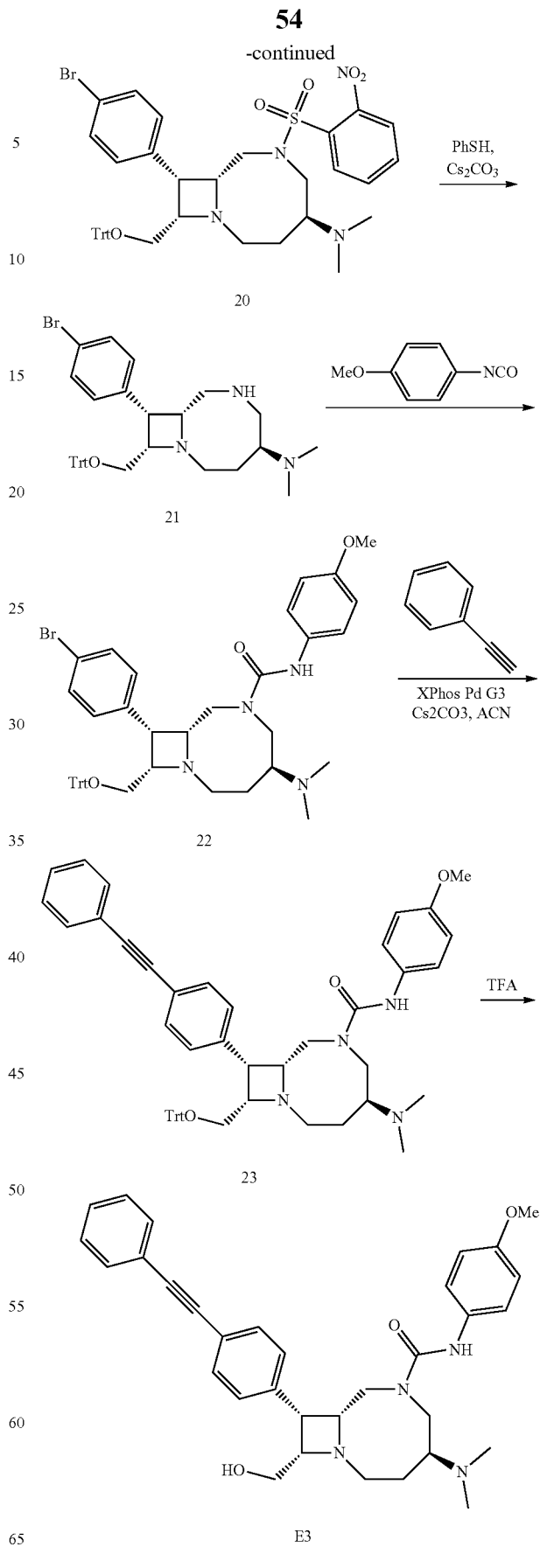

Intermediate 16: tert-butyl N-[(1S)-3-[(2R,3R,4S)-3-(4-bromophenyl)-2-[[(2-nitrophenyl)sulfonylamino]methyl]-4-(trityloxymethyl)azetidin-1-yl]-1-[[tert-butyl(diphenyl)silyl]oxymethyl]propyl]carbamate To a solution of N-(((2R,3R,4S)-3-(4-bromophenyl)-4-((trityloxy)methyl)azetidin-2-yl)methyl)-2-nitrobenzenesulfonamide (WO2015070204) (1.20 g, 1.72 mmol) and (S)-tert-butyl (1-((tert-butyldiphenylsilyl)oxy)-4-oxobutan-2-yl)carbamate (US 20150266867) (911.52 mg, 2.06 mmol) in DCM (40.00 mL) was added MgSO4 (2.07 g, 17.20 mmol) and NaBH(OAc)$_3$ (729.07 mg, 3.44 mmol). After stirring at 15° C. for 2 hours, the reaction mixture was quenched by addition sat. NaHCO$_3$ aqueous (15 mL) and extracted with DCM (2×5 mL). The combined organic layers were dried over Na$_2$SO$_4$, filtered and concentrated under reduced pressure to give a residue. The residue was purified by column chromatography (SiO$_2$, petroleum ether/ethyl acetate=20:1 to 3:1) to afford Intermediate 16 (2.00 g) as a white solid: $^1$H NMR (400 MHz, CHLOROFORM-d) δ=7.81-7.69 (m, 3H), 7.66-7.58 (m, 6H), 7.45-7.34 (m, 8H), 7.15-7.04 (m, 18H), 4.87-4.76 (m, 2H), 3.68-3.59 (m, 3H), 3.50-3.42 (m, 3H), 3.14 (br. s., 1H), 3.03-2.97 (m, 1H), 2.95-2.82 (m, 2H), 2.46 (br. s., 2H), 1.40 (s, 9H), 1.05 (s, 9H).

Intermediate 17: tert-butyl ((S)-4-((2R,3R,4S)-3-(4-bromophenyl)-2-((2-nitrophenylsulfonamido)methyl)-4-((trityloxy)methyl)azetidin-1-yl)-1-hydroxybutan-2-yl)carbamate To a solution of Intermediate 16 (500.00 mg, 444.74 μmol) in THF (6 mL) was added TBAF (174.42 mg, 667.11 μmol) at 15° C. After stirring at 15° C. for 1 hour, the reaction mixture was concentrated under reduced pressure to give a residue. The residue was purified by column chromatography (SiO$_2$, DCM:MeOH=100:1 to 20:1) to afford Intermediate 17 (300.00 mg, 338.65 μmol, 76.15% yield) as a white solid: 1H NMR (400 MHz, CHLOROFORM-d) δ=7.83 (dd, J=7.8, 17.3 Hz, 2H), 7.76-7.63 (m, 2H), 7.22-7.12 (m, 15H), 7.01 (d, J=8.0 Hz, 2H), 5.05 (br. s., 1H), 4.45 (br. s., 1H), 3.78-3.70 (m, 1H), 3.59 (br. s., 3H), 3.43 (d, J=9.5 Hz, 1H), 3.33-3.16 (m, 2H), 3.05 (d, J=6.0 Hz, 2H), 2.96-2.87 (m, 1H), 2.83-2.72 (m, 1H), 2.58-2.48 (m, 1H), 1.74 (dd, J=4.8, 14.8 Hz, 1H), 1.43 (s, 9H).

Intermediate 18: N-[[(2R,3R,4S)-1-[(3S)-3-amino-4-hydroxy-butyl]-3-(4-bromophenyl)-4-(trityloxymethyl)azetidin-2-yl]methyl]-2-nitro-benzenesulfonamide To a solution of Intermediate 17 (800.00 mg, 903.08 μmol) in DCM (16.00 mL) was added TMSOTf (602.15 mg, 2.71 mmol, 489.55 μL) and 2,6-lutidine (387.06 mg, 3.61 mmol, 420.72 μL, 4 eq). After stirring at 15° C. for 16 h, the reaction mixture was concentrated under reduced pressure to give a residue. The residue was purified by column chromatography (SiO$_2$, DCM:MeOH=1:0 to 20:1) to afford Intermediate 18 (700 mg, crude) as a white solid (containing TEA): 1H NMR (400 MHz, CHLOROFORM-d) δ=7.85 (td, J=2.3, 4.7 Hz, 1H), 7.76-7.72 (m, 1H), 7.70-7.63 (m, 2H), 7.25-7.16 (m, 15H), 6.98 (d, J=8.4 Hz, 2H), 3.72-3.60 (m, 3H), 3.52-3.42 (m, 3H), 3.27 (dd, J=6.6, 14.1 Hz, 1H), 3.14-3.00 (m, 3H), 2.83-2.68 (m, 2H), 1.85-1.62 (m, 2H)

Intermediate 19: N-[[(2R,3R,4S)-3-(4-bromophenyl)-1-[(3S)-3-(dimethylamino)-4-hydroxy-butyl]-4-(trityloxymethyl)azetidin-2-yl]methyl]-2-nitro-benzenesulfonamide To a solution of Intermediate 18 (700.00 mg, 890.88 μmol) in DCM (15.00 mL) was added HCHO (86.77 mg, 1.07 mmol, 79.61 μL, 37% purity), MgSO4 (1.07 g, 8.91 mmol) and then NaBH(OAc)$_3$ (377.63 mg, 1.78 mmol) added in portions. After stirring at 15° C. for 1 hour, the reaction mixture was quenched by addition saturated NaHCO$_3$ aqueous (100 mL) and extracted with DCM (2×30 mL). The combined organic layers were dried over Na$_2$SO$_4$, filtered and concentrated under reduced pressure to give a residue. The residue was purified by column chromatography (SiO$_2$, DCM:MeOH=1:0 to 15:1) to afford Intermediate 19 (500 mg, 614.40 μmol, 68.97% yield) as a white solid: 1H NMR (400 MHz, CHLOROFORM-d) δ=7.87 (dd, J=1.5, 7.5 Hz, 1H), 7.78-7.73 (m, 1H), 7.72-7.61 (m, 2H), 7.23-7.12 (m, 18H), 7.05 (d, J=8.0 Hz, 2H), 3.64-3.54 (m, 3H), 3.22-3.06 (m, 4H), 3.03-2.98 (m, 1H), 2.87-2.70 (m, 2H), 2.56 (td, J=6.0, 12.0 Hz, 1H), 2.45 (br. s., 1H), 2.22 (s, 6H), 1.57 (d, J=14.1 Hz, 1H), 1.41 (d, J=6.0 Hz, 1H)

Intermediate 20: (4S,8R,9R,10S)-9-(4-bromophenyl)-N,N-dimethyl-6-(2-nitrophenyl)sulfonyl-10-(trityloxymethyl)-1,6-diazabicyclo[6.2.0]decan-4-amine To a solution of triphenylphosphine (1 g, 3.76 mmol) in THF (19 ml) at 0° C. was slowly added diisopropyl azodicarboxylate (0.72 mL, 3.76 mmol). This mixture was then added to a solution of Intermediate 19 (500 mg, 614.40 μmol) in THF (75 mL) at 0° C. After stirring at 15° C. for 4 h, the reaction mixture was concentrated under reduced pressure to give a residue. The residue was purified by column chromatography (SiO$_2$, DCM:MeOH=20:1) to afford Intermediate 20 (200.00 mg, 251.33 μmol, 40.91% yield) as a white solid: 1H NMR (400 MHz, CHLOROFORM-d) δ=8.14 (d, J=7.5 Hz, 1H), 7.65-7.55 (m, 3H), 7.25-7.19 (m, 19H), 3.62-3.50 (m, 4H), 3.42 (br. s., 1H), 3.17-2.98 (m, 4H), 2.85 (dd, J=7.1, 9.3 Hz, 1H), 2.69-2.60 (m, 1H), 2.44-2.31 (m, 2H), 2.04 (br. s., 6H), 1.89 (br. s., 1H)

Intermediate 21: (4S,8R,9R,10S)-9-(4-bromophenyl)-N,N-dimethyl-10-(trityloxymethyl)-1,6-diazabicyclo[6.2.0]decan-4-amine To a solution of Intermediate 20 (150.00 mg, 188.49 μmol) in acetonitrile (3.00 mL) was added Cs$_2$CO$_3$ (368.49 mg, 1.13 mmol) and benzenethiol (83.07 mg, 753.96 μmol, 76.92 μL). After stirring at 40° C. for 16 h, the reaction mixture was quenched by addition water (15 mL) and extracted with ethyl acetate (2×5 mL). The combined organic layers were washed with brine (2×5 mL), dried over Na$_2$SO$_4$, filtered and concentrated under reduced pressure to give a residue. The residue was purified by prep-TLC (SiO$_2$, DCM:MeOH=10:1) to afford Intermediate 21 (90.00 mg, 147.39 μmol, 78.20% yield) as a white solid used directly.

Intermediate 22: (4S,8R,9R,10S)-9-(4-bromophenyl)-4-(dimethylamino)-N-(4-methoxyphenyl)-10-(trityloxymethyl)-1,6-diazabicyclo[6.2.0]decane-6-carboxamide To a solution of Intermediate 21 (90.00 mg, 147.39 μmol) in DCM (3.00 mL) was added 1-isocyanato-4-methoxybenzene (26.38 mg, 176.87 µmol). After stirring at 15° C. for 1 hour, the reaction mixture was quenched by addition water (15 mL) and extracted with DCM (2×5 mL). The combined organic layers were washed with brine (2×10 mL), dried over Na₂SO₄, filtered and concentrated under reduced pressure to give a residue. The residue was purified by prep-TLC (SiO₂, DCM:MeOH=20:1) to afford Intermediate 22 (90.00 mg, 118.46 µmol, 80.37% yield) as a white solid: 1H NMR (400 MHz, CHLOROFORM-d) δ=7.28-7.18 (m, 21H), 6.82 (d, J=8.8 Hz, 2H), 4.15-4.06 (m, 1H), 3.77 (s, 3H), 3.64-3.47 (m, 4H), 3.18-2.98 (m, 3H), 2.92-2.82 (m, 2H), 2.70 (d, J=13.2 Hz, 1H), 2.43-2.33 (m, 7H), 2.10 (br. s., 1H), 1.95 (br. s., 1H)

Intermediate 23: (4S,8R,9R,10S)-4-(dimethylamino)-N-(4-methoxyphenyl)-9-[4-(2-phenylethynyl)phenyl]-10-(trityloxymethyl)-1,6-diazabicyclo[6.2.0]decane-6-carboxamide To a solution of Intermediate 22 (64.00 mg, 84.24 µmol) and ethynylbenzene (25.81 mg, 252.71 µmol) in acetonitrile (1 mL) was added XPhos Pd G3 (7.13 mg, 8.42 µmol) and Cs₂CO₃ (54.89 mg, 168.47 µmol). After stirring at 70° C. for 2 h, the reaction mixture was concentrated to give the residue. The residue was purified by pre-TLC (ethyl acetate: methanol=10:1) to the give Intermediate 23 (47.00 mg, 60.18 µmol, 71.44% yield) as a brown solid. 1H NMR (400 MHz, MeOD-d4) δ 7.54 (d, J=4.8 Hz, 2H), 7.38-7.35 (m, 7H), 7.33-7.21 (m, 18H), 6.83 (d, J=8.8 Hz, 2H), 4.13 (s, 1H), 3.77 (s, 3H), 3.61-3.52 (m, 4H), 3.19-3.17 (m, 2H), 2.94-2.90 (m, 2H), 2.73-2.44 (m, 1H), 2.17-1.97 (m, 1H).

Synthesis of E3: (4S,8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide To a solution of Intermediate 23 (40.00 mg, 51.22 µmol) in DCM (1 mL) was added TFA (58.40 mg, 512.17 µmol, 37.92 µL). After stirring at 25° C. for 12 h, the reaction mixture was quenched by sat. NaHCO₃ and extracted with DCM (3×5 mL to give organic layer. The layer was dried over anhydrous Na₂SO₄ and concentrated to give the residue. The residue was purified by prep-HPLC (column: Waters Xbridge Prep OBD C18 150*30 5u; A: water (0.225% formic acid) B: acetonitrile) to the give compound E3 (21.70 mg, 40.28 µmol, 78.6% yield) as a white solid. HRMS (ESI): calcd for C₃₃H₃₈N₄O₃ [M+H]⁺ 539.29, found 539.30. ¹H NMR: (400 MHz, MeOD-d4) δ 7.60 (d, J=4.8 Hz, 2H), 7.49-7.46 (m, 4H), 7.38-7.36 (m, 2H), 7.23-7.24 (d, J=8.8 Hz, 2H), 6.87 (d, J=8.8 Hz, 2H), 3.76 (s, 3H), 3.55-3.52 (m, 2H), 3.48-3.3.42 (m, 6H), 3.34-3.31 (m, 1H), 3.19 (s, 1H), 2.89 (s, 6H), 2.62 (s, 1H), 2.04 (m, 2H).

Example 4: (3Z,8R,9S,10S)-10-[(dimethylamino)methyl]-N-(4-methoxyphenyl)-9-[4-(2-phenylethynyl)phenyl]-1,6-diazabicyclo[6.2.0]dec-3-ene-6-carboxamide ("E4")

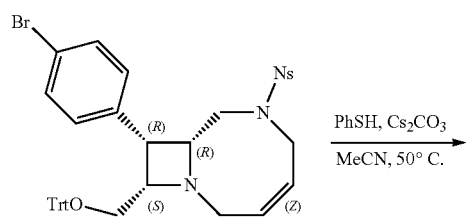

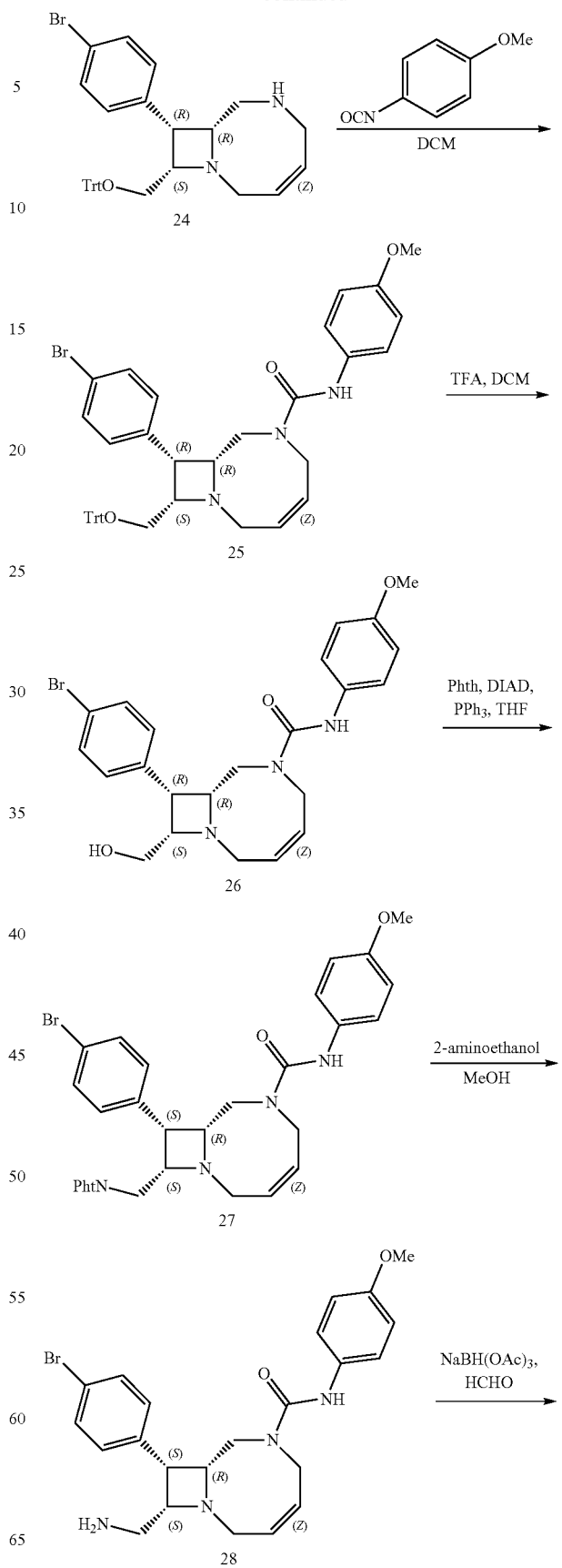

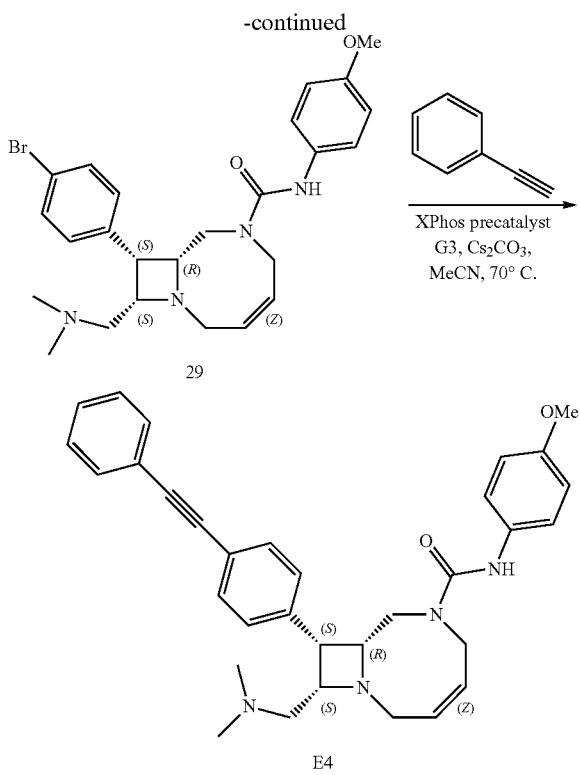

Intermediate 24: (3Z,8R,9R,10S)-9-(4-bromophenyl)-10-(trityloxymethyl)-1,6-diazabicyclo[6.2.0]dec-3-ene To a solution of (8R,9R,10S,Z)-10-((bis(4-methoxyphenyl)(phenyl)methoxy)methyl)-9-(4-bromophenyl)-6-((2-nitrophenyl)sulfonyl)-1,6-diazabicyclo[6.2.0]dec-3-ene and benzenethiol (132.09 mg, 1.20 mmol, 122.31 µL) in acetonitrile (6 mL) was added Cs₂CO₃ (260.41 mg, 799.25 µmol) at 25° C. After stirring at 50° C. for 12 h, the reaction mixture was quenched with H₂O (5 mL) and extracted with DCM (10 mL) to give the organic phase. The organic phase was concentrated and purified by prep-TLC (petroleum ether:ethyl acetate=1:1) to Intermediate 24 (450 mg, 795.70 µmol, 99.56% yield) as a white solid. ¹H NMR (400 MHz, CDCl₃-d1) δ7.26-7.16 (m, 19H), 5.90-5.84 (m, 1H), 5.67-5.60 (m, 1H), 3.61-3.53 (m, 4H), 3.61-3.52 (m, 4H), 3.11-3.09 (m, 2H), 2.86-2.84 (m, 2H), 2.48 (d, J=5.2 Hz, 1H).

Intermediate 25: (3Z,8R,9R,10S)-9-(4-bromophenyl)-N-(4-methoxyphenyl)-10-(trityloxymethyl)-1,6-diazabicyclo[6.2.0]dec-3-ene-6-carboxamide To a solution of Intermediate 24 (400 mg, 707.29 µmol) and Et₃N (196.08 µL, 1.41 mmol) in DCM (2 mL) was added 1-isocyanato-4-methoxy-benzene (116.04 mg, 778.02 µmol) dropwise at 0° C. After stirring at 25° C. for 5 h, the reaction mixture was concentrated to give the residue. The residue was purified prep-TLC (petroleum ether:ethyl acetate=1:1) to give Intermediate 25 (400 mg, 559.68 µmol, 79.13% yield) as a white solid. ¹H NMR (400 MHz, CDCl₃-d1) δ7.31-7.19 (m, 19H), 6.85-6.81 (m, 2H), 6.04 (s, 1H), 5.81-5.80 (m, 1H), 5.73-5.68 (m, 1H), 4.15 (d, J=16 Hz, 1H), 5.72 (d, J=16 Hz, 1H), 4.15-4.00 (m, 1H), 3.99-3.70 (m, 1H), 3.66-3.56 (m, 5H), 3.21-3.19 (m, 2H), 3.19-3.00 (m, 1H), 2.81-2.77 (m, 1H).

Intermediate 26: (3Z,8R,9R,10S)-9-(4-bromophenyl)-10-(hydroxymethyl)-N-(4-methoxyphenyl)-1,6-diazabicyclo[6.2.0]dec-3-ene-6-carboxamide To a solution of Intermediate 25 (360.00 mg, 503.71 µmol) in DCM (1 mL) was added TFA (3 mL, 5037 µmol) dropwise at 0° C. After stirring at 25° C. for 1 h, the reaction mixture was quenched with saturated NaHCO₃ (3 mL) and extracted with DCM (5 mL) to give the organic phase. The organic layer was dried over anhydrous Na₂SO₄, concentrated and purified pre-TLC (petroleum ether:ethyl acetate=1:2) to give Intermediate 26 (210 mg, 444.57 µmol, 88.26% yield) as a white solid. ¹H NMR (400 MHz, CDCl₃-d1) δ7.48 (d, J=8.4 Hz, 2H), 7.38 (d, J=8.4 Hz, 2H), 7.21 (d, J=9.6 Hz, 2H), 6.83 (d, J=8.8 Hz, 2H), 6.06 (s, 2H), 5.85 (s, 1H), 5.74-5.71 (m, 1H), 4.26 (m, 1H), 4.03-3.95 (m, 1H), 3.77-3.59 (m, 6H), 3.28 (m, 1H), 2.90 (s, 1H).

Intermediate 27: (3Z,8R,9S,10S)-9-(4-bromophenyl)-10-[(1,3-dioxoisoindolin-2-yl)methyl]-N-(4-methoxyphenyl)-1,6-diazabicyclo[6.2.0]dec-3-ene-6-carboxamide To a solution of Intermediate 26 (210.00 mg, 444.57 µmol), isoindoline-1,3-dione (71.95 mg, 489.03 µmol) and PPh₃ (233.21 mg, 889.13 µmol) in THF (2 mL) was added DIAD (179.79 mg, 889.13 µmol) dropwise at 25° C. After stirring at 25° C. for 5 h, the reaction mixture was concentrated to give the residue. The residue was purified by prep-TLC (petroleum ether:ethyl acetate=1:1) to give Intermediate 27 (200 mg, 332.51 µmol, 74.79% yield) as a light brown solid. ¹H NMR (400 MHz, CDCl₃-d1) δ7.80-7.67 (m, 17H), 7.54-7.67 (m, 22H), 7.25-7.20 (m, 2H), 6.80 (s, 2H), 6.06 (s, 2H), 5.85 (s, 1H), 5.74 (s, 1H), 4.22 (s, 1H) 4.02 (m, 1H), 3.77-3.75 (m, 4H), 3.70-3.66 (m, 3H), 3.50 (s, 3H), 3.12 (m, 1H), 2.88 (s, 1H).

Intermediate 28: (3Z,8R,9S,10S)-10-(aminomethyl)-9-(4-bromophenyl)-N-(4-methoxyphenyl)-1,6-diazabicyclo[6.2.0]dec-3-ene-6-carboxamide To a solution of Intermediate 27 (60.00 mg, 99.75 µmol) in MeOH (1 mL) was added 2-aminoethanol (60.33 µL, 997.52 µmol) dropwise. After stirring at 25° C. for 3 h, the reaction mixture was concentrated to give the residue. The residue was purified by prep-TLC (dichloromethane:methanol=12:1) to give Intermediate 28 (33.00 mg, 70.01 µmol, 70.18% yield) as a white solid ¹H NMR (400 MHz, CDCl₃-d1) δ7.50 (d, J=13.6 Hz, 2H), 7.46 (m, 2H), 7.21 (d, J=5.5 Hz, 2H), 6.82 (d, J=9.6 Hz, 1H), 6.08 (s, 1H), 5.83 (s, 1H), 5.73 (s, 1H), 4.22 (m, 2H), 4.02-4.00 (m, 1H), 3.77 (s, 3H), 3.71-3.63 (m, 2H), 3.55-3.50 (m, 1H), 3.36-3.17 (m, 1H), 2.81-2.76 (m, 3H).

Intermediate 29: (3Z,8R,9S,10S)-9-(4-bromophenyl)-10-[(dimethylamino)methyl]-N-(4-methoxyphenyl)-1,6-diazabicyclo[6.2.0]dec-3-ene-6-carboxamide To a stirred solution of Intermediate 28 (23.00 mg, 48.79 µmol) in DCM (2 mL) was added NaBH(OAc)₃ (51.70 mg, 243.96 µmol) at 25° C. After stirring at 25° C. for 2 h, the reaction mixture was concentrated to give the residue. The residue was purified by prep-TLC (dichloromethane:methanol=12:1) to give Intermediate 29 (20 mg, 40.04 µmol, 82% yield) as a white solid. ¹H NMR (400 MHz, CDCl₃-d1) δ7.53 (d, J=8.4 Hz, 2H), 7.31-7.26 (m, 2H), 7.19 (d, J=8.8

Hz, 3H), 6.82 (d, J=8.8 Hz, 3H), 6.14 (s, 1H), 5.83-5.86 (m, 2H), 4.12-4.02 (m, 3H), 3.90-3.59 (m, 9H), 3.19 (m, 1H), 3.01-2.80 (m, 2H), 2.38 (s, 6H).

Synthesis of E4: (3Z,8R,9S,10S)-10-[(dimethyl-amino)methyl]-N-(4-methoxyphenyl)-9-[4-(2-phenylethynyl)phenyl]-1,6-diazabicyclo[6.2.0]dec-3-ene-6-carboxamide To a solution of Intermediate 29 (20.00 mg, 40.04 μmol) and ethynylbenzene (12.27 mg, 120.13 μmol, 13.19 μL) in acetonitrile (1 mL) was added XPhos Pd G3 (3.39 mg, 4.00 μmol) and Cs$_2$CO$_3$ (26.09 mg, 80.09 μmol). After stirring at 70° C. for 2 hr, the reaction mixture was concentrated to give the residue. The residue was purified by prep-HPLC (0.04% HCl/acetonitrile/H$_2$O system) to give (3Z,8R,9S,10S)-10-[(dimethylamino)methyl]-N-(4-methoxyphenyl)-9-[4-(2-phenylethynyl)phenyl]-1,6-diazabicyclo[6.2.0]dec-3-ene-6-carboxamide (2.00 mg, 3.84 μmol, 9.59% yield) as a white solid. HRMS (ESI) calcd for C$_{32}$H$_{33}$N$_4$O [M+H]$^+$ 489.27, found 520.10 $^1$H NMR (400 MHz, MeOD-d4) δ7.74 (d, J=5.5 Hz, 2H), 7.67 (d, J=8.8 Hz, 2H), 7.53 (d, J=3.6 Hz, 2H), 7.20 (d, J=8.8 Hz, 2H), 7.18 (d, J=8.8 Hz, 2H), 6.13 (d, J=5.6 Hz, 1H), 5.78 (d, J=12.4 Hz, 1H), 4.33 (s, 2H), 4.30-4.21 (m, 9H), 3.90-3.75 (m, 5H), 3.50-3.31 (m, 3H), 2.77 (s, 6H).

Example 5: (3S,4R,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide ("E5")

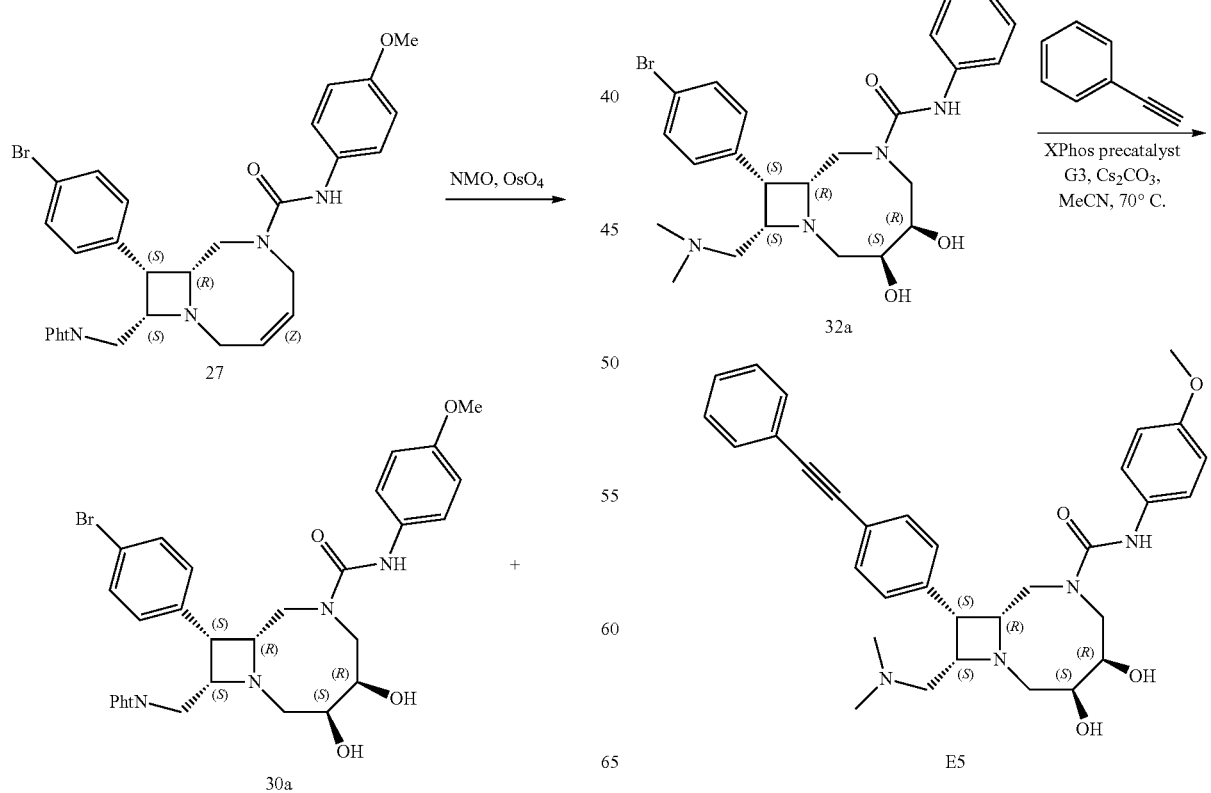

Intermediate 30a and 30b: (3S,4R,8R,9S,10S)-9-(4-bromophenyl)-10-((1,3-dioxoisoindolin-2-yl)methyl)-3,4-dihydroxy-N-(4-methoxyphenyl)-1,6-diazabicyclo[6.2.0]decane-6-carboxamide (30a) and (3R,4S,8R,9S,10S)-9-(4-bromophenyl)-10-((1,3-dioxoisoindolin-2-yl)methyl)-3,4-dihydroxy-N-(4-methoxyphenyl)-1,6-diazabicyclo[6.2.0]decane-6-carboxamide (30b)

To a stirred solution of Intermediate 27 (60 mg, 99.75 μmol) in acetone/H$_2$O=10:1 (1 mL) was added NMO (17.53 mg, 149.62 μmol) and OsO$_4$ (2.54 mg, 9.98 μmol) at room temperature. After stirring at 25° C. for 2 h, the reaction mixture was concentrated to give the residue. The residue was purified by prep-TLC (petroleum ether:ethyl acetate=1: 5) to give Intermediate 30a (less polar) (25 mg, 39.34 μmol, 39.44% yield) as a light brown solid and Intermediate 30b (more polar) (25 mg, 39.34 μmol, 39.44% yield) as a light brown solid. Intermediate 30a $^1$H NMR (400 MHz, CDCl$_3$-d1) δ7.82 (d, J=2.8 Hz, 2H), 7.81 (d, J=2.0 Hz, 2H), 7.71-7.02 (m, 4H), 7.26 (m, 2H), 6.80 (d, J=1.2 Hz, 2H), 4.24-4.07 (m, 2H), 3.93-3.81 (m, 2H), 3.74 (s, 3H), 3.62-3.54 (m, 3H), 3.28-2.88 (m, 1H), 2.65-2.49 (m, 2H). Intermediate 30b $^1$H NMR (400 MHz, CDCl$_3$-d1) δ7.83 (d, J=2.8 Hz, 2H), 7.81 (d, J=2.0 Hz, 2H), 7.73-7.47 (m, 4H), 7.24 (m, 2H), 6.80 (d, J=8.8 Hz, 2H), 6.58 (s, 1H), 3.96-3.90 (m, 2H), 3.70-3.68 (m, 4H), 3.56-3.50 (m, 3H), 3.00 (s, 1H), 2.87-2.76 (m, 2H).

Intermediate 31a: (3S,4R,8R,9S,10S)-10-(aminomethyl)-9-(4-bromophenyl)-3,4-dihydroxy-N-(4-methoxyphenyl)-1,6-diazabicyclo[6.2.0]decane-6-carboxamide To a stirred solution of Intermediate 30a (120 mg, 188.83 μmol) in MeOH (2 mL) was added 2-aminoethanol (115.34 mg, 1.89 mmol). After stirring at 25° C. for 2 h, the reaction mixture was concentrated to give the residue. The residue was purified by prep-TLC (dichloromethane:methanol=8:1) to give Intermediate 31a (70 mg, 138.50 μmol, 73.35% yield) as a white solid. $^1$H NMR (400 MHz, CDCl$_3$-d1) δ7.47-7.43 (m, 3H), 7.42-7.40 (m, 1H), 7.35-7.20 (m, 3H), 7.18-6.79 (m, 2H), 4.31-4.27 (m, 1H), 3.89 (s, 1H), 3.89-3.79 (m, 5H), 3.76-3.23 (m, 2H), 2.91-2.86 (m, 2H), 2.72-2.61 (m, 2H).

Intermediate 32a: (3S,4R,8R,9S,10S)-9-(4-bromophenyl)-10-((dimethylamino)methyl)-3,4-dihydroxy-N-(4-methoxyphenyl)-1,6-diazabicyclo[6.2.0]decane-6-carboxamide To a stirred solution of 31a (70.00 mg, 138.50 μmol) in DCM (2 mL) was added HCHO (112.41 mg, 1.39 mmol, 103.13 μL, 37% solution) and MgSO$_4$ (166.72 mg, 1.39 mmol). After stirring at 25° C. for 0.5 h, additional NaBH(OAc)$_3$ (146.77 mg, 692.52 μmol) was added. After an additional 1.5 h, the reaction mixture was concentrated to give the residue. The residue was purified by prep-TLC (dichloromethane:methanol=5:1) to give Intermediate 32a (60 mg, 112.47 μmol, 81% yield) as light brown solid. $^1$H NMR (400 MHz, CDCl$_3$-d1) δ7.48-7.43 (m, 4H), 7.42-7.40 (m, 1H), 7.27-7.20 (m, 2H), 6.81-6.78 (m, 2H), 4.26-4.03 (m, 3H), 3.64-3.54 (m, 5H), 3.27-3.24 (m, 1H).

Synthesis of E5: (3S,4R,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide To a solution of Intermediate 32a (20.00 mg, 40.04 μmol) and ethynylbenzene (12.27 mg, 120.13 μmol, 13.19 μL) in acetonitrile (1 mL) was added XPhos Pd G3 (3.39 mg, 4.00 μmol, 0.10 eq) and Cs$_2$CO$_3$ (26.09 mg, 80.09 μmol). After stirring at 70° C. for 2 hr, the reaction mixture was concentrated to give the residue. The residue was purified by prep-HPLC (Column: Waters Xbridge Prep OBD C18 150*30 5u; A: water (0.225% formic acid) B: acetonitrile) to give (3S,4R,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide (2.00 mg, 3.84 μmol, 9.59% yield) as a white solid. HRMS (ESI) calcd for C$_{33}$H$_{38}$N$_4$O$_4$ [M+H]$^+$ 554.29, found 554.20 $^1$H NMR (400 MHz, MeOD-d4) δ7.59 (s, 4H), 7.51 (d, J=3.6 Hz, 2H), 7.38 (s, 3H), 7.16 (d, J=8.8 Hz, 2H), 6.85 (d, J=8.8 Hz, 2H), 4.20-4.11 (s, 3H), 3.85-3.82 (m, 4H), 3.75 (s, 3H), 3.57-3.44 (m, 3H), 3.12-2.97 (m, 4H), 2.97-2.56 (m, 6H).

Example 6: (3R,4S,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide ("E6")

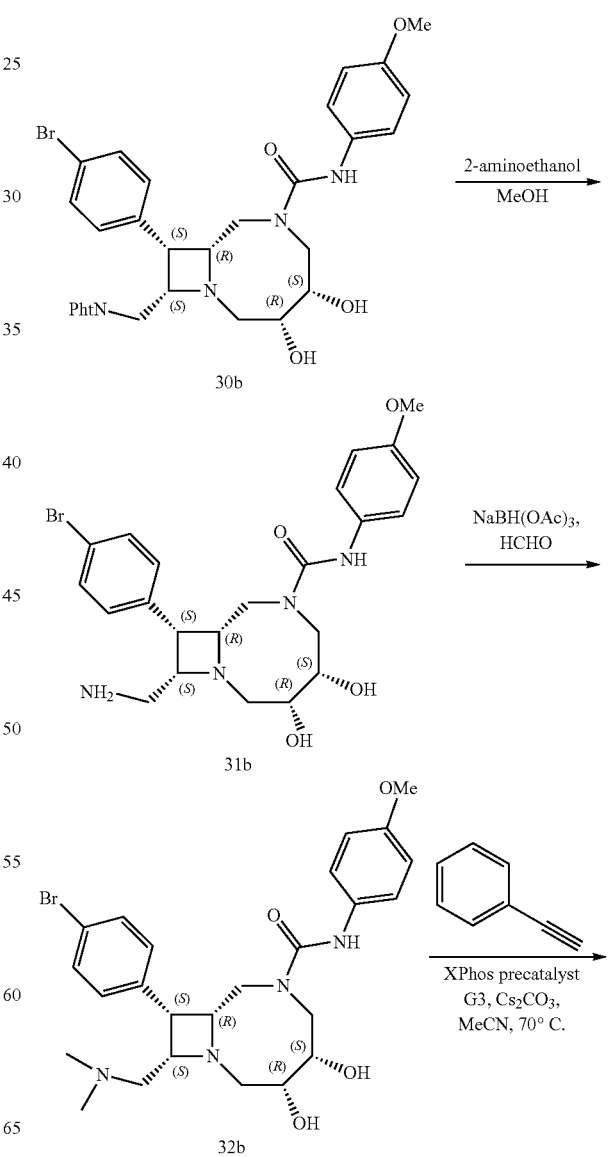

-continued

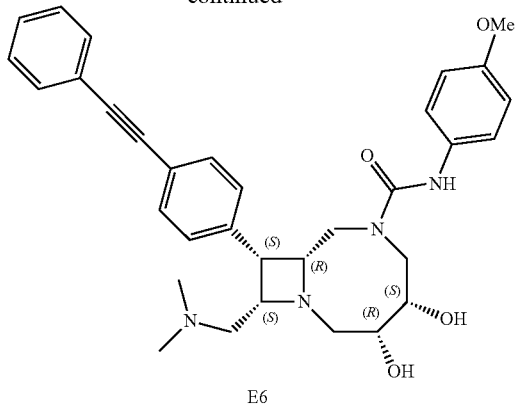

E6

Intermediate 31b: (3R,4S,8R,9S,10S)-10-(aminomethyl)-9-(4-bromophenyl)-3,4-dihydroxy-N-(4-methoxyphenyl)-1,6-diazabicyclo[6.2.0]decane-6-carboxamide To a stirred solution of Intermediate 30b (30 mg, 47.21 µmol) in MeOH (2 mL) was added 2-aminoethanol (28.84 mg, 472.10 µmol) at 25° C. After stirring at 25° C. for 2 h, the reaction mixture was concentrated to give the residue. The residue was purified by prep-TLC (dichloromethane:methanol=8:1) to give Intermediate 31b (20 mg, 39.57 µmol, 83.82% yield) as a white solid. $^1$H NMR (400 MHz, CDCl$_3$-d1) δ7.51-7.48 (m, 3H), 7.46-7.43 (m, 4H), 6.83 (d, J=8.8 Hz, 2H), 7.77-3.73 (m, 3H), 3.65-3.51 (m, 2H), 3.23-3.15 (m, 1H), 2.80-2.73 (m, 3H).

Intermediate 32b: (3R,4S,8R,9S,10S)-9-(4-bromophenyl)-10-((dimethylamino)methyl)-3,4-dihydroxy-N-(4-methoxyphenyl)-1,6-diazabicyclo[6.2.0]decane-6-carboxamide To a stirred solution of Intermediate 31a (10 mg, 19.79 µmol) in DCM (2 mL) was added HCHO (16.06 mg, 197.90 µmol, 14.73 µL, 37% solution) and MgSO$_4$ (23.82 mg, 197.90 µmol) at 25° C. After stirring at 25° C. for 0.5 h, additional NaBH(OAc)$_3$ (20.97 mg, 98.95 µmol) was added. After stirring for at 25° C. for 1.5 h additionally, the reaction mixture was concentrated to give the residue. The residue was purified by prep-TLC (dichloromethane:methanol=5:1) to give Intermediate 32b (10 mg, 18.75 µmol, 47.36% yield) as light brown solid. $^1$H NMR (400 MHz, CDCl$_3$-d1) δ7.54-7.46 (m, 4H), 7.30-7.25 (m, 7H), 6.83-6.80 (d, J=8.8 Hz, 2H), 3.89-3.78 (m, 2H), 3.67-3.63 (m, 6H), 3.56-3.48 (m, 3H), 2.74-2.64 (m, 3H), 2.28 (s, 6H).

Synthesis of E6: (3R,4S,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide To a solution of Intermediate 32b (10 mg, 18.75 µmol) and ethynylbenzene (5.74 mg, 56.24 µmol, 6.18 µL) in acetonitrile (1 mL) was added XPhos Pd G3 (1.59 mg, 1.87 µmol) and Cs$_2$CO$_3$ (12.22 mg, 37.49 µmol). After stirring at 70° C. for 2 hr, the reaction mixture was concentrated to give the residue. The residue was purified by prep-HPLC (0.04% HCl/ACN/H$_2$O system) to give (3R,4S,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide (2 mg, 3.61 µmol, 19.23% yield) as a white solid. HRMS (ESI) calcd for C$_{33}$H$_{38}$N$_4$O$_4$ [M+H]$^+$ 554.29, found 554.2. $^1$H NMR (400 MHz, MeOD-d4) δ7.62 (s, 4H), 7.53-7.51 (m, 2H), 7.40 (d, J=4.8 Hz, 3H), 7.24 (d, J=4.8 Hz, 2H), 6.87 (d, J=8.8 Hz, 2H), 4.18 (s, 3H), 4.08 (s, 1H), 3.94-3.93 (m, 3H), 3.76 (s, 4H), 3.56-3.52 (m, 2H), 3.42-3.40 (m, 2H), 3.23-3.21 (m, 2H), 2.99-2.95 (m, 1H), 3.70 (s, 6H).

Examples 7-9

The following example compounds (E7-E9) were prepared according to example 6 with the listed alkynes and the specified aldehyde (where indicated) in Table 3 starting with either Intermediate ("Int.") 32a or 32b.

TABLE 3

| | Alkyne | Aldehyde | Int. | NMR |
|---|---|---|---|---|
| Example 7 (3S,4R,8R,9S,10S)-10-[(dimethylamino)methyl]-9-[4-[2-(2-fluorophenyl)ethynyl]phenyl]-3,4-dihydroxy-N-(4-methoxyphenyl)-1,6-diazabicyclo[6.2.0]decane-6-carboxamide ("E7") | 1-ethynyl-2-fluorobenzene | formaldehyde | 32a | $^1$H NMR (400 MHz, CHLOROFORM-d) δ = 8.65-8.29 (m, 1H), 7.58-7.49 (m, 3H), 7.43 (d, J = 8.0 Hz, 2H), 7.38-7.32 (m, 1H), 7.27 (d, J = 9.0 Hz, 2H), 7.21-7.08 (m, 2H), 6.83 (d, J = 9.0 Hz, 2H), 4.31 (d, J = 11.0 Hz, 2H), 4.14 (br. s., 1H), 4.02 (d, J = 13.1 Hz, 1H), 3.85-3.69 (m, 5H), 3.61 (br. s., 1H), 3.54 (d, J = 8.0 Hz, 1H), 3.23 (d, J = 16.1 Hz, 1H), 2.99 (br. s., 1H), 2.82-2.48 (m, 4H), 2.11 (br. s., 6H) |
| Example 8 (3R,4S,8R,9S,10S)-10-[(dimethylamino)methyl]-9-[4-[2-(2-fluorophenyl)ethynyl]phenyl]-3,4-dihydroxy-N-(4-methoxyphenyl)-1,6-diazabicyclo[6.2.0]decane-6-carboxamide ("E8") | 1-ethynyl-2-fluorobenzene | formaldehyde | 32b | $^1$H NMR (400 MHz, CHLOROFORM-d) δ = 8.52 (br. s., 1H), 7.61-7.52 (m, 3H), 7.40 (d, J = 8.0 Hz, 2H), 7.37-7.30 (m, 2H), 7.21-7.10 (m, 2H), 6.84 (d, J = 9.0 Hz, 2H), 3.89 (d, J = 5.0 Hz, 2H), 3.79 (s, 6H), 3.73-3.64 (m, 3H), 3.63-3.50 (m, 2H), 3.24 (dd, J = 6.0, 14.1 Hz, 1H), 2.90 (br. s., 1H), 2.78 (d, J = 14.1 Hz, 1H), 2.67 (d, J = 10.0 Hz, 1H), 2.49 (dd, J = 7.0, 13.1 Hz, 1H), 2.16 (s, 6H) |

TABLE 3-continued

| | Alkyne | Aldehyde | Int. | NMR |
|---|---|---|---|---|
| Example 9 (3S,4R,8R,9S,10S)-10-(diethylaminomethyl)-3,4-dihydroxy-N-(4-methoxyphenyl)-9-[4-(2-phenylethynyl)phenyl]-1,6-diazabicyclo[6.2.0]decane-6-carboxamide ("E9") BIMH2W60 | ethynylbenzene | acetaldehyde | 32a | $^1$H NMR (400 MHz, CHLOROFORM-d) δ = 8.61 (br s, 1H), 8.46 (br s, 1H), 7.55 (br d, J = 3.5 Hz, 2H), 7.52-7.47 (m, 1H), 7.50 (br d, J = 8.2 Hz, 1H), 7.44-7.33 (m, 5H), 7.24 (br d, J = 8.8 Hz, 2H), 6.81 (br d, J = 8.8 Hz, 2H), 5.14 (br s, 2H), 4.34-4.21 (m, 1H), 4.12 (br s, 1H), 3.96 (br d, J = 14.1 Hz, 1H), 3.81 (br d, J = 7.9 Hz, 1H), 3.75 (s, 4H), 3.55 (br t, J = 7.1 Hz, 1H), 3.48 (br d, J = 9.0 Hz, 1H), 3.21 (br d, J = 15.7 Hz, 1H), 2.93-2.71 (m, 4H), 2.60 (br dd, J = 7.7, 12.6 Hz, 3H), 2.52-2.38 (m, 2H), 0.85 (br t, J = 6.7 Hz, 6H) |

Example 10: (3S,4R,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide ("E10")

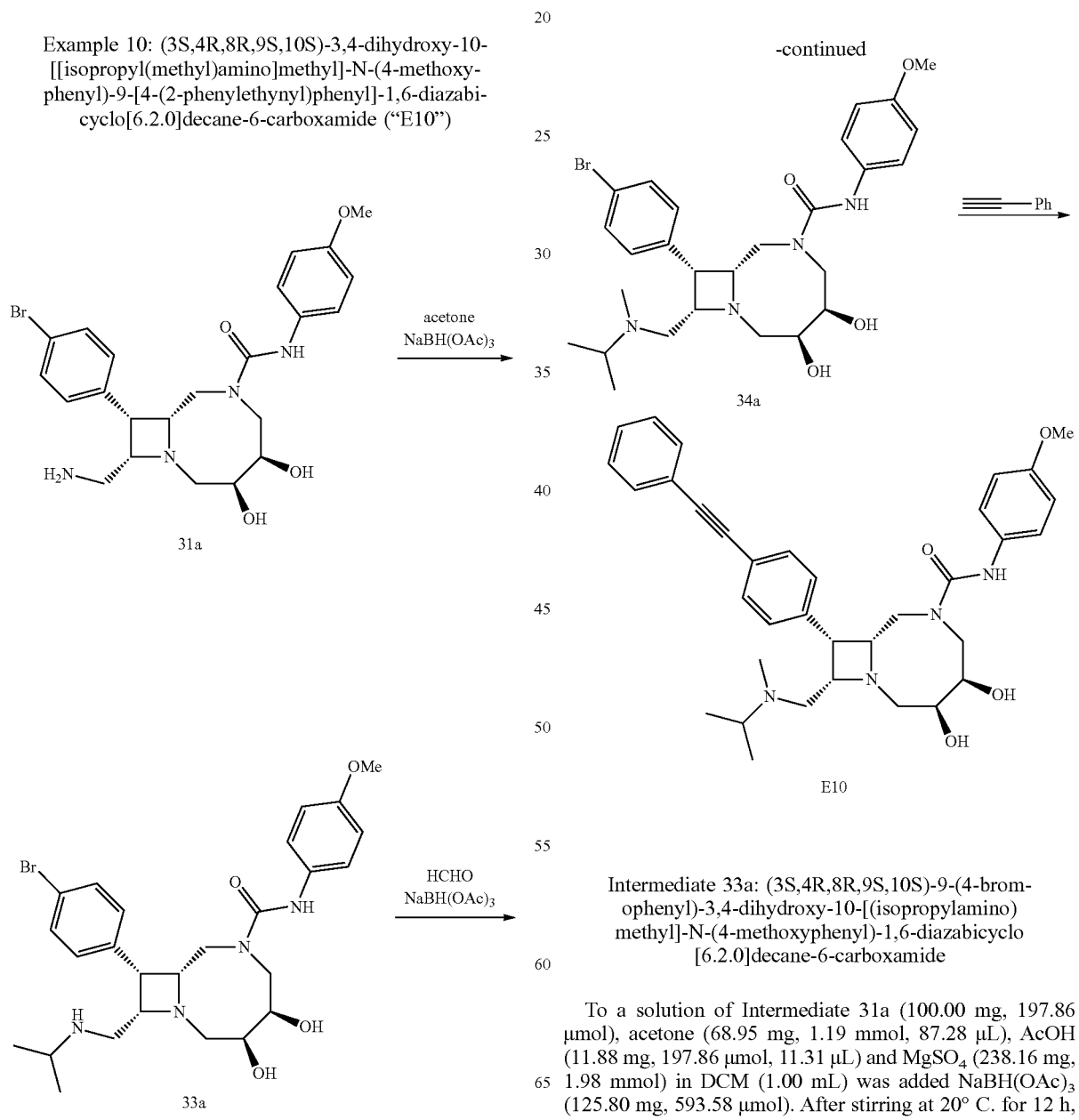

Intermediate 33a: (3S,4R,8R,9S,10S)-9-(4-bromophenyl)-3,4-dihydroxy-10-[(isopropylamino)methyl]-N-(4-methoxyphenyl)-1,6-diazabicyclo[6.2.0]decane-6-carboxamide To a solution of Intermediate 31a (100.00 mg, 197.86 μmol), acetone (68.95 mg, 1.19 mmol, 87.28 μL), AcOH (11.88 mg, 197.86 μmol, 11.31 μL) and MgSO$_4$ (238.16 mg, 1.98 mmol) in DCM (1.00 mL) was added NaBH(OAc)$_3$ (125.80 mg, 593.58 μmol). After stirring at 20° C. for 12 h, the reaction mixture filtered through a celite and concentrated under reduced pressure to give the crude Intermediate 33a (116.00 mg) as a pale yellow brown solid.

Intermediate 34a: (3S,4R,8R,9S,10S)-9-(4-bromophenyl)-3,4-dihydroxy-10-[[isopropyl(methyl)amino]methyl]-N-(4-methoxyphenyl)-1,6-diazabicyclo[6.2.0]decane-6-carboxamide To a solution of Intermediate 33a (116.00 mg, 211.88 µmol), formaldehyde (103.08 mg, 1.27 mmol, 94.57 µL), MgSO₄ (255.04 mg, 2.12 mmol) and AcOH (12.72 mg, 211.88 µmol, 12.11 µL) in DCM (1.00 mL) was added NaBH(OAc)₃ (134.72 mg, 635.64 µmol). After stirring at 20° C. for 2 h, the reaction mixture was filtered through a celite and concentrated under reduced pressure to give the crude Intermediate 34b (138.00 mg, crude) as a dark yellow solid.

Synthesis of E10: (3S,4R,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide To a solution of Intermediate 34a (30.00 mg, 53.43 µmol) and ethynylbenzene (10.91 mg, 106.86 µmol, 11.73 µL) in CH₃CN (1.00 mL) was added Et₃N (16.22 mg, 160.29 µmol, 22.22 µL) and XPhos Pd G3 (4.52 mg, 5.34 µmol). After stirring at 70° C. for 2 h, the reaction mixture was filtered through a celite and concentrated under reduced pressure to give a residue, which was purified by prep-HPLC (Column: Waters Xbridge Prep OBD C18 150*30 5u; A: water (0.225% formic acid) B: acetonitrile) to give (3S,4R,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide (11.20 mg, 17.81 µmol, 33.34% yield, formic acid salt) as a light yellow solid. ¹H NMR (400 MHz, CHLOROFORM-d) δ=8.65-8.37 (m, 1H), 7.57-7.52 (m, 2H), 7.49 (d, J=8.0 Hz, 2H), 7.42-7.34 (m, 5H), 7.25 (d, J=9.0 Hz, 2H), 6.81 (d, J=9.0 Hz, 2H), 4.36-4.21 (m, 1H), 4.13 (br. s., 1H), 3.96 (d, J=14.1 Hz, 1H), 3.84-3.73 (m, 5H), 3.62-3.46 (m, 2H), 3.21 (d, J=15.6 Hz, 1H), 2.83 (d, J=14.1 Hz, 4H), 2.75-2.54 (m, 2H), 2.11 (br. s., 3H), 0.99 (d, J=5.5 Hz, 3H), 0.71 (d, J=5.0 Hz, 3H)

Example 11: (3R,4S,8R,9S,10S)-3,4-dihydroxy-10-[[isopropyl(methyl)amino]methyl]-N-(4-methoxyphenyl)-9-[4-(2-phenylethynyl)phenyl]-1,6-diazabicyclo[6.2.0]decane-6-carboxamide ("E11")

Example E11 was prepared using the synthesis described in Example 10 beginning with Intermediate 31b. ¹H NMR (400 MHz, CHLOROFORM-d) δ=8.73-8.47 (m, 1H), 7.56-7.51 (m, 4H), 7.41-7.34 (m, 5H), 7.28 (d, J=8.9 Hz, 2H), 6.81 (d, J=8.9 Hz, 2H), 3.88 (d, J=5.4 Hz, 1H), 3.80-3.74 (m, 5H), 3.72-3.48 (m, 5H), 3.24 (dd, J=6.8, 14.1 Hz, 1H), 2.88 (t, J=11.9 Hz, 1H), 2.82-2.75 (m, 1H), 2.72 (d, J=14.2 Hz, 2H), 2.65-2.56 (m, 1H), 2.09 (s, 3H), 0.95 (d, J=6.5 Hz, 3H), 0.71 (d, J=6.4 Hz, 3H).

Example 12: (3S,4R,8R,9S,10S)-9-[4-[2-(2,3-difluorophenyl)ethynyl]phenyl]-10-[(dimethylamino)methyl]-3,4-dihydroxy-N-(4-methoxyphenyl)-1,6-diazabicyclo[6.2.0]decane-6-carboxamide ("E12")

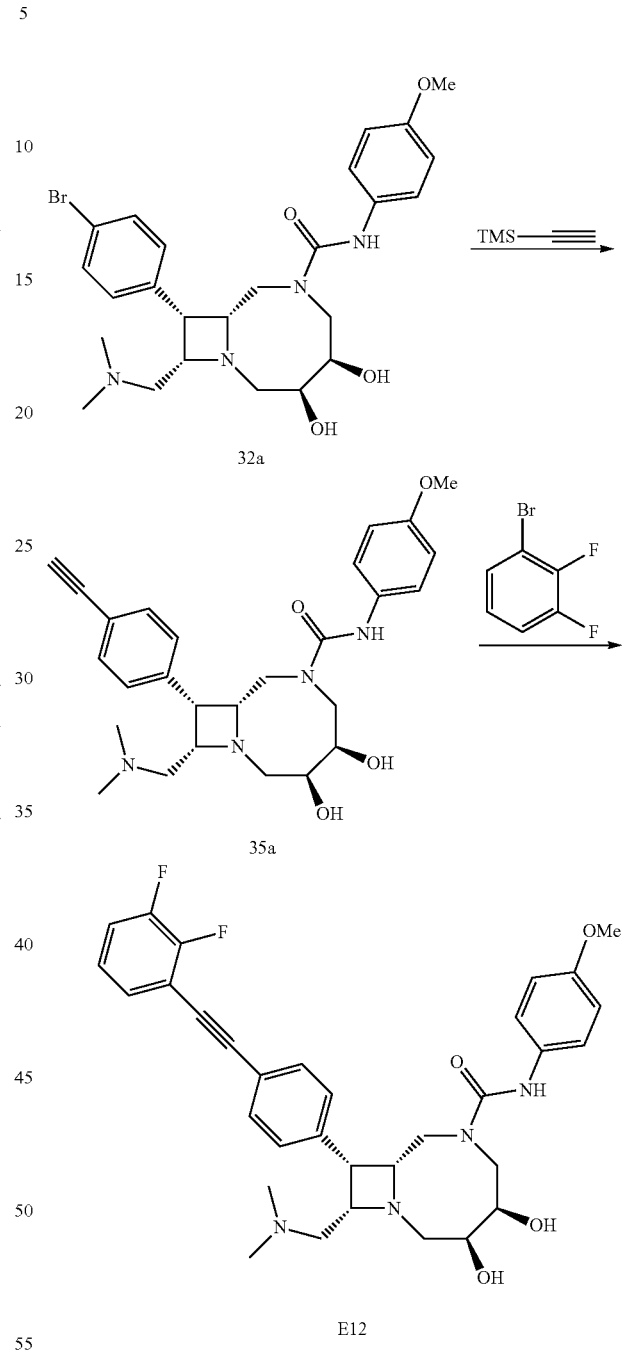

Intermediate 35a: (3S,4R,8R,9S,10S)-10-[(dimethylamino)methyl]-9-(4-ethynylphenyl)-3,4-dihydroxy-N-(4-methoxyphenyl)-1,6-diazabicyclo[6.2.0]decane-6-carboxamide To a solution of Intermediate 32a (54.00 mg, 101.23 µmol) and ethynyltrimethylsilane (29.83 mg, 303.69 µmol, 42.01 µL) in CH₃CN (1.00 mL) was added Cs₂CO₃ (131.93 mg, 404.92 µmol) and XPhos Pd G3 (8.57 mg, 10.12 µmol). After stirring with N₂ atmosphere at 70° C. for two hours, the reaction mixture was filtered through a celite and concentrated under reduced pressure to give the crude product 2 (78.00 mg, crude) as a dark yellow solid.

Synthesis of E12: (3S,4R,8R,9S,10S)-9-[4-[2-(2,3-difluorophenyl)ethynyl]phenyl]-10-[(dimethylamino)methyl]-3,4-dihydroxy-N-(4-methoxyphenyl)-1,6-diazabicyclo[6.2.0]decane-6-carboxamide To a solution of (3R,4S,8R,9S,10S)-10-[(dimethylamino)methyl]-9-(4-ethynylphenyl)-3,4-dihydroxy-N-(4-methoxyphenyl)-1,6-diazabicyclo[6.2.0]decane-6-carboxamide (Intermediate 35a) (21.60 mg, 45.13 μmol) and 1-bromo-2,3-difluorobenzene (8.71 mg, 45.13 μmol, 5.06 μL) in CH₃CN (500 μL) was added Cs₂CO₃ (29.41 mg, 90.26 μmol) and XPhos Pd G3 (3.82 mg, 4.51 μmol). After stirring with N₂ atmosphere at 40° C. for 1 h, the residue was purified by prep-TLC (SiO₂, DCM:MeOH=8:1) to remove the catalyst and then purified by prep-HPLC(Column: Waters Xbridge Prep OBD C18 150*30 5u; A: water (0.225% formic acid) B: acetonitrile) to give (3S,4R,8R,9S,10S)-9-[4-[2-(2,3-difluorophenyl)ethynyl]phenyl]-10-[(dimethylamino)methyl]-3,4-dihydroxy-N-(4-methoxyphenyl)-1,6-diazabicyclo[6.2.0]decane-6-carboxamide (2.00 mg, 3.14 μmol, 6.96% yield, formic acid salt)) as a white solid. ¹H NMR (400 MHz, CHLOROFORM-d) δ=8.48-8.27 (m, 1H), 7.58 (d, J=7.9 Hz, 2H), 7.40 (d, J=7.9 Hz, 2H), 7.29 (d, J=8.4 Hz, 3H), 7.22-7.13 (m, 1H), 7.11-7.03 (m, 1H), 6.83 (d, J=8.8 Hz, 2H), 6.73 (br. s., 1H), 3.89 (br. s., 2H), 3.77 (s, 4H), 3.75-3.62 (m, 3H), 3.61-3.48 (m, 2H), 3.28 (dd, J=6.6, 14.1 Hz, 1H), 2.89 (d, J=12.8 Hz, 3H), 2.80 (d, J=14.6 Hz, 2H), 2.68 (d, J=7.5 Hz, 1H), 2.27 (s, 6H)

Example 13: (3R,4S,8R,9S,10S)-9-(4-((2,3-difluorophenyl)ethynyl)phenyl)-10-((dimethylamino)methyl)-3,4-dihydroxy-N-(4-methoxyphenyl)-1,6-diazabicyclo[6.2.0]decane-6-carboxamide ("E13")

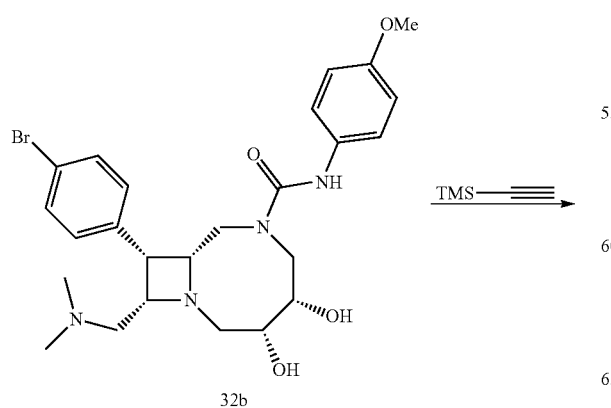

32b

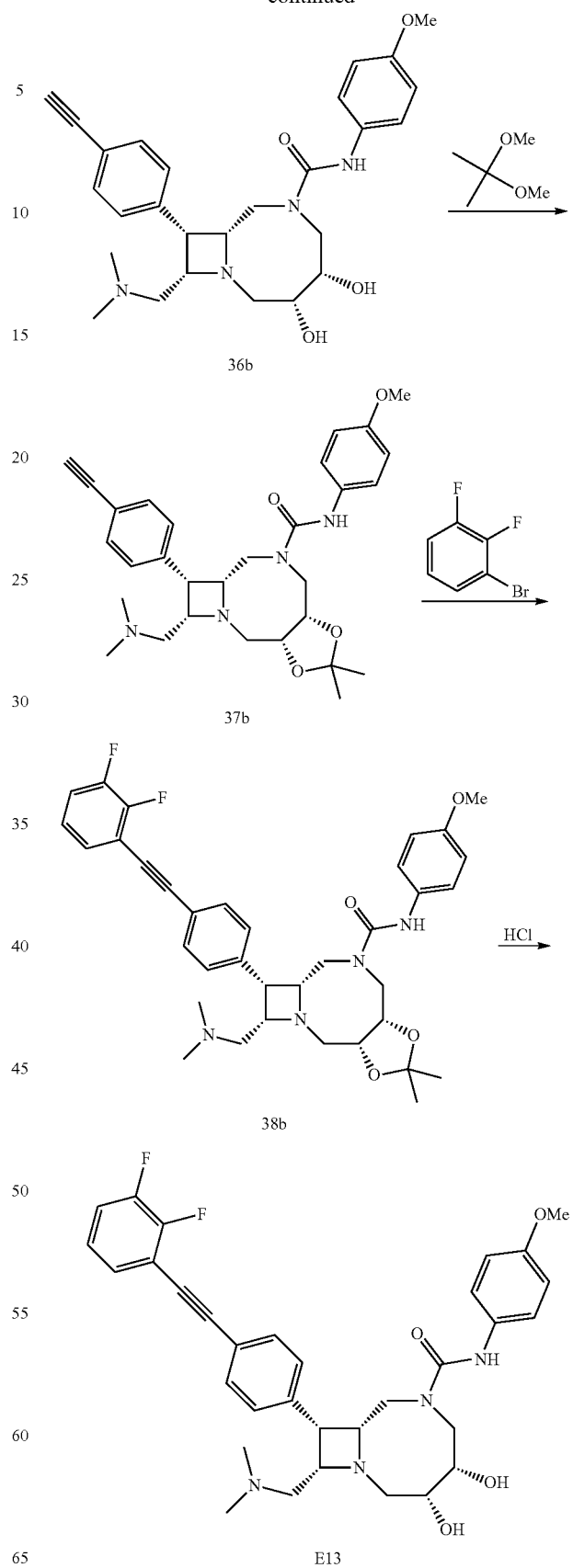

Intermediate 36b: (3R,4S,8R,9S,10S)-10-((dimethylamino)methyl)-9-(4-ethynylphenyl)-3,4-dihydroxy-N-(4-methoxyphenyl)-1,6-diazabicyclo[6.2.0]decane-6-carboxamide To a solution of (3R,4S,8R,9S,10S)-9-(4-bromophenyl)-10-[(dimethylamino)methyl]-3,4-dihydroxy-N-(4-methoxyphenyl)-1,6-diazabicyclo[6.2.0]decane-6-carboxamide (Intermediate 32b) (40.00 mg, 74.98 μmol) and ethynyl (trimethyl)silane (22.09 mg, 224.95 μmol, 31.12 μL) in CH$_3$CN (1.00 mL) was added Cs$_2$CO$_3$ (97.72 mg, 299.93 μmol) and XPhos Pd G3 (6.35 mg, 7.50 μmol). After stirring with N$_2$ atmosphere at 70° C. for 1 h, the reaction mixture was filtered through a celite and concentrated under reduced pressure to give a residue which was purified by prep-TLC (DCM:MeOH=10:1, Rf=0.2) to give the Intermediate 36b (30.00 mg, 62.69 μmol, 83.60% yield) as a light yellow solid.

Intermediate 37b: (3aS,6aR,7S,8S,10aR)-8-((dimethylamino)methyl)-7-(4-ethynylphenyl)-N-(4-methoxyphenyl)-2,2-dimethylhexahydro-3aH-azeto[1,2-a][1,3]dioxolo[4,5-f][1,4]diazocine-5 (4H)-carboxamide To a solution of Intermediate 36b (30.00 mg, 62.69 μmol) in 2,2-dimethoxypropane (500 μL) and DCM (500 μL) was added TsOH (1.08 mg, 6.27 μmol). After stirring at 20° C. for 1 h, the reaction was concentrated and purified by prep-TLC (DCM:MeOH=10:1) to give the Intermediate 37b (20.00 mg, 38.56 μmol, 61.51% yield) as a yellow oil.

Intermediate 38b: (3aS,6aR,7S,8S,10aR)-7-(4-((2,3-difluorophenyl)ethynyl)phenyl)-8-((dimethylamino)methyl)-N-(4-methoxyphenyl)-2,2-dimethylhexahydro-3aH-azeto[1,2-a][1,3]dioxolo[4,5-J][1,4]diazocine-5 (4H)-carboxamide To a solution of Intermediate 37b (20.00 mg, 38.56 μmol) and 1-bromo-2,3-difluorobenzene (22.33 mg, 115.68 μmol, 12.98 μL) in CH$_3$CN (500 μL) was added Cs$_2$CO$_3$ (50.25 mg, 154.24 μmol) and XPhos Pd G3 (3.26 mg, 3.86 μmol). After stirring under N$_2$ atmosphere at 70° C. for one hour, the reaction mixture was purified by prep-TLC (DCM:MeOH=10:1) to give the Intermediate 38b (15.00 mg, 23.78 μmol, 61.68% yield) as a yellow oil.

Synthesis of E13: (3R,4S,8R,9S,10S)-9-(4-((2,3-difluorophenyl)ethynyl)phenyl)-10-((dimethylamino)methyl)-3,4-dihydroxy-N-(4-methoxyphenyl)-1,6-diazabicyclo[6.2.0]decane-6-carboxamide To a mixture of Intermediate 38b (15.00 mg, 23.78 μmol, 1.00 eq) in CH$_3$CN (500.00 μL) was added 1 M HCl (500.00 μL). After stirring at 15° C. for 12 h., the reaction mixture was concentrated under reduced pressure to give a residue which was purified by prep-HPLC (Column: Waters Xbridge Prep OBD C18 150*30 5u; A: water (0.225% formic acid) B: acetonitrile) to give (3S,4R,8R,9S,10S)-9-(4-((2,3-difluorophenyl)ethynyl)phenyl)-10-((dimethylamino)methyl)-3,4-dihydroxy-N-(4-methoxyphenyl)-1,6-diazabicyclo[6.2.0]decane-6-carboxamide (11.00 mg, 17.28 μmol, 72.65% yield, formic acid salt)) as a white solid. $^1$H NMR (400 MHz, METHANOL-d$_4$) δ=8.69-8.45 (m, 1H), 7.61 (s, 4H), 7.40-7.29 (m, 2H), 7.25-7.13 (m, 3H), 6.85 (d, J=9.0 Hz, 2H), 4.22 (dd, J=6.0, 15.6 Hz, 1H), 4.12 (d, J=6.0 Hz, 1H), 3.87-3.80 (m, 2H), 3.80-3.72 (m, 5H), 3.53-3.46 (m, 1H), 3.36 (br. s., 1H), 3.00-2.88 (m, 3H), 2.84-2.73 (m, 2H), 2.41 (s, 6H)

Example 14: (4aR,7aR,8S,9S,11aS)-9-((dimethylamino)methyl)-N-(4-methoxyphenyl)-8-(4-(phenylethynyl)phenyl)octahydro-2H-azeto[1,2-a][1,4]dioxino[2,3-f][1,4]diazocine-6 (3H)-carboxamide ("E14")

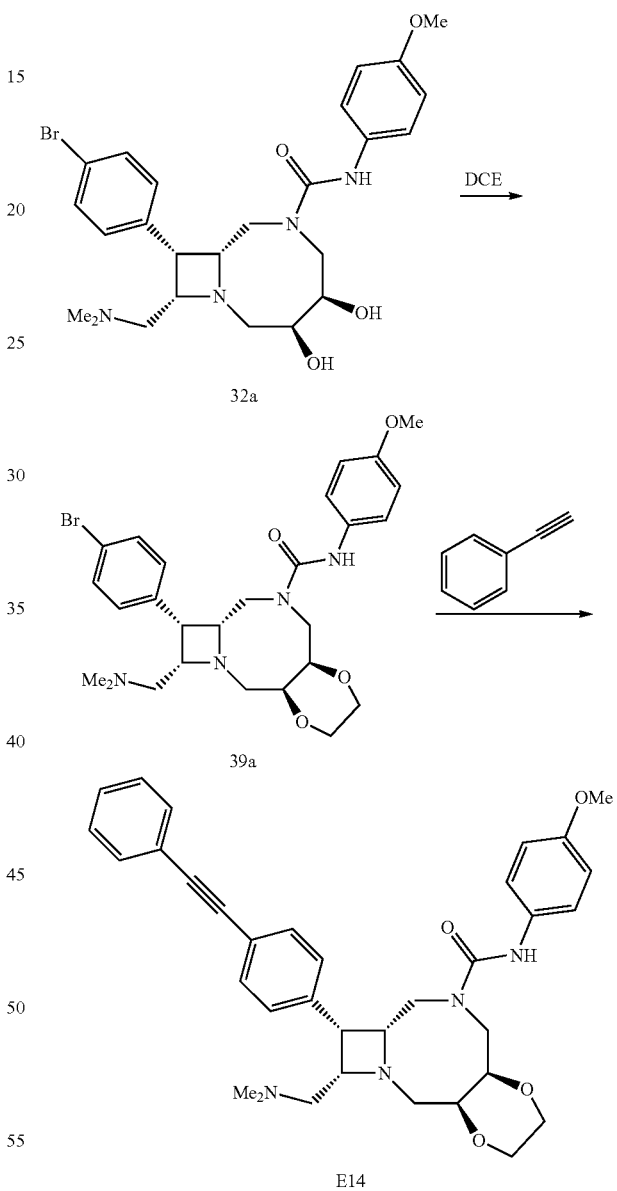

Intermediate 39a: (4aR,7aR,8S,9S,11aS)-8-(4-bromophenyl)-9-((dimethylamino)methyl)-N-(4-methoxyphenyl)octahydro-2H-azeto[1,2-a][1,4]dioxino[2,3-f][1,4]diazocine-6 (3H)-carboxamide A mixture of Intermediate 32a (30.00 mg, 56.24 μmol), NaOH (15.00 mg, 112.48 μmol, 180.30 μL, 30% m/v) and TBAB (3.63 mg, 11.25 μmol) in DCE (1.00 mL) was stirred at 55° C. for 12 h. LC-MS showed ~40% of Reactant 1 was remained. One new peak with desired Intermediate MS was detected. The reaction mixture was diluted with DCM 10 mL and washed with H$_2$O 15 mL*5. Then washed with brine 3 mL*2, dried over Na$_2$SO$_4$, filtered and concentrated under reduced pressure to give a residue which was purified by prep-TLC (SiO$_2$, DCM:MeOH=10:1) to give the Intermediate 39 (10.00 mg, 17.87 µmol, 31.78% yield) as a colorless oil.

Synthesis of E14: (4aR,7aR,8S,9S,11aS)-9-((dimethylamino)methyl)-N-(4-methoxyphenyl)-8-(4-(phenylethynyl)phenyl)octahydro-2H-azeto[1,2-a][1,4]dioxino[2,3-f][1,4]diazocine-6 (3H)-carboxamide To a solution of Intermediate 39a (20.00 mg, 35.75 µmol) and ethynylbenzene (10.95 mg, 107.25 µmol, 11.77 µL) in CH$_3$CN (500 µL) was added Cs$_2$CO$_3$ (46.59 mg, 143.00 µmol) and XPhos Pd G3 (3.03 mg, 3.58 µmol). After stirring under N$_2$ atmosphere at 70° C. for 1 hour under N$_2$ atmosphere, the reaction mixture was concentrated, purified by prep-TLC (SiO$_2$, DCM:MeOH=10:1) to remove the catalyst and then purified by pre-HPLC (Column: Waters Xbridge Prep OBD C18 150*30 5u; A: water (0.225% formic acid) B: acetonitrile) to give (4aR,7aR,8S,9S,11aS)-9-((dimethylamino)methyl)-N-(4-methoxyphenyl)-8-(4-(phenylethynyl)phenyl)octahydro-2H-azeto[1,2-a][1,4]dioxino[2,3-f][1,4]diazocine-6 (3H)-carboxamide (formic acid salt), 6.00 mg, 10.33 µmol, 28.90% yield) as a white solid. 1H NMR (400 MHz, CHLOROFORM-d) δ=8.26 (br s, 1H), 7.55 (dd, J=2.0, 7.0 Hz, 2H), 7.51-7.42 (m, 4H), 7.40-7.33 (m, 3H), 7.20 (d, J=9.0 Hz, 2H), 6.83 (d, J=9.0 Hz, 2H), 4.21 (br d, J=15.6 Hz, 1H), 4.10 (br d, J=14.1 Hz, 1H), 4.06-3.94 (m, 3H), 3.86-3.76 (m, 5H), 3.66 (br s, 1H), 3.59-3.52 (m, 2H), 3.48-3.29 (m, 3H), 2.89 (br d, J=13.1 Hz, 1H), 2.60-2.33 (m, 3H), 2.03 (s, 6H), 1.83 (br s, 1H).

Example 15: (3S,8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide ("E15")

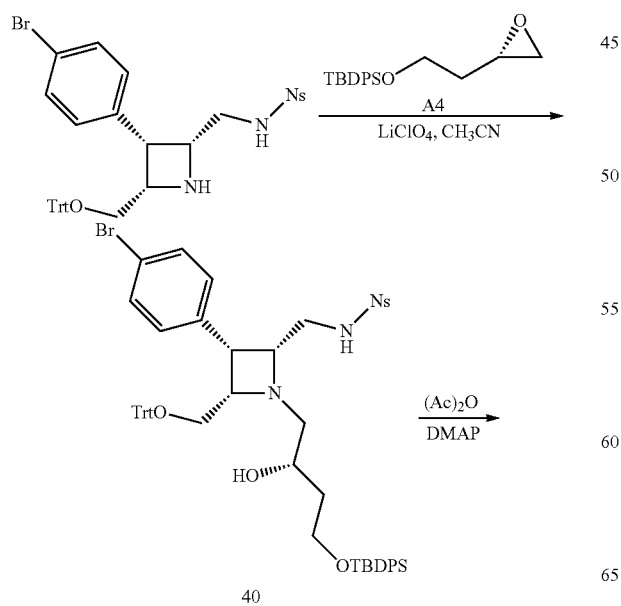

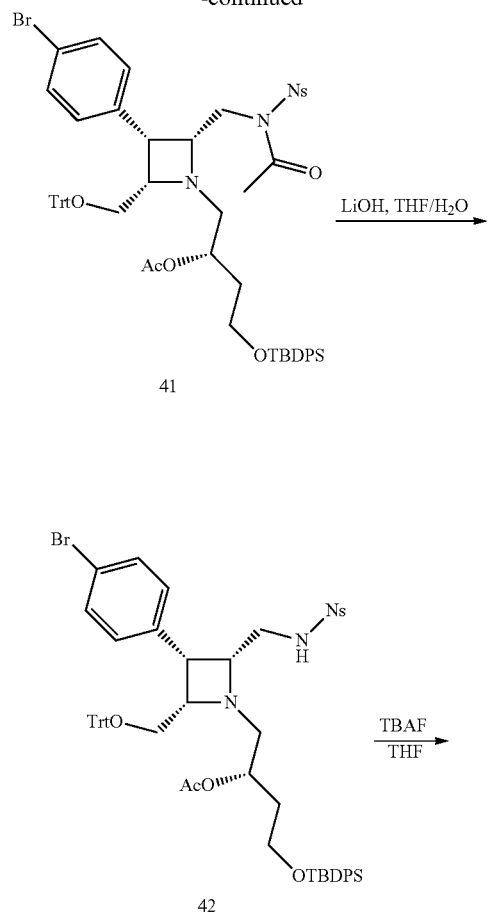

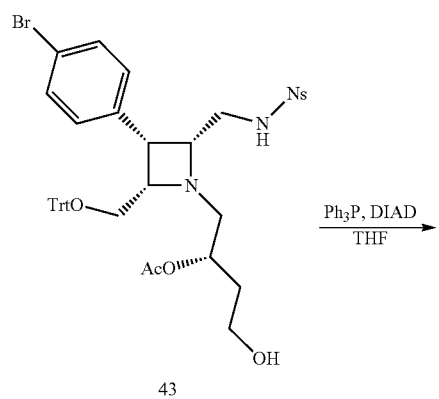

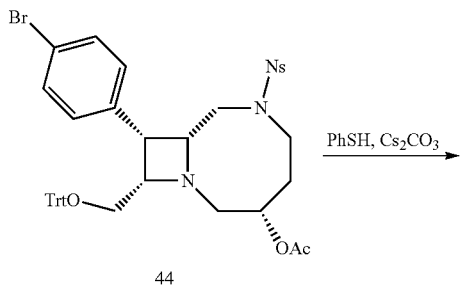

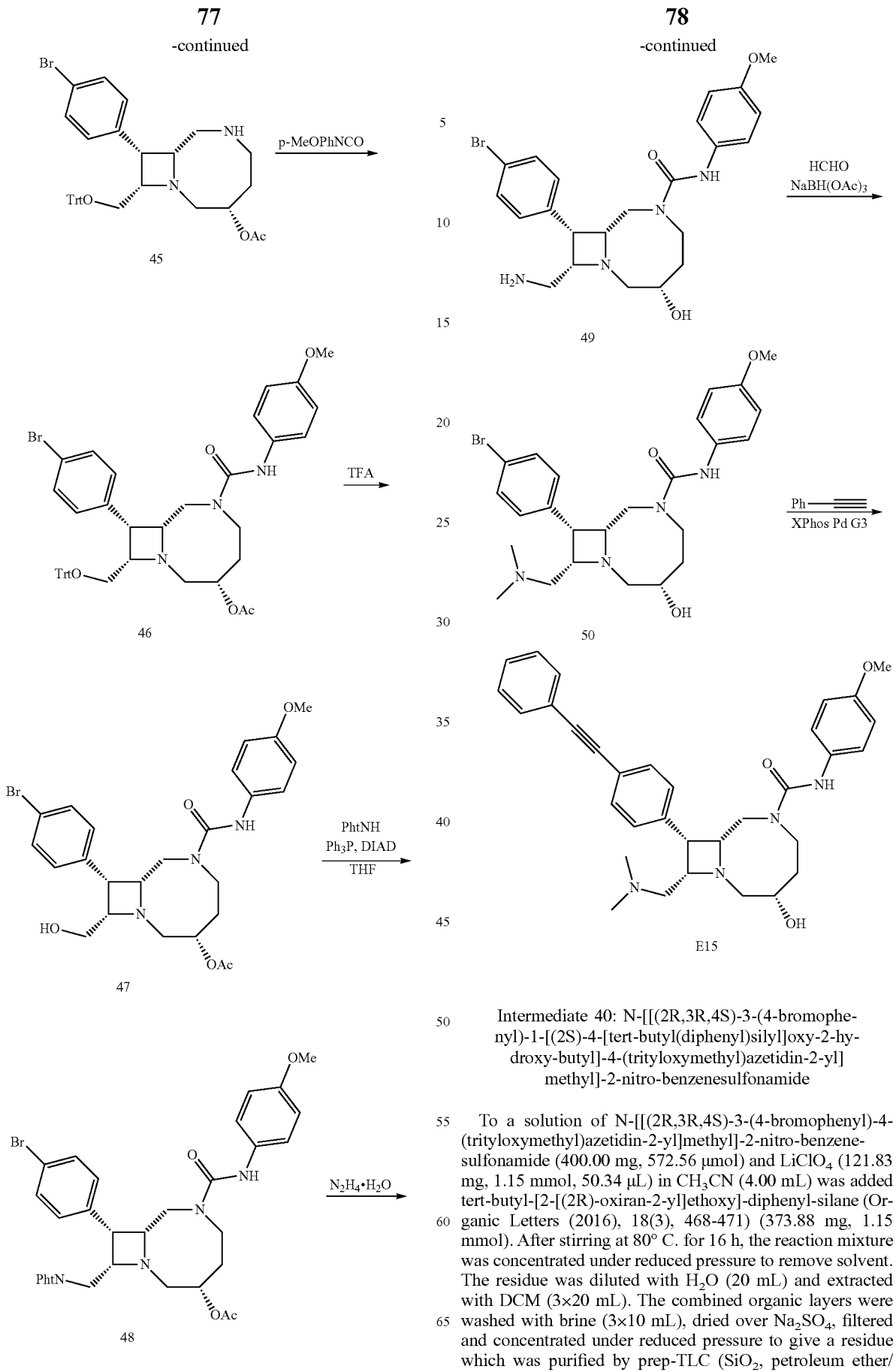

Intermediate 40: N-[[(2R,3R,4S)-3-(4-bromophenyl)-1-[(2S)-4-[tert-butyl(diphenyl)silyl]oxy-2-hydroxy-butyl]-4-(trityloxymethyl)azetidin-2-yl]methyl]-2-nitro-benzenesulfonamide To a solution of N-[[(2R,3R,4S)-3-(4-bromophenyl)-4-(trityloxymethyl)azetidin-2-yl]methyl]-2-nitro-benzene-sulfonamide (400.00 mg, 572.56 μmol) and LiClO₄ (121.83 mg, 1.15 mmol, 50.34 μL) in CH₃CN (4.00 mL) was added tert-butyl-[2-[(2R)-oxiran-2-yl]ethoxy]-diphenyl-silane (Organic Letters (2016), 18(3), 468-471) (373.88 mg, 1.15 mmol). After stirring at 80° C. for 16 h, the reaction mixture was concentrated under reduced pressure to remove solvent. The residue was diluted with H₂O (20 mL) and extracted with DCM (3×20 mL). The combined organic layers were washed with brine (3×10 mL), dried over Na₂SO₄, filtered and concentrated under reduced pressure to give a residue which was purified by prep-TLC (SiO₂, petroleum ether/ ethyl acetate=2/1) to give the Intermediate 40 (250.00 mg, 243.87 µmol, 42.59% yield) as a light yellow solid.

Intermediate 41: [(1S)-1-[[(2R,3R,4S)-2-[[acetyl-(2-nitrophenyl)sulfonyl-amino]methyl]-3-(4-bromophenyl)-4-(trityloxymethyl)azetidin-1-yl]methyl]-3-[tert-butyl(diphenyl)silyl]oxy-propyl] acetate To a solution of N-[[(2R,3R,4S)-3-(4-bromophenyl)-1-[(2S)-4-[tert-butyl(diphenyl)silyl]oxy-2-hydroxy-butyl]-4-(trityloxymethyl)azetidin-2-yl]methyl]-2-nitro-benzenesulfonamide (Intermediate 40) (250.00 mg, 243.87 µmol), Et$_3$N (24.68 mg, 243.87 µmol, 33.81 µL) and DMAP (2.98 mg, 24.39 µmol) in DCM (3.00 mL) was added Ac$_2$O (62.24 mg, 609.68 µmol, 57.10 µL). After stirring at 15° C. for 16 h, the reaction mixture was quenched by addition H$_2$O (20 mL), and then extracted with DCM (3×15 mL). The combined organic layers were washed with brine (10 mL), dried over Na$_2$SO$_4$, filtered and concentrated under reduced pressure to give a residue which was purified by prep-TLC (SiO$_2$, petroleum ether/ethyl acetate=3/1, plate 2) to give Intermediate 41 (270.00 mg, 243.42 µmol, 99.81% yield) as a white solid.

Intermediate 42: [(1S)-1-[[(2R,3R,4S)-3-(4-bromophenyl)-2-[[(2-nitrophenyl)sulfonylamino]methyl]-4-(trityloxymethyl)azetidin-1-yl]methyl]-3-[tert-butyl(diphenyl)silyl]oxy-propyl] acetate To a solution of [(1S)-1-[[(2R,3R,4S)-2-[[acetyl-(2-nitrophenyl)sulfonyl-amino]methyl]-3-(4-bromophenyl)-4-(trityloxymethyl)azetidin-1-yl]methyl]-3-[tert-butyl(diphenyl)silyl]oxy-propyl] acetate (Intermediate 41) (270.00 mg, 243.42 µmol) in THF (2 mL) and H$_2$O (2 mL) was added LiOH·H$_2$O (20.43 mg, 486.84 µmol). After stirring at 15° C. for 1 h, the reaction mixture was diluted with H$_2$O (30 mL) and extracted with DCM (20 mL*4). The combined organic layers were washed with brine (20 mL*3), dried over Na$_2$SO$_4$, filtered and concentrated under reduced pressure to give a residue which was purified by prep-TLC (SiO$_2$, petroleum ether/ethyl acetate=3/1, plate 1) to give Intermediate 42 (200.00 mg, 187.41 µmol, 76.99% yield) as a white solid.

Intermediate 43: [(1S)-1-[[(2R,3R,4S)-3-(4-bromophenyl)-2-[[(2-nitrophenyl)sulfonylamino]methyl]-4-(trityloxymethyl)azetidin-1-yl]methyl]-3-hydroxy-propyl] acetate To a solution of [(1S)-1-[[(2R,3R,4S)-3-(4-bromophenyl)-2-[[(2-nitrophenyl)sulfonylamino]methyl]-4-(trityloxymethyl)azetidin-1-yl]methyl]-3-[tert-butyl(diphenyl)silyl]oxy-propyl] acetate (Intermediate 42) (200.00 mg, 187.41 µmol) in THF (3 mL) was added TBAF (98.00 mg, 374.82 µmol). After stirring at 15° C. for 2 h, the reaction mixture was concentrated under reduced pressure to remove solvent. The residue was diluted with DCM (30 mL) and washed with H$_2$O (15 mL*5), then brine (10 mL*3), dried over Na$_2$SO$_4$, filtered and concentrated under reduced pressure to give a residue which was purified by prep-TLC (SiO$_2$, petroleum ether/ethyl acetate=1/1, plate 1) to give Intermediate 43 (150.00 mg, 180.99 µmol, 96.57% yield) as a white solid.

Intermediate 44: [(3S,8R,9R,10S)-9-(4-bromophenyl)-6-(2-nitrophenyl)sulfonyl-10-(trityloxymethyl)-1,6-diazabicyclo[6.2.0]decan-3-yl] acetate A mixture of PPh$_3$ (94.94 mg, 361.98 µmol, 2.00 eq) and DIAD (73.20 mg, 361.98 µmol, 70.38 µL, 2.00 eq) in THF (2 mL) was stirred at 0° C. under N$_2$ atmosphere to give the milky mixture. To this mixture was added a solution of [(1S)-1-[[(2R,3R,4S)-3-(4-bromophenyl)-2-[[(2-nitrophenyl)sulfonylamino]methyl]-4-(trityloxymethyl)azetidin-1-yl]methyl]-3-hydroxy-propyl] acetate (Intermediate 43) (150.00 mg, 180.99 µmol) in THF (1 mL). After stirring at 15° C. for 16 h, the reaction mixture was concentrated under reduced pressure to remove solvent. The residue was diluted with DCM (30 mL) washed with H$_2$O (10 mL*2), dried over Na$_2$SO$_4$, filtered and concentrated under reduced pressure to give a residue which was purified by prep-TLC (SiO$_2$, Petroleum ether/Ethyl acetate=1/1, plate 1) to give Intermediate 44 (150.00 mg, crude) as a white solid.

Intermediate 45: [(3S,8R,9R,10S)-9-(4-bromophenyl)-10-(trityloxymethyl)-1,6-diazabicyclo[6.2.0]decan-3-yl] acetate To a solution of [(3S,8R,9R,10S)-9-(4-bromophenyl)-6-(2-nitrophenyl)sulfonyl-10-(trityloxymethyl)-1,6-diazabicyclo[6.2.0]decan-3-yl] acetate (Intermediate 44) (150 mg, 185.01 µmol) in CH$_3$CN (3 mL) was added Cs$_2$CO$_3$ (120.56 mg, 370.02 µmol) and benzenethiol (30.58 mg, 277.52 µmol, 28.31 µL). After stirring at 40° C. for 2 h, the reaction mixture was concentrated under reduced pressure to remove solvent. The residue was diluted with H$_2$O (30 mL) and extracted with DCM (20 mL*5). The combined organic layers were washed with brine (20 mL*3), dried over Na$_2$SO$_4$, filtered and concentrated under reduced pressure to give a residue which was purified by prep-TLC (SiO$_2$, Petroleum ether/Ethyl acetate=1/1, plate 1) to give the Intermediate 45 (180.00 mg, crude) as a yellow solid.

Intermediate 46: [(3S,8R,9R,10S)-9-(4-bromophenyl)-6-[(4-methoxyphenyl)carbamoyl]-10-(trityloxymethyl)-1,6-diazabicyclo[6.2.0]decan-3-yl] acetate To a solution of [(3S,8R,9R,10S)-9-(4-bromophenyl)-10-(trityloxymethyl)-1,6-diazabicyclo[6.2.0]decan-3-yl] acetate (Intermediate 45) (180 mg, 287.73 µmol) in DCM (3 mL) was added 1-isocyanato-4-methoxybenzene (42.91 mg, 287.73 µmol, 36.99 µL). After stirring at 15° C. for 1 h, the reaction mixture was quenched by addition H$_2$O (15 mL), and then extracted with DCM (20 mL*4). The combined organic layers were washed with NaHCO$_3$ solution (15 mL), brine (15 mL*2), dried over Na$_2$SO$_4$, filtered and concentrated under reduced pressure to give a residue which was purified by prep-TLC (SiO$_2$, petroleum ether/ethyl acetate=1/1, plate 1) to give the Intermediate 46 (200 mg, 258.15 µmol, 89.72% yield) as a white solid.

Intermediate 47: [(3S,8R,9R,10S)-9-(4-bromophenyl)-10-(hydroxymethyl)-6-[(4-methoxyphenyl)carbamoyl]-1,6-diazabicyclo[6.2.0]decan-3-yl] acetate To a solution of [(3S,8R,9R,10S)-9-(4-bromophenyl)-6-[(4-methoxyphenyl)carbamoyl]-10-(trityloxymethyl)-1,6-diazabicyclo[6.2.0]decan-3-yl] acetate (Intermediate 46) (200 mg, 258.15 µmol, 1.00 eq) in DCM (3 mL) was added TFA (294.34 mg, 2.58 mmol, 191.13 µL). After stirring at 15° C. for 2 h, the reaction mixture was quenched by addition NaHCO$_3$ solution (20 mL), and extracted with DCM (20 mL*5). The combined organic layers were washed with brine (10 mL*3), dried over Na$_2$SO$_4$, filtered and concentrated under reduced pressure to give a residue which was purified by prep-TLC (SiO$_2$, petroleum ether/ethyl acetate=1/1, plate 1) to give the Intermediate 47 (130.00 mg, 244.16 μmol, 94.58% yield) as a white solid.

Intermediate 48: [(3S,8R,9S,10S)-9-(4-bromophenyl)-10-[(1,3-dioxoisoindolin-2-yl)methyl]-6-[(4-methoxyphenyl)carbamoyl]-1,6-diazabicyclo[6.2.0] decan-3-yl] acetate A mixture of PPh$_3$ (128.08 mg, 488.32 μmol, 2.00 eq) and DIAD (98.74 mg, 488.32 μmol, 94.94 μL, 2.00 eq) in THF (1 mL) was stirred at 0° C. under N$_2$ atmosphere to give a milky mixture. To this milky mixture was added to the solution of (3S,8R,9R,10S)-9-(4-bromophenyl)-10-(hydroxymethyl)-6-[(4-methoxyphenyl)carbamoyl]-1,6-diazabicyclo[6.2.0]decan-3-yl] acetate (Intermediate 47) (130 mg, 244.16 μmol) and isoindoline-1,3-dione (53.88 mg, 366.24 μmol) in THF (1 mL) at 0° C. After stirring at 15° C. for 12 h, the reaction mixture was concentrated under reduced pressure to remove solvent and then purified by prep-TLC (SiO$_2$, petroleum ether/ethyl acetate=1/1, plate 1) to give Intermediate 48 (200 mg, crude) as a yellow oil.

Intermediate 49: (3S,8R,9S,10S)-10-(aminomethyl)-9-(4-bromophenyl)-3-hydroxy-N-(4-methoxyphenyl)-1,6-diazabicyclo[6.2.0]decane-6-carboxamide To a solution of [(3S,8R,9S,10S)-9-(4-bromophenyl)-10-[(1,3-dioxoisoindolin-2-yl)methyl]-6-[(4-methoxyphenyl) carbamoyl]-1,6-diazabicyclo[6.2.0]decan-3-yl] acetate (Intermediate 48) (200 mg, 302.32 μmol) in EtOH (2 mL) was added N$_2$H$_4$·H$_2$O (29.39 μL, 604.64 μmol). After stirring at 70° C. for 2 h, the reaction mixture was concentrated under reduced pressure to remove solvent. The residue was diluted with H$_2$O (10 mL) and extracted with DCM (10 mL*5). The combined organic layers were washed with brine (10 mL*2), dried over Na$_2$SO$_4$, filtered and concentrated under reduced pressure to give a residue which was purified by prep-TLC (SiO$_2$, DCM:MeOH=10:1, plate 1) to give the Intermediate 49 (60 mg, 122.60 μmol, 40.55% yield) as a white solid.

Intermediate 50: (3S,8R,9S,10S)-9-(4-bromophenyl)-10-[(dimethylamino)methyl]-3-hydroxy-N-(4-methoxyphenyl)-1,6-diazabicyclo[6.2.0]decane-6-carboxamide To a solution of (3S,8R,9S,10S)-10-(aminomethyl)-9-(4-bromophenyl)-3-hydroxy-N-(4-methoxyphenyl)-1,6-diazabicyclo[6.2.0]decane-6-carboxamide (Intermediate 49) (60 mg, 122.60 μmol), formaldehyde (54.77 μL, 735.60 μmol), MgSO$_4$ (147.57 mg, 1.23 mmol) and AcOH (0.70 μL, 12.26 μmol) in DCM (3 mL) was added NaBH(OAc)$_3$ (77.95 mg, 367.80 μmol). After stirring at 15° C. for 2 h, the reaction mixture was filtered through a celite and washed with NaHCO$_3$ solution (10 mL*3). The combined organic layers were dried over Na$_2$SO$_4$, filtered and concentrated under reduced pressure to give Intermediate 50 (50 mg, 96.63 μmol, 78.81% yield) as a white solid.

Synthesis of E15: (3S,8R,9S,10S)-10-[(dimethylamino)methyl]-3-hydroxy-N-(4-methoxyphenyl)-9-[4-(2-phenylethynyl)phenyl]-1,6-diazabicyclo[6.2.0] decane-6-carboxamide To a solution of (3S,8R,9S,10S)-9-(4-bromophenyl)-10-[(dimethylamino)methyl]-3-hydroxy-N-(4-methoxyphenyl)-1,6-diazabicyclo[6.2.0]decane-6-carboxamide (Intermediate 50) (50 mg, 96.63 μmol) and ethynylbenzene (29.61 mg, 289.89 μmol, 31.84 μL) in CH$_3$CN (1 mL) was added Cs$_2$CO$_3$ (125.94 mg, 386.52 μmol) and XPhos Pd G3 catalyst (8.18 mg, 9.66 μmol). After stirring under N$_2$ atmosphere at 70° C. for 1 h, the reaction mixture was purified by prep-TLC (SiO$_2$, DCM:MeOH=10:1, plate 1) to remove the catalyst giving the crude product which was further purified by prep-HPLC (prep-HPLC (column: Luna C18 150*25 5u; mobile phase: A: water (0.225% formic acid) B: acetonitrile) to give the product phenylethynyl) phenyl]-1,6-diazabicyclo[6.2.0]decane-6-carboxamide (10 mg, 17.10 μmol, 17.7% yield, formic acid salt)) as a white solid. $^1$H NMR (400 MHz, CHLOROFORM-d) δ=8.44 (br s, 1H), 7.54 (br d, J=7.0 Hz, 4H), 7.44-7.34 (m, 5H), 7.29-7.24 (m, 2H), 6.83 (br d, J=8.8 Hz, 2H), 6.29 (s, 1H), 5.71 (br s, 1H), 3.87 (br s, 2H), 3.77 (s, 3H), 3.75-3.62 (m, 4H), 3.52-3.38 (m, 1H), 3.18 (br dd, J=6.1, 13.6 Hz, 1H), 2.93-2.79 (m, 1H), 2.77-2.66 (m, 2H), 2.66-2.58 (m, 1H), 2.19 (s, 6H), 2.08-1.97 (m, 1H), 1.96-1.85 (m, 1H)

Examples 16-17: Isomers of (8R,9S,10S)-10-[(dimethylamino)methyl]-3-hydroxy-N-(4-methoxyphenyl)-9-[4-(2-phenylethynyl)phenyl]-1,6-diazabicyclo [6.2.0]decane-6-carboxamide

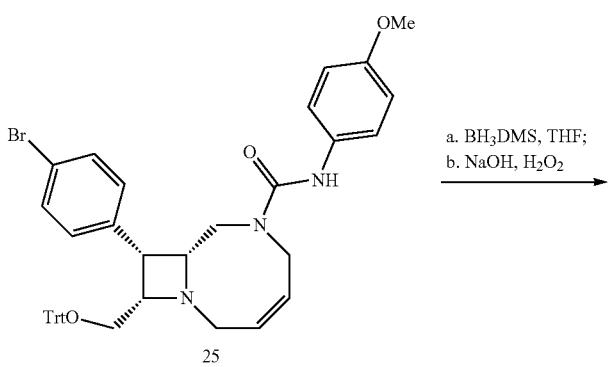

25

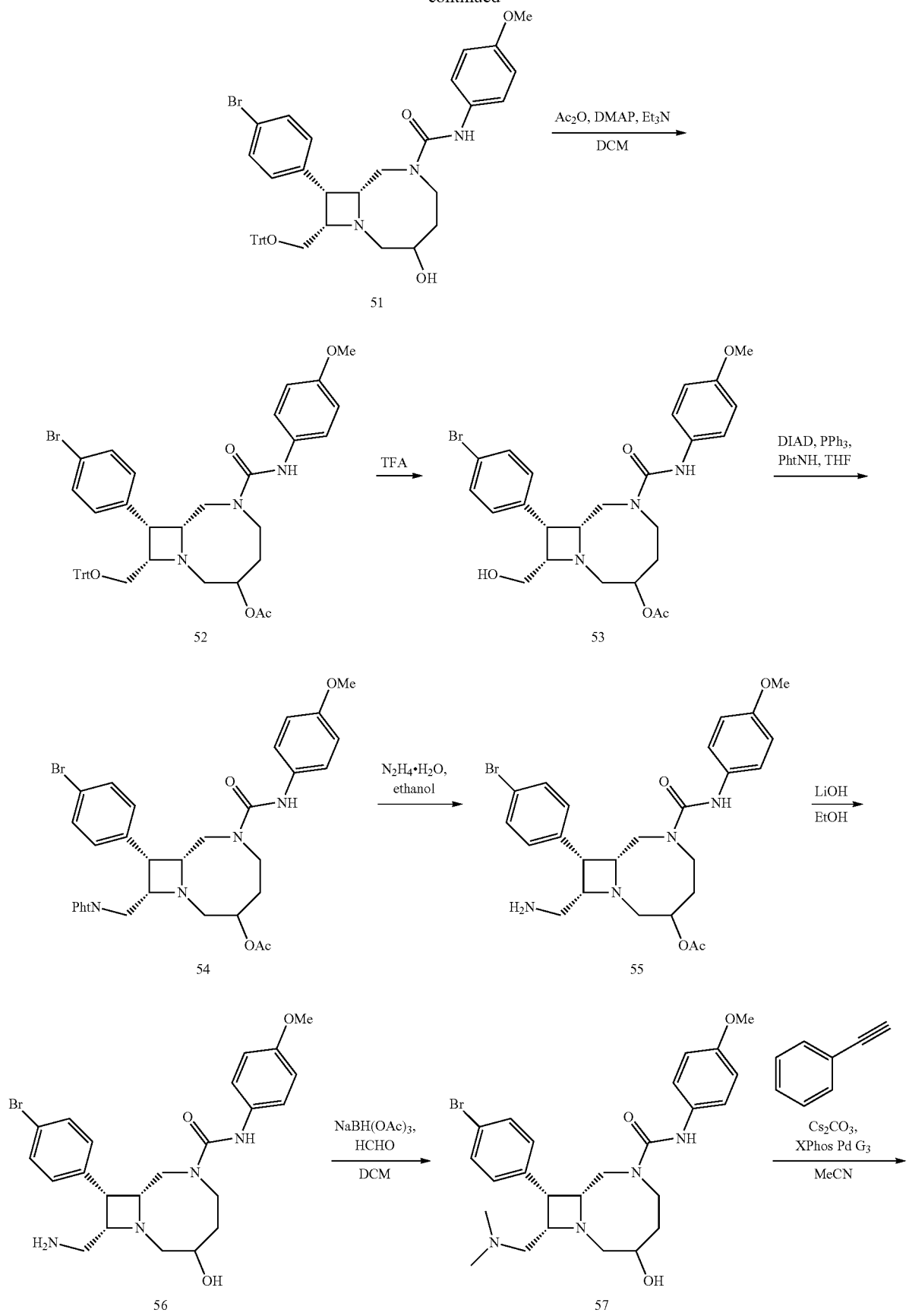

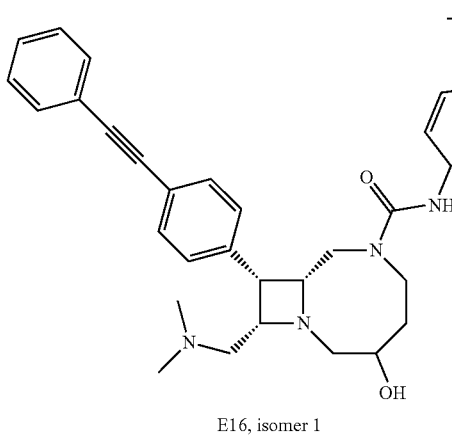

E16, isomer 1

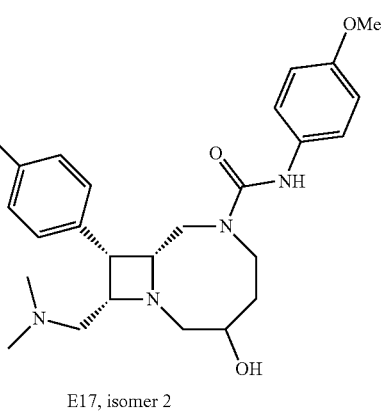

E17, isomer 2

Intermediate 51: (8R,9S,10S)-10-trityloxymethyl-3-hydroxy-N-(4-methoxyphenyl)-9-[4-bromophenyl]-1,6-diazabicyclo[6.2.0]decane-6-carboxamide To a solution of (3Z,8R,9R,10S)-9-(4-bromophenyl)-N-(4-methoxyphenyl)-10-(trityloxymethyl)-1,6-diazabicyclo[6.2.0]dec-3-ene-6-carboxamide (Intermediate 25, 980.00 mg, 1.37 mmol, 1.00 eq) in THF (1.00 mL) was added $BH_3$-$Me_2S$ (10 M, 686 µL, 5.00 eq) at 0° C. and the reaction mixture was stirred at 25° C. for 3 h. $H_2O$ (1.24 g, 68.56 mmol, 1.24 mL, 50.00 eq) was added slowly and the reaction mixture was stirred at 25° C. for 30 min. Then to the reaction solution was added $NaOH/H_2O$ (18.27 g, 68.50 mmol, 15% purity, 50.00 eq) and $H_2O_2$ (6.66 g, 68.56 mmol, 5.65 mL, 35% purity, 50.00 eq). The resulting reaction mixture was stirred at 25° C. for 3 h. The reaction was quenched with $H_2O$ (10 mL) and extracted with DCM (50 mL). The combined organic layers were dried over anhydrous $Na_2SO_4$ and concentrated to give a crude product as a white solid (mixtures), which was used into next step without further purification.

Intermediate 52: [(8R,9R,10S)-9-(4-bromophenyl)-6-[(4-methoxyphenyl)carbamoyl]-10-(trityloxymethyl)-1,6-diazabicyclo[6.2.0]decan-4-yl] acetate To a solution of Intermediate 51 (1.2 g, 1.64 mmol), $Et_3N$ (497.85 mg, 4.92 mmol) and DMAP (20.04 mg, 164 µmol) in DCM (2 mL) at 0° C. was added $Ac_2O$ (334.86 mg, 3.28 mmol). After stirring at 25° C. for 3 h, the reaction was quenched with $H_2O$ (10 mL) and extracted with DCM (20 mL) to give the organic layer. The organic layer was dried over anhydrous $Na_2SO_4$ and concentrated to give the residue. The residue was purified by prep-TLC (petroleum ether:ethyl acetate=1:1) to give two isomers of [(8R,9R,10S)-9-(4-bromophenyl)-6-[(4-methoxyphenyl)carbamoyl]-10-(trityloxymethyl)-1,6-diazabicyclo[6.2.0]decan-4-yl] acetate. Each isomer was separated by prep-TLC to produce Isomer 1 (126 mg, 9.92% yield, Rf=0.5) as a white solid and Isomer 2 (197 mg, 15.50% yield, Rf=0.4) as a white solid and mixed fractions [(8R,9R,10S)-9-(4-bromophenyl)-6-[(4-methoxy phenyl)carbamoyl]-10-(trityloxymethyl)-1,6-diazabicyclo[6.2.0]decan-4-yl] acetate (624 mg, 49.11% yield, Rf=0.3) as a white solid. Although each stereoisomer was separated individually, the stereochemistry of the 4 position for each compound could not be determined.

Isomer 1: $^1$H NMR (400 MHz, $CDCl_3$-d1) δ8.25 (s, 1H), 7.47 (d, J=8.8 Hz, 2H), 7.19-7.11 (m, 23H), 6.77 (d, J=8.8 Hz, 2H), 4.62 (s, 1H), 3.92-3.88 (m, 1H), 3.74-3.70 (m, 1H), 3.56-3.55 (m, 4H), 3.45-3.41 (m, 1H), 3.30-3.29 (m, 1H), 3.08-3.07 (m, 3H), 2.89-2.87 (m, 1H), 2.73-2.70 (m, 1H), 2.55-2.52 (m, 1H), 2.43 (s, 1H), 2.06 (s, 3H), 1.92-1.88 (m, 2H), 1.12-1.1.10 (m, 3H), 0.9-0.87 (m, 3H).

Isomer 2: $^1$H NMR (400 MHz, $CDCl_3$-d1) δ7.34-7.22 (m, 23H), 7.09 (d, J=8 Hz, 2H), 6.83 (d, J=8.8 Hz, 2H), 5.07-5.04 (m, 1H), 3.92-3.88 (m, 1H), 3.77 (m, 5H), 3.65-3.58 (m, 3H), 3.25-3.27 (m, 2H), 3.03-3.00 (m, 1H), 3.02-2.99 (m, 1H), 2.61-2.57 (m, 1H), 2.45-2.44 (m, 1H), 2.16 (s, 3H), 2.08-2.05 (m, 1H), 1.74-1.71 (m, 2H), 1.00-0.95 (m, 1H).

Mixed Fractions $^1$H NMR (400 MHz, $CDCl_3$-d1) δ7.52-7.17 (m, 21H), 6.84-6.82 (m, 3H), 4.81 (s, 1H), 4.29-4.16 (m, 1H), 3.99-3.77 (m, 1H), 3.67-3.66 (m, 1H), 3.65-3.63 (m, 6H), 3.63-3.56 (m, 5H), 3.40-3.39 (m, 3H), 3.16-3.12 (m, 2H), 2.96-2.94 (m, 1H), 2.63-0.59 (m, 1H), 2.28-2.25 (m, 1H), 1.97 (s, 3H), 1.89-1.86 (m, 1H), 1.28-1.25 (m, 2H), 0.88-0.84 (m, 1).

Intermediate 53: (8R,9R,10S)-9-(4-bromophenyl)-10-(hydroxymethyl)-6-((4-methoxyphenyl)carbamoyl)-1,6-diazabicyclo[6.2.0]decan-3-yl acetate To a solution of [(8R,9R,10S)-9-(4-bromophenyl)-6-[(4-methoxy phenyl)carbamoyl]-10-(trityloxymethyl)-1,6-diazabicyclo[6.2.0]decan-4-yl] acetate (624 mg, 805.43 µmol) in DCM (2 mL) was added TFA (918.35 mg, 8.05 mmol, 596.33 µL). After stirring at 25° C. for 3 h, the reaction mixture was quenched by $NaHCO_3$ (10 mL) and extracted with DCM (20 mL) to give the organic layer. The organic layer was dried over anhydrous $Na_2SO_4$ and concentrated to give the residue and purified by prep-TLC (petroleum ether: ethyl acetate=1:1) to Intermediate 53 (265 mg, 61.80% yield) as a white solid. $^1$H NMR (400 MHz, $CDCl_3$-d1) δ7.46 (d, J=8 Hz, 2H), 7.38 (d, J=8 Hz, 2H), 7.26 (d, J=8 Hz, 2H), 6.83 (d, J=8 Hz, 2H), 6.47 (s, 1H), 4.80 (s, 1H), 3.81-3.77 (m, 4H), 3.64-3.57 (m, 5H), 3.52-3.47 (m, 3H), 3.25-3.22 (m, 1H), 3.21 (s, 1H), 2.97-2.84 (m, 1H), 22.33-2.23 (m, 2H), 2.24 (s, 2H), 2.15-1.96 (m, 2H).

Intermediate 54: [(8R,9S,10S)-9-(4-bromophenyl)-10-[(1,3-dioxoisoindolin-2-yl)methyl]-6-[(4-methoxyphenyl)carbamoyl]-1,6-diazabicyclo[6.2.0]decan-3-yl] acetate To a solution of Intermediate 53 (275 mg, 516.5 µmol), isoindoline-1,3-dione (83.59 mg, 568.15 µmol) and $PPh_3$ (203.21 mg, 774.75 µmol) in THF (2 mL) was added DIAD (156.66 mg, 774.75 µmol) dropwise at 25° C. After stirring at 25° C. for 5 h, the reaction mixture was concentrated to give the residue. The residue was purified by prep-TLC (petroleum ether:ethyl acetate=1:1) to give Intermediate 54 (460 mg, crude) as a light yellow solid. $^1$H NMR (4400 MHz, CDCl$_3$-d1) δ7.79 (s, 2H), 7.70-7.65 (m, 20H), 7.55-7.53 (m, 20H), 7.48-7.45 (m, 30H), 6.86 (m, 3H), 6.62 (s, 1H), 4.76 (s, 2H), 3.86-3.83 (m, 6H), 3.79-7.77 (m, 3H), 3.65-3.64 (m, 3H), 3.54-3.49 (m, 1H), 3.09-3.04 (m, 1H), 2.85-2.81 (m, 1H), 2.56-2.53 (m, 1H), 3.37-3.14 (m, 1H), 2.21-2.14 (m, 1H).

Intermediate 55: [(8R,9S,10S)-10-(aminomethyl)-9-(4-bromophenyl)-6-[(4-methoxyphenyl)carbamoyl]-1,6-diazabicyclo[6.2.0]decan-3-yl] acetate To a solution of Intermediate 54 (460 mg, 695.35 µmol) in EtOH (1 mL) was added hydrazine hydrate (53.28 mg, 1.04 mmol, 51.73 µL) dropwise. After stirring at 80° C. for 2 h, the reaction mixture was filtered and concentrated to give Intermediate 55 (500 mg, crude) as a brown liquid without purification and will be used directly in next step. HRMS (ESI): calcd for C$_{24}$H$_{28}$BrN$_4$O$_3$ [M+H]$^+$ 531.15, found 531.1.

Intermediate 56: (8R,9S,10S)-10-(aminomethyl)-9-(4-bromophenyl)-3-hydroxy-N-(4-methoxyphenyl)-1,6-diazabicyclo[6.2.0]decane-6-carboxamide To a solution of Intermediate 55 (300 mg, 564.50 µmol) in EtOH:H$_2$O=2:1 (1 mL) was added LiOH·H$_2$O (47.37 mg, 1.13 mmol). After stirring at 40° C. for 2 h, the reaction mixture was diluted with H$_2$O (3 mL) and extracted with DCM (10 mL) to give organic layer. The organic layer was concentrated and purified by pre-TLC (dichloromethane:methanol=10:1) to give Intermediate 56 (90 mg, 32.58% yield) as a white solid. $^1$H NMR (4400 MHz, CDCl$_3$-d1) δ7.52-7.47 (m, 2H), 7.34-7.32 (m, 18H), 7.27-7.22 (m, 3H), 6.84 (d, J=9.2 Hz, 2H), 6.17 (s, 1H), 3.87-3.84 (m, 1H), 3.78-3.74 (m, 3H), 3.70-3.66 (m, 3H), 3.57-3.55 (m, 2H), 3.13-3.10 (m, 1H), 2.77-2.71 (m, 1H), 2.04-1.88 (m, 5H).

Intermediate 57: (8R,9S,10S)-9-(4-bromophenyl)-10-[(dimethylamino)methyl]-3-hydroxy-N-(4-methoxyphenyl)-1,6-diazabicyclo[6.2.0]decane-6-carboxamide To a stirred solution of Intermediate 56 (90 mg, 183.9 µmol) in DCM (2 mL) was added HCHO (149.26 mg, 1.84 mmol, 136.93 µL, 37% solution) and MgSO$_4$ (442.72 mg, 3.68 mmol). After stirring at 25° C. for 0.5 h, NaBH(OAc)$_3$ (194.88 mg, 919.49 µmol) was added. After stirring at 25° C. for 1.5 h, the reaction mixture was concentrated to give the residue. The residue was purified by prep-TLC (dichloromethane:methanol=10:1) to give Intermediate 57 (58 mg, 60.95% yield) as light brown solid. $^1$H NMR (400 MHz, CDCl$_3$-d1) δ7.51-7.44 (m, 2H), 7.30-7.23 (m, 5H), 6.85 (d, J=8.8 Hz, 2H), 6.15 (s, 1H), 3.89-3.87 (m, 2H), 3.83-3.78 (m, 3H), 3.73-3.67 (m, 4H), 3.20-3.15 (m, 1H), 2.72-2.69 (m, 2H), 2.60-2.51 (m, 2H), 2.14 (s, 5H), 2.05-2.026 (m, 4H), 2.00-1.91 (m, 1H).

Synthesis of E16 and E17: (8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide isomer 1 (E16) and isomer 2 (E17)

To a solution of Intermediate 57 (50 mg, 96.63 µmol) and ethynylbenzene (29.61 mg, 289.89 µmol) in Acetonitrile (1 mL) was added XPhos Pd G3 (8.18 mg, 9.66 µmol) and Cs$_2$CO$_3$ (62.97 mg, 193.26 µmol). After stirring at 70° C. for 2 h, the reaction mixture was concentrated to give the residue. The residue was purified by pre-HPLC (Column: Waters Xbridge Prep OBD C18 150*30 5u; A: water (0.225% formic acid) B: acetonitrile) to the give each stereoisomer of (8R,9S,10S)-10-[(dimethylamino)methyl]-3-hydroxy-N-(4-methoxyphenyl)-9-[4-(2-phenylethynyl)phenyl]-1,6-diazabicyclo[6.2.0]decane-6-carboxamide.

Each isomer was separated to produce Isomer 1 (5.1 mg, 9.80% yield) and Isomer 2 (17.1 mg, 32.85% yield) as a white solid.

E16: Isomer 1: HRMS (ESI): calcd for C$_{32}$H$_{35}$N$_4$O$_2$ [M+H]$^+$ 539.29, found 529. $^1$H NMR (400 MHz, MeOD-d4) δ7.60-7.50 (m, 6H), 7.39-7.37 (m, 3H), 7.36-7.18 (m, 2H), 6.85 (d, J=8.8 Hz, 2H), 3.83-3.80 (m, 2H), 3.76 (s, 3H), 3.69-3.68 (m, 2H), 3.55-3.52 (m, 3H), 3.15-3.09 (m, 2H), 3.01-3.00 (m, 2H), 3.41-3.34 (m, 2H), 2.26 (m, 6H), 1.75-1.72 (m, 1H).

E17: Isomer 2: HRMS (ESI): calcd for C$_{32}$H$_{35}$N$_4$O$_2$ [M+H]$^+$ 539.29, found 529.40 $^1$H NMR (400 MHz, MeOD-d4) δ7.61-7.54 (m, 6H), 7.50 (d, J=1.6 Hz, 3H), 7.38-7.36 (m, 2H), 6.85 (d, J=8.8 Hz, 2H), 3.84-3.80 (m, 3H), 3.75 (s, 3H), 3.67-3.61 (m, 2H), 3.55-3.51 (m, 1H), 3.08-3.05 (m, 2H), 2.83-2.80 (m, 1H), 2.74-2.68 (m, 3H), 2.26 (s, 6H), 2.03-1.94 (m, 2H).

Examples 18-19: (8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide isomer 1 ("E18") and isomer 2 ("E19")

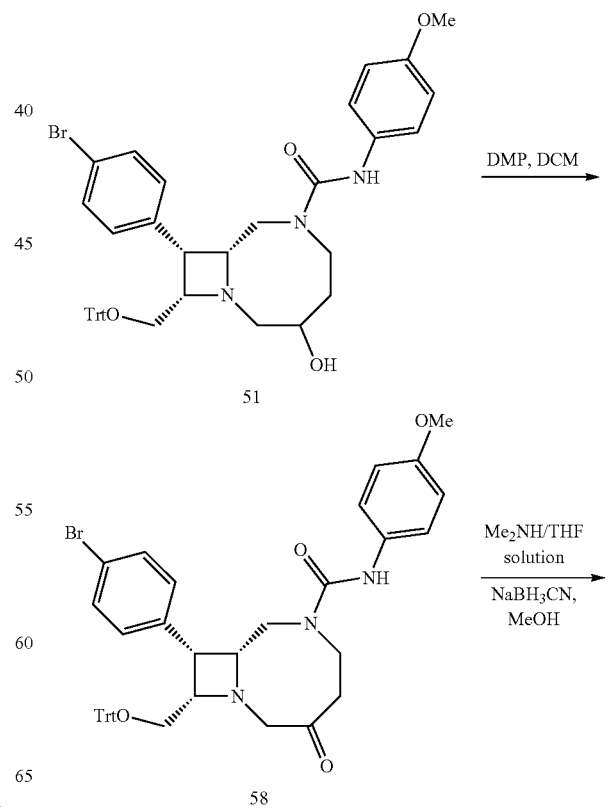

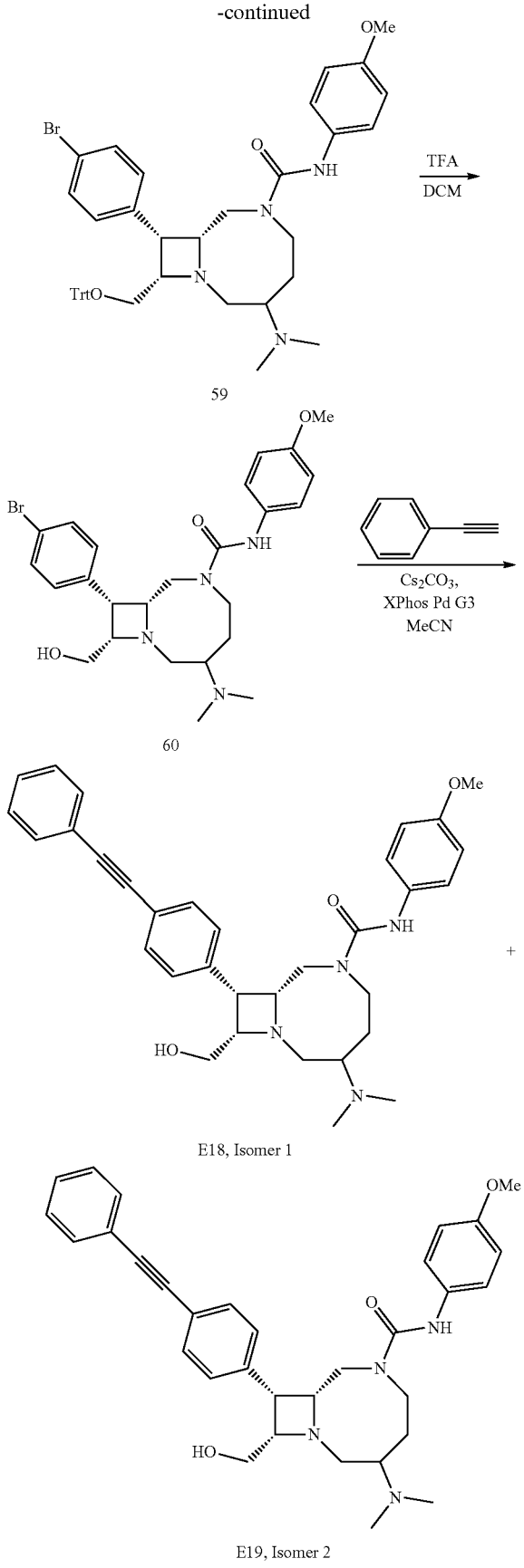

Intermediate 58: (8R,9R,10S)-9-(4-bromophenyl)-N-(4-methoxyphenyl)-3-oxo-10-((trityloxy)methyl)-1,6-diazabicyclo[6.2.0]decane-6-carboxamide To a solution of Intermediate 51 (500.00 mg, 682.41 µmol, 1 eq) in DCM (5 mL) was added Dess-Martin (347.32 mg, 818.89 µmol). After stirring at 25° C. for 3 h, the reaction mixture was quenched by saturated $Na_2SO_3$ (5 mL) and extracted with DCM (10 mL) to give the organic layer. The organic layer was concentrated and prep-TLC (petroleum ether:ethyl acetate=1:1) to give Intermediate 58 (280 mg, 56.15% yield) as a brown solid. $^1$H NMR (400 MHz, $CDCl_3$-d1) δ7.37-7.19 (m, 30H), 6.86-6.82 (m, 2H), 6.20 (s, 1H), 4.27-4.20 (m, 3H), 4.07-3.81 (m, 1H), 3.79-3.77 (m, 3H), 3.70-3.66 (m, 3H), 3.54-3.31 (m, 1H), 3.06-3.04 (m, 1H), 2.98-2.94 (m, 2H), 2.76-2.73 (m, 1H), 2.72-2.45 (m, 1H).

Intermediate 59: (8R,9R,10S)-9-(4-bromophenyl)-3-(dimethylamino)-N-(4-methoxyphenyl)-10-((trityloxy)methyl)-1,6-diazabicyclo[6.2.0]decane-6-carboxamide To a stirred solution of Intermediate 58 (250 mg, 342.14 µmol) in MeOH (2 mL) was added N-methylmethanamine (2 M, 1.71 mL) and $CH_3COOH$ (205.46 mg, 3.42 mmol). After stirring at 25° C. for 0.5 h, $NaBH_3CN$ (21.50 mg, 342.14 µmol) was added. After stirring at 25° C. for 1.5 h, the reaction mixture was concentrated to give the residue. The residue was purified by prep-TLC (dichloromethane:methanol=15:1) to give Intermediate 59 (120 mg, 46.16% yield) as light brown solid. HRMS (ESI) calcd for $C_{32}H_{33}N_4O$ $[M+H]^+$ 759.28, found 759.2.

Intermediate 60: (8R,9R,10S)-9-(4-bromophenyl)-3-(dimethylamino)-10-(hydroxymethyl)-N-(4-methoxyphenyl)-1,6-diazabicyclo[6.2.0]decane-6-carboxamide To a stirred solution of Intermediate 59 (115 mg, 151.36 µmol) in DCM (1 mL) was TFA (172.58 mg, 1.51 mmol). After stirring at 25° C. for 12 h, the reaction mixture was quenched with saturated $NaHCO_3$ (5 mL) and extracted with DCM (5 mL) to give organic layer. The organic solution was collected, concentrated and then purified by prep-TLC (dichloromethane:methanol=10:1) to give Intermediate 60 (45.00 mg, 57.45% yield) as light brown solid. $^1$H NMR (400 MHz, $CDCl_3$-d1) δ7.47-7.43 (m, 2H), 7.38-7.31 (m, 4H), 6.83 (d, J=8.8 Hz, 2H), 3.99 (s, 1H), 3.77 (s, 5H), 3.63-3.61 (m, 5H), 3.59-3.57 (m, 5H), 3.48-3.46 (m, 2H), 3.32-3.13 (m, 3H), 2.76 (s, 6H), 2.48-2.34 (m, 4H), 2.04-2.00 (m, 1H).

Synthesis of E18 and E19: (8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide isomer 1 (E18) and isomer 2 (E19)

To a solution of Intermediate 59 (30 mg, 57.98 µmol) and ethynylbenzene (17.76 mg, 173.94 µmol) in acetonitrile (1 mL) was added XPhos Pd G3 (4.91 mg, 5.80 µmol) and $Cs_2CO_3$ (37.78 mg, 115.96 µmol). After stirring at 70° C. for 2 h, the reaction mixture was concentrated to give a residue. The residue was purified by pre-HPLC (Column: Waters Xbridge Prep OBD C18 150*30 5u; A: water (0.225% formic acid) B: acetonitrile) to the give each stereoisomer of (8R,9R,10S)-4-(dimethylamino)-10-(hydroxymethyl)-N-(4-methoxyphenyl)-9-[4-(2-phenylethynyl)phenyl]-1,6-diazabicyclo[6.2.0]decane-6-carboxamide separated as isomer 1 (E18) (2.60 mg, 8.32% yield) and isomer 2 (E19) (11.40 mg, 36.50% yield) as a white solid.

E18: Isomer 1, HRMS (ESI) calcd for: $C_{33}H_{38}N_4O_3$ [M+H]$^+$ 539.29, found 539.4 $^1$H NMR (400 MHz, MeOD-d4) δ8.34 (s, 1H), 7.56-7.51 (m, 2H), 7.50-7.48 (m, 4H), 7.37 (d, J=5.2 Hz, 2H), 7.26 (d, J=9.6 Hz, 2H), 6.85 (d, J=8.8 Hz, 1H), 4.09-4.05 (m, 1H), 3.75-3.72 (m, 3H), 3.66-3.65 (m, 1H), 3.52-3.46 (m, 4H), 3.26-3.20 (m, 2H), 2.64 (s, 6H), 2.55-2.52 (m, 1H), 1.97 (s, 2H).

E19: Isomer 2, HRMS (ESI) calcd for: $C_{33}H_{38}N_4O_3$ [M+H]$^+$ 539.29, found 539.4 $^1$H NMR (400 MHz, MeOD-d4) δ8.55 (s, 1H), 7.61 (d, J=8 Hz, 2H), 7.51-7.49 (m, 4H), 7.38-7.36 (m, 3H), 7.23 (d, J=8.8 Hz, 2H), 6.86 (d, J=8.8 Hz, 2H), 4.21-4.11 (m, 1H), 3.76-3.73 (m, 5H), 3.76-3.73 (m, 2H), 3.62-3.40 (m, 3H), 3.31-3.13 (m, 3H), 2.81-2.77 (s, 6H), 2.64 (s, 1H), 2.46 (s, 1H), 2.06-2.03 (m, 1H).

Examples 20-21: (8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide isomer 1 ("E20") and isomer 2 Example 21 ("E21")

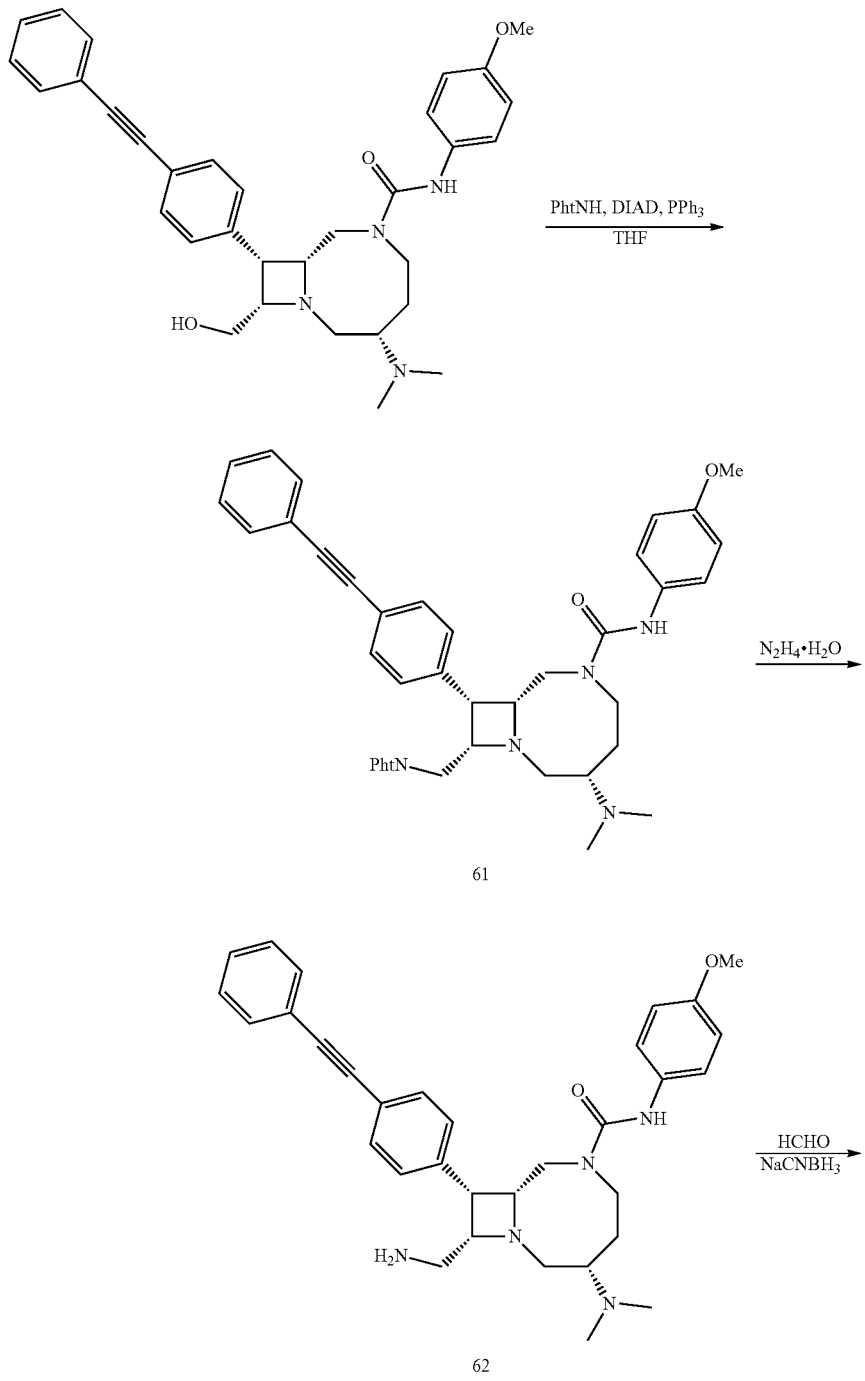

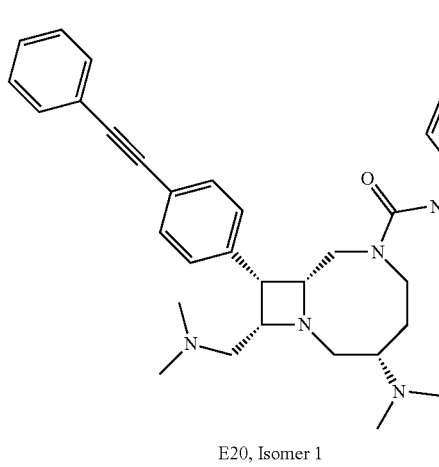

E20, Isomer 1

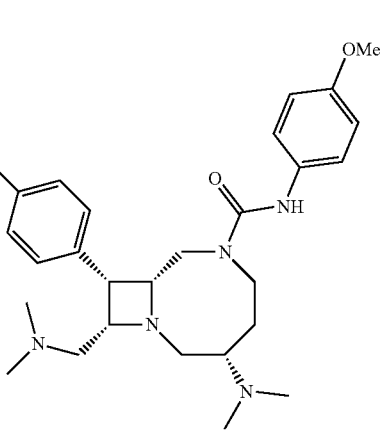

E21, Isomer 2

Intermediate 61: (8R,9S,10S)-3-(dimethylamino)-10-((1,3-dioxoisoindolin-2-yl)methyl)-N-(4-methoxyphenyl)-9-(4-(phenylethynyl)phenyl)-1,6-diazabicyclo[6.2.0]decane-6-carboxamide To a solution of a mixture of Examples 18 and 19 (165 mg, 318.87 μmol, 1 eq), isoindoline-1,3-dione (51.61 mg, 350.75 μmol) and PPh$_3$ (125.45 mg, 478.30 μmol) in THF (2 mL) was added DIAD (96.72 mg, 478.30 μmol) dropwise. After stirring at 25° C. for 12 h, the residue was purified by prep-TLC (petroleum ether:ethyl acetate=0:1) to give Intermediate 61 (184 mg, 89.25% yield) as a light yellow solid. $^1$H NMR (400 MHz, CDCl$_3$-d1) δ7.83-7.81 (m, 1H), 7.73-7.72 (m, 2H), 7.55-7.26 (m, 5H), 6.82-6.79 (m, 2H), 3.94-3.74 (m, 2H), 3.72 (s, 3H), 3.67-3.56 (m, 5H), 3.54-3.55 (m, 2H), 3.35-3.06 (m, 1H), 2.77 (s, 6H), 1.26 (s, 1H).

Intermediate 62: (8R,9S,10S)-10-(aminomethyl)-3-(dimethylamino)-N-(4-methoxyphenyl)-9-(4-(phenylethynyl)phenyl)-1,6-diazabicyclo[6.2.0]decane-6-carboxamide To a solution of Intermediate 61 (174 mg, 260.56 μmol) in EtOH (1 mL) was added hydrazine hydrate (19.96 mg, 390.84 μmol) dropwise. After stirring at 80° C. for 2 h, the reaction mixture was filtered and concentrated to give the residue. The residue was purified by prep-TLC (dichloromethane:methanol=6:1) to give Intermediate 62 (50.00 mg, 35.69% yield) as a brown liquid. HRMS (ESI) calcd for C$_{33}$H$_{39}$N$_5$O$_2$ [M+H]$^+$ 538.31, found 538.2.

Synthesis of E20 and E21: (4S,8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide (E20) and (4R,8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide (E21)

To a stirred solution of Intermediate 61 (50 mg, 96.81 μmol) in DCM (2.00 mL) was added HCHO (78.57 mg, 968.10 μmol, 72.08 μL) and MgSO$_4$ (116.53 mg, 968.10 μmol). After stirring at 25° C. for 0.5 h, CH$_3$COOH (5.81 mg, 96.81 μmol) and NaBH(OAc)$_3$ (102.59 mg, 484.05 μmol) were added. After stirring at 25° C. for 1.5 h, the reaction mixture was quenched by H$_2$O (5 mL) and extract with DCM (20 mL*3) to give organic layer. The organic layer was dried over anhydrous Na$_2$SO$_4$ and concentrated to give the residue. The residue was purified by prep-HPLC to give and separate each isomer of (8R,9S,10S)-9-(4-bromophenyl)-4-(dimethylamino)-10-[(dimethylamino)methyl]-N-(4-methoxyphenyl)-1,6-diazabicyclo[6.2.0]decane-6-carboxamide as isomer 1 (E20) (2.90 mg, 5.33 μmol, 5.51% yield) as light brown solid (HRMS (ESI) calcd for: C$_{35}$H$_{43}$N$_5$O$_2$ [M+H]$^+$ 566.34, found 566.4; $^1$H NMR (400 MHz, MeOD-d4) δ7.61-7.51 (m, 5H), 7.44-7.38 (m, 4H), 7.37-7.23 (m, 2H), 6.87-6.85 (m, 2H), 4.05-3.77 (m, 1H), 3.77 (s, 3H), 3.66-3.51 (m, 2H), 3.19-3.16 (m, 1H), 2.50-2.47 (m, 1H), 2.35-2.19 (m, 1H), 1.86-1.80 (m, 1H))) and isomer 2 (E21) (15.20 mg, 27.91 μmol, 28.83% yield) as light brown solid ($^1$H NMR (400 MHz, MeOD-d4) δ7.56-7.54 (m, 6H), 7.52-7.51 (m, 3H), 7.23-7.22 (m, 2H), 6.83-6.84 (m, 2H), 4.14-4.12 (m, 1H), 3.87-3.81 (m, 1H), 3.76 (s, 3H), 3.67-3.48 (m, 2H), 3.24-3.22 (m, 2H), 2.77 (s, 6H), 2.71-2.60 (m, 4H), 2.32-2.31 (m, 2H), 2.31-2.30 (m, 1H)).

Example 22: (3S,4R,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide ("E22")

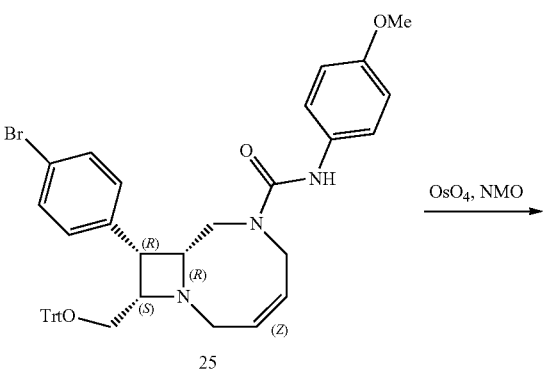

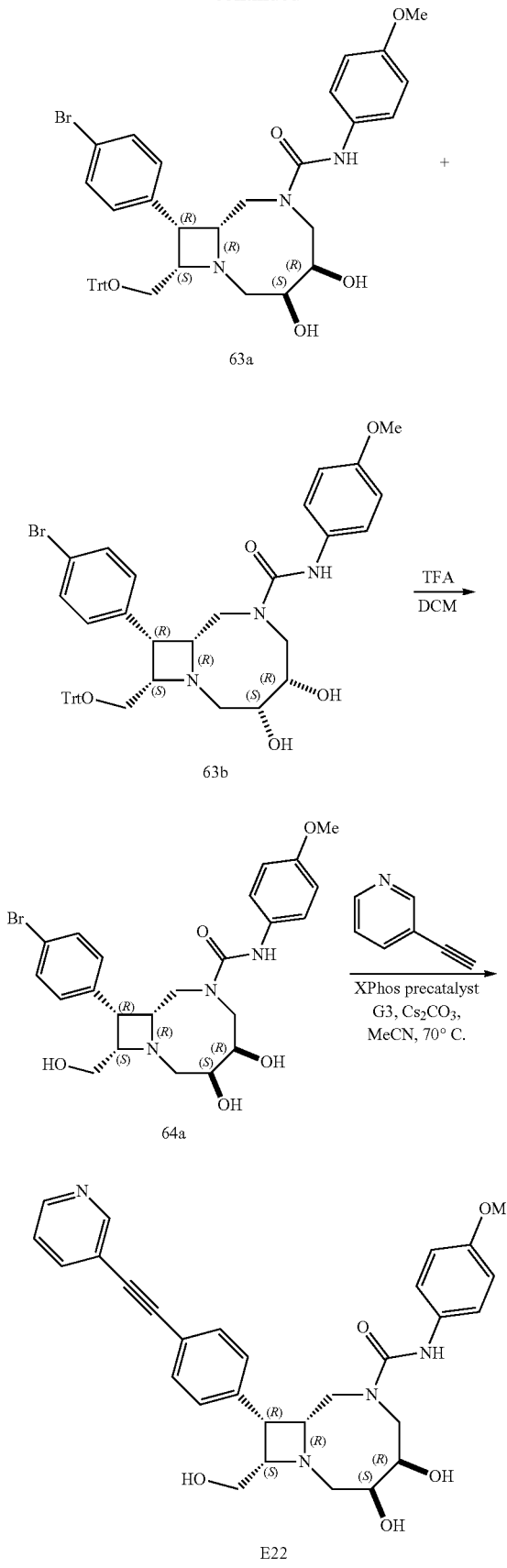

Intermediate 63a and 63b: (3S,4R,8R,9R,10S)-9-(4-bromophenyl)-3,4-dihydroxy-N-(4-methoxyphenyl)-10-(trityloxymethyl)-1,6-diazabicyclo[6.2.0]decane-6-carboxamide (63a) and (3R,4S,8R,9R,10S)-9-(4-bromophenyl)-3,4-dihydroxy-N-(4-methoxyphenyl)-10-(trityloxymethyl)-1,6-diazabicyclo[6.2.0]decane-6-carboxamide (63b)

To a solution of Intermediate 25 (220 mg, 307.83 μmol) and NMO (43.27 mg, 369.4 μmol) in acetone/H$_2$O=10:1 (1 mL) was added OsO$_4$ (7.83 mg, 30.78 μmol) at 25° C. After stirring at 25° C. for 12 h, the reaction mixture was concentrated to give a residue. The residue was purified by pre-TLC (petroleum ether:ethyl acetate=1:5) to give Intermediate 63a (120 mg, 52.07% yield) as a white solid $^1$H NMR (400 MHz, CDCl$_3$-d1) δ7.31-7.05 (m, 23H), 6.85-6.81 (m, 2H), 6.82 (d, J=8 Hz, 2H), 4.23-4.19 (m, 1H), 3.99 (s, 1H), 3.76-3.73 (m, 6H), 3.50-3.43 (m, 2H), 3.19-3.13 (m, 2H), 2.98-2.96 (m, 1H), 2.86-2.84 (m, 1H), 2.78-2.59 (m, 1H)) and Intermediate 63b (134 mg, 58.14% yield) as a white solid ($^1$H NMR (400 MHz, CDCl$_3$-d1) δ7.39-7.24 (m, 23H), 7.09-7.05 (m, 2H), 6.84 (d, J=8.8 Hz, 2H), 3.85-3.78 (m, 5H), 3.69-3.61 (m, 4H), 3.45-3.40 (m, 3H), 3.14-3.13 (m, 1H), 3.05-3.04 (m, 1H), 2.78-2.75 (m, 1H)).

Intermediate 64a: (3S,4R,8R,9R,10S)-9-(4-bromophenyl)-3,4-dihydroxy-10-(hydroxymethyl)-N-(4-methoxyphenyl)-1,6-diazabicyclo[6.2.0]decane-6-carboxamide To a solution of Intermediate 63a (60 mg, 80.14 μmol) in DCM (2 mL) was added TFA (91.37 mg, 801.39 μmol). After stirring at 25° C. for 3 h, the reaction was quenched with NaHCO$_3$ (10 mL) and extracted with DCM (20 mL) to give the organic layer. The organic layer was dried over anhydrous Na$_2$SO$_4$ and concentrated to give the residue. The residue was purified by prep-TLC (petroleum ether:ethyl acetate) to give the Intermediate 64a (35 mg, 86.24% yield) as a white solid. $^1$H NMR (400 MHz, CDCl$_3$-d1) δ7.43 (d, J=7.6 Hz, 2H), 7.30 (d, J=8.4 Hz, 2H), 7.20 (d, J=8.8 Hz, 2H), 6.82 (d, J=8.8 Hz, 2H), 4.32-4.28 (m, 1H), 4.13-4.06 (m, 2H), 3.85 (m, 1H), 3.76 (s, 3H), 3.61 (s, 1H), 3.48 (s, 3H), 3.22 (m, 1H), 2.98-2.88 (m, 2H), 2.77-2.70 (m, 2H), 2.0 (s, 1H).

Synthesis of E22: (3S,4R,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide To a solution of Intermediate 64a (20 mg, 39.5 μmol) and 3-ethynylpyridine (8.15 mg, 78.99 μmol) in acetonitrile (1 mL) was added XPhos Pd G3 (3.34 mg, 3.95 μmol) and Cs$_2$CO$_3$ (25.74 mg, 78.99 μmol). After stirring at 70° C. for 1 h, the reaction mixture was concentrated to give the residue. The residue was purified by pre-HPLC (Column: Waters Xbridge Prep OBD C18 150*30 5u; A: water (0.225% formic acid) B: acetonitrile) to the give (3S,4R,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide (6.8 mg, 29.69% yield) as a white solid (HRMS (ESI) calcd for C$_{30}$H$_{32}$N$_4$O$_5$ [M+H]$^+$ 529.24, found 529.30; $^1$H NMR (400 MHz, MeOD-d4) δ8.69 (s, 1H), 8.51 (d, J=4 Hz, 1H), 7.98 (d, J=8 Hz, 1H), 7.60-7.52 (m, 4H), 7.48-7.45 (m, 1H), 7.16 (d, J=8.8 Hz, 2H), 6.84 (d, J=8.8 Hz, 2H), 4.16-4.11 (m, 2H), 3.84-3.82 (m, 2H), 3.75 (s, 3H), 3.64-3.58 (m, 4H), 3.39-3.60 (m, 2H), 2.88-2.79 (m, 3H)).

Example 23: (3R,4S,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide ("E23")

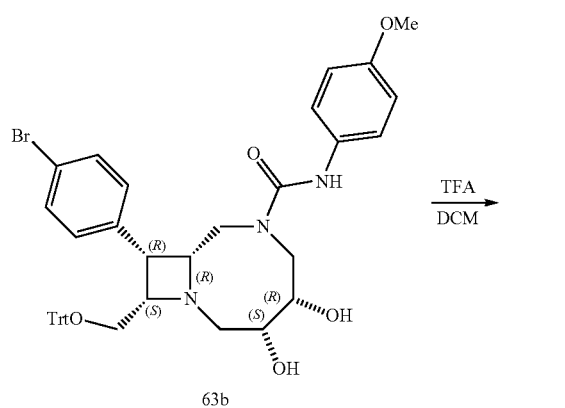

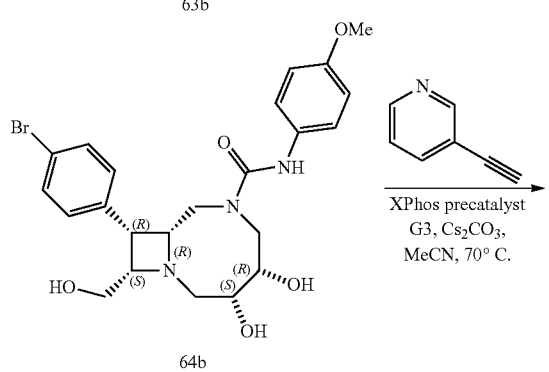

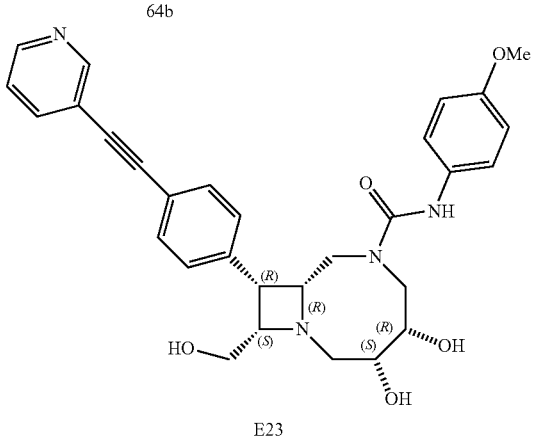

Intermediate 64b: (3R,4S,8R,9R,10S)-9-(4-bromophenyl)-3,4-dihydroxy-10-(hydroxymethyl)-N-(4-methoxyphenyl)-1,6-diazabicyclo[6.2.0]decane-6-carboxamide To a solution of Intermediate 63b (130 mg, 173.63 μmol) in DCM (2 mL) was added TFA (197.98 mg, 1.74 mmol). After stirring at 25° C. for 3 h, the reaction was quenched with NaHCO₃ (10 mL) and extracted with DCM (20 mL) to give the organic layer. The organic layer was dried over anhydrous Na$_2$SO$_4$ and concentrated to give the residue. The residue was purified by prep-TLC (petroleum ether:ethyl acetate) to give the Intermediate 64b (75 mg 85.30% yield) as a white solid ($^1$H NMR (400 MHz, CDCl$_3$-d1) δ7.48 (d, J=7.6 Hz, 2H), 7.09-7.28 (m, 7H), 6.84 (d, J=8.8 Hz, 2H), 3.78 (d, J=10.8 Hz, 1H), 3.72-3.66 (m, 4H), 3.59-3.57 (m, 5H), 3.53-3.51 (m, 4H), 3.27-3.25 (m, 1H), 2.88-2.74 (m, 2H)).

Synthesis of E23: (3R,4S,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide To a solution of Intermediate 64b (20 mg, 39.50 μmol) and 3-ethynylpyridine (8.15 mg, 78.99 μmol) in acetonitrile (1 mL) was added XPhos Pd G3 (3.34 mg, 3.95 μmol) and Cs$_2$CO$_3$ (25.74 mg, 78.99 μmol). After stirring at 70° C. for 2 h, the reaction mixture was concentrated to give the residue. The residue was purified by pre-HPLC (Column: Waters Xbridge Prep OBD C18 150*30 5u; A: water (0.225% formic acid) B: acetonitrile) to the give (3R,4S,8R,9R,10S)-3,4-dihydroxy-10-(hydroxymethyl)-N-(4-methoxyphenyl)-9-(4-(pyridin-3-ylethynyl)phenyl)-1,6-diazabicyclo[6.2.0]decane-6-carboxamide (7.4 mg, 29.69% yield) as a white solid. HRMS (ESI) calcd for C$_{30}$H$_{32}$N$_4$O$_5$ [M+H]$^+$ 529.24, found 529.30. $^1$H NMR (400 MHz, MeOD-d4) δ8.69 (s, 1H), 8.52 (d, J=5.2 Hz, 1H), 7.98 (d, J=8 Hz, 1H), 7.61-7.56 (m, 4H), 7.48-7.46 (m, 1H), 7.23 (d, J=8.8 Hz, 2H), 6.86 (d, J=9.2 Hz, 2H), 3.84-3.80 (m, 3H), 3.76 (s, 3H), 3.65-3.50 (m, 7H), 3.31-3.28 (m, 1H), 3.08-3.26 (m, 1H), 2.74-2.71 (m, 1H).

Synthesis of Intermediate A5: [(1S)-1-[[tert-butyl(diphenyl)silyl]oxymethyl]-3-oxo-propyl]acetate

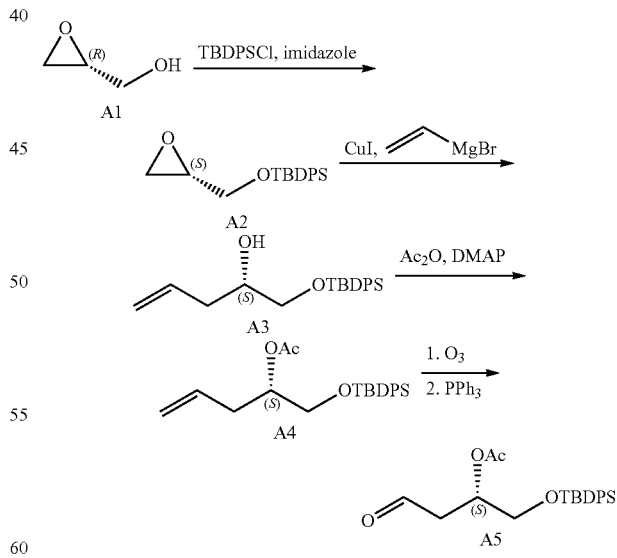

Intermediate A2: tert-butyl-[[(2S)-oxiran-2-yl]methoxy]-diphenyl-silane

To a solution of (R)-oxiran-2-ylmethanol (3.00 g, 40.50 mmol, 2.68 mL) and imidazole (5.51 g, 80.99 mmol) in DCM (80 mL) at 0° C. was added TBDPSCl (13.36 g, 48.60 mmol, 12.48 mL). After stirring at 25° C. for 12 h, the reaction mixture was quenched with H₂O (20 mL) and extracted by DCM (60 mL*2) to give the organic layer. The layer was dried over anhydrous Na₂SO₄ and concentrated to give the residue. The residue was purified by column chromatography on silica gel (petroleum ether:ethyl acetate=10:1) to give Intermediate A2 (12.66 g, 100.00% yield) as a colorless liquid. ¹H NMR (400 MHz, CDCl₃-d1) δ7.69-7.68 (m, 4H), 7.46-7.40 (m, 5H), 8.87-3.85 (m, 1H), 3.73-3.70 (m, 1H), 3.14-3.13 (m, 1H), 2.76-2.74 (m, 1H), 1.05 (s, 9H).

Intermediate A3: (2S)-1-[tert-butyl(diphenyl)silyl]oxypent-4-en-2-ol

CuI (1.83 g, 9.60 mmol, 1.5 eq) was placed in a three-necked flask under nitrogen and then anhydrous THF (20 mL) was added. The resulting mixture was cooled to −78° C., and then vinyl magnesium bromide (1 M, 22.40 mL, 3.5 eq) was added dropwise while maintaining the internal temperature below −78° C. The heterogeneous mixture was warmed to −20° C. and stirred at this temperature for 30 min. After cooling the solution back to −78° C., Intermediate A2 (2.00 g, 6.40 mmol, 1 eq) was added dropwise. The mixture was stirred, and allowed to gradually warm to 20° C. for 12 h. The reaction mixture was quenched with H₂O (20 mL) and extracted by DCM (60 mL*2) to give the organic layer. The layer was dried over anhydrous Na₂SO₄ and concentrated to give the residue. The residue was purified by column chromatography on silica gel (petroleum ether:ethyl acetate=7:1) to give Intermediate A3 (2.18 g, 100.00% yield) as a colorless liquid. ¹H NMR (400 MHz, CDCl₃-d1) δ7.67-7.65 (m, 4H), 7.44-7.37 (m, 7H), 5.82-5.76 (m, 1H), 5.10-4.90 (m, 2H), 3.81-3.78 (m, 1H), 3.68-3.65 (m, 1H), 3.57-3.54 (m, 1H), 2.46-2.44 (m, 1H), 2.25-2.22 (m, 1H), 1.05 (m, 9H).

Intermediate A4: [(1S)-1-[[tert-butyl(diphenyl)silyl]oxymethyl]but-3-enyl] acetate To a solution of Intermediate A3 (2.18 g, 6.40 mmol, 1 eq), Et₃N (1.94 g, 19.21 mmol, 3 eq) and DMAP (78.21 mg, 640.18 μmol, 0.1 eq) in DCM (2 mL) at 0° C. was added acetic anhydride (980.06 mg, 9.60 mmol, 1.5 eq). The resulting reaction mixture was stirred at 25° C. for 3 h. TLC (petroleum ether:ethyl acetate=10:1) showed the reaction was complete, the reaction mixture was quenched with H₂O (10 mL) and extracted with DCM (20 mL*3) to give organic layer. The layer was dried over anhydrous Na₂SO₄ and concentrated to give the residue. The residue was purified by column chromatography on silica gel (petroleum ether:ethyl acetate=10:1) to give Intermediate A4 (2.30 g, 93.94% yield) as a colorless liquid. ¹H NMR (400 MHz, CDCl₃-d1) δ7.67-7.65 (m, 4H), 7.40-7.26 (m, 6H), 5.77-5.69 (m, 1H), 5.11-5.01 (m, 3H), 3.73-3.66 (m, 2H), 2.48-2.32 (m, 1H), 2.02 (m, 3H), 1.09 (m, 9H).

Intermediate A5: [(1S)-1-[[tert-butyl(diphenyl)silyl]oxymethyl]-3-oxo-propyl] acetate A −78° C. solution of Intermediate A4 (1.70 g, 4.44 mmol, 1 eq) in DCM/MeOH=1:1 (30 mL) was treated with a stream of O3 in O2 until the solution turned blue. N₂ was then bubbled through the solution until the color disappeared. The resulting solution was treated with Me₂S (2.76 g, 44.44 mmol, 10 eq), warmed to 20° C. and stirred for 2 h. TLC (petroleum ether:ethyl acetate=5:1) showed the reaction was complete, the reaction mixture was diluted with DCM (50 mL) and washed with H₂O (10 mL) to give the organic layer. The organic layer was dried over anhydrous Na₂SO₄ and concentrated to give Intermediate A5 (1.70 g, crude) as a colorless liquid without further purification.

Example 24: (4S,8R,9S,10S)-10-[(dimethylamino)methyl]-4-hydroxy-N-(4-methoxyphenyl)-9-[4-(2-phenylethynyl)phenyl]-1,6-diazabicyclo[6.2.0]decane-6-carboxamide ("E24")

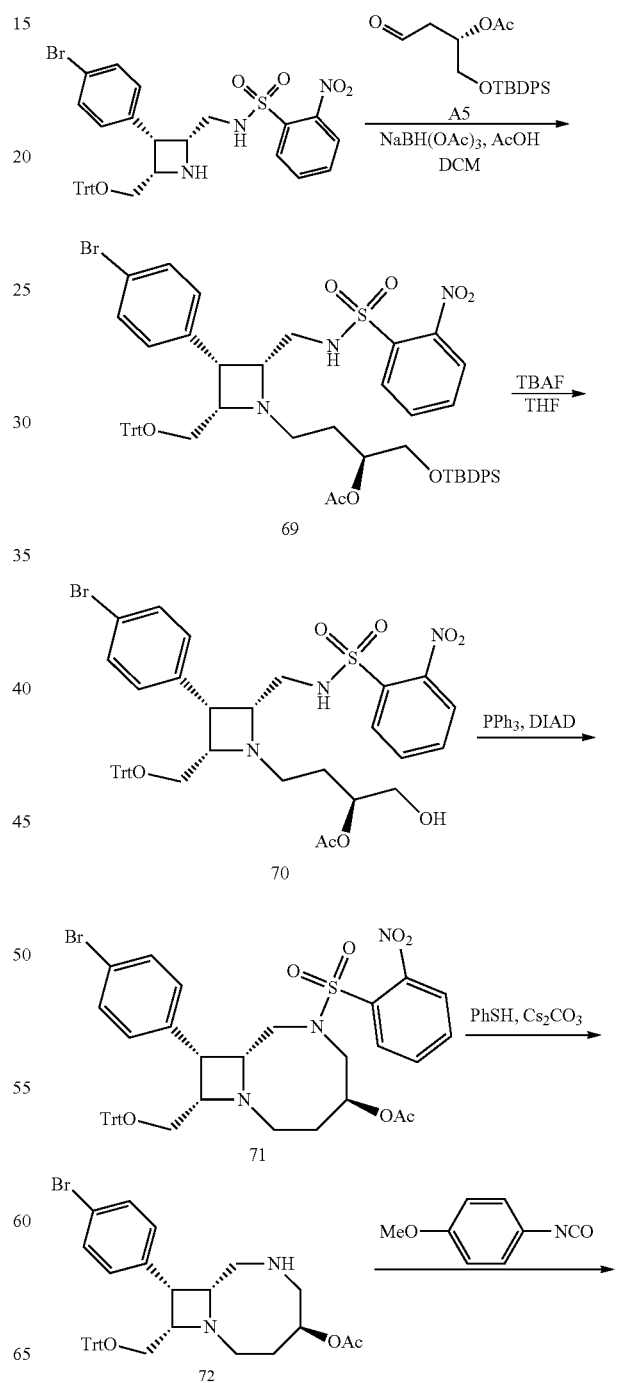

101
-continued

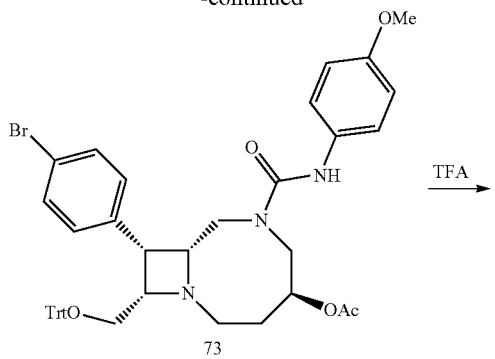
73

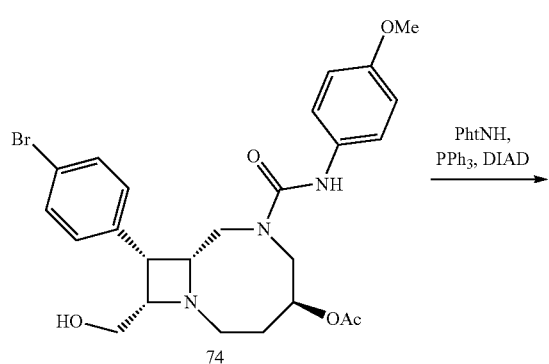
74

75

76

102
-continued

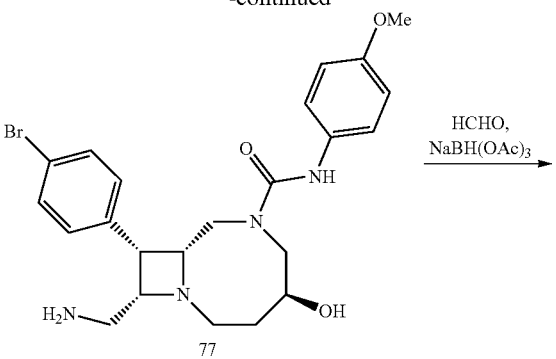
77

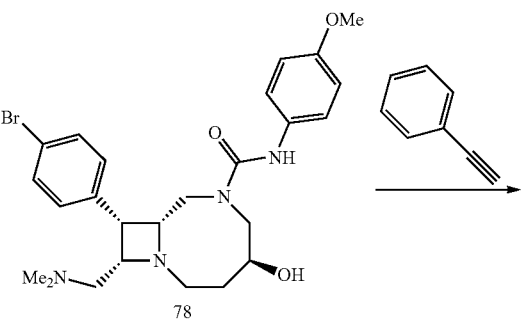
78

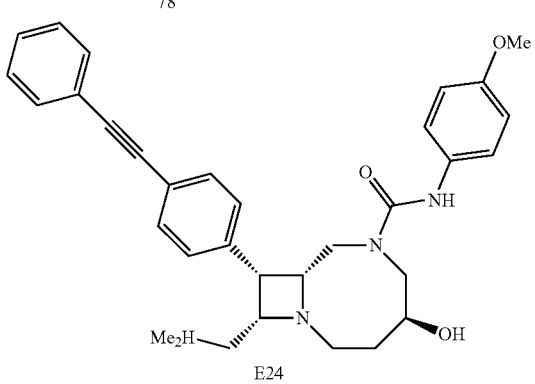
E24

Intermediate 69: [(1S)-3-[(2R,3R,4S)-3-(4-bromophenyl)-2-[[(2-nitrophenyl)sulfonylamino]methyl]-4-(trityloxymethyl)azetidin-1-yl]-1-[[tert-butyl(diphenyl)silyl]oxymethyl]propyl] acetate To a stirred solution of N-(((2R,3R,4S)-3-(4-bromophenyl)-4-((trityloxy)methyl)azetidin-2-yl)methyl)-2-nitrobenzenesulfonamide (WO2015070204) (1.20 g, 1.72 mmol, 1 eq) in DCM (12 mL) was added Intermediate A5 (1.46 g, 3.78 mmol, 2.2 eq) at 25° C. and CH₃COOH (103.29 mg, 1.72 mmol, 1 eq). The resulting reaction mixture was stirred at 25° C. for 0.5 h. To the mixture was added NaBH(OAc)₃ (1.09 g, 5.16 mmol, 3 eq). The resulting reaction mixture was stirred at 25° C. for 1.5 h. LCMS showed the reaction was complete, the reaction mixture was quenched by H₂O (5 mL) and extracted with DCM (10 mL*3) to give the organic layer. The layer was dried over anhydrous Na₂SO₄ and concentrated to give the residue. The residue was purified by column chromatography on silica gel (petroleum ether:ethyl acetate=1:1) to give Intermediate 69 (1.67 g, crude) as light brown solid.

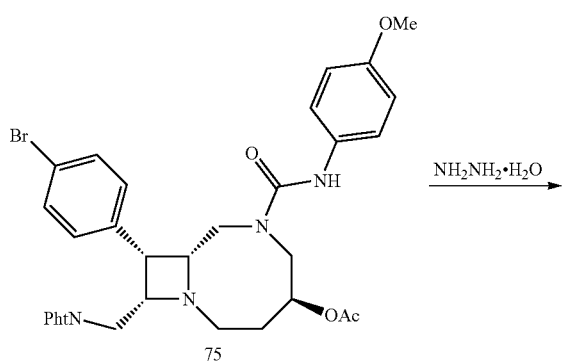

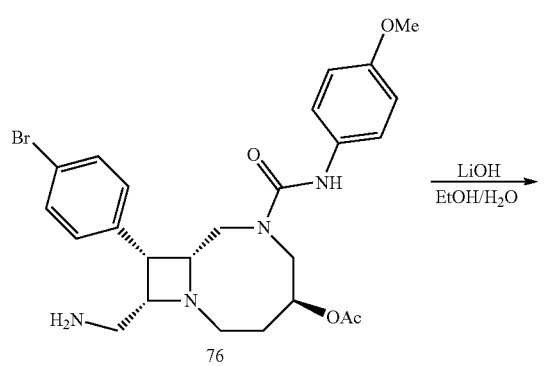

¹H NMR (400 MHz, CDCl₃-d1) δ5.15-5.11 (m, ¹H), 4.96-4.95 (m, 1H), 4.10-4.07 (m, 1H), 3.62-3.44 (m, 4H), 3.17-3.12 (m, 1H), 2.88-2.81 (m, 3H), 2.51-2.44 (m, 2H), 2.06-2.08 (m, 3H).

Intermediate 70: [(1S)-3-[(2R,3R,4S)-3-(4-bromophenyl)-2-[[(2-nitrophenyl)sulfonylamino]methyl]-4-(trityloxymethyl)azetidin-1-yl]-1-(hydroxymethyl)propyl] acetate To a stirred solution of Intermediate 69 (1.67 g, 1.56 mmol, 1 eq) in THF (16 mL) was TBAF (1.22 g, 4.68 mmol, 3 eq). The resulting reaction mixture was stirred at 25° C. for 12 h. LCMS showed the reaction was complete, the reaction mixture concentrated to give the residue. The residue was purified by column chromatography on silica gel (petroleum ether:ethyl acetate=1:1) to give Intermediate 70 (920.00 mg, 71.16% yield) as a white solid. ¹H NMR (400 MHz, CDCl₃-d1) δ 7.85-7.66 (m, 10), 7.26-6.97 (m, 20H), 5.02 (m, 1H), 4.85-4.82 (m, 1H), 4.05-3.76 (m, 1H), 3.70-3.52 (m, 3H), 3.12-2.86 (m, 3H), 2.03 (s, 5H), 1.52-1.46 (m, 2H).

Intermediate 71: [(4S,8R,9R,10S)-9-(4-bromophenyl)-6-(2-nitrophenyl)sulfonyl-10-(trityloxymethyl)-1,6-diazabicyclo[6.2.0]decan-4-yl] acetate To a stirred solution of Intermediate 70 (660.00 mg, 796.36 μmol, 1 eq) in THF (20 mL) was a mixture of PPh₃ (835.51 mg, 3.19 mmol, 4 eq) and DIAD (644.13 mg, 3.19 mmol, 619.35 μL, 4 eq). The resulting reaction mixture was stirred at 25° C. for 12 h. LCMS showed the reaction was complete, the reaction mixture was concentrated to give the residue. The residue was purified by prep-TLC (petroleum ether:ethyl acetate=1:1) to give Intermediate 71 (445.00 mg, crude) as a white solid. ¹H NMR (400 MHz, CDCl₃-d1) δ7.92-7.90 (m, 1H), 7.69-7.61 (m, 3H), 7.26-7.16 (m, 20H), 4.42-4.40 (m, 2H), 4.14-4.10 (m, 1H), 3.57 (s, 3H), 3.56-3.45 (m, 1H), 3.10-3.03 (m, 3H), 2.85-2.84 (m, 1H), 2.37-2.31 (m, 1H), 2.13-1.98 (m, 1H), 1.87-1.54 (m, 1H), 01.28-1.26 (m, 3H).

Intermediate 72: [(4S,8R,9R,10S)-9-(4-bromophenyl)-6-(2-nitrophenyl)sulfonyl-10-(trityloxymethyl)-1,6-diazabicyclo[6.2.0]decan-4-yl] acetate To a stirred solution of Intermediate 71 (660.00 mg, 796.36 μmol, 1 eq) in THF (20.00 mL) was a mixture of PPh₃ (835.51 mg, 3.19 mmol, 4 eq) and DIAD (644.13 mg, 3.19 mmol, 619.35 μL, 4 eq). The resulting reaction mixture was stirred at 25° C. for 12 h. LCMS showed the reaction was complete, the reaction mixture was concentrated to give the residue. The residue was purified by prep-TLC (petroleum ether:ethyl acetate=1:1) to give Intermediate 72 (445.00 mg, crude) as a white solid. ¹H NMR (400 MHz, CDCl₃-d1) δ7.26-7.22 (m, 25H), 4.01-4.00 (m, 1H), 3.83-3.81 (m, 1H), 3.62-3.47 (m, 1H), 3.51-3.47 (m, 1H), 3.49-3.48 (m, 1H), 3.21-3.11 (m, 1H), 2.92-2.88 (m, 1H), 2.49-2.47 (m, 2H), 2.05 (s, 3H), 1.85-1.084 (m, 1H), 1.60 (s, 3H).

Intermediate 73: [(4S,8R,9R,10S)-9-(4-bromophenyl)-6-[(4-methoxyphenyl)carbamoyl]-10-(trityloxymethyl)-1,6-diazabicyclo[6.2.0]decan-4-yl] acetate To a stirred solution of Intermediate 72 (154.00 mg, 246.17 μmol, 1 eq) and Et₃N (49.82 mg, 492.34 μmol, 68.25 μL, 2 eq) in DCM (2 mL) was 1-isocyanato-4-methoxybenzene (40.39 mg, 270.78 μmol, 34.82 μL, 1.1 eq). The resulting reaction mixture was stirred at 25° C. for 12 h. LCMS showed the reaction was complete, the reaction mixture was quenched by H₂O (2 mL) and extracted with DCM (10 mL*3) to give the organic layer. The layer was dried over anhydrous Na₂SO₄ and concentrated to give the residue. The residue was purified by prep-TLC (petroleum ether:ethyl acetate=1:1) to give Intermediate 73 (169 mg, 88.61% yield) as a white solid. ¹H NMR (400 MHz, CDCl₃-d1) δ7.33-7.23 (m, 20H), 6.83-6.82 (m, 2H), 4.59-4.57 (m, 1H), 4.30-4.27 (m, 1H), 3.78-3.75 (m, 4), 3.63-3.3.62 (m, 1H), 3.54-3.53 (m, 1H), 3.15-3.13 (m, 2H), 2.92-2.90 (m, 2H), 2.08-2.00 (m, 3H), 1.89-1.85 (s, 2H), 1.57 (m, 1H).

Intermediate 74: [(4S,8R,9R,10S)-9-(4-bromophenyl)-10-(hydroxymethyl)-6-[(4-methoxyphenyl)carbamoyl]-1,6-diazabicyclo[6.2.0]decan-4-yl] acetate To a stirred solution of Intermediate 73 (169.00 mg, 218.14 μmol, 1 eq) in DCM (2 mL) was TFA (248.72 mg, 2.18 mmol, 10 eq). The resulting reaction mixture was stirred at 25° C. for 12 h. LCMS showed the reaction was complete, the reaction mixture was quenched by NaHCO₃ and extracted with DCM (10 mL*3) to give the organic layer. The layer was dried over anhydrous Na₂SO₄ and concentrated to give the residue. The residue was purified by prep-TLC (petroleum ether:ethyl acetate=1:2) to give Intermediate 74 (81.00 mg, 152.13 μmol, 69.74% yield) as a white solid. HRMS (ESI): calcd for $C_{25}H_{30}BrN_3O_5$ [M+H]+ 532.14, found 534.1.

Intermediate 75: [(4S,8R,9S,10S)-9-(4-bromophenyl)-10-[(1,3-dioxoisoindolin-2-yl)methyl]-6-[(4-methoxyphenyl)carbamoyl]-1,6-diazabicyclo[6.2.0]decan-4-yl] acetate To a solution of Intermediate 74 (81.00 mg, 104.55 μmol, 1 eq), isoindoline-1,3-dione (16.92 mg, 115.01 μmol, 1.1 eq) and PPh₃ (41.13 mg, 156.82 μmol, 1.5 eq) in THF (2 mL) was added DIAD (31.71 mg, 156.82 μmol, 30.49 μL, 1.5 eq) dropwise at 25° C. under N₂. The resulting reaction mixture was stirred at 25° C. for 12 h. LCMS showed the reaction was complete, the reaction mixture was concentrated to give the residue. The residue was purified by pre-TLC (Petroleum ether:Ethyl acetate=1:1) to give Intermediate 75 (58.00 mg, 83.86% yield) as a yellow solid. ¹H NMR (400 MHz, CDCl₃-d1) δ7.83-7.81 (m, 2H), 7.73-7.71 (m, 2H), 7.51-7.49 (m, 4H), 7.25-7.23 (m, 2H), 6.89-6.84 (m, 2H), 6.56 (s, 1H), 4.59-4.55 (m, 1H), 4.28-4.27 (m, 1H), 3.82-3.78 (m, 4H), 3.58-3.55 (m, 3.50H), 3.50-3.25 (m, 2H), 2.99-2.98 (m, 1H), 2.37-2.12 (m, 1H), 2.08 (s, 5H).

Intermediate 76: (4S,8R,9S,10S)-10-(aminomethyl)-9-(4-bromophenyl)-6-((4-methoxyphenyl)carbamoyl)-1,6-diazabicyclo[6.2.0]decan-4-yl acetate To a solution of Intermediate 75 (58.00 mg, 87.67 μmol, 1 eq) in EtOH (1 mL) was added hydrazine hydrate (6.72 mg, 131.51 μmol, 6.52 μL, 98% purity, 1.5 eq) dropwise at 25° C. under N₂. The resulting reaction mixture was stirred at 70° C. for 1 h. LCMS showed the reaction was complete, the reaction mixture was concentrated to give the residue Intermediate 76 without further purification. HRMS (ESI): calcd for $C_{25}H_{31}BrN_4O_4$ [M+H]⁺ 531.15, found 531.1.

Intermediate 77: (4S,8R,9S,10S)-10-(aminomethyl)-9-(4-bromophenyl)-4-hydroxy-N-(4-methoxyphenyl)-1,6-diazabicyclo[6.2.0]decane-6-carboxamide To a solution of Intermediate 76 (46.00 mg, 86.56 µmol, 1 eq) in EtOH:H$_2$O=1:1 (1 mL) was added LiOH·H$_2$O (7.26 mg, 173.12 µmol, 2 eq) at 25° C. The resulting reaction mixture was stirred at 25° C. for 2 h. LCMS showed the reaction was complete, the reaction mixture was quenched by H$_2$O (2 mL) and extracted with DCM (10 mL*3) to give the organic layer. The layer was dried over anhydrous Na$_2$SO$_4$ and concentrated to give Intermediate 77 (80.00 mg, crude) as a white solid. HRMS (ESI): ET6538-397-P1P calcd for C$_{23}$H$_{29}$BrN$_4$O$_3$ [M+H]$^+$ 489.14, found 491.1.

Intermediate 78: (4S,8R,9S,10S)-9-(4-bromophenyl)-10-((dimethylamino)methyl)-4-hydroxy-N-(4-methoxyphenyl)-1,6-diazabicyclo[6.2.0]decane-6-carboxamide To a solution of Intermediate 77 (757.00 mg, 1.01 mmol, 1 eq), isoindoline-1,3-dione (164.07 mg, 1.12 mmol, 1.1 eq) and PPh$_3$ (398.85 mg, 1.52 mmol, 1.5 eq) in THF (2 mL) was added DIAD (307.49 mg, 1.52 mmol, 1.5 eq) dropwise at 25° C. under N$_2$. The resulting reaction mixture was stirred at 25° C. for 12 h. LCMS showed the reaction was complete, the reaction mixture was concentrated to give the residue. The residue was purified by pre-TLC (petroleum ether:ethyl acetate=1:1) to give Intermediate 78 (1.13 g, crude) as a yellow solid. $^1$H NMR (400 MHz, CDCl$_3$-d1) δ7.45-7.44 (m, 3H), 7.39-7.37 (m, 2H), 6.83-6.81 (m, 2H), 4.08-3.97 (m, 2H), 3.77-3.76 (m, 2H), 3.45-3.44 (m, 1H), 3.29-3.10 (m, 3H), 2.02 (s, 6H), 0.87 (s, 2H).

Synthesis of E24: (4S,8R,9S,10S)-10-[(dimethylamino)methyl]-4-hydroxy-N-(4-methoxyphenyl)-9-[4-(2-phenylethynyl)phenyl]-1,6-diazabicyclo[6.2.0]decane-6-carboxamide (E24)

To a solution of Intermediate 78 (40.00 mg, 77.30 µmol, 1 eq) and ethynylbenzene (23.68 mg, 231.90 µmol, 25.47 µL, 3.00 eq) in acetonitrile (1 mL) was added XPhos Pd G3 (6.54 mg, 7.73 µmol, 0.1 eq) and Cs$_2$CO$_3$ (50.37 mg, 154.60 µmol, 2 eq). The resulting reaction mixture was stirred at 70° C. for 2 h. LCMS showed the reaction was complete, the reaction mixture was concentrated to give the residue. The residue was purified by prep-HPLC (Column: Waters Xbridge Prep OBD C18 150*30 5u; A: water (0.225% formic acid) B: acetonitrile) to give (4S,8R,9S,10S)-10-[(dimethylamino)methyl]-4-hydroxy-N-(4-methoxyphenyl)-9-[4-(2-phenylethynyl)phenyl]-1,6-diazabicyclo[6.2.0]decane-6-carboxamide (6.10 mg, 14.65% yield) as a white solid. HRMS (ESI): calcd for C$_{33}$H$_{38}$N$_4$O$_3$ [M+H]$^+$ 539.29, found 539.4 $^1$H NMR (400 MHz, MeOD-d4) δ7.55-7.50 (m, 2H), 7.49-7.37 (m, 4H), 6.86-6.84 (m, 2H), 4.18-4.05 (m, 1H), 4.02-4.00 (m, 1H), 3.75 (s, 3H), 3.64-3.31 (m, 1H), 2.90-2.85 (m, 3H), 2.43 (s, 6H), 2.35-2.34 (m, 1H), 2.34-2.06 (m, 1H).

Example 25: (8R,9S,10S)-3,10-bis[(dimethylamino)methyl]-N-(4-methoxyphenyl)-9-[4-(2-phenylethynyl)phenyl]-1,6-diazabicyclo[6.2.0]decane-6-carboxamide ("E25")

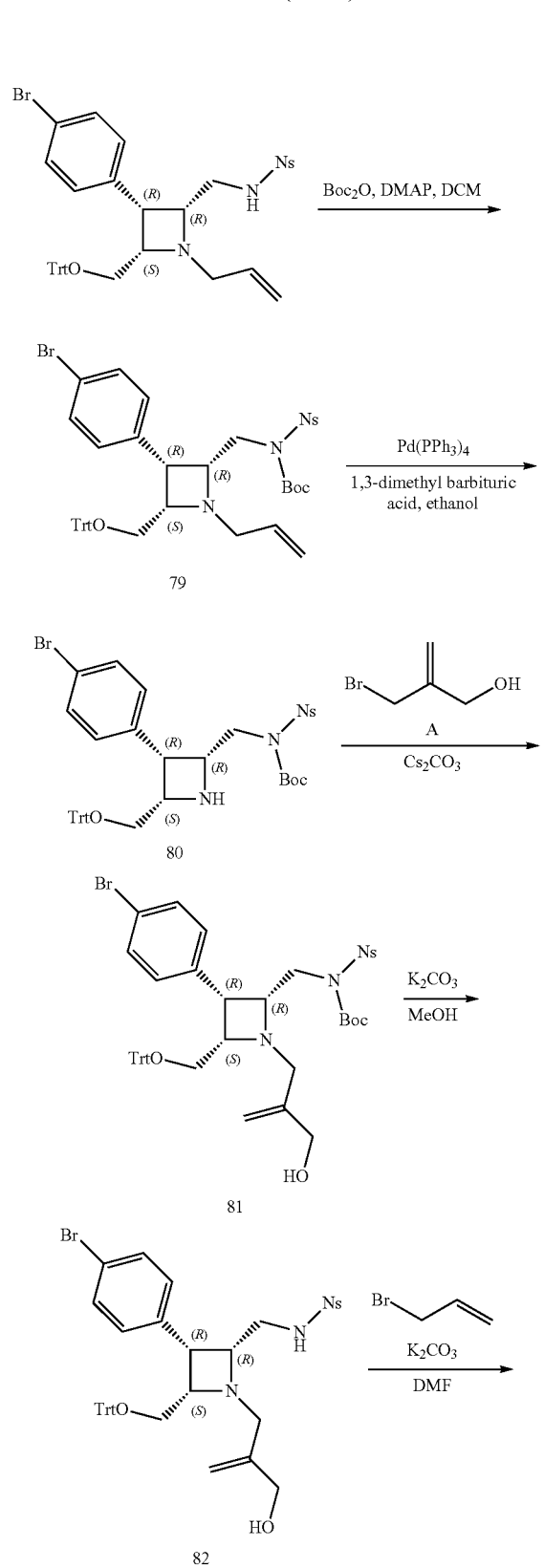

107
-continued
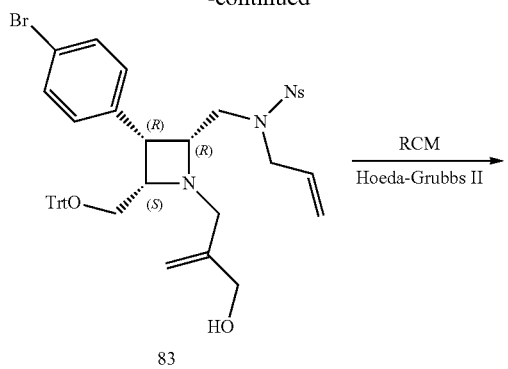
83
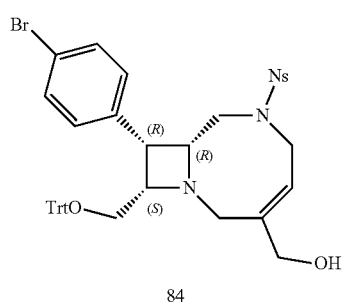
84
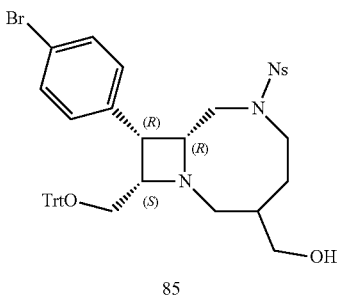
85
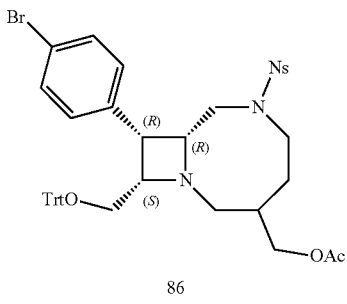
86
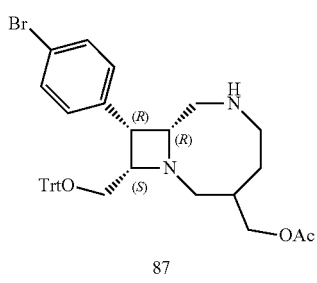
87
108
-continued
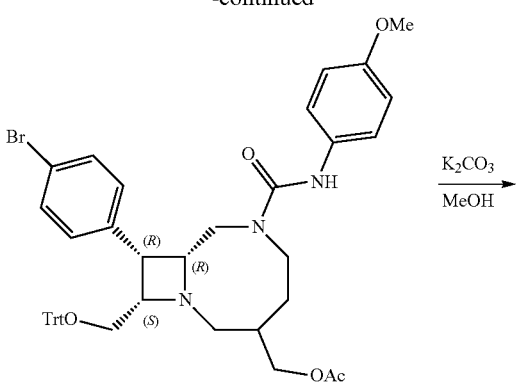
88
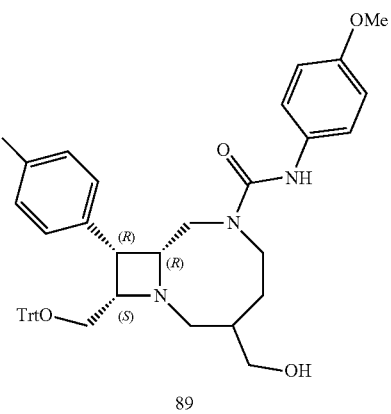
89
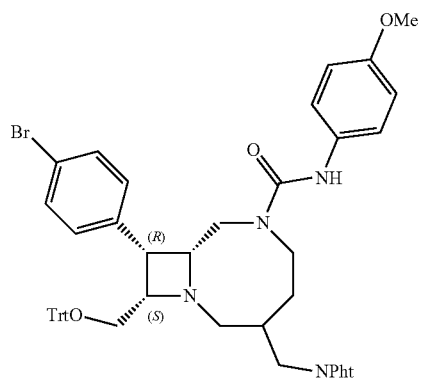
90
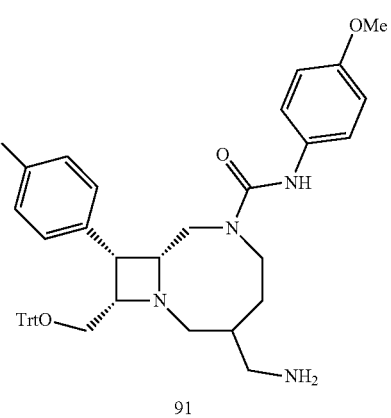
91

109
-continued

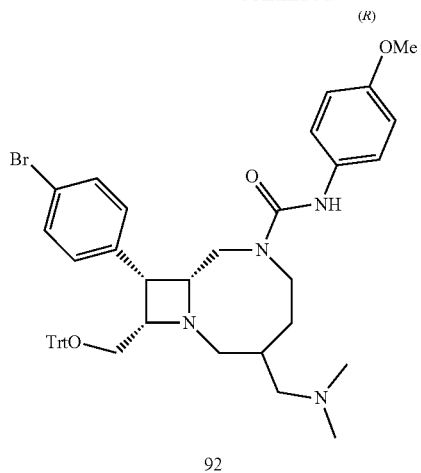

92

TFA/DCM →

110
-continued

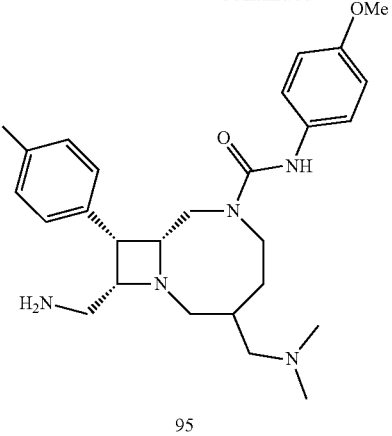

95

HCHO, NaBH(OAc)₃ →

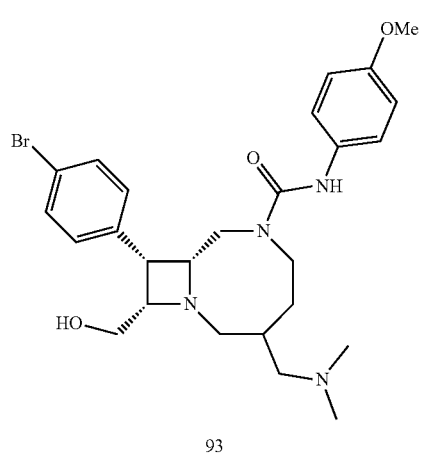

93

Mitsunobu →

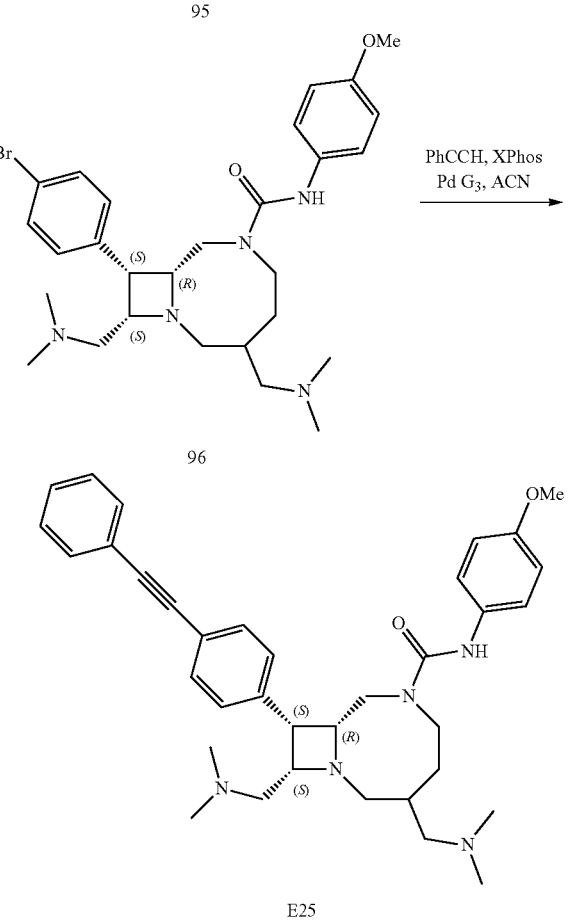

96

PhCCH, XPhos
Pd G₃, ACN →

E25

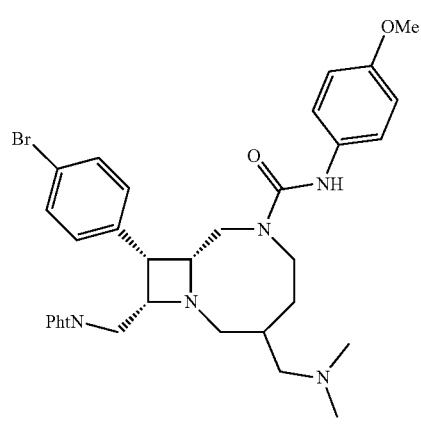

94

N₂H₄·H₂O
EtOH →

Intermediate 79: tert-butyl N-[[(2R,3R,4S)-1-allyl-3-(4-bromophenyl)-4-(trityloxymethyl)azetidin-2-yl]methyl]-N-(2-nitrophenyl)sulfonyl-carbamate To a solution of N-(((2R,3R,4S')-3-(4-bromophenyl)-4-((trityloxy)methyl)azetidin-2-yl)methyl)-2-nitrobenzenesulfonamide (WO2015070204) (8.50 g, 11.51 mmol, 1 eq), DMAP (140.58 mg, 1.15 mmol, 0.1 eq) and Et₃N (3.49 g, 34.52 mmol, 4.79 mL, 3 eq) in DCM (60 mL) was added BOC₂O (2.76 g, 12.66 mmol, 1.1 eq) and the reaction mixture was stirred at 25° C. for 4 h. TLC (petroleum ether:DCM=3:1) showed the reaction was complete, the reaction was quenched with H₂O (100 mL) and extracted with DCM (300 mL) to give the organic layer. The organic layer was dried over anhydrous Na₂SO₄ and concentrated to give the residue. The residue was purified by chromatography on silica gel (petroleum ether:ethyl acetate=3:1) to give Intermediate 79 (8.19 g, 84.83% yield) as a brown solid. ¹H NMR (400 MHz, CDCl₃-d1) δ8.20 (d, J=4.4 Hz, 1H), 7.70 (s, 3H), 7.35-7.32 (m, 5H), 7.19-7.13 (m, 10H), 7.11 (m, 7H), 5.73-5.63 (m, 1H), 5.09-5.05 (m, 1H), 4.90-4.87 (m, 1H), 3.95-3.91 (m, 1H), 3.65-3.64 (m, 3H), 3.54-3.49 (m, 1H), 3.09-3.04 (m, 1H), 2.85-2.81 (m, 1H), 2.56-2.53 (m, 1H), 3.06-3.05 (m, 1H), 2.94-2.89 (m, 1H).

Intermediate 80: tert-butyl N-[[(2R,3R,4S)-3-(4-bromophenyl)-4-(trityloxymethyl)azetidin-2-yl]methyl]-N-(2-nitrophenyl)sulfonyl-carbamate To a solution of Intermediate 79 (7.70 g, 9.18 mmol, 1 eq) in EtOH (10 mL) was added 1,3-dimethylhexahydropyrimidine-2,4,6-trione (2.15 g, 13.77 mmol, 1.5 eq) and Pd(PPh₃)₄ (1.06 g, 917.98 μmol, 0.1 eq) and the reaction mixture was stirred at 40° C. for 2 h. LCMS showed the reaction was complete, the reaction was quenched with 10% NaOH (20 mL) and extracted with DCM (500 mL) to give the organic layer. The organic layer was dried over anhydrous Na₂SO₄ and concentrated to give the residue. The residue was purified by column chromatography on silica gel (petroleum ether:ethyl acetate=3:1) to give Intermediate 80 (6.44 g, 8.06 mmol, 87.83% yield) as a light brown solid. ¹H NMR (400 MHz, CDCl₃-d1) δ8.24-8.22 (m, 1H), 7.72-7.65 (m, 3H), 7.33 (s, 4H), 7.22-7.19 (m, 16H), 7.42-7.34 (m, 2H), 3.95-3.89 (m, 1H), 3.06-3.04 (m, 1H), 3.02-2.95 (m, 1H), 2.05 (s, 1H), 1.03 (s, 9H).

Intermediate 81: tert-butyl N-[[(2R,3R,4S)-3-(4-bromophenyl)-1-[2-(hydroxymethyl)allyl]-4-(trityloxymethyl) azetidin-2-yl]methyl]-N-(2-nitrophenyl)sulfonyl-carbamate To a solution of Intermediate 80 (6.44 g, 8.06 mmol, 1 eq) and K₂CO₃ (3.34 g, 24.18 mmol, 3 eq) in DMF (60 mL) was added 2-(bromomethyl)prop-2-en-1-ol (1.83 g, 12.09 mmol, 1.5 eq) at 25° C. and the reaction mixture was stirred at 25° C. for 12 h. LCMS showed the reaction was complete, the reaction was quenched with H₂O (50 mL) and extracted with DCM (100 mL) to give the organic layer. The organic layer was dried over anhydrous Na₂SO₄ and concentrated to give the residue. The residue was purified by chromatography on silica gel (petroleum ether:ethyl acetate=2:1) to give Intermediate 81 (5.52 g, 78.83% yield) as a white solid. ¹H NMR (400 MHz, CDCl₃-d1) δ8.20 (d, J=4.8 Hz, 2H), 8.02 (s, 1H), 7.72-7.67 (m, 3H), 7.42-7.40 (m, 2H), 7.30-7.26 (m, 2H), 7.18-7.16 (m, 10H), 7.08-7.07 (m, 7H), 4.80 (s, 1H), 4.65 (s, 1H), 4.06-3.98 (m, 3H), 3.84 (m, 1H), 3.65-3.62 (m, 2H), 3.55-3.51 (m, 2H), 3.03-3.00 (m, 2H), 1.30 (s, 9H).

Intermediate 82: N-[[(2R,3R,4S)-3-(4-bromophenyl)-1-[2-(hydroxymethyl)allyl]-4-(trityloxymethyl)azetidin-2-yl]methyl]-2-nitro-benzenesulfonamide To a solution of Intermediate 81 (5.00 g, 5.75 mmol, 1 eq) in MeOH (50 mL) was added K₂CO₃ (3.97 g, 28.75 mmol, 5 eq) and the reaction mixture was stirred at 80° C. for 3 h. LCMS showed the reaction was complete, the reaction was quenched with H₂O (100 mL) and extracted with DCM (300 mL) to give the organic layer. The organic layer was dried over anhydrous Na₂SO₄ and concentrated to give the residue. The residue was purified by chromatography on silica gel (petroleum ether:ethyl acetate=1:1) to give Intermediate 82 (2.50 g, 3.25 mmol, 56.56% yield) as a white solid. ¹H NMR (400 MHz, CDCl₃-d1) δ 7.82-7.78 (m, 2H), 7.71-7.69 (m, 1H), 7.18-7.13 (m, 18H), 5.10 (s, 1H), 5.01-4.97 (m, 2H), 4.12-4.07 (m, 2H), 3.70-3.58 (m, 3H), 3.34-3.23 (m, 1H), 3.07-3.06 (m, 1H), 2.93-2.89 (m, 2H).

Intermediate 83: N-allyl-N-[[(2R,3R,4S)-3-(4-bromophenyl)-1-[2-(hydroxymethyl)allyl]-4-(trityloxymethyl)azetidin-2-yl]methyl]-2-nitro-benzenesulfonamide To a solution of Intermediate 82 (2.50 g, 3.25 mmol, 1 eq) in DMF (1.00 mL) was added 3-bromoprop-1-ene (590.18 mg, 4.88 mmol, 1.5 eq) and K₂CO₃ (1.35 g, 9.76 mmol, 3 eq) at 25° C. and the reaction mixture was stirred at 25° C. for 12 h. LCMS showed the reaction was complete, the reaction was quenched with H₂O (100 mL) and extracted with DCM (500 mL) to give the organic layer. The organic layer was dried over anhydrous Na₂SO₄ and concentrated to give the residue. The residue was purified by chromatography on silica gel (petroleum ether:ethyl acetate=1:1) to give Intermediate 83 (2.62 g, 99.68% yield) as a white solid. ¹H NMR (400 MHz, CDCl₃-d1) δ8.02 (s, 1H), 7.66-7.53 (m, 1H), 7.37-7.35 (m, 3H), 7.15-7.11 (m, 19H), 5.43-5.36 (m, 1H), 5.00-4.98 (m, 1H), 4.88 (s, 1H), 4.80-4.76 (m, 2H), 4.04- (s, 2H), 3.82-3.79 (m, 2H), 3.52-3.32 (m, 3H), 3.16 (m, 1H), 3.06-3.02 (m, 2H), 2.96-2.88 (m, 2H).

Intermediate 84: [(3E,8R,9R,10S)-9-(4-bromophenyl)-6-(2-nitrophenyl)sulfonyl-10-(trityloxymethyl)-1,6-diazabicyclo[6.2.0]dec-3-en-3-yl]methanol To a solution of Intermediate 83 (2.20 g, 2.72 mmol, 1 eq) in DCM (20 mL) was added [1,3-bis(2,4,6-trimethylphenyl)imidazolidin-2-ylidene]-dichloro-[(2-isopropoxyphenyl)methylene]ruthenium (Hoyveda-Grubbs 2$^{nd}$ Generation Catalyst) (426.12 mg, 680.04 μmol, 0.25 eq) and the reaction mixture was stirred at 40° C. for 12 h. LCMS showed the reaction was complete, the reaction was concentrated to give the residue. The residue was purified by column chromatography on silica (petroleum ether:ethyl acetate=1:1) to give Intermediate 84 (2.12 g, 100.00% yield) as a white solid. ¹H NMR (400 MHz, CDCl₃-d1) δ7.89-7.87 (m, 1H), 7.70-7.61 (m, 3H), 7.26-7.22 (m, 17H), 7.11-7.08 (m, 2H), 5.68-5.64 (m, 1H), 4.15-4.05 (m, 1H), 3.99-3.64 (m, 2H), 3.53-3.52 (m, 1H), 3.31-3.22 (m, 2H), 3.12-3.09 (m, 2H), 2.85-2.84 (m, 1H), 2.17 (s, 1H).

Intermediate 85: [(8R,9R,10S)-9-(4-bromophenyl)-6-(2-nitrophenyl)sulfonyl-10-(trityloxymethyl)-1,6-diazabicyclo[6.2.0]decan-3-yl]methanol To a solution of Intermediate 84 (750.00 mg, 960.65 μmol, 1 eq) and Et₃N (1.94 g, 19.21 mmol, 2.66 mL, 20 eq) in THF (15 mL) was added 2-nitrobenzenesulfonohydrazide (2.09 g, 9.61 mmol, 10 eq) and the reaction mixture was stirred at 40° C. for 12 h. LCMS showed the reaction was complete, the reaction was quenched with H₂O (3 mL) and extracted with DCM (10 mL*2) to give the organic layer. The organic layer was dried over anhydrous Na₂SO₄ and concentrated to give the residue. The residue was purified by column chromatography on silica gel (petroleum ether:ethyl acetate=1:1) to give Intermediate 85 (1.50 g, 100.00% yield) as a yellow solid. ¹H NMR (400 MHz, CDCl₃-d1) δ7.76-7.74 (d, J=5.6 Hz, 2H), 7.65-7.55 (m, 4H), 7.26-7.22 (m, 19H), 7.10-7.08 (d, J=8.4 Hz, 2H), 3.75-3.61 (m, 6H), 3.26-3.22 (m, 1H), 3.16-3.12 (m, 1H), 3.00-2.99 (m, 2H), 2.89-2.87 (m, 2H), 2.72-2.69 (m, 1H), 2.17 (s, 1H), 1.97-1.90 (m, 3H), 1.40-1.26 (m, 2H).

Intermediate 86: [(8R,9R,10S)-9-(4-bromophenyl)-6-(2-nitrophenyl)sulfonyl-10-(trityloxymethyl)-1,6-diazabicyclo[6.2.0]decan-3-yl]methyl acetate To a solution of Intermediate 85 (1.49 g, 1.90 mmol, 1 eq), Et$_3$N (576.78 mg, 5.70 mmol, 3 eq) and DMAP (23.21 mg, 190.00 µmol, 0.1 eq) in DCM (15 mL) at 0° C. was added acetic anhydride (387.94 mg, 3.80 mmol, 355.91 µL, 2 eq). The resulting reaction mixture was stirred at 25° C. for 3 h. LCMS showed the reaction was complete, the reaction mixture was quenched with H$_2$O (10 mL) and extracted with DCM (30 mL*2) to give the organic layer. The layer was dried over anhydrous Na$_2$SO$_4$ and concentrated to give the residue. The residue was purified by column chromatography on silica gel (petroleum ether:ethyl acetate=1:1) to give Intermediate 86 (1.51 g, 96.32% yield) as a white solid. $^1$H NMR (400 MHz, CDCl$_3$-d1) δ7.80-7.76 (m, 1H), 7.61-7.56 (m, 3H), 7.27-7.22 (m, 15H), 7.13-7.11 (d, J=8.4 Hz, 2H), 4.01-3.99 (m, 2H), 3.69-3.63 (m, 4H), 3.22-3.12 (m, 3H), 2.94-2.88 (m, 2H), 2.62-2.61 (m, 1H), 2.20-2.05 (m, 1H), 1.92 (s, 1H), 1.82 (s, 3H), 1.32-1.27 (m, 1H).

Intermediate 87: [(8R,9R,10S)-9-(4-bromophenyl)-10-(trityloxymethyl)-1,6-diazabicyclo[6.2.0]decan-3-yl]methyl acetate To a solution of Intermediate 86 (1.51 g, 1.83 mmol, 1. eq) and benzenethiol (302.57 mg, 2.75 mmol, 280.16 µL, 1.5 eq) in acetonitrile (15 mL) was added Cs$_2$CO$_3$ (1.19 g, 3.66 mmol, 2 eq) dropwise at 25° C. The resulting reaction mixture was stirred at 25° C. for 12 h. LCMS showed the reaction was complete, the reaction mixture was quenched with H$_2$O (10 mL) and extracted with DCM (20 mL*3) to give the organic layer. The organic was dried over anhydrous Na$_2$SO$_4$ and concentrated to give the residue. The residue was purified by column chromatography on silica gel (dichloromethane:methanol=10:1) to give Intermediate 87 (1.09 g, crude) as a white solid. HRMS (ESI): calcd for C$_{37}$H$_{39}$BrN$_2$O$_3$ [M+H]$^+$ 639.21, found 639.1.

Intermediate 88: [(8R,9R,10S)-9-(4-bromophenyl)-6-[(4-methoxyphenyl)carbamoyl]-10-(trityloxymethyl)-1,6-diazabicyclo[6.2.0]decan-3-yl]methyl acetate To a solution of Intermediate 87 and Et$_3$N (344.05 mg, 3.40 mmol, 2 eq) in DCM (10 mL) was added 1-isocyanato-4-methoxy-benzene (278.91 mg, 1.87 mmol, 1.1 eq) dropwise at 0° C. The resulting reaction mixture was stirred at 25° C. for 3 h. LCMS showed the reaction was complete, the reaction mixture was quenched with H$_2$O (20 mL) and extracted with DCM (50 mL*3) to give the organic layer. The layer was dried over anhydrous Na$_2$SO$_4$ and concentrated to give the residue. The residue was purified by column chromatography on silica gel (petroleum ether:ethyl acetate=1:1) to give Intermediate 87 (1.10 g, 81.76% yield) as a white solid. $^1$H NMR (400 MHz, CDCl$_3$-d1) δ7.30-7.23 (m, 20H), 6.84-6.82 (m, 2H), 6.09 (s, 1H), 4.07-4.03 (m, 1H), 3.79-3.78 (m, 3H), 3.72 (m, 1H), 3.62-3.55 (m, 3H), 3.19-3.17 (m, 1H), 3.00-2.94 (m, 2H), 2.55-2.54 (m, 1H), 2.52-2.50 (m, 1H), 2.00 (s, 1H), 1.87 (s, 3H), 1.86-1.77 (m, 1H).

Intermediate 89: (8R,9R,10S)-9-(4-bromophenyl)-3-(hydroxymethyl)-N-(4-methoxyphenyl)-10-(trityloxymethyl)-1,6-diazabicyclo[6.2.0]decane-6-carboxamide To a solution of Intermediate 88 (750.00 mg, 950.85 µmol, 1 eq) in MeOH (7 mL) was added K$_2$CO$_3$ (394.25 mg, 2.85 mmol, 3 eq). The resulting reaction mixture was stirred at 25° C. for 12 h. LCMS showed the reaction was complete, the reaction mixture was filtered to give the filtrate and concentrated to give the residue. The residue was purified by pre-TLC (petroleum ether:ethyl acetate=1:1) to give Intermediate 88 (757.00 mg, crude) as a white solid. $^1$H NMR (400 MHz, CDCl$_3$-d1) δ7.29-7.23 (m, 24H), 7.09-7.07 (m, 1H), 6.84-6.81 (m, 2H), 3.77 (s, 3H), 3.66-3.63 (m, 2H), 3.62 (m, 4H), 3.15-3.07 (m, 1H), 2.82-2.79 (m, 1H), 2.66-2.64 (m, 1H), 1.77 (s, 1H), 1.28-1.25 (s, 2H).

Intermediate 90: (8R,9R,10S)-9-(4-bromophenyl)-3-[(1,3-dioxoisoindolin-2-yl)methyl]-N-(4-methoxyphenyl)-10-(trityloxymethyl)-1,6-diazabicyclo[6.2.0]decane-6-carboxamide To a solution of Intermediate 89 (757.00 mg, 1.01 mmol, 1 eq), isoindoline-1,3-dione (164.07 mg, 1.12 mmol, 1.1 eq) and PPh$_3$ (398.85 mg, 1.52 mmol, 1.5 eq) in THF (2 mL) was added DIAD (307.49 mg, 1.52 mmol, 1.5 eq) dropwise at 25° C. under N$_2$. The resulting reaction mixture was stirred at 25° C. for 12 h. LCMS showed the reaction was complete, the reaction mixture was concentrated to give the residue. The residue was purified by pre-TLC (petroleum ether:ethyl acetate=1:1) to give Intermediate 90 (1.13 g, crude) as a yellow solid $^1$H NMR (400 MHz, CDCl$_3$-d1) δ7.70-7.68 (m, 3H), 7.68-7.65 (m, 8H), 7.49-7.47 (m, 3H), 7.22-7.17 (m, 3H), 6.74-6.72 (m, 2H), 5.99 (s, 1H), 3.84-3.77 (m, 2H), 3.75 (s, 3H), 3.64-3.60 (m, 4H), 3.54-3.50 (m, 3H), 3.16 (s, 1H), 3.05 (s, 1H), 2.94 (m, 1H), 2.64-2.62 (m, 1H), 1.88 (s, 1H).

Intermediate 91: (8R,9R,10S)-3-(aminomethyl)-9-(4-bromophenyl)-N-(4-methoxyphenyl)-10-(trityloxymethyl)-1,6-diazabicyclo[6.2.0]decane-6-carboxamide To a solution of Intermediate 90 (1.13 g, 1.29 mmol, 1 eq) in EtOH (2 mL) was added NH$_2$NH$_2$·H$_2$O (98.86 mg, 1.94 mmol, 98% purity, 1.5 eq) dropwise. The resulting reaction mixture was stirred at 70° C. for 1 h. LCMS showed the reaction was complete, the reaction mixture was quenched by H$_2$O (2 mL) and extracted with DCM (10 mL*3) to give the organic layer. The layer was dried over anhydrous Na$_2$SO$_4$ and concentrated to give the residue. The residue was purified by prep-TLC (dichloromethane:methanol=12:1) to give Intermediate 91 (586.00 mg, 60.91% yield) as a white solid. $^1$H NMR (400 MHz, CDCl$_3$-d1) δ7.21-7.14 (m, 20H), 7.12-7.09 (m, 3H), 6.81-6.78 (m, 2H), 3.76-3.70 (m, 5H), 3.59-3.51 (m, 5H), 3.17-3.14 (m, 1H), 3.00-2.99 (m, 1H), 2.77-2.72 (m, 1H), 2.68-2.46 (m, 3H), 1.91 (m, 2H), 1.69 (s, 1H), 1.63 (s, 1H).

Intermediate 92: (8R,9R,10S)-9-(4-bromophenyl)-3-[(dimethylamino)methyl]-N-(4-methoxyphenyl)-10-(trityloxymethyl)-1,6-diazabicyclo[6.2.0]decane-6-carboxamide To a stirred solution of Intermediate 91 (586.00 mg, 785.80 µmol, 1 eq) in DCM (6 mL) was added HCHO (637.77 mg, 7.86 mmol, 585.11 µL, 10 eq) and MgSO$_4$ (945.86 mg, 7.86 mmol, 10 eq). The resulting reaction mixture was stirred at 25° C. for 0.5 h. To the mixture was added CH$_3$COOH (47.19 mg, 785.80 µmol, 1 eq) and NaBH(OAc)$_3$ (832.71 mg, 3.93 mmol, 5 eq). The resulting reaction mixture was stirred at 25° C. for 1.5 h. LCMS showed the reaction was complete, the reaction mixture was quenched by H$_2$O (5 mL) and extract with DCM (20 mL*3) to give organic layer. The organic layer was dried over anhydrous Na$_2$SO$_4$ and concentrated to give the residue. The residue was purified by prep-TLC (dichloromethane:methanol=12:1) to give Intermediate 92 (370.00 mg, 60.85% yield) as light brown solid. $^1$H NMR (400 MHz, CDCl$_3$-d1) δ7.34-7.29 (m, 2H), 7.76-7.22 (m, 10H), 7.14-7.12 (m, 2H), 6.83 (s, 1H), 6.83-6.79 (m, 2H), 3.76-3.67 (m, 4H), 3.63-3.60 (m, 4H), 3.15-3.14 (m, 1H), 2.97-2.96 (m, 1H), 2.73-2.64 (m, 3H), 2.73-2.65 (m, 1H), 2.02-1.88 (m, 3H).

Intermediate 93: (8R,9R,10S)-9-(4-bromophenyl)-3-[(dimethylamino)methyl]-10-(hydroxymethyl)-N-(4-methoxyphenyl)-1,6-diazabicyclo[6.2.0]decane-6-carboxamide To a stirred solution of Intermediate 92 (370.00 mg, 478.16 µmol, 1 eq) in DCM (1 mL) was TFA (545.20 mg, 4.78 mmol, 10 eq). The resulting reaction mixture was stirred at 25° C. for 12 h. LCMS showed the reaction was complete, the reaction mixture was quenched by NaHCO$_3$ (5 mL) and extracted with DCM (10 mL*3) to give the organic layer. The layer was dried over anhydrous Na$_2$SO$_4$ and concentrated to give the residue. The residue was purified by prep-TLC (dichloromethane:methanol=8:1) to give (172.00 mg, 67.68% yield) as a light brown solid.
$^1$H NMR (400 MHz, CDCl$_3$-d1) δ7.44 (d, J=8.0 Hz, 2H), 7.35 (d, J=8.0 Hz, 2H), 7.28-7.25 (m, 3H), 6.84 (d, J=8.8 Hz, 2H), 3.78-3.73 (m, 4H), 3.70-3.61 (m, 1H), 3.60-3.56 (m, 4H), 3.51-3.39 (m, 1H), 3.23-3.14 (m, 1H), 2.89-2.63 (m, 1H), 2.29 (m, 6H), 2.17-2.12 (m, 1H), 1.89 (s, 2H), 1.64-1.61 (m, 1H).

Intermediate 94: (8R,9S,10S)-9-(4-bromophenyl)-3-[(dimethylamino)methyl]-10-[(1,3-dioxoisoindolin-2-yl)methyl]-N-(4-methoxyphenyl)-1,6-diazabicyclo[6.2.0]decane-6-carboxamide To a solution of Intermediate 93 (172.00 mg, 323.62 µmol, 1 eq), isoindoline-1,3-dione (52.38 mg, 355.98 µmol, 1.1 eq) and PPh$_3$ (127.32 mg, 485.43 µmol, 1.5 eq) in THF (2 mL) was added DIAD (98.16 mg, 485.43 µmol, 1.5 eq) dropwise at 25° C. under N$_2$. The resulting reaction mixture was stirred at 25° C. for 12 h. LCMS showed the reaction was complete, the reaction mixture was concentrated to give the residue. The residue was purified by pre-TLC (dichloromethane:methanol=10:1) to give Intermediate 94 (152.00 mg, 71.10% yield) as a yellow solid. $^1$H NMR (400 MHz, CDCl$_3$-d1) δ7.81 (d, J=4.8 Hz, 2H), 7.70 (d, J=4.8 Hz, 2H), 7.51 (d, J=8.4 Hz, 2H), 7.44 (d, J=8.4 Hz, 2H), 7.26-7.23 (m, 3H), 6.82 (d, J=8.8 Hz, 2H), 3.92-3.89 (m, 1H), 3.76 (s, 3H), 3.70-3.68 (m, 2H), 3.66-3.64 (m, 2H), 3.57-3.53 (m, 4H), 2.79 (m, 1H), 2.67-2.61 (m, 1H), 2.39-2.38 (m, 1H), 2.36 (m, 3H), 2.16-1.99 (m, 1H), 1.26 (s, 1H).

Intermediate 95: (8R,9S,10S)-10-(aminomethyl)-9-(4-bromophenyl)-3-[(dimethylamino)methyl]-N-(4-methoxyphenyl)-1,6-diazabicyclo[6.2.0]decane-6-carboxamide To a solution of Intermediate 94 (152.00 mg, 230.09 µmol, 1 eq) in EtOH (2 mL) was added NH$_2$NH$_2$·H$_2$O (17.63 mg, 345.14 µmol, 17.12 µL, 98% purity, 1.5 eq) dropwise. The resulting reaction mixture was stirred at 70° C. for 1 h. LCMS showed the reaction was complete, the reaction mixture was quenched by H$_2$O (2 mL) and extracted with DCM (10 mL*3) to give the organic layer. The layer was dried over anhydrous Na$_2$SO$_4$ and concentrated to give the residue. The residue was purified by prep-TLC (dichloromethane:methanol=5:1) to give Intermediate 95 (80.00 mg, 65.54% yield) as a white solid. HRMS (ESI): calcd for C$_{26}$H$_{36}$BrN$_5$O$_2$ [M+H]$^+$ 530.21, found 530.1.

Intermediate 96: (8R,9S,10S)-9-(4-bromophenyl)-3,10-bis[(dimethylamino)methyl]-N-(4-methoxyphenyl)-1,6-diazabicyclo[6.2.0]decane-6-carboxamide To a stirred solution of Intermediate 95 (120.00 mg, 226.20 µmol, 1 eq) in DCM (2 mL) was added HCHO (183.43 mg, 2.26 mmol, 168.28 µL, 10 eq) and MgSO$_4$ (272.28 mg, 2.26 mmol, 10 eq). The resulting reaction mixture was stirred at 25° C. for 0.5 h. To the mixture was added CH$_3$COOH (13.58 mg, 226.20 µmol, 1 eq) and NaBH(OAc)$_3$ (239.71 mg, 1.13 mmol, 5 eq). The resulting reaction mixture was stirred at 25° C. for 1.5 h. LCMS showed the reaction was complete, the reaction mixture was quenched by H$_2$O (5 mL) and extract with DCM (20 mL*3) to give organic layer. The organic layer was dried over anhydrous Na$_2$SO$_4$ and concentrated to give the residue. The residue was purified by prep-TLC (dichloromethane:methanol=2:1) to give (100.00 mg, 79.15% yield) as a white solid. $^1$H NMR (400 MHz, CDCl$_3$-d1) δ7.46 (d, J=8.4 Hz, 2H), 7.32 (d, J=8.4 Hz, 2H), 7.25 (d, J=12.8 Hz, 2H), 6.83 (d, J=8.4 Hz, 2H), 6.12 (s, 1H), 3.77 (s, 3H), 3.61-3.59 (m, 2H), 3.57-3.55 (m, 2H), 3.41-3.39 (m, 2H), 2.78-2.75 (m, 1H), 2.42-2.38 (m, 1H), 2.28-2.26 (m, 2H), 2.16 (s, 6H), 2.00 (m, 1H), 1.76 (m, 1H).

Synthesis of E25: (8R,9S,10S)-3,10-bis[(dimethylamino)methyl]-N-(4-methoxyphenyl)-9-[4-(2-phenylethynyl)phenyl]-1,6-diazabicyclo[6.2.0]decane-6-carboxamide (E25)

To a solution of Intermediate 96 (50.00 mg, 89.52 µmol, 1 eq) and ethynylbenzene (27.43 mg, 268.55 µmol, 29.49 µL, 3 eq) in acetonitrile (1 mL) was added XPhos Pd G3 (7.58 mg, 8.95 µmol, 0.1 eq) and Cs$_2$CO$_3$ (58.33 mg, 179.04 µmol, 2 eq). The resulting reaction mixture was stirred at 70° C. for 2 h. LCMS showed the reaction was complete, the reaction mixture was quenched by H$_2$O (5 mL) and extracted with DCM (10 mL*3) to give the organic layer. The layer was dried over anhydrous Na$_2$SO$_4$ and concentrated to give the residue. The residue was purified by prep-HPLC (Column: Waters Xbridge Prep OBD C18 150*30 5u; A: water (0.225% formic acid) B: acetonitrile) to give Example 25 (10.00 mg, 17.25 µmol, 19.27% yield) as a white solid. HRMS (ESI): calcd for C$_{36}$H$_{45}$N$_5$O$_2$ [M+H]+ 580.36, found 580.5 $^1$H NMR (400 MHz, MeOD-d4) δ7.56-7.51 (m, 6H), 7.38-7.37 (m, 2H), 7.37 (d, J=13.2 Hz, 2H), 6.85 (d, J=8.8 Hz, 2H), 4.02-3.98 (m, 2H), 3.853-3.82 (m, 2H), 3.75 (s, 3H), 3.54-3.51 (m, 1H), 2.99-2.91 (m, 3H), 2.87 (m, 1H), 2.71 (s, 6H), 2.44 (s, 6H), 2.02 (m, 2H), 1.84-1.81 (m, 1H).

Example 26: (8R,9S,10S)-10-[(dimethylamino)methyl]-3-(hydroxymethyl)-N-(4-methoxyphenyl)-9-[4-(2-phenylethynyl)phenyl]-1,6-diazabicyclo[6.2.0]decane-6-carboxamide ("E26")
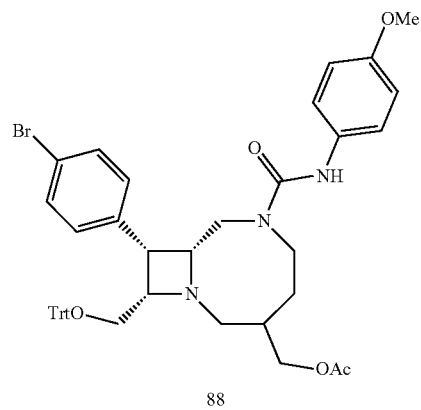
88
TFA / DCM →
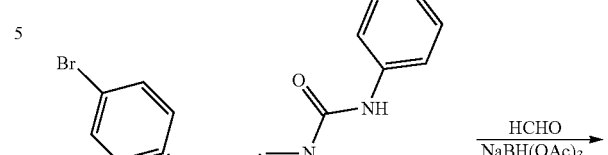
98
HCHO / NaBH(OAc)₃ →
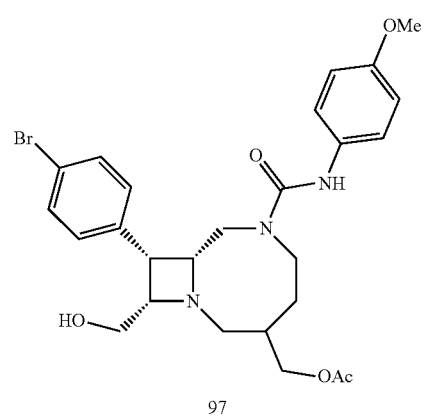
97
PPh₃, DIAD / Pth →
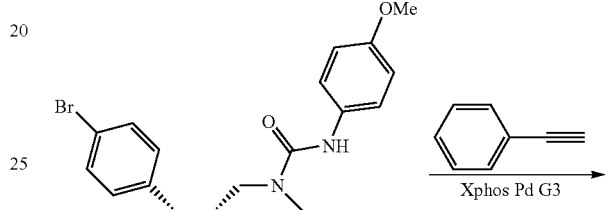
100
PhC≡CH / Xphos Pd G3 →
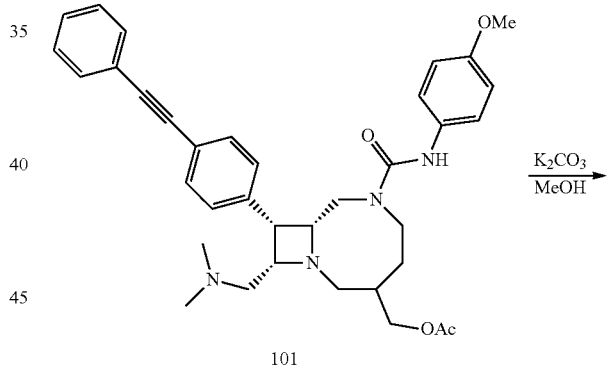
101
K₂CO₃ / MeOH →
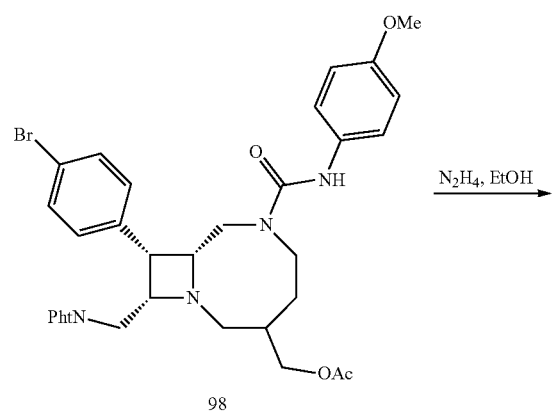
98
N₂H₄, EtOH →
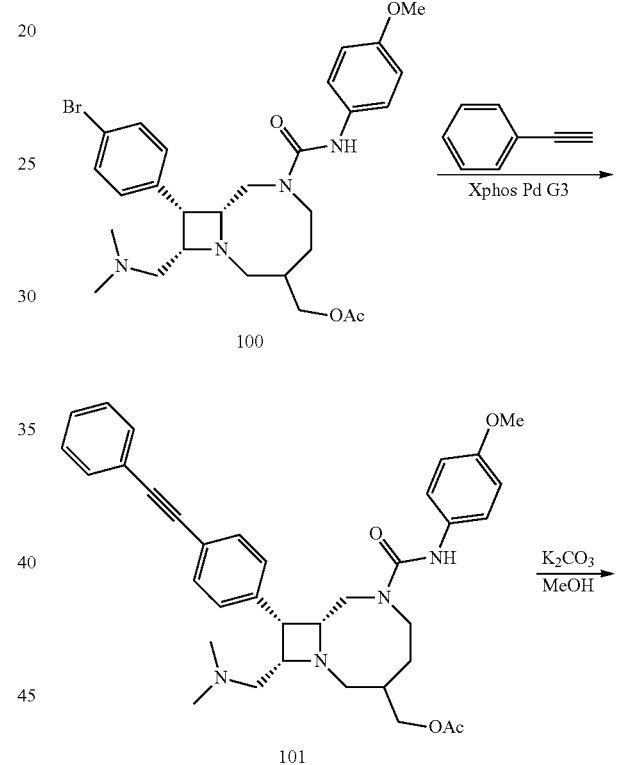
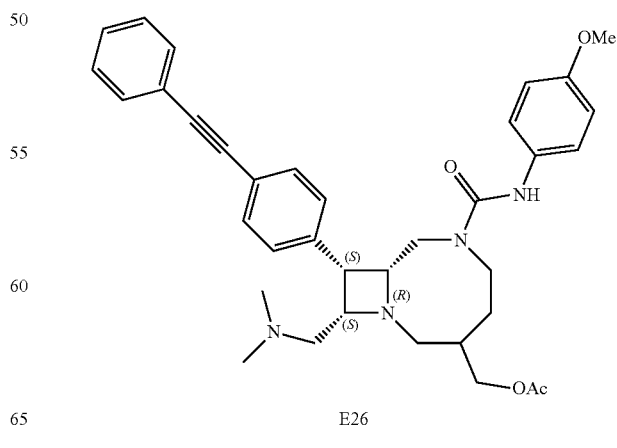
E26

Intermediate 97: [(8R,9R,10S)-9-(4-bromophenyl)-10-(hydroxymethyl)-6-[(4-methoxyphenyl)carbamoyl]-1,6-diazabicyclo[6.2.0]decan-3-yl]methyl acetate To a stirred solution of Intermediate 88 (180.00 mg, 228.20 µmol, 1 eq) in DCM (3.6 mL) was TFA (2.28 mmol, 168.96 µL, 10 eq). The resulting reaction mixture was stirred at 25° C. for 12 h. LCMS showed the reaction was complete, the reaction mixture was quenched with saturated NaHCO$_3$ (10 mL) and extracted with DCM (50 mL*3) to give organic layer and the layer was concentrated to give the residue. The residue was purified by prep-TLC (dichloromethane:methanol=12:1) to give Intermediate 97 (300.00 mg, crude) as a white solid. $^1$H NMR (400 MHz, CDCl$_3$-d1) δ7.47-7.45 (m, 1H), 7.38-7.32 (m, 2H), 7.26-7.22 (m, 3H), 6.84-6.82 (d, J=8.8 Hz, 2H), 6.08 (s, 1H), 4.24-4.20 (m, 1H), 4.11-4.07 (m, 1H), 3.80-3.77 (m, 4H), 3.65 (s, 4H), 3.55-3.54 (m, 2H), 3.48-3.43 (m, 1H), 2.97 (s, 1H), 2.83 (s, 1H), 2.08-2.03 (m, 4H), 1.96-1.94 (m, 1H), 1.86-1.84 (m, 1H).

Intermediate 98: [(8R,9S,10S)-9-(4-bromophenyl)-10-[(1,3-dioxoisoindolin-2-yl)methyl]-6-[(4-methoxyphenyl)carbamoyl]-1,6-diazabicyclo[6.2.0]decan-3-yl]methyl acetate To a solution of Intermediate 97 (300.00 mg, 549.00 µmol, 1 eq), isoindoline-1,3-dione (88.85 mg, 603.90 µmol, 1.1 eq) and PPh$_3$ (216.00 mg, 823.50 µmol, 1.5 eq) in THF (2 mL) was added DIAD (166.52 mg, 823.50 µmol, 1.5 eq) dropwise at 25° C. The resulting reaction mixture was stirred at 25° C. for 12 h. LCMS showed the reaction was complete, the reaction mixture was concentrated to give the residue. The residue was purified by pre-TLC (petroleum ether:ethyl acetate=1:1) to give Intermediate 98 (458.00 mg, crude) as a yellow solid. $^1$H NMR (400 MHz, CDCl$_3$-d1) δ7.80-7.70 (m, 2H), 7.68-7.65 (m, 12H), 7.49-7.46 ((m, 19H), 7.46-7.44 (m, 3H), 6.85-6.80 (m, 3H), 6.06 (s, 1H), 4.12-4.06 (m, 2H), 3.84-3.77 (m, 1H), 3.67-3.65 (m, 4H), 3.59-3.55 (m, 5H), 2.87-2.83 (m, 2H), 2.46-2.42 (m, 1H), 1.98 (s, 3H), 1.30-1.26 (m, 3H).

Intermediate 99: [(8R,9S,10S)-10-(aminomethyl)-9-(4-bromophenyl)-6-[(4-methoxyphenyl)carbamoyl]-1,6-diazabicyclo[6.2.0]decan-3-yl]methyl acetate To a solution of Intermediate 98 (458.00 mg, 677.95 µmol, 1 eq) in EtOH (2 mL) was added NH$_2$NH$_2$·H$_2$O (51.95 mg, 1.02 mmol, 98% purity, 1.5 eq) dropwise. The resulting reaction mixture was stirred at 70° C. for 1 h. LCMS showed the reaction was complete, the reaction mixture was quenched by H$_2$O (2 mL) and extracted with DCM (10 mL*3) to give the organic layer. The layer was dried over anhydrous Na$_2$SO$_4$ and concentrated to give the residue. The residue was purified by prep-TLC (dichloromethane:methanol=12:1) to give Intermediate 99 (180.00 mg, 48.67% yield) as a white solid. $^1$H NMR (400 MHz, CDCl$_3$-d1) δ7.47-7.45 (m, 3H), 7.38-7.34 (m, 2H), 7.24-7.22 (m, 2H), 6.84-6.81 (m, 2H), 6.07 (s, 1H), 4.20-4.18 (m, 1H), 4.10-4.09 (m, 1H), 3.77-3.62 (m, 5H), 3.60-3.57 (m, 3H), 3.45-3.33 (m, 2H), 3.35-3.32 (m, 2H), 2.95-2.92 (m, 1H), 2.77-2.76 (m, 2H), 2.55-2.54 (m, 1H), 2.03 (s, 3H), 1.94-1.74 (m, 2H), 1.27-1.24 (m, 2H).

Intermediate 100: [(8R,9S,10S)-9-(4-bromophenyl)-10-[(dimethylamino)methyl]-6-[(4-methoxyphenyl)carbamoyl]-1,6-diazabicyclo[6.2.0]decan-3-yl] methyl acetate To a stirred solution of Intermediate 99 (180.00 mg, 329.99 µmol, 1 eq) in DCM (2 mL) was added HCHO (267.83 mg, 3.30 mmol, 245.71 µL, 10 eq) and MgSO$_4$ (397.21 mg, 3.30 mmol, 10 eq). The resulting reaction mixture was stirred at 25° C. for 0.5 h. To the mixture was added CH$_3$COOH (19.82 mg, 329.99 µmol, 1 eq) and NaBH(OAc)$_3$ (349.69 mg, 1.65 mmol, 5 eq). The resulting reaction mixture was stirred at 25° C. for 1.5 h. LCMS showed the reaction was complete, the reaction mixture was quenched by H$_2$O (5 mL) and extract with DCM (20 mL*3) to give organic layer. The organic layer was dried over anhydrous Na$_2$SO$_4$ and concentrated to give the residue. The residue was purified by prep-TLC (dichloromethane:methanol=12:1) to give Intermediate 100 (134.00 mg, 70.80% yield) as a white solid. $^1$H NMR (400 MHz, CDCl$_3$-d1) δ7.49-7.47 (m, 2H), 7.35-7.26 (m, 2H), 7.24-7.22 (m, 2H), 6.84-6.81 (m, 2H), 6.08 (s, 1H), 4.23-4.19 (m, 1H), 3.77 (s, 4H), 3.73-3.58 (m, 4H), 3.60-3.58 (m, 1H), 2.98-2.93 (m, 1H), 2.95-2.93 (m, 1H), 2.76 (m, 2H), 2.56-2.51 (m, 2H), 2.05 (s, 6H), 1.92-1.88 (m, 2H).

Intermediate 101: [(8R,9S,10S)-10-[(dimethylamino)methyl]-6-[(4-methoxyphenyl)carbamoyl]-9-[4-(2-phenylethynyl)phenyl]-1,6-diazabicyclo[6.2.0]decan-3-yl]methyl acetate To a solution of Intermediate 100 (60.00 mg, 104.62 µmol, 1 eq) and ethynylbenzene (32.05 mg, 313.85 µmol, 34.47 µL, 3 eq) in acetonitrile (1 mL) was added XPhos Pd G3 (8.86 mg, 10.46 µmol, 0.1 eq) and Cs$_2$CO$_3$ (68.17 mg, 209.23 µmol, 2 eq). The resulting reaction mixture was stirred at 70° C. for 2 h. LCMS showed the reaction was complete, the reaction mixture was concentrated to give the residue. The residue was purified by pre-TLC (dichloromethane:methanol=7:1) to the give Intermediate 101 (42.00 mg, 67.50% yield) as a brown solid. HRMS (ESI): calcd for C$_{36}$H$_{42}$N$_4$O$_4$ [M+H]$^+$ 595.32, found 565.2 Synthesis of E26: (8R,9S,10S)-10-[(dimethylamino)methyl]-3-(hydroxymethyl)-N-(4-methoxyphenyl)-9-[4-(2-phenylethynyl)phenyl]-1,6-diazabicyclo[6.2.0]decane-6-carboxamide (E26)

To a solution of Intermediate 101 (42.00 mg, 70.62 µmol, 1 eq) in MeOH (2 mL) was added K$_2$CO$_3$ (29.28 mg, 211.86 µmol, 3 eq). The resulting reaction mixture was stirred at 25° C. for 12 h. LCMS showed the reaction was complete, the reaction mixture was quenched by H$_2$O (5 mL) and extracted with DCM (10 mL*3) to give the organic layer. The layer was dried over anhydrous Na$_2$SO$_4$ and concentrated to give the residue. The residue was purified by prep-HPLC (Column: Waters Xbridge Prep OBD C18 150*30 5u; A: water (0.225% formic acid) B: acetonitrile) to give compound E26 (10.80 mg, 27.67% yield) as a white solid. HRMS (ESI): calcd for C$_{34}$H$_{40}$N$_4$O$_3$ [M+H]$^+$ 553.31, found 553.4 $^1$H NMR (400 MHz, MeOD-d4) δ7.57-7.51 (m, 6H), 7.39-7.38 (m, 3H), 6.85-6.83 (m, 2H), 3.91-3.82 (m, 1H), 3.76-3.71 (m, 1H), 3.71-3.69 (m, 4H), 3.76 (m, 1H), 3.03-2.94 (m, 3H), 2.59-2.47 (m, 4H), 1.95-1.92 (m, 1H), 1.91-1.82 (m, 2H).

Example 27: (8R,9R,10S)-3-[(dimethylamino)methyl]-10-(hydroxymethyl)-N-(4-methoxyphenyl)-9-[4-(2-phenylethynyl)phenyl]-1,6-diazabicyclo[6.2.0]decane-6-carboxamide ("E27")

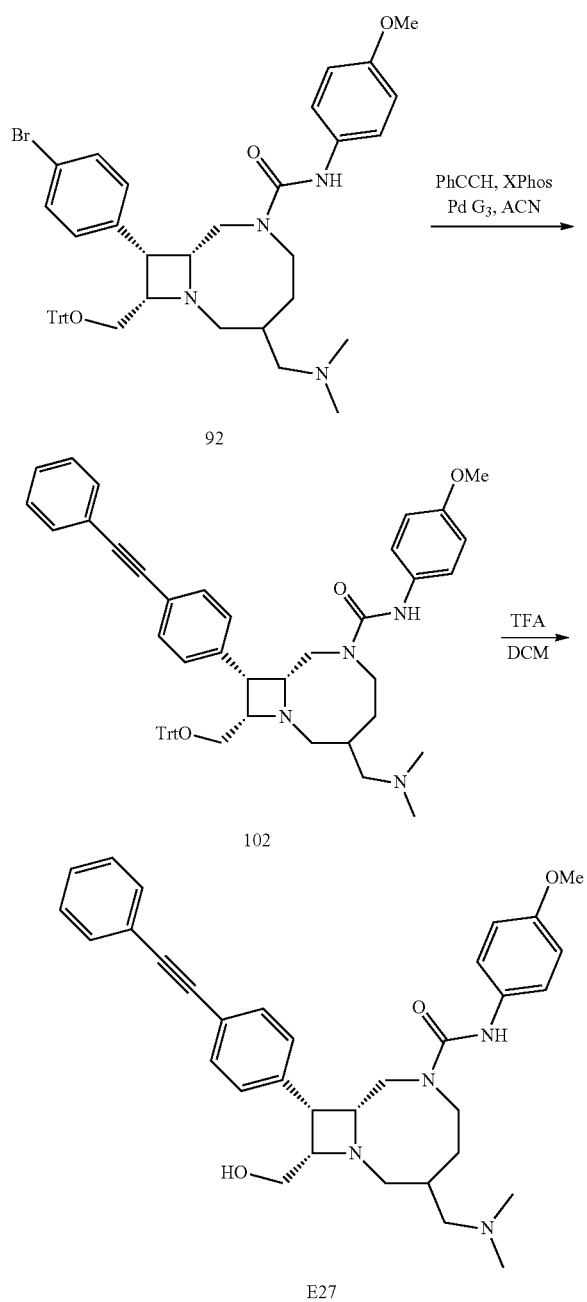

Intermediate 102: (8R,9R,10S)-3-[(dimethylamino)methyl]-N-(4-methoxyphenyl)-9-[4-(2-phenylethynyl)phenyl]-10-(trityloxymethyl)-1,6-diazabicyclo[6.2.0]decane-6-carboxamide To a solution of Intermediate 92 (30.00 mg, 38.77 µmol, 1 eq) and ethynylbenzene (11.88 mg, 116.31 µmol, 12.77 µL, 3 eq) in acetonitrile (1 mL) was added XPhos Pd G3 (3.28 mg, 3.88 µmol, 0.1 eq) and $Cs_2CO_3$ (25.26 mg, 77.54 µmol, 2 eq). The resulting reaction mixture was stirred at 70° C. for 2 h. LCMS showed the reaction was complete, the reaction mixture was concentrated to give the residue. The residue was purified by pre-TLC (dichloromethane:methanol=7:1) to the give Intermediate 102 (50.00 mg, crude) as a brown solid. HRMS (ESI): calcd for $C_{53}H_{54}N_4O_3$ $[M+H]^+$ 795.42, found 795.4.

Synthesis of E27: (8R,9R,10S)-3-[(dimethylamino)methyl]-10-(hydroxymethyl)-N-(4-methoxyphenyl)-9-[4-(2-phenylethynyl)phenyl]-1,6-diazabicyclo[6.2.0]decane-6-carboxamide (E27)

To a stirred solution of Intermediate 102 (50.00 mg, 62.89 µmol, 1 eq) in DCM (1 mL) was added TFA (71.71 mg, 628.91 µmol, 46.56 µL, 10.00 eq). The resulting reaction mixture was stirred at 25° C. for 12 h. LCMS showed the reaction was complete, the reaction mixture was quenched by $NaHCO_3$ (5 mL) and extracted with DCM (10 mL*3) to give the organic layer. The layer was dried over anhydrous $Na_2SO_4$ and concentrated to give the residue. The residue was purified by prep-HPLC (Column: Waters Xbridge Prep OBD C18 150*30 5u; A: water (0.225% formic acid) B: acetonitrile) to give compound E27 (4.70 mg, 13.52% yield) as a white solid. HRMS (ESI): calcd for $C_{33}H_{37}N_4O_2$ $[M+H]^+$ 553.29, found 553.4.

$^1$H NMR (400 MHz, MeOD-d4) δ7.544-7.51 (m, 6H), 7.39-7.37 (m, 3H), 7.34-7.22 (m, 2H), 6.86-6.81 (m, 2H), 4.02-3.99 (m, 1H), 3.76-3.72 (m, 4H), 3.70-3.66 (m, 1H), 3.41-3.40 (m, 1H), 3.38-3.35 (m, 1H), 3.12 (m, 1H), 2.85-2.75 (m, 1H), 2.16-2.09 (m, 2H), 1.81-1.77 (m, 1H).

Example 28: (3R,8R,9R,10S)-3-(dimethylamino)-10-(hydroxymethyl)-N-(4-methoxyphenyl)-9-[4-(2-phenylethynyl)phenyl]-1,6-diazabicyclo[6.2.0]decane-6-carboxamide ("E28")

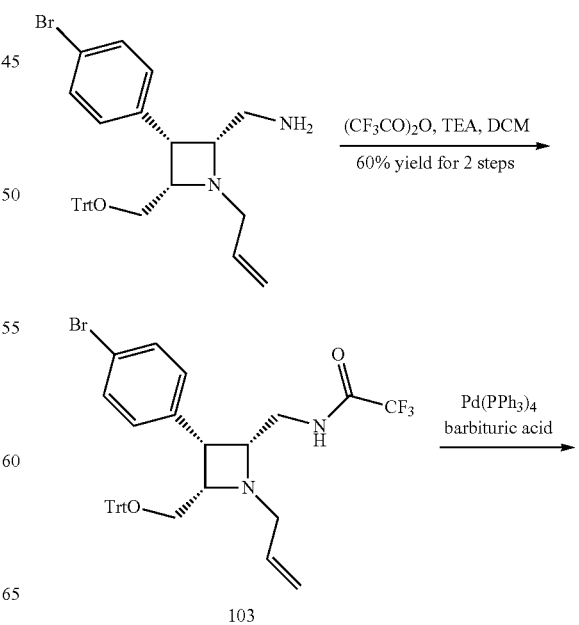

123
-continued
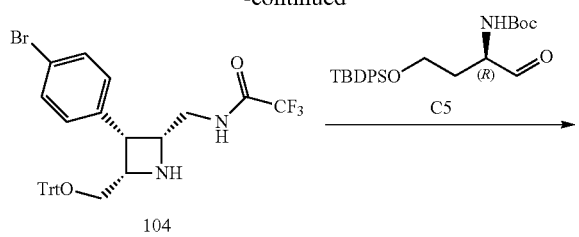
104
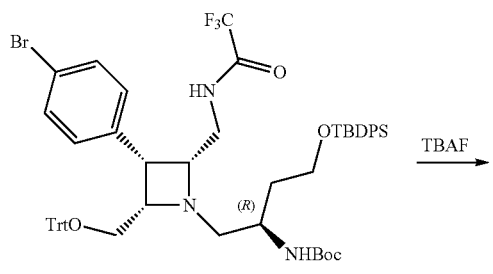
105
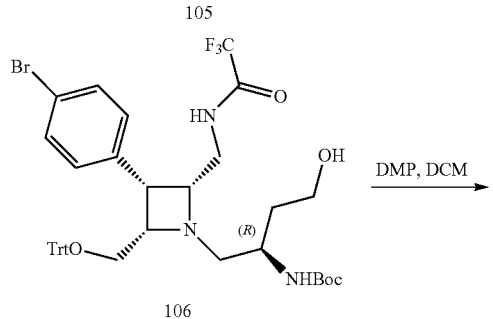
106
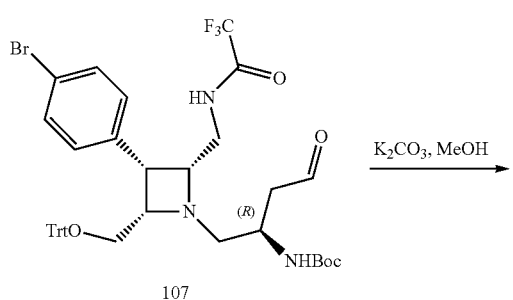
107
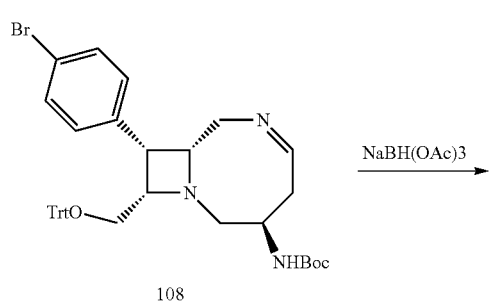
108
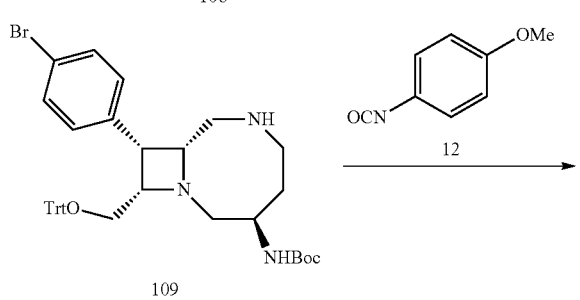
109
124
-continued
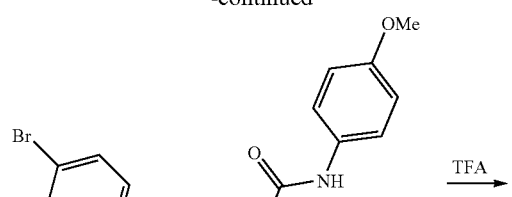
110
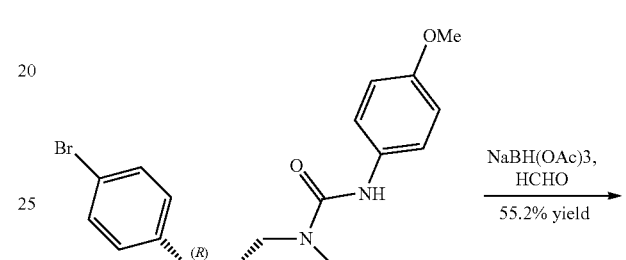
111
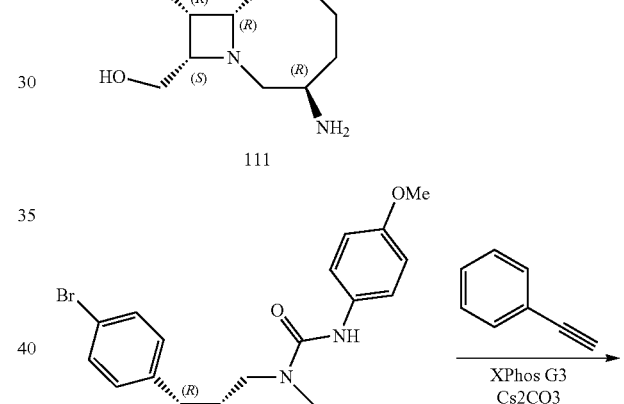
112
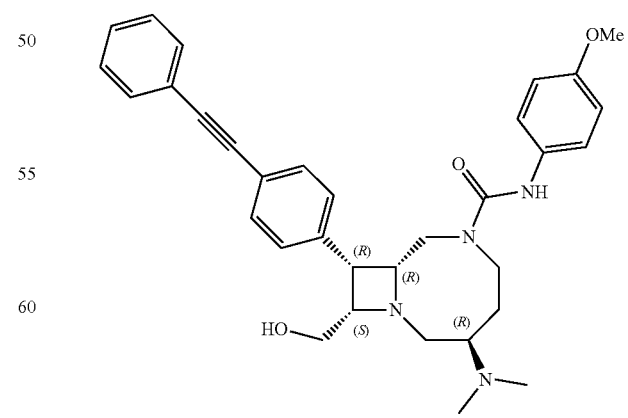
E28

Intermediate 103: N-[[(2R,3R,4S)-1-allyl-3-(4-bromophenyl)-4-(trityloxymethyl)azetidin-2-yl]methyl]-2,2,2-trifluoro-acetamide To a solution of [(2R,3R,4S)-1-allyl-3-(4-bromophenyl)-4-(trityloxymethyl)azetidin-2-yl]methanamine (J.O.C. (2012), 77(17), 7187-7211) (25.00 g, 31.62 mmol, 1.00 eq) in DCM (250.00 mL) was added TEA (25.59 g, 252.92 mmol, 35.06 mL, 8.00 eq), then it was cooled to 0° C. TFAA (26.56 g, 126.46 mmol, 17.59 mL, 4.00 eq) was added to the reaction mixture dropwise. After stirring at 20° C. for 16 h, the reaction mixture was quenched by NaHCO$_3$ solution (100 mL), extracted with DCM (50 mL×3), the combined organic layer was concentrated to give a residue. The residue was purified by column chromatography (SiO$_2$, petroleum ether/ethyl acetate=20/1 to 1:1) yielding Intermediate 103 (11.00 g, 16.94 mmol, 53.56% yield) as a yellow solid. $^1$H NMR (400 MHz, CHLOROFORM-d) δ ppm 2.87-3.08 (m, 2H) 3.09-3.24 (m, 2H) 3.30-3.51 (m, 3H) 3.57-3.69 (m, 2H) 5.10 (br d, J=10.14 Hz, 1H) 5.18-5.33 (m, 1H) 5.80 (dddd, J=17.28, 10.01, 7.44, 5.40 Hz, 1H) 6.11 (br s, 1H) 7.17-7.23 (m, 16H) 7.33 (d, J=8.38 Hz, 2H)

Intermediate 104: N-[[(2R,3R,4S)-3-(4-bromophenyl)-4-(trityloxymethyl)azetidin-2-yl]methyl]-2,2,2-trifluoro-acetamide To a solution of Intermediate 103 (11.00 g, 16.94 mmol, 1.00 eq) in EtOH (169.00 mL) was added 1,3-dimethylbarbituric acid (3.97 g, 25.41 mmol, 1.50 eq) and Pd(PPh$_3$)$_4$ (1.96 g, 1.69 mmol, 0.10 eq) under N$_2$ atmosphere. The mixture was stirred at 40° C. for 16 h. The reaction mixture was quenched by NaHCO$_3$ solution (200 mL), extracted with DCM (50 mL×3), the combined organic layer was concentrated to give a residue. The residue was purified by column chromatography (SiO$_2$, petroleum ether/ethyl acetate=10/1 to 5:1) yielding Intermediate 104 (7.80 g, 12.80 mmol, 75.55% yield as a yellow solid. $^1$H NMR (400 MHz, CHLOROFORM-d) δ ppm 2.26 (br s, 1H) 2.20-2.31 (m, 1H) 2.99-3.07 (m, 1H) 3.10-3.23 (m, 2H) 3.30-3.39 (m, 1H) 3.76 (br t, J=7.28 Hz, 1H) 4.27-4.49 (m, 2H) 6.10 (br s, 1H) 7.17-7.24 (m, 16H) 7.32-7.38 (m, 2H)

Intermediate 105: tert-butyl N-[(1R)-1-[[(2R,3R,4S)-3-(4-bromophenyl)-2-[[(2,2,2-trifluoroacetyl)amino]methyl]-4-(trityloxymethyl)azetidin-1-yl]methyl]-3-[tert-butyl(diphenyl)silyl]oxy-propyl]carbamate To a solution of Intermediate 104 (4.00 g, 6.56 mmol, 1.00 eq), tert-butyl N-[(1R)-3-[tert-butyl(diphenyl)silyl]oxy-1-formyl-propyl]carbamate (synthesized as described in Bioorganic & Medicinal Chemistry (2006), 14(1), 214-236, hereby incorporated by reference in its entirety) (2.90 g, 6.56 mmol, 1.00 eq) in DCM (50.00 mL) was added MgSO$_4$ (158.00 mg, 1.31 mmol, 20.00 eq) and NaBH(OAc)$_3$ (139.10 mg, 656.30 μmol, 10.00 eq). After stirring at 20° C. for 16 h, additional tert-butyl N-[(1R)-3-[tert-butyl(diphenyl)silyl]oxy-1-formyl-propyl]carbamate (1 g) was added. After an additional 0.5 h, the reaction mixture was quenched by NaHCO$_3$ solution (200 mL), extracted with DCM (50 mL×3), the combined organic layer was concentrated to give a residue. The residue was purified by column chromatography (SiO$_2$, petroleum ether/ethyl acetate=20/1 to 10:1) to give Intermediate 105 (4.20 g, 4.06 mmol, 61.85% yield as a yellow gum. $^1$H NMR (400 MHz, CHLOROFORM-d) δ ppm 1.01-1.05 (m, 9H) 1.41-1.47 (m, 10H) 1.63-1.78 (m, 1H) 1.82-1.92 (m, 1H) 2.65-2.76 (m, 1H) 2.82-3.01 (m, 2H) 3.13 (br dd, J=9.60, 6.09 Hz, 1H) 3.29-3.79 (m, 7H) 4.67 (br d, J=9.29 Hz, 1H) 7.11-7.25 (m, 17H) 7.31-7.50 (m, 8H) 7.63 (td, J=7.37, 1.44 Hz, 4H) 8.40-8.73 (m, 1H)

Intermediate 106: tert-butyl N-[(1R)-1-[[(2R,3R,4S)-3-(4-bromophenyl)-2-[[(2,2,2-trifluoroacetyl)amino]methyl]-4-(trityloxymethyl)azetidin-1-yl]methyl]-3-hydroxy-propyl]carbamate To a solution of Intermediate 105 (4.20 g, 4.06 mmol, 1.00 eq) in THF (50.00 mL) was added TBAF (1.59 g, 6.09 mmol, 1.50 eq). After stirring at 20° C. for 16 hour, the reaction mixture was concentrated to give a residue. The residue was purified by column chromatography (SiO$_2$, petroleum ether/ethyl acetate=10/1 to 2:1) to give Intermediate 106 (2.30 g, 2.89 mmol, 71.23% yield as a yellow solid. $^1$H NMR (400 MHz, CHLOROFORM-d) δ ppm 1.41 (s, 3H) 1.45-1.53 (m, 9H) 1.58-1.77 (m, 2H) 2.49 (br dd, J=12.74, 4.33 Hz, 2H) 2.82 (t, J=12.17 Hz, 1H) 2.88-2.98 (m, 2H) 3.08-3.29 (m, 3H) 3.47 (td, J=7.87, 3.20 Hz, 1H) 3.60-3.72 (m, 1H) 4.51 (br d, J=9.41 Hz, 1H) 7.12 (d, J=8.41 Hz, 1H) 7.09-7.14 (m, 1H) 7.16-7.26 (m, 17H) 7.34 (d, J=8.41 Hz, 1H) 8.13 (br s, 1H)

Intermediate 107: tert-butyl N-[(1R)-1-[[(2R,3R,4S)-3-(4-bromophenyl)-2-[[(2,2,2-trifluoroacetyl)amino]methyl]-4-(trityloxymethyl)azetidin-1-yl]methyl]-3-oxo-propyl]carbamate To a solution of Intermediate 106 (2.30 g, 2.89 mmol, 1.00 eq) in DCM (30.00 mL) was added DMP (2.45 g, 5.78 mmol, 1.79 mL, 2.00 eq) at 0° C. under N$_2$. The mixture was stirred at 0° C. for 1 hour. LCMS showed reactant 106 was consumed completely and the majority was the desired product, the reaction mixture was quenched by a solution of NaHCO$_3$ (2.5 g) and Na$_2$SO$_3$ (2.5 g) in H$_2$O (20 mL), extracted with DCM (20 mL×3), the combined organic layer was concentrated to give a residue. The residue was purified by column chromatography (SiO$_2$, petroleum ether/ethyl acetate=2/1 to 0:1) to give Intermediate 107 (1.80 g, 2.27 mmol, 78.37% yield as a yellow solid. $^1$H NMR (400 MHz, CHLOROFORM-d) δ ppm 1.47 (s, 9H) 1.51-1.69 (m, 3H) 2.46-2.54 (m, 2H) 2.78-2.88 (m, 1H) 2.89-3.00 (m, 2H) 3.08-3.20 (m, 2H) 3.49-3.69 (m, 4H) 3.91-4.07 (m, 1H) 4.50-4.76 (m, 1H) 7.08-7.13 (m, 3H) 7.17-7.26 (m, 22H) 8.25 (br s, 1H) 9.63 (s, 1H)

Intermediate 108: tert-butyl N-[(3R,5Z,8R,9R,10S)-9-(4-bromophenyl)-10-(trityloxymethyl)-1,6-diazabicyclo[6.2.0]dec-5-en-3-yl]carbamate To a solution of Intermediate 107 (1.70 g, 2.14 mmol, 1.00 eq) in MeOH (20.00 mL) and H$_2$O (77.13 mg, 4.28 mmol, 77.13 μL, 2.00 eq) was added K$_2$CO$_3$ (591.32 mg, 4.28 mmol, 2.00 eq). After stirring at 20° C. for 16 h, additional K$_2$CO$_3$ (200 mg) was added. After 2 h additional, the reaction mixture was dissolved in water (30 mL), extracted with DCM (20 mL×3), the organic layer was dried over Na$_2$SO$_4$, then concentrated to give a residue. The residue was purified by column chromatography (SiO$_2$, petroleum ether/ethyl acetate=5/1 to 0:1) to give Intermediate 108 (750.00 mg, 771.30 μmol, 45.05% yield, 70% purity) as a yellow solid.

Intermediate 109: tert-butyl N-[(3R,8R,9R,10S)-9-(4-bromophenyl)-10-(trityloxymethyl)-1,6-diazabicyclo[6.2.0]decan-3-yl]carbamate To a solution of Intermediate 108 (750.00 mg, 1.10 mmol, 1.00 eq) in DCM (18.00 mL) was added AcOH (66.17 mg, 1.10 mmol, 63.02 μL, 1.00 eq) and NaBH(OAc)₃ (2.34 g, 11.02 mmol, 10.00 eq). The mixture was stirred at 20° C. for 0.5 hour. LCMS showed reactant 108 was consumed completely, the majority was the desired product, the reaction mixture was quenched by NaHCO₃ solution (20 mL), extracted with DCM (10 mL×3), the combined organic layer was concentrated to give Intermediate 109 as a yellow solid (750 mg, crude), which was used directly in next step.

Intermediate 110: tert-butyl N-[(3R,8R,9R,10S)-9-(4-bromophenyl)-6-[(4-methoxyphenyl)carbamoyl]-10-(trityloxymethyl)-1,6-diazabicyclo[6.2.0]decan-3-yl]carbamate To a solution of Intermediate 109 (750.00 mg, 769.02 μmol, 1.00 eq) in DCM (10.00 mL) was added TEA (38.91 mg, 384.51 μmol, 53.30 μL, 0.50 eq) and 1-isocyanato-4-methoxy-benzene (137.64 mg, 922.82 μmol, 118.66 μL, 1.20 eq). The mixture was stirred at 20° C. for 0.5 hour. LCMS showed reactant 109 was consumed completely, and the majority was the desired product. The reaction mixture was concentrated to give a residue. The residue was purified by column chromatography (SiO₂, petroleum ether/ethyl acetate), further purified by pre-HPLC (Column: Waters Xbridge Prep OBD C18 150*30 5u; A: water (0.225% formic acid) B: acetonitrile). Intermediate 110 (150.00 mg, 180.33 μmol, 23.45% yield) was obtained as a white solid. ¹H NMR (400 MHz, CHLOROFORM-d) δ ppm 1.45 (br d, J=6.15 Hz, 9H) 2.18 (br s, 2H) 3.20-3.68 (m, 3H) 3.72-4.51 (m, 11H) 5.14-5.42 (m, 1H) 6.78 (br s, 1H) 6.88 (br t, J=7.97 Hz, 2H) 7.22-7.38 (m, 20H) 7.47-7.53 (m, 1H).

Intermediate 111: (3R,8R,9R,10S)-3-amino-9-(4-bromophenyl)-10-(hydroxymethyl)-N-(4-methoxyphenyl)-1,6-diazabicyclo[6.2.0]decane-6-carboxamide To a solution of Intermediate 110 (120.00 mg, 144.26 μmol, 1.00 eq) in DCM (3.00 mL) was added TFA (1.54 g, 13.51 mmol, 1.00 mL, 93.63 eq) at 0° C. The mixture was stirred at 20° C. for 1 hour. LCMS showed reactant 110 consumed completely, the majority was the desired product, the reaction mixture was quenched by NaHCO₃ solution (20 mL), then washed with NH₃·H₂O (1 mL), extracted with DCM (10 mL×3), the combined organic layer was concentrated to give a residue. The residue was purified by prep-TLC (SiO₂, DCM:MeOH=10:1) to give Intermediate 111 (60.00 mg, 122.60 μmol, 84.98% yield) as a white solid.

Intermediate 112: (3R,8R,9R,10S)-9-(4-bromophenyl)-3-(dimethylamino)-10-(hydroxymethyl)-N-(4-methoxyphenyl)-1,6-diazabicyclo[6.2.0]decane-6-carboxamide To a solution of Intermediate 111 (60.00 mg, 122.60 μmol, 1.00 eq), HCHO (99.50 mg, 1.23 mmol, 91.28 μL, 10.00 eq) in DCM (3.00 mL) was added MgSO₄ (147.57 mg, 1.23 mmol, 10.00 eq) and NaBH(OAc)₃ (259.84 mg, 1.23 mmol, 10.00 eq) at 20° C. The mixture was stirred at 20° C. for 1 hour. LCMS showed reactant 111 consumed completely, the majority was the desired product, the reaction mixture was quenched by NaHCO₃ solution (10 mL), extracted with DCM (5 mL×3), the combined organic layer was concentrated to give a residue. The residue was purified by prep-TLC (SiO₂, DCM:MeOH=10:1) to give Intermediate 112 (38.00 mg, 73.44 μmol, 59.90% yield) as a yellow solid. ¹H NMR (400 MHz, CHLOROFORM-d) δ ppm 1.84-1.99 (m, 1H) 2.49 (br s, 6H) 2.55 (br d, J=9.26 Hz, 2H) 2.88 (br d, J=11.69 Hz, 1H) 3.02-3.16 (m, 3H) 3.41 (br dd, J=11.58, 4.52 Hz, 1H) 3.51-3.61 (m, 3H) 3.62-3.86 (m, 6H) 3.98-4.17 (m, 1H) 4.73 (s, 1H) 6.78-6.91 (m, 2H) 7.23 (d, J=8.82 Hz, 2H) 7.34-7.53 (m, 4H).

Synthesis of E28: (3R,8R,9R,10S)-3-(dimethylamino)-10-(hydroxymethyl)-N-(4-methoxyphenyl)-9-[4-(2-phenylethynyl)phenyl]-1,6-diazabicyclo[6.2.0]decane-6-carboxamide (E28)

To a solution of Intermediate 112 (25.00 mg, 48.31 μmol, 1.00 eq), ethynylbenzene (14.80 mg, 144.93 μmol, 15.91 μL, 3.00 eq) in CH₃CN (350.00 μL) was added Cs₂CO₃ (47.22 mg, 144.93 μmol, 3.00 eq) and XPhos Pd G3 (4.09 mg, 4.83 μmol, 0.10 eq) under N₂ atmosphere. The mixture was stirred at 70° C. for 3 hour. LCMS showed reactant 1 consumed completely, the majority was the desired product, the reaction mixture was dissolved in water (2 mL), extracted with DCM (2 mL×3), the organic layer was dried over Na₂SO₄, then concentrated to give a residue. The residue was purified by prep-TLC (SiO₂, DCM:MeOH=10:1), then further purified by pre-HPLC (Column: Waters Xbridge Prep OBD C18 150*30 5u; A: water (0.225% formic acid) B: acetonitrile) to give compound E28 (13.00 mg, 24.13 μmol, 49.95% yield as a formic acid salt) as a white solid. ¹H NMR (400 MHz, CHLOROFORM-d) δ ppm 1.88 (br d, J=7.65 Hz, 1H) 2.38 (s, 7H) 2.49 (br dd, J=13.30, 9.29 Hz, 3H) 2.71 (br s, 1H) 2.79-2.96 (m, 1H) 3.09 (br d, J=15.94 Hz, 1H) 3.25 (br dd, J=13.30, 5.02 Hz, 1H) 3.41-3.73 (m, 6H) 3.78 (s, 3H) 3.90-4.03 (m, 1H) 6.84 (d, J=8.91 Hz, 2H) 7.21 (d, J=8.91 Hz, 2H) 7.32-7.40 (m, 3H) 7.46-7.57 (m, 6H).

Example 29: (3S,8R,9R,10S)-3-(dimethylamino)-10-(hydroxymethyl)-N-(4-methoxyphenyl)-9-(4-(phenylethynyl)phenyl)-1,6-diazabicyclo[6.2.0]decane-6-carboxamide ("E29")

Synthesis was performed similarly to that described in Example 28 after the synthesis of Intermediate 105 (Intermediate 105) utilizing the enantiomeric tert-butyl N-[(1S)-3-[tert-butyl(diphenyl)silyl]oxy-1-formyl-propyl]carbamate (Bioorganic & Medicinal Chemistry (2006)) in place of Intermediate 105. ¹H NMR (400 MHz, CHLOROFORM-d) δ=7.64-7.46 (m, 6H), 7.44-7.34 (m, 3H), 7.33-7.29 (m, 1H), 7.29-7.25 (m, 2H), 6.85 (d, J=8.9 Hz, 2H), 6.29 (br s, 1H), 3.86 (br d, J=10.8 Hz, 1H), 3.80 (s, 3H), 3.78-3.72 (m, 2H), 3.72-3.65 (m, 1H), 3.65-3.54 (m, 4H), 3.21-3.11 (m, 1H), 2.99-2.87 (m, 1H), 2.72-2.60 (m, 2H), 2.37 (s, 6H), 2.15 (br s, 1H), 2.01 (br d, J=7.9 Hz, 1H).

Example 30: (4R,8R,9R,10S)-4-(dimethylamino)-10-(hydroxymethyl)-N-(4-methoxyphenyl)-9-(4-(phenylethynyl)phenyl)-1,6-diazabicyclo[6.2.0]decane-6-carboxamide ("E30")

Synthesis was performed as shown in Example 3 utilizing the enantiomeric (R)-tert-butyl (1-((tert-butyldiphenylsilyl)oxy)-4-oxobutan-2-yl)carbamate (US 20150266867) as the starting material. ¹H NMR (400 MHz, CHLOROFORM-d)

δ=7.59-7.54 (m, 2H), 7.52-7.45 (m, 4H), 7.41-7.30 (m, 5H), 6.89-6.80 (m, 2H), 3.80 (s, 3H), 3.77-3.58 (m, 5H), 3.57 (br d, J=8.2 Hz, 1H), 3.51-3.43 (m, 2H), 3.29 (br d, J=13.6 Hz, 1H), 3.02 (br s, 1H), 2.67-2.44 (m, 2H), 2.34 (s, 6H), 1.81 (br s, 1H), 1.66 (br s, 1H).
Example 31: (8R,9R,10S)-4-((dimethylamino)methyl)-10-(hydroxymethyl)-N-(4-methoxyphenyl)-9-(4-(phenylethynyl)phenyl)-1,6-diazabicyclo[6.2.0]decane-6-carboxamide ("E31")
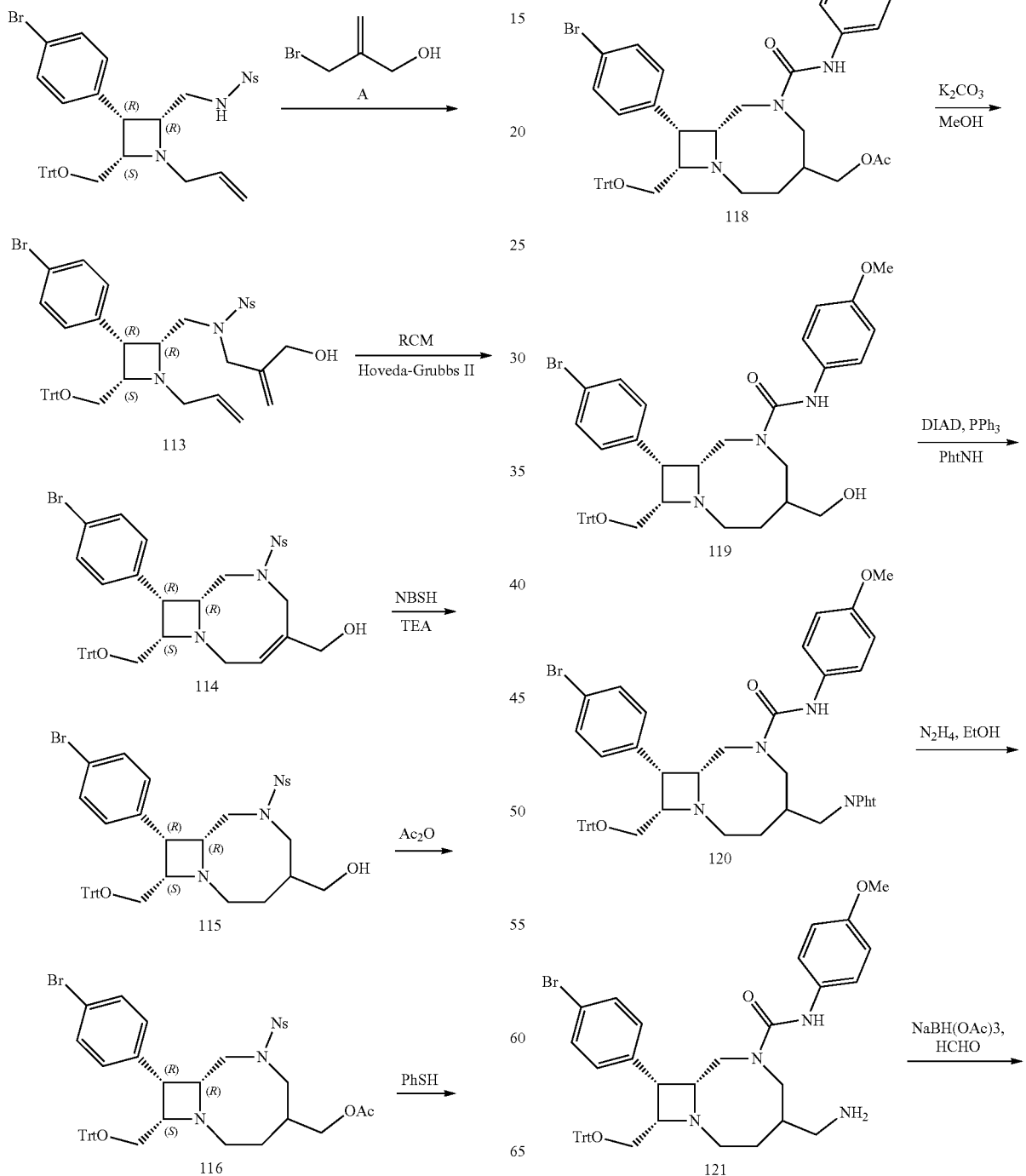

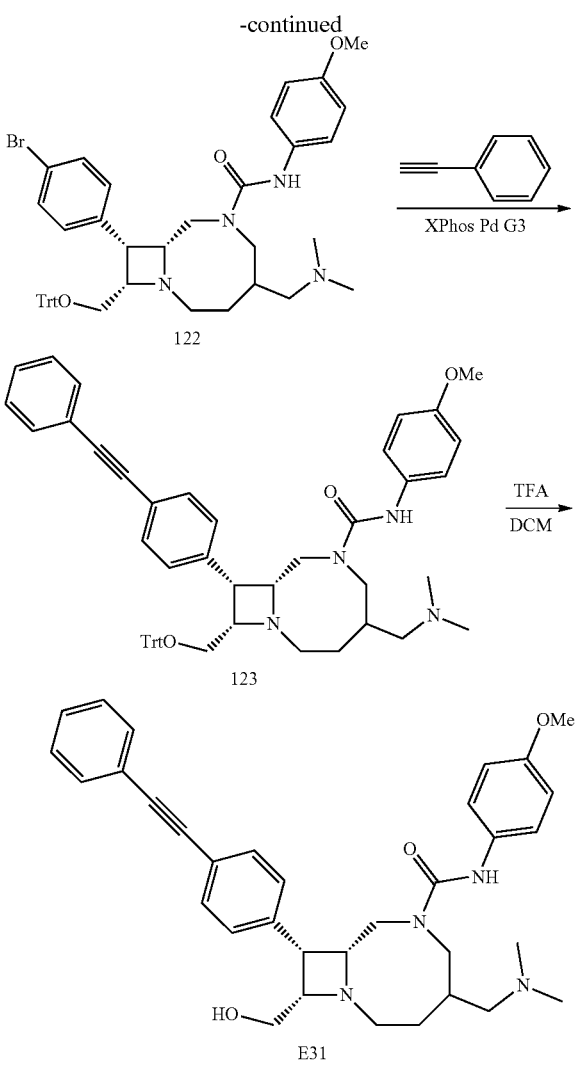

Hz, 6H), 5.57 (tdd, J=6.6, 10.4, 17.0 Hz, 1H), 5.10-5.00 (m, 2H), 4.89 (d, J=10.1 Hz, 1H), 4.69 (s, 1H), 3.91 (d, J=8.8 Hz, 3H), 3.70-3.61 (m, 1H), 3.54-3.38 (m, 3H), 3.26-3.14 (m, 3H), 2.98 (dd, J=4.4, 9.3 Hz, 1H), 2.85-2.73 (m, 2H)

Intermediate 114: [(3E,8R,9R,10S)-9-(4-bromophenyl)-6-(2-nitrophenyl)sulfonyl-10-(trityloxymethyl)-1,6-diazabicyclo[6.2.0]dec-3-en-4-yl]methanol To a solution of Intermediate 113 (5.00 g, 6.18 mmol, 1.00 eq) in DCM (500.00 mL) was added Hoveyda-Grubbs Catalyst $2^{nd}$ Generation (774.77 mg, 1.24 mmol, 0.20 eq). The mixture was stirred at 55° C. for 2 hour. TLC (petroleum ether:ethylacetate=1:1) showed Intermediate 113 was consumed completely and desired MS was detected. The reaction mixture was concentrated under reduced pressure to give a residue. The residue was purified by column chromatography ($SiO_2$, petroleum ether/ethyl acetate=20:1 to 1:1) to afford Intermediate 114 (4.00 g, 5.12 mmol, 82.90% yield) as a brown solid: 1H NMR (400 MHz, CHLOROFORM-d) δ=7.88-7.83 (m, 1H), 7.64-7.51 (m, 3H), 7.18 (d, J=6.0 Hz, 2H), 7.13 (s, 14H), 7.06 (d, J=8.5 Hz, 2H), 5.81 (t, J=6.3 Hz, 1H), 4.07-4.02 (m, 3H), 3.96-3.88 (m, 1H), 3.59-3.32 (m, 6H), 3.19 (d, J=14.1 Hz, 1H), 3.09-2.93 (m, 3H), 2.83-2.79 (m, 1H).

Intermediate 115: [(8R,9R,10S)-9-(4-bromophenyl)-6-(2-nitrophenyl)sulfonyl-10-(trityloxymethyl)-1,6-diazabicyclo[6.2.0]decan-4-yl]methanol To a solution of Intermediate 114 (4.00 g, 5.12 mmol, 1.00 eq) in THF (51.00 mL) was added 2-nitrobenzenesulfonohydrazide (5.56 g, 25.60 mmol, 4.00 eq) and TEA (5.18 g, 51.23 mmol, 7.10 mL, 10.00 eq). After stirring at 40° C. for 16 hour, the reaction mixture was quenched by addition water (100 mL) and extracted with ethyl acetate (50 mL*2). The combined organic layers were dried over $Na_2SO_4$, filtered and concentrated under reduced pressure to give a residue. The residue was purified by column chromatography ($SiO_2$, petroleum ether/ethyl acetate=10/1 to 1:1) to afford Intermediate 115 (3.60 g, crude) as a white solid.

Intermediate 116: [(8R,9R,10S)-9-(4-bromophenyl)-6-(2-nitrophenyl)sulfonyl-10-(trityloxymethyl)-1,6-diazabicyclo[6.2.0]decan-4-yl]methyl acetate To a solution of Intermediate 115 (3.60 g, 4.60 mmol, 1.00 eq) in DCM (80.00 mL) was added DMAP (56.19 mg, 460.00 μmol, 0.1 eq) and TEA (465.40 mg, 4.60 mmol, 637.53 μL, 1.00 eq), then $Ac_2O$ (939.07 mg, 9.20 mmol, 861.53 μL, 2.00 eq) at 0° C. After stirring at 20° C. for 2 h, the reaction mixture was quenched by addition sat. $NaHCO_3$ aqueous (150 mL) and extracted with DCM (50 mL*2). The combined organic layers were dried over $Na_2SO_4$, filtered and concentrated under reduced pressure to give a residue. The residue was purified by column chromatography ($SiO_2$, petroleum ether/ethyl acetate=30/1 to 1:1) to afford Intermediate 116 (3.00 g, 3.64 mmol, 79.07% yield) as a white solid.

Intermediate 117: [(8R,9R,10S)-9-(4-bromophenyl)-10-(trityloxymethyl)-1,6-diazabicyclo[6.2.0]decan-4-yl]methyl acetate To a solution of Intermediate 116 6 (3.00 g, 3.64 mmol, 1.00 eq) in acetonitrile (80.00 mL) was added $Cs_2CO_3$ (1.42 g, 4.37 mmol, 1.20 eq) and benzenethiol ("PhSH") (601.14

Intermediate 113: N-[[(2R,3R,4S)-1-allyl-3-(4-bromophenyl)-4-(trityloxymethyl)azetidin-2-yl]methyl]-N-[2-(hydroxymethyl)allyl]-2-nitro-benzenesulfonamide To a solution of N-[[(2R,3R,4S)-1-allyl-3-(4-bromophenyl)-4-(trityloxymethyl)azetidin-2-yl]methyl]-2-nitro-benzenesulfonamide (WO2015070204) (5.00 g, 6.77 mmol, 1.00 eq) in DMF (62.5 mL) was added $K_2CO_3$ (2.11 g, 15.23 mmol, 2.25 eq) and cooled to 0° C., whereby 2-(bromomethyl)prop-2-en-1-ol (2.04 g, 13.54 mmol, 2.00 eq) in DMF (7.5 mL) was added. The mixture was stirred at 20° C. for 16 hour. LC-MS showed Reactant 113 was consumed completely and desired MS was detected. The reaction mixture was quenched by addition water (300 mL) and extracted with ethyl acetate (100 mL*2). The combined organic layers were washed with brine (100 mL*2), dried over $Na_2SO_4$, filtered and concentrated under reduced pressure to give a residue. The residue was purified by column chromatography ($SiO_2$, petroleum ether/ethyl acetate=20:1 to 2:1) to afford Intermediate 113 (5.00 g, 6.18 mmol, 91.32% yield) as a white solid: $^1$H NMR (400 MHz, CHLOROFORM-d) δ=8.00 (s, 1H), 7.68-7.62 (m, 1H), 7.60-7.46 (m, 3H), 7.30-7.23 (m, 3H), 7.19-7.12 (m, 10H), 7.07 (dd, J=2.9, 6.8 mg, 5.46 mmol, 1.50 eq) at 0° C. After stirring at 20° C. for 16 h, the reaction mixture was quenched by addition water (100 mL) and extracted with ethyl acetate (30 mL*2). The combined organic layers were washed with brine (50 mL*2), dried over $Na_2SO_4$, filtered and concentrated under reduced pressure to give a residue. The residue was purified by column chromatography ($SiO_2$, petroleum ether/ethyl acetate=10:1 to 1:1) to afford Intermediate 117 (2.00 g, 3.13 mmol, 85.90% yield) as a white solid.

Intermediate 118: [(8R,9R,10S)-9-(4-bromophenyl)-6-[(4-methoxyphenyl)carbamoyl]-10-(trityloxymethyl)-1,6-diazabicyclo[6.2.0]decan-4-yl]methyl acetate To a solution of Intermediate 117 (2.00 g, 3.13 mmol, 1.00 eq) in DCM (50.00 mL) was added 1-isocyanato-4-methoxy-benzene (560.21 mg, 3.76 mmol, 1.20 eq) at 0° C. The mixture was stirred at 15° C. for 2 hour. LC-MS showed Intermediate 117 was consumed completely and desired MS was detected. The reaction mixture was quenched by addition water (100 mL) and extracted with DCM (30 mL*2). The combined organic layers were dried over $Na_2SO_4$, filtered and concentrated under reduced pressure to give a residue. The residue was purified by column chromatography ($SiO_2$, DCM:MeOH=100:1 to 20:1) to afford Intermediate 118 (2.20 g, 2.79 mmol, 89.11% yield) as a white solid. 1H NMR (400 MHz, CHLOROFORM-d) δ=7.28-7.16 (m, 23H), 6.83 (d, J=9.0 Hz, 2H), 4.01-3.95 (m, 1H), 3.92-3.85 (m, 1H), 3.80-3.73 (m, 5H), 3.63-3.54 (m, 2H), 3.42 (t, J=8.0 Hz, 1H), 3.20-2.90 (m, 5H), 2.74 (dd, J=11.0, 14.1 Hz, 1H), 2.50-2.40 (m, 1H), 2.06 (s, 3H), 1.66 (dd, J=6.8, 13.8 Hz, 1H), 1.53-1.45 (m, 1H).

Intermediate 119: (8R,9R,10S)-9-(4-bromophenyl)-4-(hydroxymethyl)-N-(4-methoxyphenyl)-10-(trityloxymethyl)-1,6-diazabicyclo[6.2.0]decane-6-carboxamide To a solution of Intermediate 118 (200.00 mg, 253.56 μmol, 1.00 eq) in DCM (1.00 mL) and MeOH (1 mL) was added $K_2CO_3$ (175.22 mg, 1.27 mmol, 5.00 eq). The mixture was stirred at 15° C. for 4 hour. LC-MS showed Intermediate 118 was consumed completely and one main peak with desired MS was detected. The reaction mixture was quenched by addition water (10 mL) and extracted with DCM (5 mL*2). The combined organic layers were dried over $Na_2SO_4$, filtered and concentrated under reduced pressure to give a residue. The residue was purified by column chromatography ($SiO_2$, petroleum ether/ethyl acetate=10:1 to 1:1) to afford Intermediate 119 (150.00 mg, 200.88 μmol, 79.22% yield) as a white solid. 1H NMR (400 MHz, CHLOROFORM-d) δ=7.37 (d, J=8.5 Hz, 2H), 7.27 (s, 4H), 7.22 (s, 15H), 6.80 (d, J=8.5 Hz, 2H), 3.90 (d, J=16.1 Hz, 2H), 3.77 (s, 3H), 3.70-3.57 (m, 3H), 3.43-3.32 (m, 2H), 3.19-3.07 (m, 2H), 3.05-2.94 (m, 2H), 2.75 (d, J=11.5 Hz, 1H), 2.47 (t, J=12.0 Hz, 1H), 1.89 (br. s., 1H), 1.52-1.38 (m, 2H).

Intermediate 120: (8R,9R,10S)-9-(4-bromophenyl)-4-[(1,3-dioxoisoindolin-2-yl)methyl]-N-(4-methoxyphenyl)-10-(trityloxymethyl)-1,6-diazabicyclo[6.2.0]decane-6-carboxamide To a solution of $PPh_3$ (0.15 g) in 3 mL THF was added DIAD (0.11 mL) at 0° C. After 5 minutes, this mixture was added to a solution of Intermediate 119 (20.00 mg, 26.78 μmol, 1.00 eq) and isoindoline-1,3-dione (5.91 mg, 40.17 μmol, 1.50 eq) in THF (1 mL) at 0° C. The mixture was stirred at 15° C. for 16 h. LC-MS showed Intermediate 9 was consumed completely and desired MS was detected. The reaction mixture was concentrated under reduced pressure to give a residue. The residue was purified by prep-TLC ($SiO_2$, petroleum ether/ethyl acetate=1:1) to afford Intermediate 120 (10.00 mg, 11.42 μmol, 42.63% yield) as a white solid. 1H NMR (400 MHz, CHLOROFORM-d) δ=7.87 (dd, J=3.0, 5.5 Hz, 1H), 7.75 (dd, J=3.3, 5.3 Hz, 2H), 7.32-7.28 (m, 7H), 7.27-7.20 (m, 15H), 6.80 (d, J=9.0 Hz, 2H), 6.17 (s, 1H), 3.83-3.75 (m, 3H), 3.74-3.56 (m, 5H), 3.52 (d, J=7.5 Hz, 1H), 3.24-3.12 (m, 3H), 3.03-2.96 (m, 1H), 2.83-2.74 (m, 1H), 2.45-2.30 (m, 2H), 1.83 (d, J=7.5 Hz, 1H).

Intermediate 121: (8R,9R,10S)-4-(aminomethyl)-9-(4-bromophenyl)-N-(4-methoxyphenyl)-10-(trityloxymethyl)-1,6-diazabicyclo[6.2.0]decane-6-carboxamide To a solution of Intermediate 120 (500.00 mg, 570.87 μmol, 1.00 eq) in EtOH (10.00 mL) was added $N_2H_4·H_2O$ (28.58 mg, 570.87 μmol, 27.75 μL, 1.00 eq). The mixture was stirred at 70° C. for 1 hour. LC-MS showed Intermediate 120 was consumed and desired MS was detected. The reaction mixture was quenched by addition water (30 mL) and extracted with DCM (10 mL*2). The combined organic layers were washed with brine (10 mL*2), dried over $Na_2SO_4$, filtered and concentrated under reduced pressure to give a residue. The residue was purified by column chromatography ($SiO_2$, DCM:MeOH=100:1 to 10:1) to afford Intermediate 121 (150.00 mg, crude) as a yellow solid contain Ph3PO. 1H NMR (400 MHz, CHLOROFORM-d) δ=7.64-7.56 (m, 4H), 7.51-7.45 (m, 3H), 7.39 (dt, J=2.8, 7.4 Hz, 5H), 7.14 (s, 13H), 6.71 (d, J=9.0 Hz, 2H), 3.79-3.62 (m, 4H), 3.56-3.46 (m, 2H), 3.31 (br. s., 1H), 3.11-2.85 (m, 5H), 2.74 (d, J=12.5 Hz, 1H), 2.44-2.18 (m, 2H), 1.62-1.39 (m, 3H).

Intermediate 122: (8R,9R,10S)-9-(4-bromophenyl)-4-((dimethylamino)methyl)-N-(4-methoxyphenyl)-10-((trityloxy)methyl)-1,6-diazabicyclo[6.2.0]decane-6-carboxamide To a solution of Intermediate 121 (150.00 mg, 201.14 μmol, 1.00 eq) in DCM (5.00 mL) was added $MgSO_4$ (290.53 mg, 2.41 mmol, 12.00 eq) and HCHO (98.21 mg, 1.21 mmol, 90.10 μL, 37% purity, 6.02 eq) then $NaBH(OAc)_3$ (639.44 mg, 3.02 mmol, 15.00 eq). The mixture was stirred at 15° C. for 16 hour. LC-MS showed Intermediate 121 was consumed and one desired MS was detected. The reaction mixture was quenched by addition sat. $NaHCO_3$ aqueous (20 mL) and extracted with DCM (5 mL*2). The combined organic layers were dried over $Na_2SO_4$, filtered and concentrated under reduced pressure to give a residue. The residue was purified by prep-TLC ($SiO_2$, DCM:MeOH=20:1) to afford Intermediate 122 (60.00 mg, 77.54 μmol, 38.55% yield) as a yellow solid. 1H NMR (400 MHz, CHLOROFORM-d) δ=7.24-7.08 (m, 24H), 6.72 (d, J=9.0 Hz, 2H), 3.88 (d, J=14.1 Hz, 1H), 3.67 (s, 3H), 3.57-3.48 (m, 3H), 3.33-3.25 (m, 1H), 3.10-2.86 (m, 5H), 2.64 (dd, J=10.8, 14.3 Hz, 1H), 2.44-2.36 (m, 1H), 2.21 (s, 6H), 1.90 (d, J=12.0 Hz, 1H), 1.51 (br. s., 2H), 1.36 (d, J=4.5 Hz, 2H).

Intermediate 123: (8R,9R,10S)-4-[(dimethylamino)methyl]-N-(4-methoxyphenyl)-9-[4-(2-phenylethynyl)phenyl]-10-(trityloxymethyl)-1,6-diazabicyclo[6.2.0]decane-6-carboxamide To a solution of Intermediate 122 (60.00 mg, 77.54 μmol, 1.00 eq) in acetonitrile (1.00 mL) was added ethynylbenzene (23.76 mg, 232.62 μmol, 25.55 μL, 3.00 eq), Cs₂CO₃ (101.06 mg, 310.16 μmol, 4.00 eq) and Xphos Pd G3 (6.56 mg, 7.75 μmol, 0.1 eq). The mixture was stirred at 70° C. for 2 hour. LC-MS showed reactant was consumed completely and desired MS was detected. The reaction mixture was quenched by addition water (10 mL) and extracted with DCM (5 mL*2). The combined organic layers were washed with brine (5 mL*2), dried over Na₂SO₄, filtered and concentrated under reduced pressure to give a residue. The residue was purified by prep-TLC (SiO₂, DCM:MeOH=20:1) to afford Intermediate 123 (50.00 mg, 62.89 μmol, 81.11% yield) as a yellow solid.

Synthesis of E31: (8R,9R,10S)-4-((dimethylamino)methyl)-10-(hydroxymethyl)-N-(4-methoxyphenyl)-9-(4-(phenylethynyl)phenyl)-1,6-diazabicyclo[6.2.0]decane-6-carboxamide (E31)

To a solution of Intermediate 123 (50.00 mg, 62.89 μmol, 1.00 eq) in DCM (1.00 mL) was added TFA (71.71 mg, 628.90 μmol, 46.56 μL, 10.00 eq). The mixture was stirred at 25° C. for 1 hour. LC-MS showed Intermediate 123 was consumed completely and desired MS was detected. The reaction mixture was quenched by addition sat. NaHCO₃ aqueous (10 mL) and extracted with DCM (5 mL*2). The combined organic layers were dried over Na₂SO₄, filtered and concentrated under reduced pressure to give a residue. The residue was purified by prep-TLC (SiO₂, DCM:MeOH=10:1) to afford compound E31 (4.50 mg, 8.14 μmol, 12.95% yield) as a white solid. 1H NMR (400 MHz, CHLOROFORM-d) δ=7.54 (dd, J=2.0, 7.5 Hz, 2H), 7.48 (s, 4H), 7.37-7.29 (m, 5H), 6.82 (d, J=9.0 Hz, 2H), 4.05 (d, J=14.1 Hz, 1H), 3.78 (s, 3H), 3.73-3.62 (m, 4H), 3.60-3.52 (m, 2H), 3.46 (t, J=8.5 Hz, 1H), 3.15 (dd, J=5.3, 16.3 Hz, 2H), 2.86 (dd, J=10.5, 14.6 Hz, 1H), 2.58 (br. s., 1H), 2.32 (s, 6H), 2.25 (t, J=12.3 Hz, 2H), 2.03 (d, J=12.5 Hz, 1H), 1.59 (br. s., 2H), 1.53 (br. s., 1H)

Example 32: (8R,9S,10S)-10-[(dimethylamino)methyl]-4-(hydroxymethyl)-N-(4-methoxyphenyl)-9-[4-(2-phenylethynyl)phenyl]-1,6-diazabicyclo[6.2.0]decane-6-carboxamide ("E32")

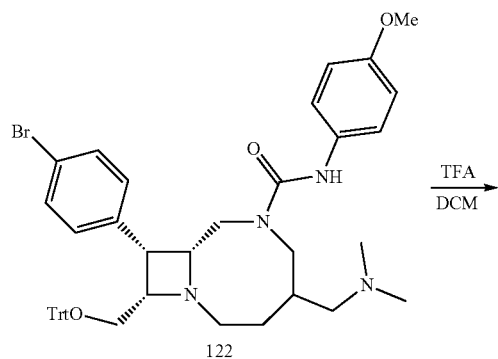

122

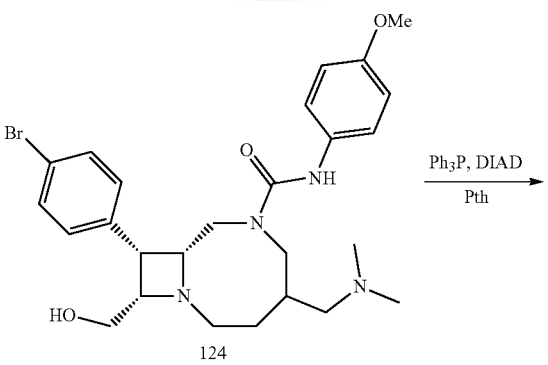

124

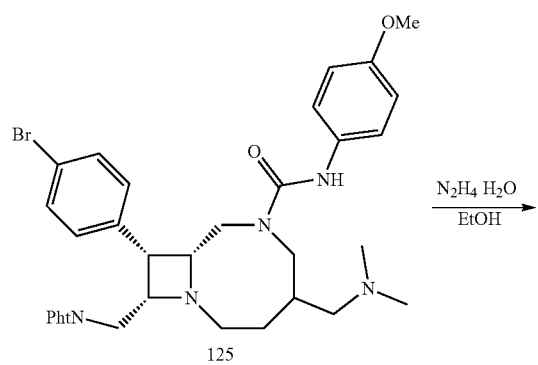

125

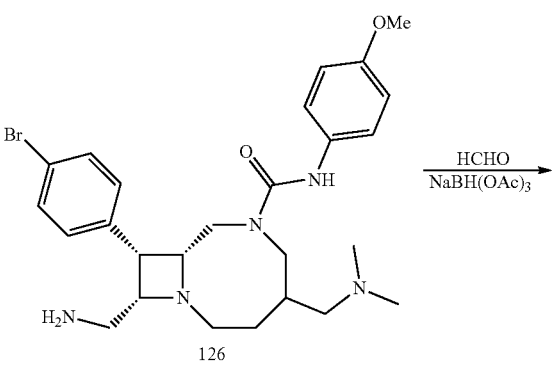

126

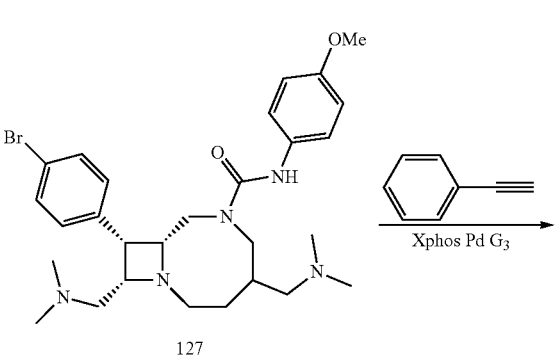

127

-continued

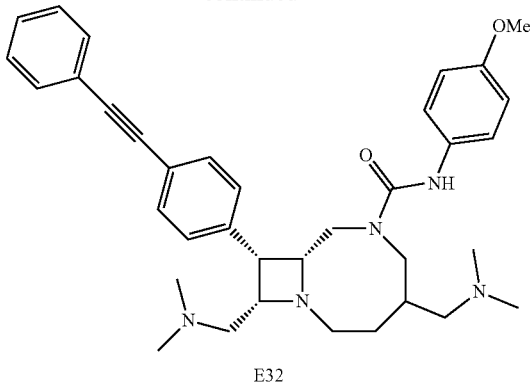

E32

Intermediate 124: (8R,9R,10S)-9-(4-bromophenyl)-4-[(dimethylamino)methyl]-10-(hydroxymethyl)-N-(4-methoxyphenyl)-1,6-diazabicyclo[6.2.0]decane-6-carboxamide To a solution of Intermediate 122 (400.00 mg, 516.93 µmol, 1.00 eq) in DCM (10.00 mL) was added TFA (589.40 mg, 5.17 mmol, 382.73 µL, 10.00 eq). The mixture was stirred at 25° C. for 1 hour. LC-MS showed Intermediate 122 was consumed completely and desired MS was detected. The reaction mixture was quenched by addition sat. NaHCO$_3$ aqueous (10 mL) and extracted with DCM (5 mL*2). The combined organic layers were dried over Na$_2$SO$_4$, filtered and concentrated under reduced pressure to give a residue. The residue was purified by column chromatography (SiO$_2$, DCM:MeOH=100:1 to 10:1) to afford Intermediate 124 (130.00 mg, crude) as a yellow solid. 1H NMR (400 MHz, CHLOROFORM-d) δ=7.47 (d, J=8.8 Hz, 1H), 7.39-7.32 (m, 3H), 7.32-7.26 (m, 9H), 7.23 (d, J=9.3 Hz, 3H), 6.91 (d, J=8.4 Hz, 1H), 3.93 (d, J=14.1 Hz, 1H), 3.69 (s, 3H), 3.60-3.52 (m, 4H), 3.04 (d, J=14.1 Hz, 2H), 2.75-2.63 (m, 2H), 2.23 (s, 6H), 2.15 (d, J=11.9 Hz, 1H), 1.65-1.46 (m, 4H).

Intermediate 125: (8R,9S,10S)-9-(4-bromophenyl)-4-[(dimethylamino)methyl]-10-[(1,3-dioxoisoindolin-2-yl)methyl]-N-(4-methoxyphenyl)-1,6-diazabicyclo[6.2.0]decane-6-carboxamide To a solution of PPh$_3$ (0.15 g) in 3 mL THF was added DIAD (0.11 mL) at 0° C. This mixture (1.16 mL) were added to a solution of Intermediate 124 (30.00 mg, 56.45 µmol, 1.00 eq) and isoindoline-1,3-dione (12.46 mg, 84.67 µmol, 1.50 eq) in THF (1.00 mL) at 0° C. The mixture was stirred at 25° C. for 16 hour. LC-MS showed Intermediate 124 was consumed completely and desired MS was detected. The reaction mixture was concentrated under reduced pressure to give a residue. The residue was purified by prep-TLC (SiO$_2$, DCM:MeOH=20:1) to afford Intermediate 125 (30.00 mg, crude) as a white solid contain Ph$_3$PO.

Intermediate 126: (8R,9S,10S)-10-(aminomethyl)-9-(4-bromophenyl)-4-[(dimethylamino)methyl]-N-(4-methoxyphenyl)-1,6-diazabicyclo[6.2.0]decane-6-carboxamide To a solution of Intermediate 125 (100.00 mg, 151.38 µmol, 1.00 eq) in EtOH (2.00 mL) was added N$_2$H$_4$·H$_2$O (7.58 mg, 151.38 µmol, 7.36 µL, 1.00 eq). The mixture was stirred at 70° C. for 1 hour. LC-MS showed Intermediate 125 was consumed completely and desired MS was detected. The reaction mixture was quenched by addition water (10 mL) and extracted with DCM (5 mL*2). The combined organic layers were washed with brine (5 mL*2), dried over Na$_2$SO$_4$, filtered and concentrated under reduced pressure to give a residue. The residue was purified by prep-TLC (SiO$_2$, DCM:MeOH=8:1) to afford Intermediate 126 (90.00 mg, crude) as a yellow solid.

Intermediate 127: (8R,9S,10S)-9-(4-bromophenyl)-4,10-bis[(dimethylamino)methyl]-N-(4-methoxyphenyl)-1,6-diazabicyclo[6.2.0]decane-6-carboxamide To a solution of Intermediate 126 (45.00 mg, 84.83 µmol, 1.00 eq) in DCM (2.00 mL) was added HCHO (41.31 mg, 508.98 µmol, 37.90 µL, 37% solution, 6.00 eq) and MgSO$_4$ (122.53 mg, 1.02 mmol, 12.00 eq), after stirred for 30 min, NaBH(OAc)$_3$ (269.68 mg, 1.27 mmol, 15.00 eq) was added. The mixture was stirred at 15° C. for 16 hour. LC-MS showed Intermediate 126 was consumed completely and desired MS was detected. The reaction mixture was quenched by addition sat. NaHCO$_3$ aqueous (10 mL) and extracted with DCM (3 mL*2). The combined organic layers were washed with brine (3 mL*2), dried over Na$_2$SO$_4$, filtered and concentrated under reduced pressure to give a residue. The residue was purified by prep-TLC (SiO$_2$, DCM: MeOH=10:1) to afford Intermediate 127 (20.00 mg, 35.81 µmol, 42.21% yield) as a yellow solid. 1H NMR (400 MHz, CHLOROFORM-d) δ=7.46-7.40 (m, 2H), 7.37-7.33 (m, 2H), 7.30 (d, J=9.0 Hz, 2H), 6.81 (d, J=9.0 Hz, 2H), 3.97 (d, J=14.1 Hz, 1H), 3.77 (s, 3H), 3.67 (d, J=15.6 Hz, 1H), 3.60-3.54 (m, 1H), 3.45-3.32 (m, 2H), 3.15-3.03 (m, 2H), 2.74 (dd, J=10.8, 14.3 Hz, 1H), 2.47-2.34 (m, 4H), 2.30 (s, 6H), 2.25-2.17 (m, 1H), 2.02 (s, 6H), 1.62-1.48 (m, 3H).

Synthesis of E32: (8R,9S,10S)-4,10-bis[(dimethylamino)methyl]-N-(4-methoxyphenyl)-9-[4-(2-phenylethynyl)phenyl]-1,6-diazabicyclo[6.2.0]decane-6-carboxamide (E32)

To a solution of Intermediate 127 (15.00 mg, 26.86 µmol, 1.00 eq) in acetonitrile (1.00 mL) was added ethynylbenzene (10.97 mg, 107.42 µmol, 3.00 eq), Xphos Pd G3 (2.27 mg, 2.69 µmol, 0.10 eq) and Cs$_2$CO$_3$ (35.00 mg, 107.42 µmol, 4.00 eq). The mixture was stirred at 70° C. for 1 hour. LC-MS showed Intermediate 127 was consumed completely and desired MS was detected. The reaction mixture was quenched by addition water (10 mL) and extracted with ethyl acetate (3 mL*2). The combined organic layers were washed with brine (3 mL*2), dried over Na$_2$SO$_4$, filtered and concentrated under reduced pressure to give a residue. The residue was purified by prep-TLC (SiO$_2$, DCM: MeOH=8:1) to afford compound E32 (4.30 mg, 7.42 µmol, 27.61% yield) as a yellow solid. 1H NMR (400 MHz, CHLOROFORM-d) δ=7.50-7.44 (m, 2H), 7.44-7.36 (m, 4H), 7.31-7.21 (m, 5H), 6.74 (d, J=8.5 Hz, 2H), 3.93 (d, J=14.6 Hz, 1H), 3.70 (s, 3H), 3.63-3.52 (m, 2H), 3.42-3.28 (m, 2H), 3.09-2.99 (m, 2H), 2.72 (dd, J=10.5, 14.1 Hz, 1H), 2.36 (d, J=10.0 Hz, 3H), 2.23 (s, 6H), 2.16 (t, J=12.5 Hz, 2H), 1.96 (br. s., 6H), 1.54 (br. s., 1H), 1.45 (br. s., 2H).

Example 33: (8R,9S,10S)-10-[(dimethylamino)methyl]-4-(hydroxymethyl)-N-(4-methoxyphenyl)-9-[4-(2-phenylethynyl)phenyl]-1,6-diazabicyclo[6.2.0]decane-6-carboxamide ("E33")

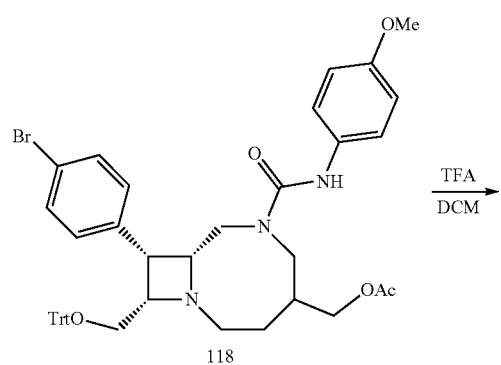

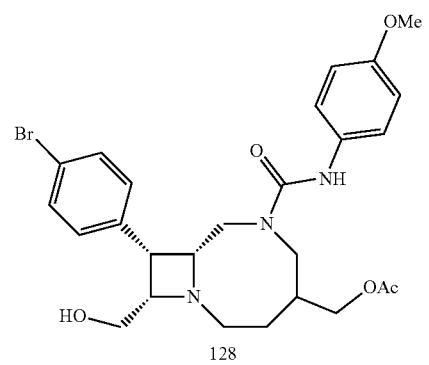

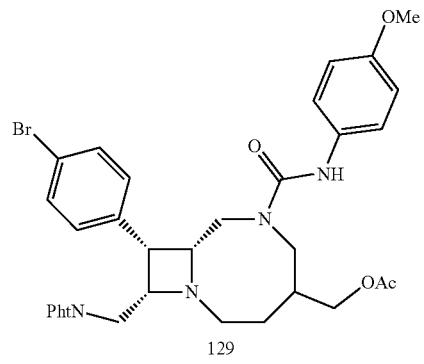

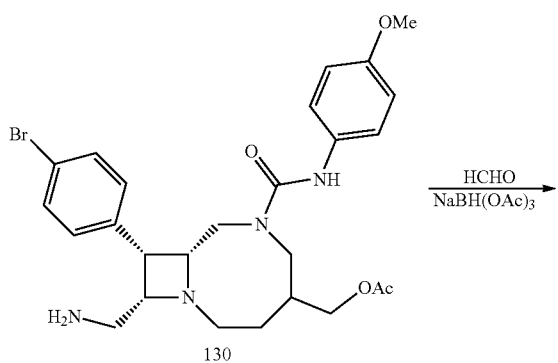

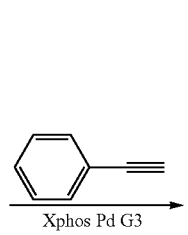

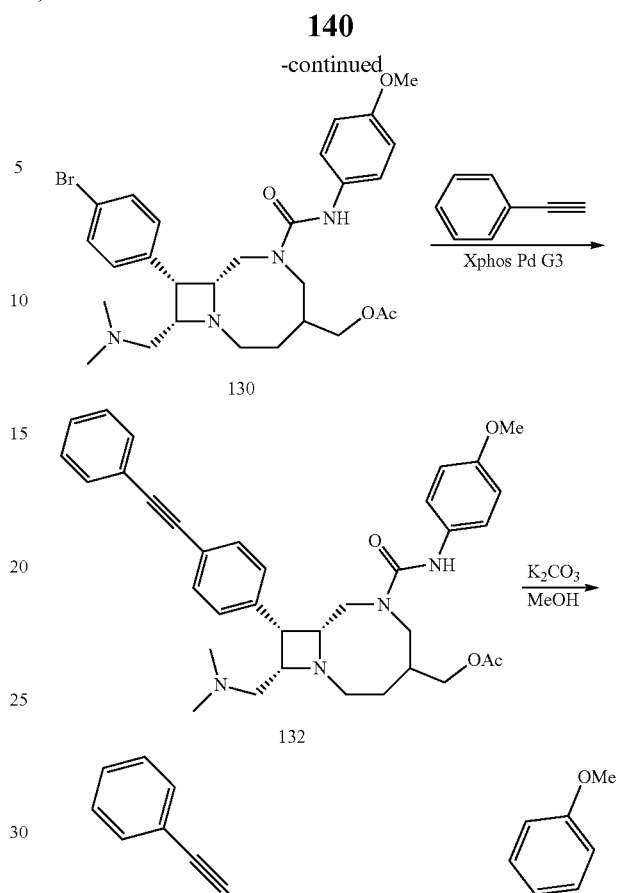

Intermediate 128: [(8R,9R,10S)-9-(4-bromophenyl)-10-(hydroxymethyl)-6-[(4-methoxyphenyl)carbamoyl]-1,6-diazabicyclo[6.2.0]decan-4-yl]methyl acetate To a solution of Intermediate 118 (600.00 mg, 760.68 μmol, 1.00 eq) in DCM (10.00 mL) was added TFA (867.33 mg, 7.61 mmol, 563.20 μL, 10.00 eq). The mixture was stirred at 20° C. for 2 hour. LC-MS showed Intermediate 118 was consumed and desired MS was detected. The reaction mixture was quenched by addition sat. NaHCO₃ aqueous (30 mL) and extracted with DCM (10 mL*2). The combined organic layers were dried over Na₂SO₄, filtered and concentrated under reduced pressure to give a residue. The residue was purified by column chromatography (SiO₂, DCM/MeOH=1:0 to 20:1) to afford Intermediate 128 (300.00 mg, 549.00 μmol, 72.17% yield) as a white solid.

Intermediate 129: [(8R,9S,10S)-9-(4-bromophenyl)-10-[(1,3-dioxoisoindolin-2-yl)methyl]-6-[(4-methoxyphenyl)carbamoyl]-1,6-diazabicyclo[6.2.0]decan-4-yl]methyl acetate To a solution of triphenylphosphine (1 g, 3.76 mmol) in THF (19 ml) at 0° C. was slowly added DIAD (0.73 mL, 3.76 mmol). This prepared mixture (11 mL) was added to a mixture of Intermediate 128 (300.00 mg, 549.00 µmol, 1.00 eq) and isoindoline-1,3-dione (121.16 mg, 823.50 µmol, 1.50 eq) in THF (15.00 mL) at 0° C. and then the mixture was stirred at 25° C. for 16 hour under $N_2$ atmosphere. LC-MS showed Intermediate 128 was consumed completely and desired MS was detected. The reaction mixture was concentrated under reduced pressure to give a residue. The residue was purified by column chromatography ($SiO_2$, DCM:MeOH=1:0 to 10:1) to afford Intermediate 129 (400.00 mg, crude) as a yellow solid contain $Ph_3PO$.

Intermediate 130: [(8R,9S,10S)-10-(aminomethyl)-9-(4-bromophenyl)-6-[(4-methoxyphenyl)carbamoyl]-1,6-diazabicyclo[6.2.0]decan-4-yl]methyl acetate To a solution of Intermediate 129 (400.00 mg, 592.09 µmol, 1.00 eq) in EtOH (10.00 mL) was added $N_2H_4 \cdot H_2O$ (29.64 mg, 592.09 µmol, 28.78 µL, 1.00 eq). The mixture was stirred at 70° C. for 2 h. The reaction mixture was quenched by addition water (30 mL) and extracted with DCM (30 mL*2). The combined organic layers were washed with brine (30 mL*2), dried over $Na_2SO_4$, filtered and concentrated under reduced pressure to give a residue. The residue was purified by column chromatography ($SiO_2$, DCM:MeOH=1:0 to 20:1) to afford Intermediate 130 (280.00 mg, 513.32 µmol, 86.70% yield) as a white solid.

Intermediate 131: [(8R,9S,10S)-9-(4-bromophenyl)-10-[(dimethylamino)methyl]-6-[(4-methoxyphenyl)carbamoyl]-1,6-diazabicyclo[6.2.0]decan-4-yl]methyl acetate To a solution of Intermediate 130 (140.00 mg, 256.66 µmol, 1.00 eq) in DCM (5.00 mL) was added $MgSO_4$ (370.73 mg, 3.08 mmol, 12.00 eq) and HCHO (124.99 mg, 1.54 mmol, 114.67 µL, 37% solution, 6.00 eq) then $NaBH(OAc)_3$ (815.95 mg, 3.85 mmol, 15.00 eq) was added in portions. The mixture was stirred at 15° C. for 16 hour. LC-MS showed Intermediate 130 was consumed and one desired MS was detected. The reaction mixture was quenched by addition sat. $NaHCO_3$ aqueous (20 mL) and extracted with DCM (5 mL*2). The combined organic layers were dried over $Na_2SO_4$, filtered and concentrated under reduced pressure to give a residue. The residue was purified by prep-TLC ($SiO_2$, DCM:MeOH=20:1) to afford Intermediate 131 (73.00 mg, 127.28 µmol, 49.59% yield) as a white solid.

Intermediate 132: [(8R,9S,10S)-10-[(dimethylamino)methyl]-6-[(4-methoxyphenyl)carbamoyl]-9-[4-(2-phenylethynyl)phenyl]-1,6-diazabicyclo[6.2.0]decan-4-yl]methyl acetate To a solution of Intermediate 131 (73.00 mg, 127.28 µmol, 1.00 eq) in acetonitrile (4.00 mL) was added ethynylbenzene (39 mg, 381.85 µmol, 3.00 eq), Xphos Pd G3 (10.77 mg, 12.73 µmol, 0.10 eq) and $Cs_2CO_3$ (165.89 mg, 509.14 µmol, 4.00 eq). The mixture was stirred at 70° C. for 1 hour. LC-MS showed Intermediate 131 was consumed completely and desired MS was detected. The reaction mixture was quenched by addition water (10 mL) and extracted with ethyl acetate (3 mL*2). The combined organic layers were washed with brine (3 mL*2), dried over $Na_2SO_4$, filtered and concentrated under reduced pressure to give a residue. The residue was purified by prep-TLC ($SiO_2$, DCM:MeOH=10:1) to afford Intermediate 132 (30.00 mg, 50.44 µmol, 39.63% yield) as a brown solid.

Synthesis of E33: (8R,9S,10S)-10-[(dimethylamino)methyl]-4-(hydroxymethyl)-N-(4-methoxyphenyl)-9-[4-(2-phenylethynyl)phenyl]-1,6-diazabicyclo[6.2.0]decane-6-carboxamide (E33)

To a solution of Intermediate 132 (30.00 mg, 50.44 µmol, 1.00 eq) in MeOH (500.00 µL)/DCM (0.5 mL) was added $K_2CO_3$ (34.86 mg, 252.20 µmol, 5.00 eq). The mixture was stirred at 15° C. for 1 hour. LC-MS showed Intermediate 132 was consumed completely and one main peak with desired MS was detected. The reaction mixture was quenched by addition water (10 mL) and extracted with DCM (5 mL*2). The combined organic layers were dried over $Na_2SO_4$, filtered and concentrated under reduced pressure to give a residue. The residue was purified by prep-HPLC (column: Luna C18 150*25 5u; mobile phase: [water (0.225% formic acid)-acetonitrile]; B %: 25%-45%, 12 min) to afford compound E33 (11.00 mg, 18.37 µmol, 36.42% yield, formic acid salt)) as a white solid: 1H NMR (400 MHz, METHANOL-d4) δ=7.58-7.49 (m, 6H), 7.38 (d, J=3.5 Hz, 3H), 7.29 (d, J=8.8 Hz, 2H), 6.81 (d, J=9.3 Hz, 2H), 3.92 (d, J=15.4 Hz, 1H), 3.82-3.71 (m, 5H), 3.59 (d, J=6.2 Hz, 2H), 3.45 (t, J=9.0 Hz, 1H), 3.20-3.05 (m, 2H), 3.01-2.91 (m, 2H), 2.88-2.81 (m, 1H), 2.48 (t, J=12.1 Hz, 1H), 2.40-2.29 (m, 6H), 1.83 (br. s., 1H), 1.67-1.48 (m, 2H).

Example 34: (8R,9S,10S)-10-((dimethylamino)methyl)-N-(4-methoxyphenyl)-2-methyl-9-(4-(phenylethynyl)phenyl)-1,6-diazabicyclo[6.2.0]decane-6-carboxamide ("E34")

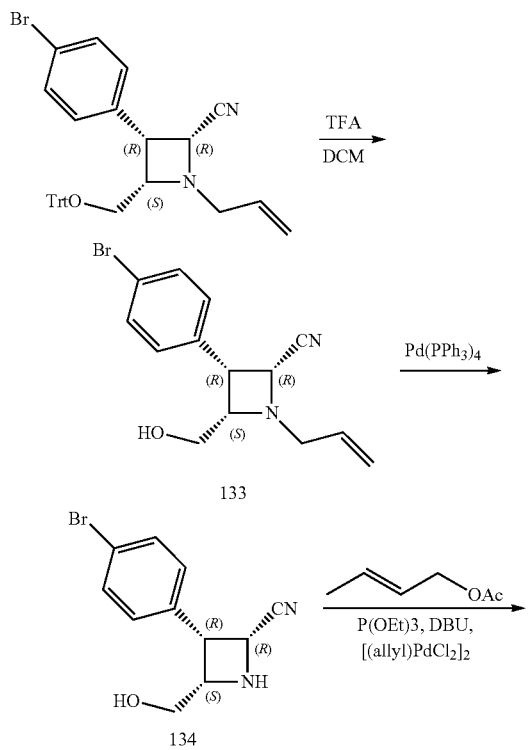

143
-continued
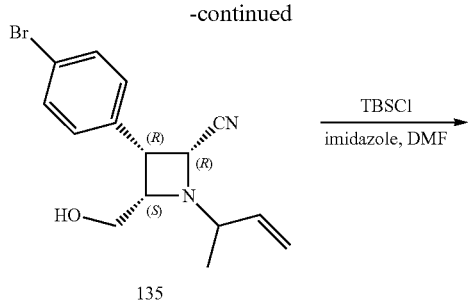
135
TBSCl
imidazole, DMF
→
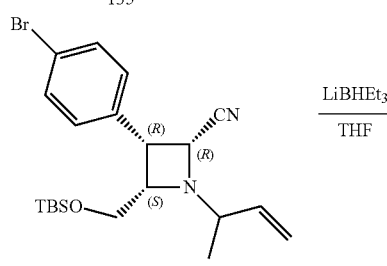
136
LiBHEt$_3$
THF
→
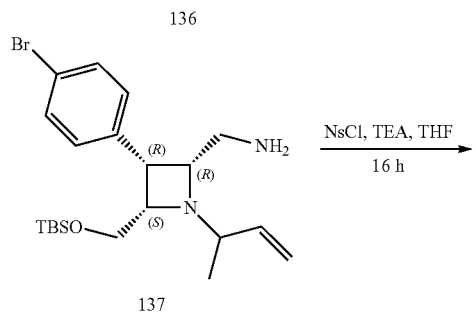
137
NsCl, TEA, THF
16 h
→
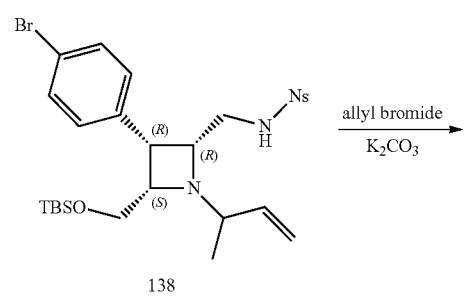
138
allyl bromide
K$_2$CO$_3$
→
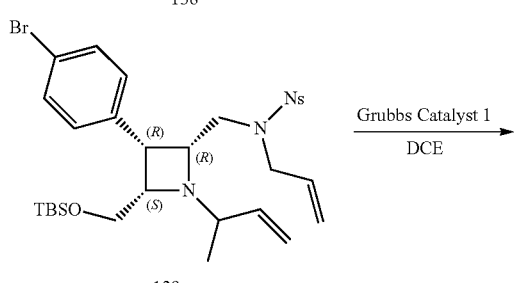
139
Grubbs Catalyst 1
DCE
→
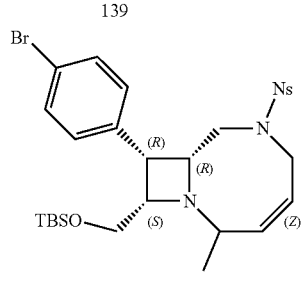
140
NBSH
DCM
→
144
-continued
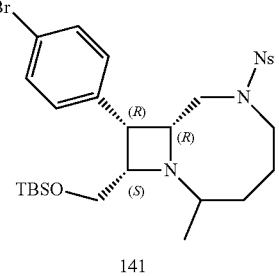
141
PhSH, Cs$_2$CO$_3$
CH$_3$CN
→
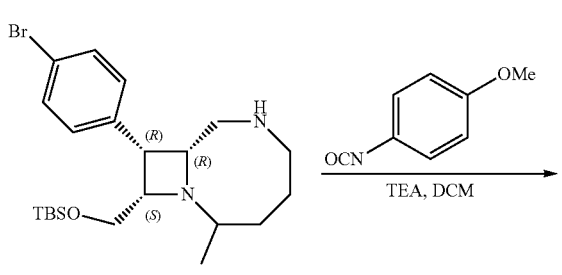
142
4-MeO-C$_6$H$_4$-NCO
TEA, DCM
→
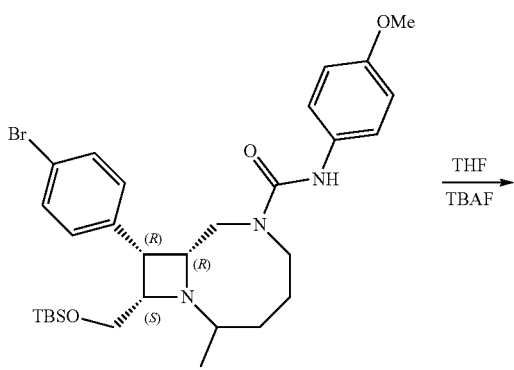
143
THF
TBAF
→
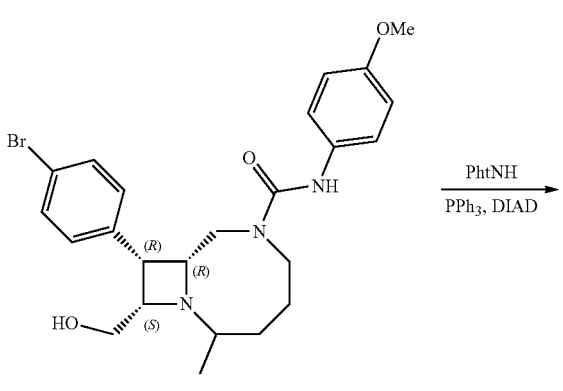
144
PhtNH
PPh$_3$, DIAD
→

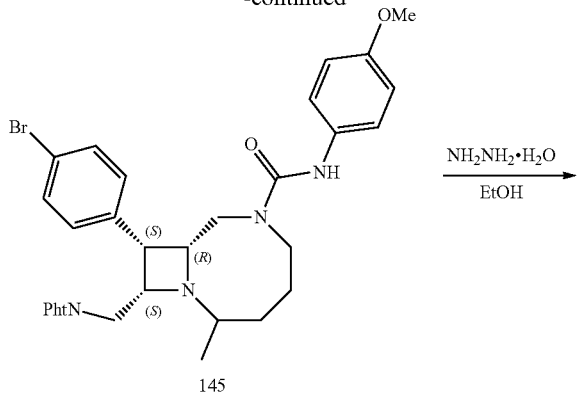

145

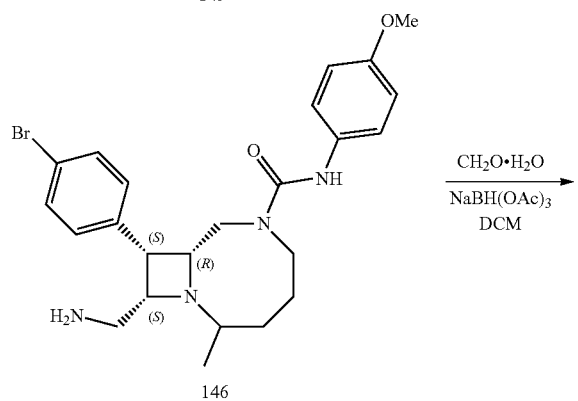

146

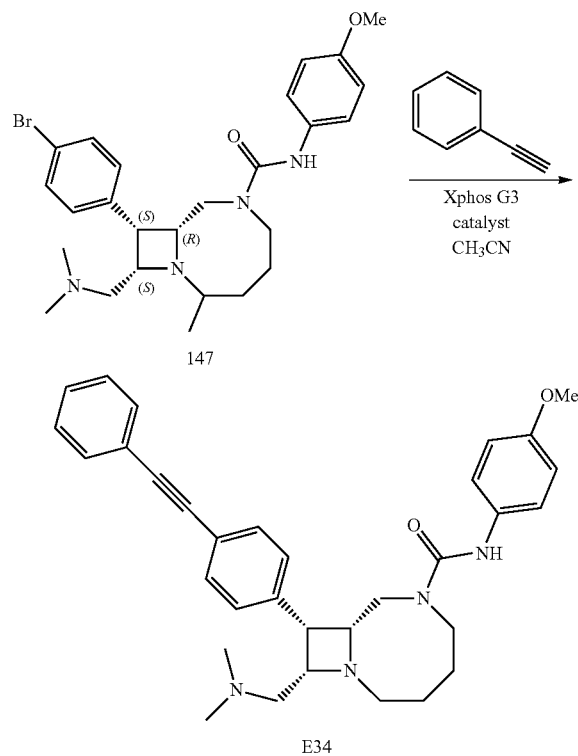

E34

Intermediate 133: (2R,3R,4S)-1-allyl-3-(4-bromophenyl)-4-(hydroxymethyl)azetidine-2-carbonitrile To a solution of (2R,3R,4S)-1-allyl-3-(4-bromophenyl)-4-((trityloxy)methyl)azetidine-2-carbonitrile (J.O.C (2012), 77(17), 7187-7211) (16.00 g, 29.12 mmol, 1.00 eq) in DCM (291.00 mL) was added TFA (33.20 g, 291.20 mmol, 21.56 mL, 10.00 eq) at 25° C. The mixture was stirred at 25° C. for 16 hour. TLC showed reactant consumed completely, desired product was observed, quenched with NaHCO₃ solution (500 mL), extracted with DCM (200 mL×3), dried over Na₂SO₄, concentrated to give a residue (8.95 g, crude) as a yellow solid, which was used directly in next step.

Intermediate 134: (2R,3R,4S)-3-(4-bromophenyl)-4-(hydroxymethyl)azetidine-2-carbonitrile A mixture of Intermediate 133 (8.95 g, 29.14 mmol, 1.00 eq), 1,3-dimethyl barbituric acid (6.82 g, 43.71 mmol, 1.50 eq), Pd(PPh₃)₄ (3.37 g, 2.91 mmol, 0.10 eq) in EtOH (290.00 mL) was degassed and purged with N₂ for 3 times, and then the mixture was stirred at 40° C. for 16 hour under N₂ atmosphere. LCMS showed reactant 133 consumed completely, desired MS was observed, concentrated to give a residue. The residue was purified by prep-HPLC (column: Waters Xbridge Prep OBD C18 150*30 5u; A: water (10 mM NH₄HCO₃); B: acetonitrile) to give Intermediate 134 (4.70 g, 17.60 mmol, 60.38% yield) as an orange solid.

Intermediate 135: (2R,3R,4S)-3-(4-bromophenyl)-4-(hydroxymethyl)-1-(1-methylallyl)azetidine-2-carbonitrile To a solution of Intermediate 134 (1.60 g, 5.99 mmol, 1.00 eq) in THF (3.50 mL) was added P(OEt)₃ (39.81 mg, 239.59 μmol, 41.04 μL, 0.04 eq), (E)-but-2-en-1-yl acetate (724.70 mg, 6.35 mmol, 1.06 eq), allyl(chloro)palladium (21.92 mg, 59.90 μmol, 0.01 eq) and DBU (911.89 mg, 5.99 mmol, 902.86 μL, 1.00 eq), the mixture was degassed and purged with N₂ for 3 times, and then the mixture was stirred at 40° C. for 16 hr under N₂ atmosphere. The reaction was quenched with water (15 mL), extracted with DCM (20 mL×3), dried over Na₂SO₄, concentrated to give a residue. The residue was purified by column chromatography (SiO₂, petroleum ether/ethyl acetate=10/1 to 0:1) to give Intermediate 135 (150.00 mg, 466.98 μmol, 7.80% yield) as a white solid. $^1$H NMR (400 MHz, METHANOL-d₄) δ=1.20 (dd, J=11.04, 6.53 Hz, 3H) 3.11 (quin, J=7.03 Hz, 1H) 3.43-3.55 (m, 2H) 3.59-3.67 (m, 1H) 3.80-3.92 (m, 1H) 4.04-4.15 (m, 1H) 4.35 (d, J=8.53 Hz, 1H) 4.41 (d, J=8.53 Hz, 1H) 5.05-5.41 (m, 2H) 5.64-5.91 (m, 1H) 7.47-7.52 (m, 2H) 7.52-7.56 (m, 2H).

Intermediate 136: (2R,3R,4S)-3-(4-bromophenyl)-4-[[tert-butyl(dimethyl)silyl]oxymethyl]-1-(1-methylallyl)azetidine-2-carbonitrile To a solution of Intermediate 135 (1.23 g, 3.83 mmol, 1.00 eq) in DMF (6.00 mL) was added imidazole (1.56 g, 22.98 mmol, 6.00 eq) and TBSCl (2.31 g, 15.32 mmol, 1.88 mL, 4.00 eq). The mixture was stirred at 25° C. for 16 hour. LCMS showed reactant consumed completely, desired MS was observed, washed with water (30 mL), extracted with ethyl acetate (30 mL×3), dried over Na₂SO₄, concentrated to give a residue. The residue was purified by column chromatography (SiO₂, petroleum ether/ethyl acetate=100/1 to 10:1) to give Intermediate 136 (1.60 g, 3.67 mmol, 95.93% yield) as a white solid. $^1$H NMR (400 MHz, METHANOL-d₄) δ ppm −0.36-−0.13 (m, 7H) 0.69-0.77 (m, 9H) 1.19 (dd, J=18.57, 6.53 Hz, 3H) 3.04-3.17 (m, 1H) 3.39-3.47 (m, 1H) 3.53-3.59 (m, 1H) 3.61-3.72 (m, 1H) 3.82-3.92 (m, 1H)

4.33-4.44 (m, 1H) 5.07-5.35 (m, 2H) 5.61-5.85 (m, 1H) 7.46-7.50 (m, 2H) 7.52-7.56 (m, 2H).

Intermediate 137: [(2R,3R,4S)-3-(4-bromophenyl)-4-[[tert-butyl(dimethyl)silyl]oxymethyl]-1-(1-methylallyl)azetidin-2-yl]methanamine To a solution of Intermediate 136 (1.85 g, 4.25 mmol, 1.00 eq) in THF (200.00 mL) was added LiBHEt$_3$ (1 M, 5.06 mL, 10.00 eq) at 0° C. under N$_2$ atmosphere. The mixture was stirred at 25° C. for 2 hours. LCMS showed reactant 136 consumed completely, desired MS was observed, quenched with H$_2$O (100 mL), extracted with ethyl acetate (300 mL×3), concentrated to give a residue. The residue was purified by column chromatography (SiO$_2$, DCM/MeOH=1/0 to 10:1) to give Intermediate 137 (1.40 g, 3.19 mmol, 74.95% yield) as an oil.

Intermediate 138: N-[[(2R,3R,4S)-3-(4-bromophenyl)-4-[[tert-butyl(dimethyl)silyl]oxymethyl]-1-(1-methylallyl)azetidin-2-yl]methyl]-2-nitro-benzenesulfonamide To a solution of Intermediate 138 (1.36 g, 3.09 mmol, 1.00 eq) in THF (55.00 mL) was added TEA (9.91 g, 97.95 mmol, 13.58 mL, 31.70 eq) and 2-nitrobenzenesulfonyl chloride (2.05 g, 9.27 mmol, 3.00 eq) at 0° C. The mixture was stirred at 25° C. for 2 hours. LCMS showed reactant 1 consumed completely, desired MS was observed, concentrated to give a residue. The residue was purified by column chromatography (SiO$_2$, petroleum ether/ethyl acetate=20/1 to 5:1) to give Intermediate 138 (1.93 g, crude) as a yellow oil.

Intermediate 139: N-allyl-N-[[(2R,3R,4S)-3-(4-bromophenyl)-4-[[tert-butyl(dimethyl)silyl]oxymethyl]-1-(1-methylallyl)azetidin-2-yl]methyl]-2-nitro-benzenesulfonamide To a solution of Intermediate 138 (1.95 g, 3.12 mmol, 1.00 eq) in DMF (15.00 mL) was added K$_2$CO$_3$ (647.17 mg, 4.68 mmol, 1.50 eq), then 3-bromoprop-1-ene (1.13 g, 9.36 mmol, 808.84 µL, 3.00 eq) was added. The mixture was stirred at 25° C. for 16 hour. LCMS showed reactant 138 consumed completely, desired MS was observed, washed with brine (20 mL×3), extracted with ethyl acetate (20 mL×3), dried over Na$_2$SO$_4$, concentrated to give a residue. The residue was purified by column chromatography (SiO$_2$, petroleum ether/ethyl acetate=20/1 to 5:1) to give Intermediate 139 (1.90 g, 2.86 mmol, 91.61% yield as a yellow gum. $^1$H NMR (400 MHz, CHLOROFORM-d) δ=ppm −0.34-−0.27 (m, 3H) −0.23-−0.18 (m, 3H) 0.70-0.75 (m, 9H) 1.14 (dd, J=16.76, 6.62 Hz, 3H) 3.11-3.42 (m, 5H) 3.15-3.79 (m, 6H) 4.69-4.82 (m, 1H) 4.93-5.04 (m, 1H) 5.05-5.22 (m, 2H) 5.28-5.50 (m, 1H) 5.67-5.81 (m, 1H) 7.32 (d, J=8.38 Hz, 2H) 7.43 (dd, J=8.38, 1.32 Hz, 2H) 7.52-7.62 (m, 3H) 7.62-7.70 (m, 1H).

Intermediate 140: [(3Z,8R,9R,10S)-9-(4-bromophenyl)-2-methyl-6-(2-nitrophenyl)sulfonyl-1,6-diazabicyclo[6.2.0]dec-3-en-10-yl]methoxy-tert-butyl-dimethyl-silane To a solution of Intermediate 139 (1.84 g, 2.77 mmol, 1.00 eq) in DCE (368.00 mL) was added Hoveyda-Grubbs Catalyst 1$^{st}$ Generation (569.51 mg, 692.50 µmol, 0.25 eq). The mixture was stirred at 90° C. for 16 hour. The reaction mixture was filtered and concentrated under reduced pressure to give a residue. The residue was purified by prep-TLC (SiO$_2$, petroleum ether/ethyl acetate=5:1). Intermediate 140 (1.25 g, 1.96 mmol, 70.88% yield) as a light black solid.

Intermediate 141: [(8R,9R,10S)-9-(4-bromophenyl)-2-methyl-6-(2-nitrophenyl)sulfonyl-1,6-diazabicyclo[6.2.0]decan-10-yl]methoxy-tert-butyl-dimethyl-silane To a solution of Intermediate 140 (1.00 g, 1.57 mmol, 1.00 eq) in THF (40.00 mL) was added TEA (1.43 g, 14.13 mmol, 1.96 mL, 9.00 eq) and 2-nitrobenzenesulfonohydrazide (1.02 g, 4.71 mmol, 3.00 eq). The mixture was stirred at 40° C. in an oil bath for 16 h. LCMS showed reactant 140 consumed completely, the majority was the desired product. The reaction mixture was quenched with a saturated solution of NaHCO$_3$ (20 mL) and extracted three times with ethyl acetate (30 mL×3). The combined organic extracts were dried over MgSO$_4$, filtered, and concentrated under reduced pressure to provide the crude product. The residue was purified by column chromatography (SiO$_2$, petroleum ether/ethyl acetate=20/1 to 5:1) to give Intermediate 141 (830.00 mg, 1.04 mmol, 66.22% yield, 80% purity) as a yellow solid. $^1$H NMR (400 MHz, CHLOROFORM-d) δ=ppm −0.29-−0.08 (m, 6H) 0.75 (d, J=14.05 Hz, 9H) 1.03-1.17 (m, 2H) 1.36-1.48 (m, 1H) 1.71-2.17 (m, 3H) 2.62 (br. s., 1H) 2.75-2.94 (m, 1H) 3.00-3.29 (m, 2H) 3.37-3.48 (m, 1H) 3.49-3.67 (m, 3H) 3.69-3.87 (m, 2H) 7.28-7.46 (m, 4H) 7.53-7.66 (m, 3H) 7.78 (d, J=6.02 Hz, 1H)

Intermediate 142: [(8R,9R,10S)-9-(4-bromophenyl)-2-methyl-1,6-diazabicyclo[6.2.0]decan-10-yl]methoxy-tert-butyl-dimethyl-silane To a solution of Intermediate 141 (830.00 mg, 1.30 mmol, 1.00 eq) in CH$_3$CN (8.00 mL) was added Cs$_2$CO$_3$ (508.28 mg, 1.56 mmol, 1.20 eq) and benzenethiol (214.77 mg, 1.95 mmol, 198.86 µL, 1.50 eq). After stirring at 20° C. for 16 hour, the reaction was diluted with water (15 mL), extracted with ethyl acetate (15 mL×3), dried over Na$_2$SO$_4$, concentrated to give a residue. The residue was purified by prep-TLC (SiO$_2$, petroleum ether/ethyl acetate=5:1) to give Intermediate 142 (580.00 mg, 1.02 mmol, 78.70% yield, 80% purity) as a yellow solid Intermediate 143: (8R,9R,10S)-9-(4-bromophenyl)-10-[[tert-butyl(dimethyl)silyl]oxymethyl]-N-(4-methoxyphenyl)-2-methyl-1,6-diazabicyclo[6.2.0]decane-6-carboxamide To a solution of Intermediate 142 (550.00 mg, 1.21 mmol, 1.00 eq) in DCM (10.00 mL) was added TEA (61.36 mg, 606.35 µmol, 84.05 µL, 0.50 eq) and 1-isocyanato-4-methoxy-benzene (180.88 mg, 1.21 mmol, 155.93 µL, 1.00 eq) at 0° C. After stirring at 20° C. for 3 hour, the reaction was diluted with water (10 mL), extracted with DCM (20 mL×3), dried over Na$_2$SO$_4$, concentrated to give a residue. The residue was purified by column chromatography (SiO$_2$, petroleum ether/ethyl acetate=10/1 to 5:1) to give Intermediate 143 (700.00 mg, 1.16 mmol, 95.99% yield) as a yellow solid.

Intermediate 144: (8R,9R,10S)-9-(4-bromophenyl)-10-(hydroxymethyl)-N-(4-methoxyphenyl)-2-methyl-1,6-diazabicyclo[6.2.0]decane-6-carboxamide To a solution of Intermediate 143 (690.00 mg, 1.14 mmol, 1.00 eq) in THF (10.00 mL) was added TBAF (596.13 mg, 2.28 mmol, 2.00 eq). The mixture was stirred at 50° C. for 16 hour. TLC showed reactant 1 consumed completely, desired product was observed, washed with water (10 mL×3), extracted with ethyl acetate (20 mL×3), dried over Na$_2$SO$_4$, concentrated to give a residue. The residue was purified by column chromatography (SiO$_2$, DCM/MeOH=1/0 to 20:1) to give Intermediate 144 (440.00 mg, 900.86 μmol, 79.02% yield) as a yellow solid. $^1$H NMR (400 MHz, CHLOROFORM-d) δ=ppm 1.09 (d, J=6.53 Hz, 3H) 1.40 (d, J=16.56 Hz, 1H) 1.77-1.99 (m, 2H) 2.72-2.90 (m, 2H) 3.51 (d, J=6.02 Hz, 1H) 3.57-3.69 (m, 4H) 3.71-3.80 (m, 4H) 3.81-3.94 (m, 2H) 6.02-6.08 (m, 1H) 6.79-6.87 (m, 2H) 7.24 (d, J=9.03 Hz, 2H) 7.36-7.43 (m, 2H) 7.43-7.49 (m, 2H)

Intermediate 145: (8R,9S,10S)-9-(4-bromophenyl)-10-[(1,3-dioxo-3a,7a-dihydroisoindol-2-yl)methyl]-N-(4-methoxyphenyl)-2-methyl-1,6-diazabicyclo[6.2.0]decane-6-carboxamide To a solution of Intermediate 144 (420.00 mg, 859.92 μmol, 1.00 eq) in THF (18.00 mL) was added isoindoline-1,3-dione (189.78 mg, 1.29 mmol, 1.50 eq), PPh$_3$ (451.09 mg, 1.72 mmol, 2.00 eq) and DIAD (347.77 mg, 1.72 mmol, 334.39 μL, 2.00 eq) at 0° C. The mixture was stirred at 25° C. for 16 hour. LCMS showed reactant 145 consumed completely, the majority was the desired product, washed with water (10 mL), extracted with ethyl acetate (10 mL×3), dried over Na$_2$SO$_4$, concentrated to give a residue. The residue was purified by column chromatography (SiO$_2$, petroleum ether/ethyl acetate=5/1 to 1:1) to give Intermediate 145 (800.00 mg, 645.63 μmol, 75.08% yield, 50% purity) as a brown gum.

Intermediate 146: (8R,9S,10S)-10-(aminomethyl)-9-(4-bromophenyl)-N-(4-methoxyphenyl)-2-methyl-1,6-diazabicyclo[6.2.0]decane-6-carboxamide To a solution of Intermediate 145 (750.00 mg, 605.28 μmol, 1.00 eq) in EtOH (14.00 mL) was added NH$_2$NH$_2$·H$_2$O (30.30 mg, 605.28 μmol, 29.42 μL, 1.00 eq). The mixture was stirred at 80° C. for 2 hour. LCMS showed Intermediate 145 consumed completely, the majority was the desired product (Intermediate 146) washed with water (40 mL), extracted with ethyl acetate (30 mL×3), dried over Na$_2$SO$_4$, concentrated to give a residue. The residue was purified by column chromatography (SiO$_2$, DCM/MEOH=0/1 to 10:1) to give (10S,10aR)-9-amino-10-(4-bromophenyl)-N-(4-methoxyphenyl)-6-methyloctahydropyrrolo[1,2-a][1,4]diazocine-2 (1H)-carboxamide ("R146") (190 mg) ($^1$H NMR (400 MHz, CHLOROFORM-d) δ=ppm 0.97 (d, J=6.02 Hz, 1H) 1.14 (d, J=8.03 Hz, 2H) 1.25-1.48 (m, 2H) 1.87-2.09 (m, 2H) 2.72-2.84 (m, 1H) 3.01 (d, J=10.04 Hz, 1H) 3.15-3.23 (m, 1H) 3.28 (d, J=6.02 Hz, 1H) 3.45 (br. s., 1H) 3.62-4.11 (m, 7H) 6.82 (d, J=10.04 Hz, 2H) 7.18-7.25 (m, 2H) 7.29 (d, J=8.03 Hz, 2H) 7.49 (d, J=8.03 Hz, 2H)) as a yellow mixture solid and Intermediate 146 (40 mg) as a yellow solid ($^1$H NMR (400 MHz, CHLOROFORM-d)=ppm 0.99-1.16 (m, 3H) 1.44 (d, J=11.04 Hz, 1H) 1.87 (br. s., 3H) 2.66 (br. s., 1H) 2.80-2.91 (m, 1H) 2.92-3.00 (m, 1H) 3.01-3.15 (m, 1H) 3.38 (br. s., 1H) 3.59 (d, J=12.55 Hz, 2H) 3.67-3.84 (m, 6H) 6.14 (s, 1H) 6.81 (d, J=8.53 Hz, 2H) 7.20 (d, J=8.53 Hz, 2H) 7.34 (d, J=8.03 Hz, 2H) 7.46 (d, J=8.03 Hz, 2)). H).

Intermediate 147: (8R,9S,10S)-9-(4-bromophenyl)-10-((dimethylamino)methyl)-N-(4-methoxyphenyl)-2-methyl-1,6-diazabicyclo[6.2.0]decane-6-carboxamide To a solution of Compound 146 (15.00 mg, 21.54 umol, 1.00 eq) in DCM (3.00 mL) was added HCHO (17.48 mg, 215.42 umol, 16.04 uL, 37% purity, 10.00 eq) and MgSO$_4$ (51.86 mg, 430.83 umol, 20.00 eq) followed by NaBH(OAc)$_3$ (45.66 mg, 215.42 umol, 10.00 eq). After the mixture was stirred at 20° C. for 2 hour, the resulting mixture was filtered and the filtrate was concentrated. The residue was purified by prep-TLC (SiO$_2$, dichloromethane:methanol=20:1) to give compound 147 (5.00 mg, 7.76 umol, 36.02% yield, 80% purity) as a light yellow solid.

Synthesis of E34: (8R,9S,10S)-10-((dimethylamino)methyl)-N-(4-methoxyphenyl)-2-methyl-9-(4-(phenylethynyl)phenyl)-1,6-diazabicyclo[6.2.0]decane-6-carboxamide (E34)

To a solution of Intermediate 147 (5.00 mg, 9.70 μmol, 1.00 eq) in CH$_3$CN (500.00 μL) was added ethynylbenzene (2.97 mg, 29.10 μmol, 3.19 μL, 3.00 eq), Cs$_2$CO$_3$ (12.64 mg, 38.80 μmol, 4.00 eq), degassed with N$_2$ for 3 times, and then XPhos Pd G3 (821.04 ug, 0.97 μmol, 0.10 eq). After stirring at 70° C. for 3 h, the reaction was diluted with water (3 mL), extracted with ethyl acetate (5 mL×3), dried over Na$_2$SO$_4$, concentrated to give a residue. The residue was purified by prep-TLC (SiO$_2$, petroleum ether/ethyl acetate=1:1) to give compound E34 (5.00 mg, 9.32 μmol, 96.04% yield) as a light yellow solid. $^1$H NMR (400 MHz, CHLOROFORM-d) δ=ppm 1.16 (d, J=6.17 Hz, 3H) 1.70-1.94 (m, 4H) 2.01 (br. s., 6H) 2.42-2.66 (m, 3H) 2.83-2.94 (m, 1H) 3.47 (br. s., 2H) 3.53-3.62 (m, 1H) 3.65-3.82 (m, 6H) 6.04 (s, 1H) 6.83 (d, J=8.82 Hz, 2H) 7.24 (d, J=8.82 Hz, 2H) 7.33-7.39 (m, 3H) 7.39-7.44 (m, 2H) 7.50 (d, J=7.94 Hz, 2H) 7.53-7.57 (m, 2H).

Example 35: (8R,9R,10S)-10-(hydroxymethyl)-N-(4-methoxyphenyl)-2-methyl-9-[4-(2-phenylethynyl)phenyl]-1,6-diazabicyclo[6.2.0]decane-6-carboxamide ("E35")

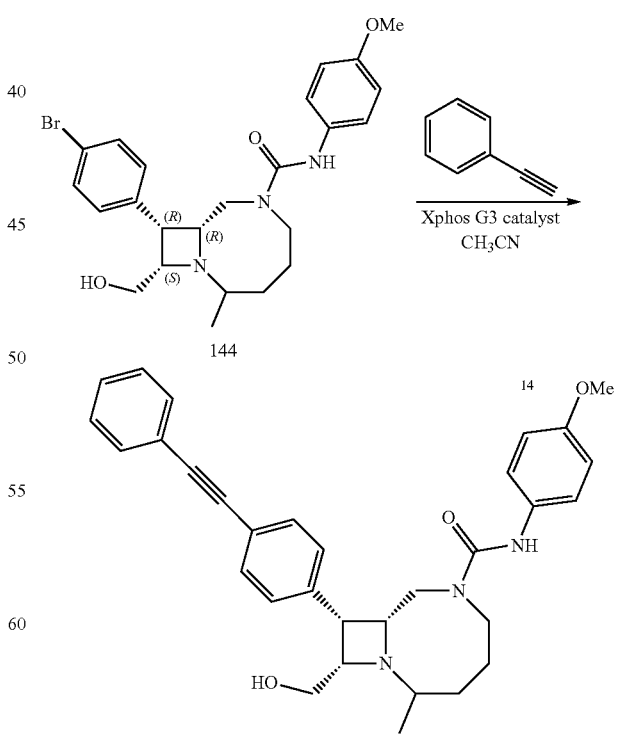

To a solution of Intermediate 144 (20.00 mg, 40.95 μmol, 1.00 eq) in CH$_3$CN (1.00 mL) was added ethynylbenzene (12.55 mg, 122.85 μmol, 13.49 μL, 3.00 eq), Cs$_2$CO$_3$ (53.37 mg, 163.80 μmol, 4.00 eq), degassed with N$_2$ for 3 times and then XPhos Pd G3 (3.47 mg, 4.10 μmol, 0.10 eq). The mixture was stirred at 70° C. for 16 hour. LCMS showed reactant 144 consumed completely, the majority was the desired product, washed with water (10 mL), extracted with ethyl acetate (10 mL×3), dried over Na$_2$SO$_4$, concentrated to give a residue. The residue was purified by prep-HPLC (column: Waters Xbridge Prep OBD C18 150*30 5u; A: water (10 mM NH$_4$HCO$_3$); B: acetonitrile) to give compound E35 (8.30 mg, 16.29 μmol, 39.77% yield) as a white solid. $^1$H NMR (400 MHz, CHLOROFORM-d) δ=1.10 (d, J=6.02 Hz, 3H) 1.40 (d, J=13.55 Hz, 1H) 1.76-2.01 (m, 3H) 2.72-3.03 (m, 1H) 2.76 (br. s., 1H) 3.43-3.81 (m, 9H) 3.82-3.96 (m, 2H) 6.03-6.11 (m, 1H) 6.80-6.88 (m, 2H) 7.24 (d, J=9.03 Hz, 2H) 7.32-7.40 (m, 3H) 7.48-7.56 (m, 6H).

Example 36: (3S,4R,8R,9S)-3,4-dihydroxy-N-(4-methoxyphenyl)-9-[4-(2-phenylethynyl)phenyl]-1,6-diazabicyclo[6.2.0]decane-6-carboxamide ("E36")

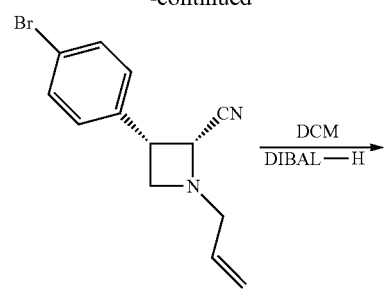

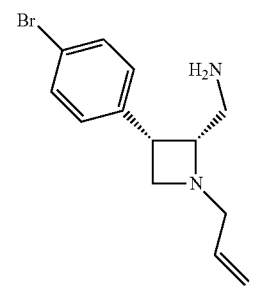

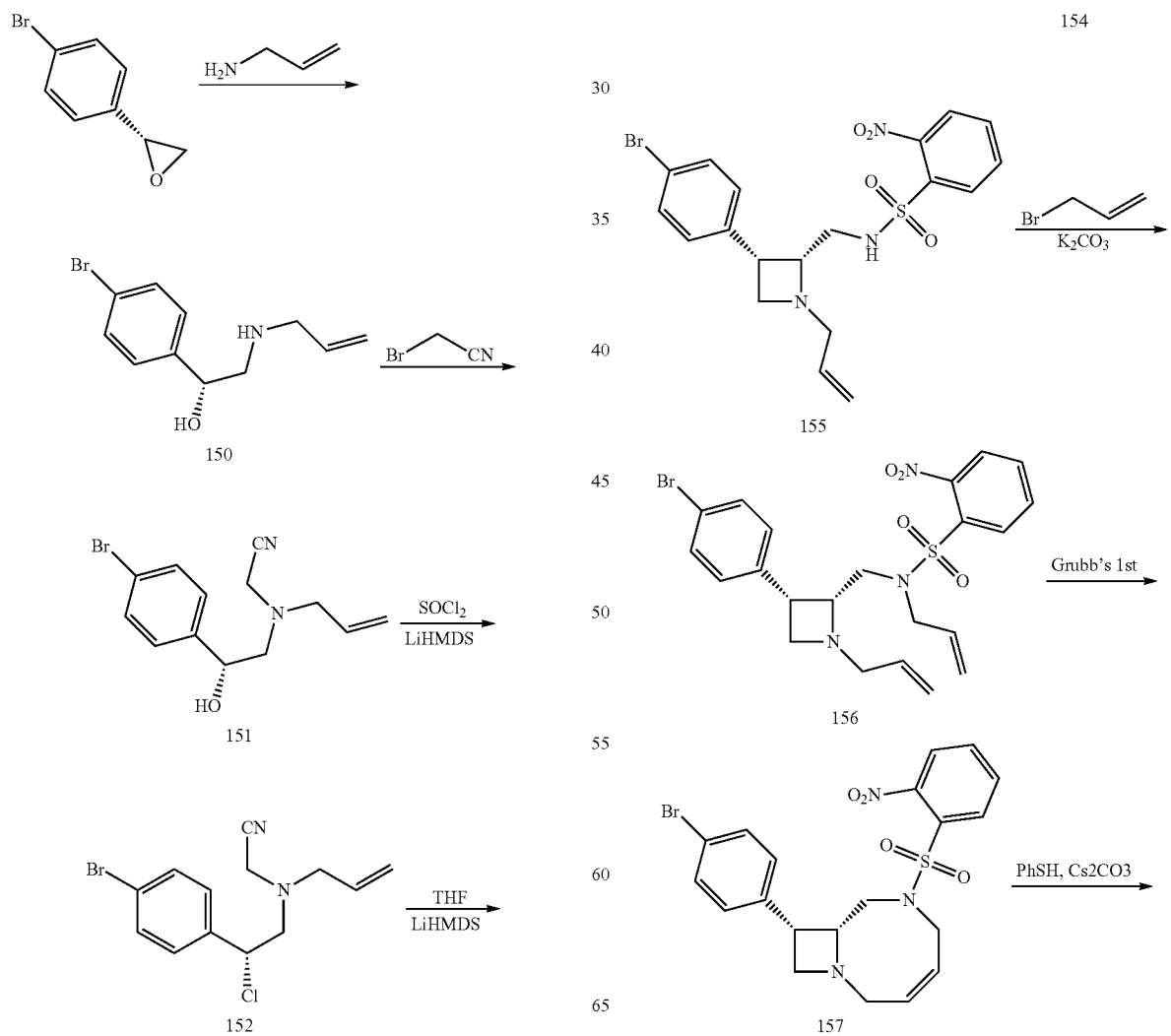

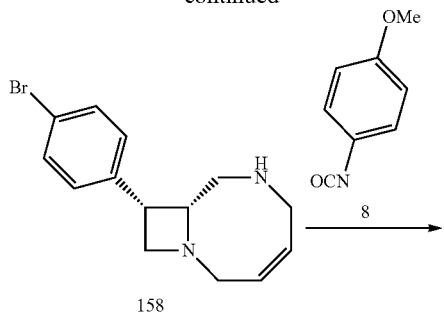

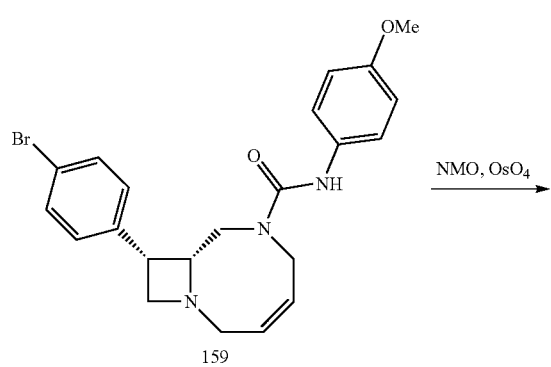

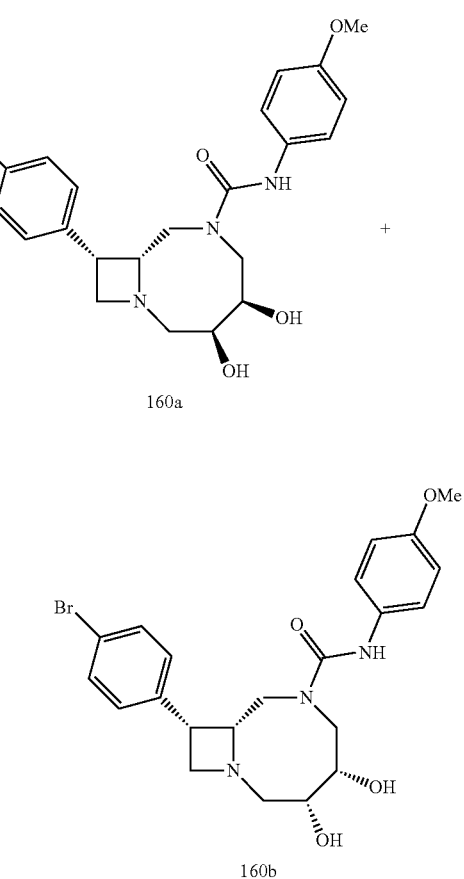

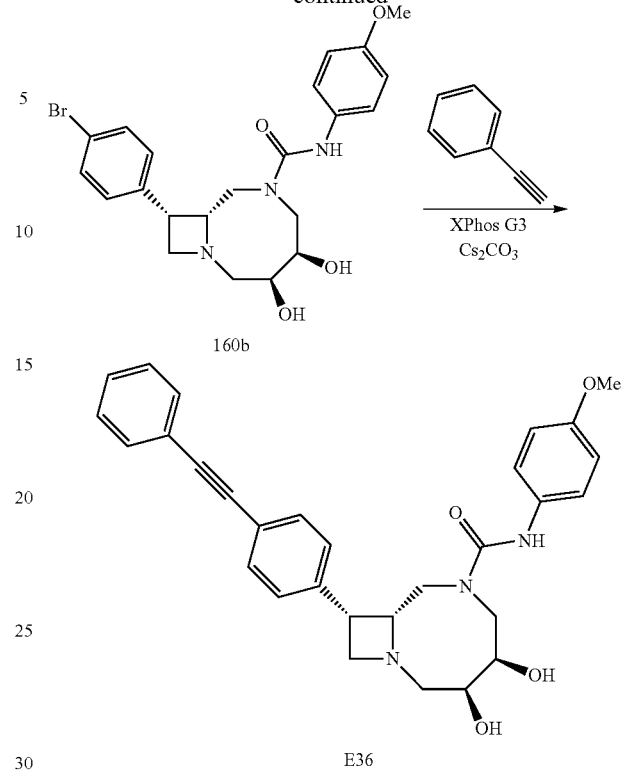

Intermediate 150: (R)-2-(allylamino)-1-(4-bromophenyl)ethan-1-ol

To a flask containing (R)-2-bromophenyl)oxirane (8.0 g, 40.2 mmol) was added allylamine (12.03 ml, 161 mmol). The mixture was stirred at 55° C. for 20 h. After this time analysis by LCMS indicated the reaction was complete and the mixture was cooled to room temperature and the organic solvent was evaporated under reduced pressure. Upon addition of hexane to the residue a white solid formed and was filtered and dried under high vacuum for 2 hours to afford the desired product (R)-2-(allylamino)-1-(4-bromophenyl)ethan-1-ol (9.66 g, 37.7 mmol, 94% yield) as a white solid. The reaction was carried on to the next step without further purification. $^1$H NMR (300 MHz, CDCl$_3$) δ 7.53-7.36 (m, 2H), 7.29-7.13 (m, 2H), 5.96-5.72 (m, 1H), 5.28-5.02 (m, 2H), 4.67 (dd, J=9.0, 3.6 Hz, 1H), 3.41-3.18 (m, 2H), 2.87 (dd, J=12.2, 3.6 Hz, 1H), 2.66 (dd, J=12.2, 8.9 Hz, 1H).

Intermediate 151: (R)-2-(allyl(2-(4-bromophenyl)-2-hydroxyethyl)amino)acetonitrile To a solution of (R)-2-(allylamino)-1-(4-bromophenyl)ethan-1-ol (9.66 g, 37.7 mmol) in anhydrous acetonitrile (60 ml) at room temperature was added K$_2$CO$_3$ (7.82 g, 56.6 mmol) and 2-bromoacetonitrile (7.88 ml, 113 mmol). The heterogeneous mixture was stirred at 85° C. under a nitrogen atmosphere for 18 h. After this time analysis by LCMS indicated the reaction was complete and the mixture was cooled to room temperature. The organic solvent was evaporated under reduced pressure, diluted with water (50 ml) and extracted with ethyl acetate. The combined organic components were dried over Na$_2$SO$_4$, filtered and concentrated under reduced pressure. The residue was purified by column chromatography (SiO$_2$, ethyl acetate/hexane=20-30%) to give (R)-2-(allyl(2-(4-bromophenyl)-2-hydroxyethyl)amino)acetonitrile (9 g, 30.5 mmol, 81% yield) as a pale yellow solid. $^1$H NMR (300 MHz, CDCl$_3$) δ 7.54-7.40 (m, 2H), 7.31-7.16 (m, 2H), 5.91-5.66 (m, 1H), 5.43-5.22 (m, 2H), 4.78-4.65 (m, 1H), 3.79-3.54 (m, 2H), 3.45-3.30 (m, 1H), 3.27-3.11 (m, 2H), 2.86-2.74 (m, 1H), 2.68-2.54 (m, 1H).

Intermediate 152: (R)-2-(allyl(2-(4-bromophenyl)-2-chloroethyl)amino)acetonitrile To a solution of pyridine (12.1 ml, 151 mmol) in anhydrous DMF (100 ml) at 0° C. was added thionyl chloride (4.38 ml, 60.3 mmol) dropwise. The mixture was stirred at 0° C. for 15 minutes. To this solution was added (R)-2-(allyl(2-(4-bromophenyl)-2-hydroxyethyl)amino)acetonitrile (8.9 g, 30.2 mmol) in DCM (10 ml) over 5 minutes. This mixture was stirred at 0° C. for 30 minutes upon which TLC analysis indicated that the reaction was complete. To the reaction mixture was added saturated aq. NaHCO$_3$ and the resulting solution was stirred vigorously for 10 min before being transferred to a separatory funnel. The layers were separated and the aqueous phase was extracted DCM and the combined organic extracts were washed with brine, dried with MgSO$_4$, filtered, and concentrated under reduced pressure to afford the crude product. The residue was purified by column chromatography (SiO$_2$, ethyl acetate/hexane=0-20%) to give the desired intermediate (5.00 g, 9.87 mmol, 92% yield) as a brown solid. $^1$H NMR (300 MHz, CDCl$_3$) δ ppm 7.57-7.42 (m, 2H), 7.32-7.23 (m, 2H), 5.84-5.58 (m, 1H), 5.37-5.14 (m, 2H), 4.91-4.71 (m, 1H), 3.65-3.38 (m, 2H), 3.26-2.94 (m, 4H).

Intermediate 153: (2R,3S)-1-allyl-3-(4-bromophenyl)azetidine-2-carbonitrile

A 100 ml round-bottomed flask was charged with (R)-2-(allyl(2-(4-bromophenyl)-2-chloroethyl)amino)acetonitrile (0.55 g, 1.754 mmol) and anhydrous THF (10 ml) to give a pale yellow solution. The flask was completely submerged in a dry ice/acetone bath and cooled to −50° C. LiHMDS (1M, THF solution) was added dropwise to this chilled solution. After complete addition, the reaction was stirred for 1 h at −50° C. LCMS and TLC analysis (20% EtOAc in hexanes, KMnO$_4$ staining) indicated complete disappearance of starting material. The reaction mixture was treated with saturated aq. NH$_4$Cl and the resulting solution was stirred vigorously for 10 min before being transferred to a separatory funnel. The layers were separated, the aqueous phase was extracted EtOAc and the combined organic extracts were washed with brine, dried with MgSO$_4$, filtered, and concentrated under reduced pressure to afford the crude product. The residue was purified by column chromatography (SiO$_2$, ethyl acetate/hexane=0-20%) to give two main sets of fractions. The first set of fractions (0.16 g, 0.577 mmol, 33% yield) gave the (2S,3S)-1-allyl-3-(4-bromophenyl)azetidine-2-carbonitrile side product. The second set of fractions (0.17 g, 0.613 mmol, 35% yield) solidified upon standing to give the desired product (2R,3S)-1-allyl-3-(4-bromophenyl)azetidine-2-carbonitrile. 1H NMR (300 MHz, CDCl$_3$) δ 7.59-7.45 (m, 2H), 7.36-7.28 (m, 2H), 5.91-5.69 (m, 1H), 5.36-5.14 (m, 2H), 4.39-4.26 (m, 1H), 3.87-3.75 (m, 1H), 3.60-3.40 (m, 2H), 3.31-3.18 (m, 2H).

Intermediate 154: ((2R,3S)-1-allyl-3-(4-bromophenyl)azetidin-2-yl)methanamine

To a solution of (2R,3S)-1-allyl-3-(4-bromophenyl)azetidine-2-carbonitrile (0.62 g, 2.25 mmol) in DCM (23 ml) and cooled to 0° C. with stirring was added DIBAL-H (2.41 ml, 13.51 mmol) slowly via syringe. After 15 minutes, the reaction was allowed to warm to room temperature over 45 min. After this time analysis by LCMS indicated the reaction was complete and the reaction was cooled to 0° C. and methanol (1.366 ml, 33.8 mmol) was added slowly. To this mixture was added Rochelle's solution (100 mL) slowly (care needed, exothermic). The aqueous phase was extracted with DCM and the combined organic phases were dried over MgSO$_4$ and concentrated under reduced pressure to give (2R,3S)-1-allyl-3-(4-bromophenyl)azetidine-2-carbonitrile as a yellow oil that was carried on to the next step without purification.

Intermediate 155: N-(((2R,3S)-1-allyl-3-(4-bromophenyl)azetidin-2-yl)methyl)-2-nitrobenzenesulfonamide To a solution of Intermediate 154 (1.454 g, 5.171 mmol) in DCM (26 ml) and cooled to 0° C. were added 2,6-lutidine (1.797 ml, 15.51 mmol) followed by 2-nitrobenzene-1-sulfonyl chloride (1.261 g, 5.69 mmol) in one portion. The solution was then allowed to warm to room temperature and stir for 16 h. To the reaction mixture was added water and the aqueous layer was extracted with DCM. The combined organic extracts were dried over MgSO$_4$, filtered, and concentrated under reduced pressure to provide the crude product. The residue was purified by column chromatography (SiO$_2$, ethyl acetate/hexane=0-20%) to give Intermediate 155 (2.4 g, 100% yield).

Intermediate 156: N-allyl-N-[[(2R,3S)-1-allyl-3-(4-bromophenyl)azetidin-2-yl]methyl]-2-nitro-benzenesulfonamide To a solution of Intermediate 155 (5.00 g, 10.72 mmol, 1.00 eq) in DMF (10.00 mL) was added K$_2$CO$_3$ (2.22 g, 16.08 mmol, 1.50 eq) and 3-bromoprop-1-ene (1.95 g, 16.08 mmol, 1.39 mL, 1.50 eq). The mixture was stirred at 25° C. for 16 hour. LCMS showed reactant 156 consumed completely, the majority was the desired product, the reaction mixture was dissolved in water (100 mL), extracted with DCM (20 mL×3), the organic layer was dried over Na$_2$SO$_4$, then concentrated to give a residue. The residue was purified by column chromatography (SiO$_2$, petroleum ether/ethyl acetate=10/1 to 5:1) to give Intermediate 156 (5.00 g, 9.87 mmol, 92.10% yield) was obtained as a brown solid. $^1$H NMR (400 MHz, CHLOROFORM-d) δ ppm 2.53 (s, 1H) 2.90 (dd, J=13.80, 6.65 Hz, 1H) 2.94-3.11 (m, 2H) 3.18-3.26 (m, 1H) 3.33 (dd, J=7.34, 2.20 Hz, 1H) 3.41 (dd, J=13.80, 5.14 Hz, 1H) 3.47-3.63 (m, 2H) 3.65-3.75 (m, 1H) 3.88 (dd, J=16.00, 5.96 Hz, 1H) 4.95 (dd, J=17.07, 1.13 Hz, 1H) 5.03-5.14 (m, 2H) 5.21 (dd, J=17.19, 1.51 Hz, 1H) 5.48 (ddt, J=16.89, 10.43, 6.23, 6.23 Hz, 1H) 5.64-5.87 (m, 1H) 7.35-7.40 (m, 2H) 7.42-7.49 (m, 2H) 7.55-7.62 (m, 2H) 7.64-7.72 (m, 2H)

Intermediate 157: (3Z,8R,9S)-9-(4-bromophenyl)-6-(2-nitrophenyl)sulfonyl-1,6-diazabicyclo[6.2.0]dec-3-ene To a solution of Intermediate 156 (5.00 g, 9.87 mmol, 1.00 eq) in toluene (500.00 mL) was added Hoveyda-Grubbs Catalyst 1$^{st}$ Generation (812 mg) under N$_2$ atmosphere. The mixture was stirred at 60° C. in an oil bath for 16 h. Additional Hoveyda-Grubbs Catalyst 1$^{st}$ Generation (1218 mg) was added, stirred for 16 h more. The reaction mixture was concentrated to give a residue. The residue was purified by column chromatography (SiO$_2$, petroleum ether/ethyl acetate=5/1 to 0:1) to give Intermediate 157 (1.20 g, 1.25 mmol, 12.71% yield, 50% purity) as a black solid along with recovered SM (2.2 g). $^1$H NMR (400 MHz, CHLOROFORM-d) δ ppm 2.62 (br s, 1H) 3.15-3.31 (m, 2H) 3.38 (br s, 1H) 3.52 (br d, J=16.98 Hz, 1H) 3.60-3.79 (m, 3H) 3.82-3.95 (m, 1H) 4.03 (br dd, J=14.33, 6.62 Hz, 1H) 5.58-5.67 (m, 1H) 5.68-5.81 (m, 1H) 7.30 (br d, J=7.94 Hz, 2H) 7.45 (br d, J=8.16 Hz, 2H) 7.56 (br d, J=7.28 Hz, 1H) 7.61-7.67 (m, 2H) 7.83 (br d, J=7.50 Hz, 1H).

Intermediate 158: (3Z,8R,9S)-9-(4-bromophenyl)-1,6-diazabicyclo[6.2.0]dec-3-ene

To a solution of Intermediate 157 (1.70 g, 1.78 mmol, 1.00 eq) in CH$_3$CN (17.00 mL) was added benzenethiol (293.67 mg, 2.67 mmol, 271.92 μL, 1.50 eq) and Cs$_2$CO$_3$ (694.74 mg, 2.13 mmol, 1.20 eq). After stirring at 40° C. for 16 hour, the reaction mixture was dissolved in water (100 mL), extracted with DCM (30 mL×3), the organic layer was dried over Na$_2$SO$_4$, then concentrated to give a residue. The residue was purified by column chromatography (SiO$_2$, petroleum ether/ethyl acetate=1/1 to dichloromethane:methanol=10:1) to give Intermediate 158 (650.00 mg, 1.55 mmol, 87.18% yield, 70% purity) as a black oil. $^1$H NMR (400 MHz, CHLOROFORM-d) δ ppm 2.42-2.50 (m, 1H) 2.52-2.61 (m, 1H) 2.77-3.10 (m, 3H) 3.22 (br dd, J=16.22, 4.38 Hz, 1H) 3.36-3.50 (m, 3H) 3.53-3.69 (m, 3H) 3.77 (br t, J=8.99 Hz, 1H) 5.67-5.86 (m, 2H) 7.21-7.28 (m, 2H) 7.44 (d, J=8.33 Hz, 2H).

Intermediate 159: (3Z,8R,9S)-9-(4-bromophenyl)-N-(4-methoxyphenyl)-1,6-diazabicyclo[6.2.0]dec-3-ene-6-carboxamide To a solution of Intermediate 158 (650.00 mg, 1.55 mmol, 1.00 eq) in DCM (10.00 mL) was added TEA (78.52 mg, 775.92 μmol, 107.56 μL, 0.50 eq) and then 1-isocyanato-4-methoxy-benzene (277.75 mg, 1.86 mmol, 239.44 μL, 1.20 eq) was added at 20° C. under N$_2$ atmosphere. The mixture was stirred at 20° C. for 1 hour. LCMS showed reactant 158 consumed completely, the majority was the desired product, the reaction mixture was dissolved in water (10 mL), extracted with DCM (5 mL×3), the organic layer was dried over Na$_2$SO$_4$, then concentrated to give a residue. The residue was purified by column chromatography (SiO$_2$, petroleum ether/ethyl acetate=5/1 to 1:1) to give Intermediate 159 (560.00 mg, 1.27 mmol, 81.84% yield) as a white solid. $^1$H NMR (400 MHz, CHLOROFORM-d) δ ppm 2.37-2.56 (m, 1H) 3.24-3.33 (m, 1H) 3.34-3.41 (m, 1H) 3.42-3.53 (m, 1H) 3.54-3.64 (m, 2H) 3.68-3.74 (m, 2H) 3.77 (s, 3H) 3.86 (br dd, J=15.88, 7.28 Hz, 1H) 4.17 (br d, J=15.44 Hz, 1H) 5.64 (br d, J=11.69 Hz, 1H) 5.74-5.91 (m, 1H) 6.06 (s, 1H) 6.82 (d, J=8.82 Hz, 2H) 7.22 (d, J=9.04 Hz, 2H) 7.34 (d, J=8.16 Hz, 2H) 7.48 (d, J=8.38 Hz, 2H).

Intermediate 160a and 160b: (3S,4R,8R,9S)-9-(4-bromophenyl)-3,4-dihydroxy-N-(4-methoxyphenyl)-1,6-diazabicyclo[6.2.0]decane-6-carboxamide (160a); (3R,4S,8R,9S)-9-(4-bromophenyl)-3,4-dihydroxy-N-(4-methoxyphenyl)-1,6-diazabicyclo[6.2.0]decane-6-carboxamide (160b)

To a solution of Intermediate 159 (500.00 mg, 1.13 mmol, 1.00 eq) in acetone (5.00 mL) and H$_2$O (500.00 μL) was added NMO (198.63 mg, 1.69 mmol, 178.95 μL, 1.50 eq) and OsO$_4$ (2.87 mg, 11.30 μmol, 0.59 μL, 0.01 eq) at −78° C. The resulting reaction mixture was then allowed to stir at 20° C. for 0.5 h. TLC showed reactant consumed completely, two desired products were observed, the reaction mixture was concentrated to give a residue. The residue was purified by prep-TLC (SiO$_2$, petroleum ether/ethyl acetate). Intermediate 160a (100.00 mg, 209.93 μmol, 61.92% yield) was obtained as a white solid ($^1$H NMR (400 MHz, CHLOROFORM-d) δ ppm 2.17-2.37 (m, 1H) 2.63 (br d, J=13.16 Hz, 1H) 2.90 (br dd, J=13.37, 8.55 Hz, 1H) 3.23 (br d, J=15.79 Hz, 1H) 3.39-3.45 (m, 1H) 3.46-3.52 (m, 2H) 3.58 (br d, J=5.26 Hz, 2H) 3.73-3.83 (m, 5H) 3.95 (br s, 1H) 4.11 (br dd, J=15.57, 5.04 Hz, 1H) 4.25 (br s, 1H) 6.81 (d, J=8.77 Hz, 2H) 7.16 (d, J=8.77 Hz, 2H) 7.32 (d, J=8.33 Hz, 2H) 7.44 (d, J=8.33 Hz, 2H) 7.92 (br s, 1H)) and Intermediate 160b (275.00 mg, 577.29 μmol, 72.98% yield) as a white solid ($^1$H NMR (400 MHz, CHLOROFORM-d) δ ppm 2.27 (br s, 1H) 2.79 (br d, J=14.03 Hz, 1H) 2.93-3.05 (m, 1H) 3.27-3.52 (m, 3H) 3.45-3.52 (m, 3H) 3.54-3.70 (m, 5H) 3.73-3.82 (m, 4H) 6.79 (d, J=9.21 Hz, 2H) 7.21 (d, J=8.77 Hz, 2H) 7.25-7.30 (m, 1H) 7.27 (d, J=6.82 Hz, 1H) 7.28-7.31 (m, 1H) 7.47 (d, J=8.33 Hz, 2H)).

Synthesis of E36: (3S,4R,8R,9S)-3,4-dihydroxy-N-(4-methoxyphenyl)-9-[4-(2-phenylethynyl)phenyl]-1,6-diazabicyclo[6.2.0]decane-6-carboxamide (E36)

To a solution of Intermediate 160a (10.00 mg, 20.99 μmol, 1.00 eq), ethynylbenzene (6.43 mg, 62.97 μmol, 6.91 μL, 3.00 eq) in CH$_3$CN (150.00 μL) was added Cs$_2$CO$_3$ (27.36 mg, 83.96 μmol, 4.00 eq) and Xphos Pd G3 (1.78 mg, 2.10 μmol, 0.10 eq) under N$_2$ atmosphere. The mixture was stirred at 70° C. for 1 hour. LCMS showed reactant 1 consumed completely, the majority was the desired product. The reaction mixture was filtered, the filter cake was washed with DCM (10 mL), the filtrate was concentrated to give a residue. The residue was purified by prep-TLC (SiO$_2$, petroleum ether/ethyl acetate=1:1) and then further purified by pre-HPLC (Column: Waters Xbridge Prep OBD C18 150*30 5u; A: water (0.225% formic acid) B: acetonitrile) to give compound E36 (4.00 mg, 8.04 μmol, 38.30% yield) as a white solid. $^1$H NMR (400 MHz, CHLOROFORM-d) δ ppm 2.31-2.44 (m, 1H) 2.73 (br d, J=13.45 Hz, 1H) 2.92-2.99 (m, 1H) 3.33 (br d, J=15.66 Hz, 1H) 3.57 (br t, J=7.39 Hz, 2H) 3.70 (br d, J=4.63 Hz, 1H) 3.75-3.85 (m, 4H) 3.87-3.94 (m, 1H) 4.00 (br s, 1H) 4.16 (br d, J=16.32 Hz, 1H) 6.83 (br d, J=8.82 Hz, 2H) 7.21 (br d, J=8.82 Hz, 2H) 7.35 (br s, 3H) 7.44 (br d, J=7.94 Hz, 2H) 7.49-7.59 (m, 4H) 7.82 (br s, 1H).

Example 37: (3R,4S,8R,9S)-3,4-dihydroxy-N-(4-methoxyphenyl)-9-[4-(2-phenylethynyl)phenyl]-1,6-diazabicyclo[6.2.0]decane-6-carboxamide ("E37")

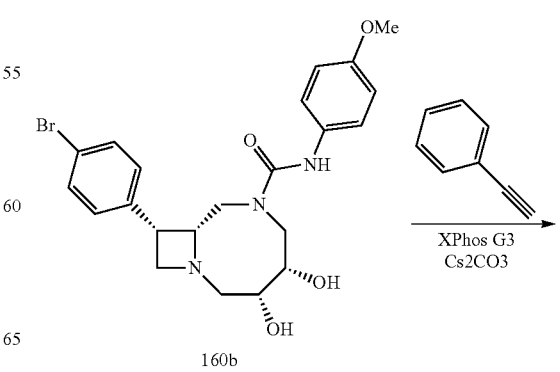

160b

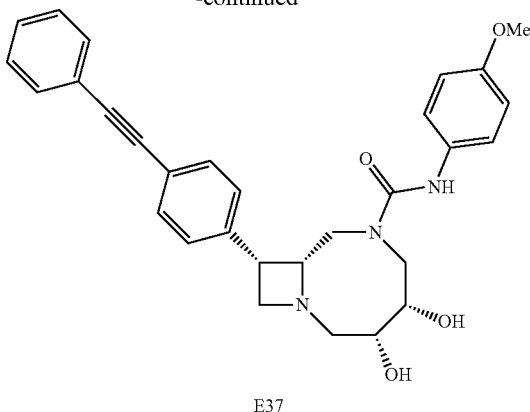

E37

To a stirred solution of Intermediate 160b (10.00 mg, 20.99 μmol, 1.00 eq), ethynylbenzene (6.43 mg, 62.98 μmol, 6.92 μL, 3.00 eq) in CH$_3$CN (150.00 μL) was added Cs$_2$CO$_3$ (27.36 mg, 83.97 μmol, 4.00 eq) and Xphos Pd G3 (1.78 mg, 2.10 μmol, 0.10 eq) under N$_2$ atmosphere. The mixture was stirred at 70° C. for 1 hour. LCMS showed reactant 160b consumed completely, the majority was the desired product. The reaction mixture was filtered, the filter cake was washed with DCM (5 mL), the filtrate was concentrated to give a residue. The residue was purified by prep-TLC (SiO$_2$, petroleum ether/ethyl acetate=1:1), then further purified by pre-HPLC (Column: Waters Xbridge Prep OBD C18 150*30 5u; A: water (0.225% formic acid) B: acetonitrile) to give compound E37 (5.00 mg, 10.05 μmol, 47.87% yield) as a white solid. $^1$H NMR (400 MHz, CHLOROFORM-d) δ ppm 2.32 (br s, 1H) 2.60 (br s, 2H) 2.87 (br d, J=14.11 Hz, 1H) 3.06 (dd, J=14.00, 6.95 Hz, 1H) 3.29-3.48 (m, 2H) 3.57-3.65 (m, 2H) 3.71 (br d, J=5.51 Hz, 4H) 3.77 (s, 3H) 3.80-3.84 (m, 1H) 6.66 (br s, 1H) 6.82 (d, J=8.82 Hz, 2H) 7.20-7.26 (m, 2H) 7.27 (s, 1H) 7.33-7.43 (m, 5H) 7.49-7.57 (m, 4H).

Example 38: (3R,4S,8R,9S,10S)—N-(4-cyclopropoxyphenyl)-10-((dimethylamino)methyl)-3,4-dihydroxy-9-(4-(phenylethynyl)phenyl)-1,6-diazabicyclo[6.2.0]decane-6-carboxamide (E38)

The synthesis of compound E38 was performed in an otherwise identical synthetic route to the synthesis of compound E1 where Intermediate 4b was used in place of Intermediate 4a. The same reactions steps as described above were then followed Measurements of Biological Activity Example 39: In Vitro P. falciparum Blood-Stage Culture and Assay Strains of P. falciparum (Dd2, 3D7, D6, K1, NF54, V1/3, HB3, 7G8, FCB and TM90C2B) were obtained from the Malaria Research and Reference Reagent Resource Center (MR4). P. falciparum isolates were maintained with 0-positive human blood in an atmosphere of 93% N$_2$, 4% CO$_2$, 3% O$_2$ at 37° C. in complete culturing medium (10.4 g/L RPMI 1640, 5.94 g/L HEPES, 5 g/L albumax II, 50 mg/L hypoxanthine, 2.1 g/L sodium bicarbonate, 10% human serum and 43 mg/L gentamicin). Parasites were cultured in medium until parasitaemia reached 3-8%. Parasitaemia was determined by checking at least 500 red blood cells from a Giemsa-stained blood smear. For the compound screening, a parasite dilution at 2.0% parasitaemia and 2.0% haematocrit was created with medium. 25 μl of medium was dispensed into 384-well black, clear-bottom plates and 100 nl of each compound in DMSO was transferred into assay plates along with the control compound (mefloquine). Next, 25 μl of the parasite suspension in medium was dispensed into the assay plates giving a final parasitaemia of 1% and a final haematocrit of 1%. The assay plates were incubated for 72 h at 37° C. 10 μl of detection reagent consisting of 10×SYBR Green I (Invitrogen; supplied in 10,000× concentration) in lysis buffer (20 mM Tris-HCl, 5 mM EDTA, 0.16% (w/v) Saponin, 1.6% (v/v) Triton X-100) was dispensed into the assay plates. For optimal staining, the assay plates were left at room temperature for 24 h in the dark. The assay plates were read with 505 dichroic mirrors with 485 nm excitation and 530 nm emission settings in an Envision (PerkinElmer).

By following the above-described protocol, the 50% effective concentration (EC$_{50}$) for compounds E1-E38 was measured against P. falciparum Dd2 and the results are shown in Table 4 below as +++ for an EC$_{50}$ less than 50 nM, ++ for an EC$_{50}$ from 50 nM to 250 nM and + for an EC$_{50}$>250 nM.

TABLE 4

| Example | Pf Dd2 (nM) |
|---|---|
| E1 | +++ |
| E2 | +++ |
| E3 | + |
| E4 | +++ |
| E5 | +++ |
| E6 | +++ |
| E7 | +++ |
| E8 | ++ |
| E9 | +++ |
| E10 | +++ |
| E11 | ++ |
| E12 | ++ |
| E13 | +++ |
| E14 | +++ |
| E15 | +++ |
| E16 | + |
| E17 | +++ |
| E18 | + |
| E19 | ++ |
| E20 | + |
| E21 | + |
| E22 | + |
| E23 | ++ |
| E24 | + |
| E25 | ++ |
| E26 | +++ |
| E27 | +++ |
| E28 | ++ |
| E29 | ++ |
| E30 | + |
| E31 | + |
| E32 | + |
| E33 | +++ |
| E34 | +++ |
| E35 | +++ |
| E36 | ++ |
| E37 | ++ |
| E38 | +++ |

Example 40: In Vitro P. berghei Liver-Stage Assay

HepG2 cells (ATCC) were maintained in DMEM, 10% (v/v) FBS (Sigma), and 1% (v/v) antibiotic-antimycotic in a standard tissue culture incubator (37° C., 5% C$_{O2}$). P. berghei (ANKA GFP-luc) infected A. stephensi mosquitoes were obtained from the New York University Langone Medical Center Insectary. For assays, ~17,500 HepG2 cells per well were added to a 384-well microtitre plate in duplicate. After 18-24 h at 37° C. the media was exchanged and compounds were added. After 1 h, parasites obtained from freshly dissected mosquitoes were added to the plates (4,000 parasites per well), the plates were spun for 10 min at 1,000 r.p.m. and then incubated at 37° C. The final assay volume was 30 µl. After a 48-h incubation at 37° C., Bright-Glo (Promega) was added to the parasite plate to measure relative luminescence. The relative signal intensity of each plate was evaluated with an EnVision (PerkinElmer) system.

Example 41: In Vitro *P. falciparum* Liver-Stage Assay

Micropatterned co-culture (MPCC) is an in vitro co-culture system of primary human hepatocytes organized into colonies and surrounded by supportive stromal cells. Hepatocytes in this format maintain a functional phenotype for up to 4-6 weeks without proliferation, as assessed by major liver-specific functions and gene expression. In brief, 96-well plates were coated homogenously with rat-tail type I collagen (50 µg/mL) and subjected to soft-lithographic techniques to pattern the collagen into 500-µm-island microdomains that mediate selective hepatocyte adhesion. To create MPCCs, cryopreserved primary human hepatocytes (BioreclamationIVT) were pelleted by centrifugation at 100 g for 6 min at 4° C., assessed for viability using Trypan blue exclusion (typically 70-90%), and seeded on micropatterned collagen plates (each well contained ~10,000 hepatocytes organized into colonies of 500 µM) in serum-free DMEM with 1% penicillin-streptomycin. The cells were washed with serum-free DMEM with 1% penicillin-streptomycin 2-3 h later and replaced with human hepatocyte culture medium 48. 3T3-J2 mouse embryonic fibroblasts were seeded (7,000 cells per well) 24 h after hepatocyte seeding.

MPCCs were infected with 75,000 sporozoites (NF54) (Johns Hopkins University) 1 day after hepatocytes were seeded. After incubation at 37° C. and 5% CO2 for 3 h, wells were washed once with PBS, and the respective compounds were added. Cultures were dosed daily. Samples were fixed on day 3.5 after infection. For immunofluorescence staining, MPCCs were fixed with −20° C. methanol for 10 min at 4° C., washed twice with PBS, blocked with 2% BSA in PBS, and incubated with mouse anti-*P. falciparum* Hsp70 antibodies (clone 4C9, 2 µg/mL) for 1 h at room temperature. Samples were washed with PBS then incubated with Alexa 488-conjugated secondary goat anti-mouse for 1 h at room temperature. Samples were washed with PBS, counterstained with the DNA dye Hoechst 33258 (Invitrogen; 1:1,000), and mounted on glass slides with fluoromount G (Southern Biotech). Images were captured on a Nikon Eclipse Ti fluorescence microscope. Diameters of developing liver stage parasites were measured and used to calculate the corresponding area.

Example 42: *P. falciparum* Cytoplasmic PheRS Biochemical Assay

Protein sequences of both α-(PF3D7_0109800) and β-(PF3D7_1104000) subunits of cytoplasmic *P. falciparum* PheRS were obtained from PlasmoDB (http://plasmodb.org/plasmo/). Full length α- and β-subunit gene sequences optimized for expression in *E. coli* were cloned into pETM11 (Kanamycin resistance) and pETM20 (ampicillin resistance) expression vectors using Nco1 and Kpn1 sites and co-transformed into *E. coli* B834 cells. Protein expression was induced by addition of 0.5 mM isopropyl β-d-1-thiogalactopyranoside (IPTG) and cells were grown until an OD600 of 0.6-0.8 was reached at 37° C. They were then allowed to grow at 18° C. for 20 h after induction. Cells were separated by centrifugation at 5,000 g for 20 min and the bacterial pellets were suspended in a buffer consisting of 50 mM Tris-HCl (pH 7.5), 200 mM NaCl, 4 mM β-mercaptoethanol, 15% (v/v) glycerol, 0.1 mg/mL lysozyme and 1 mM phenylmethylsulfonyl fluoride (PMSF). Cells were lysed by sonication and cleared by centrifugation at 20,000 g for 1 h. The supernatant was applied on to prepacked NiNTA column (GE Healthcare), and bound proteins were eluted by gradient-mixing with elution buffer (50 mM Tris-HCl (pH 7.5), 80 mM NaCl, 4 mM β-mercaptoethanol, 15% (v/v) glycerol, 1 M imidazole). Pure fractions were pooled and loaded on to heparin column for further purification. Again, bound proteins were eluted using gradient of heparin elution buffer 50 mM Tris-HCl (pH 7.5), 1 M NaCl, 4 mM β-mercaptoethanol, 15% (v/v) glycerol). Pure fractions were again pooled and dialysed overnight into a buffer containing 50 mM Tris-HCl (pH 7.5), 200 mM NaCl, 4 mM (3-mercaptoethanol, 1 mM DTT and 0.5 mM EDTA. TEV protease (1:50 ratio of protease:protein) was added to the protein sample and incubated at 20° C. for 24 h to remove the polyhistidine tag. Protein was further purified via gel-filtration chromatography on a GE HiLoad 60/600 Superdex column in 50 mM Tris-HCl (pH 7.5), 200 mM NaCl, 4 mM β-mercaptoethanol, 1 mM $MgCl_2$. The eluted protein (a heterodimer of *P. falciparum* cPheRS) were collected, assessed for purity via SDS-PAGE and stored at −80° C.

Nuclear encoded tRNAPhe from *P. falciparum* was synthesized using an in vitro transcription method as described in Nature 538, 344-349 (20 Oct. 2016) doi:10.1038/nature19804. Aminoacylation and enzyme inhibition assays for *P. falciparum* cytosolic PheRS were performed as described in Biochem. J. 465, 459-469 (2015). Enzymatic assays were performed in buffer containing 30 mM HEPES (pH 7.5), 150 mM NaCl, 30 mM KCl, 50 mM MgCl2, 1 mM DTT, 100 µM ATP, 100 µM L-phenylalanine, 15 µM *P. falciparum* tRNAPhe, 2 U/mL *E. coli* inorganic pyrophosphatase (NEB) and 500 nM recombinant *P. falciparum* PheRS at 3° C. Reactions at different time points were stopped by the addition of 40 mM EDTA and subsequent transfer to ice. Recombinant maltose binding protein was used as negative control. The cPheRS inhibition assays were performed using inhibitor concentrations of 0.01 nM, 0.1 nM, 1 nM, 10 nM, 100 nM, 1 µM, 5 µM and 10 µM for strong binders and 1 nM, 10 nM, 100 nM, 1 µM, 10 µM, 100 µM and 500 µM for weaker binders in the assay buffer. Enzymatic and inhibition experiments were performed twice in triplicate.

Example 43: Mammalian Cell Cytotoxicity Assays

Mammalian cells (HepG2, A549, and HEK293) were obtained from the ATCC and cultured routinely in DMEM with 10% FBS and 1% (v/v) antibiotic-antimycotic. For cytotoxicity assays, $1 \times 10^6$ cells were seeded into 384-well plates 1 day before compound treatment. Cells were treated with ascending doses of compound for 72 h, and viability was measured using Cell-Titer Glo (Promega). All cell lines were tested for *Mycoplasma* contamination using Universal *mycoplasma* Detection Kit (ATCC).

Example 44: In Vitro ADME/PK and Safety Assays

In vitro characterization assays (protein binding, microsomal stability, hepatocyte stability, cytochrome P450

(CYP) inhibition, and aqueous solubility) were performed according to industry-standard techniques. Ion channel inhibition studies were performed using the Q-Patch system using standard techniques.

Example 45: In Vivo *P. berghei* Blood-Stage Assay

CD-1 mice (n=4 per experimental group; female; 6-7-week-old; 20-24 g, Charles River) were intravenously inoculated with approximately $1\times10^5$ *P. berghei* (ANKA GFP-luc) blood-stage parasites 24 h before treatment and compounds were administered orally (at 0 h). Parasitaemia was monitored by the in vivo imaging system (IVIS SpectrumCT, PerkinElmer) to acquire the bioluminescence signal (150 mg $kg^{-1}$ of luciferin was intraperitoneally injected approximately 10 min before imaging). In addition, blood smear samples were obtained from each mouse periodically, stained with Giemsa, and viewed under a microscope for visual detection of blood parasitaemia. Animals with parasitaemia exceeding 25% were humanely euthanized.

Example 46: In Vivo *P. berghei* Causal Prophylaxis Assay

CD-1 mice (n=4 per experimental group; female; 6-7-week-old; 20-24 g, Charles River) were inoculated intravenously with approximately $1\times10^5$ *P. berghei* (ANKA GFP-luc) sporozoites freshly dissected from *A. stephensi* mosquitoes. Immediately after infection, the mice were treated with single oral doses of Compound; infection was monitored as described for the *P. berghei* erythrocytic-stage assay. For time-course experiments, the time of compound treatment (single oral dose of 10 mg $kg^{-1}$) was varied from 5 days before infection to 2 days after infection.

Example 47: In Vivo *P. berghei* Transmission-Stage Assay

CD-1 (n=3 per experimental group; female; 6-7-week-old; 21-24 g, Charles River) mice were infected with *P. berghei* (ANKA GFP-luc) for 96 h before treatment with vehicle or compound (day 0). On day 2, female *A. stephensi* mosquitoes were allowed to feed on the mice for 20 min. After 1 week (day 9), the midguts of the mosquitoes were dissected out and oocysts were enumerated microscopically (12.5× magnification).

Example 48: In Vivo *P. falciparum* Blood-Stage Assay

In vivo adapted *P. falciparum* (3D7HLH/BRD) were selected as described in PLoS One 3, e2252 (2008). In brief, NSG mice (n=2 per experimental group; female; 4-5-week-old; 19-21 g; The Jackson Laboratory) were intraperitoneally injected with 1 ml of human erythrocytes (0-positive, 50% haematocrit, 50% RPMI 1640 with 5% albumax) daily to generate mice with humanized circulating erythrocytes (huRBC NSG). Approximately $2\times10^7$ blood-stage *P. falciparum* 3D7HLH/BRD (*FASEB J.* 25, 3583-3593 (2011)) were intravenously infected to huRBC NSG mice and >1% parasitaemia was achieved 5 weeks after infection. After three in vivo passages, the parasites were frozen and used experimentally. Approximately 48 h after infection with $1\times10^7$ blood-stage of *P. falciparum* 3D7HLH/BRD, the mean parasitaemia was approximately 0.4%. huRBC NSG mice were orally treated with a single dose of compound and parasitaemia was monitored for 30 days by IVIS to acquire the bioluminescence signal (150 mg kg-1 of luciferin was intraperitoneally injected approximately 10 min before imaging).

Example 49: In Vivo *P. falciparum* Transmission-Stage Assay huRBCNSGmice (n=2 per experimental group; female; 4-5-week-old; 18-20 g; Jackson Laboratory) were infected with blood-stage *P. falciparum* 3D7HLH/BRD for 2 weeks to allow the development of mature gametocytes. Subsequently, the mice were treated with a single oral dose of compound. Blood samples were collected for 11 days. For molecular detection of parasite stages, 40 µl of blood was obtained from control and treated mice. In brief, total RNA was isolated from blood samples using RNeasy Plus Kit with genomic DNA eliminator columns (Qiagen). First-strand cDNA synthesis was performed from extracted RNA using SuperScript III First-Strand Synthesis System (Life Technologies). Parasite stages were quantified using a stage-specific qRT-PCR assay as described in Sci. Transl. Med. 6, 244re5 (2014). Primers were designed to measure transcript levels of PF3D7_0501300 (ring stage parasites), PF3D7_1477700 (immature gametocytes) and PF3D7_1031000 (mature gametocytes). Primers for PF3D7_1120200 (*P. falciparum* UCE) transcript were used as a constitutively expressed parasite marker. The assay was performed using cDNA in a total reaction volume of 20 µl, containing primers for each gene at a final concentration of 250 nM. Amplification was performed on a Viia7 qRT-PCR machine (Life Technologies) using SYBR Green Master Mix (Applied Biosystems) with the following reaction conditions: 1 cycle×10 min at 95° C. and 40 cycles×1 s at 95° C. and 20 s at 60° C. Each cDNA sample was run in triplicate and the mean Ct value was used for the analysis. Ct values obtained above the cut-off (negative control) for each marker were considered negative for the presence of specific transcripts. Blood samples from each mouse before parasite inoculation were also tested for 'background noise' using the same primer sets. No amplification was detected from any samples.

Example 50: In Vivo *P. falciparum* Liver-Stage Assay

FRG knockout on C57BL/6 (human repopulated, >70%) mice (huHep FRG knockout; n=2 per experimental group; female; 5.5-6-month-old; 19-21 g; Yecuris) were inoculated intravenously with approximately $1\times10^5$ *P. falciparum* (NF54HT-GFP-luc) sporozoites and Compound was administered as a single 10 mg kg-1 oral dose one day after inoculation. Infection was monitored daily by IVIS. Daily engraftment of human erythro-cytes (0.4 ml, 0-positive, 50% haematocrit, 50% RPMI 1640 with 5% albumax) was initiated 5 days after inoculation. For qPCR analysis, blood samples (40 µl) were collected 7 days after inoculation. For molecular detection of the blood-stage parasite, 40 µl of blood was obtained from control and treated mice. In brief, total RNA was isolated from blood samples using RNeasy Plus Kit with genomic DNA eliminator columns (Qiagen). First-strand cDNA synthesis was performed from extracted RNA using SuperScript III First-Strand Synthesis System (Life Technologies). The presence of the blood-stage parasites was quantified using a highly stage-specific qRT-PCR assay as described in PLOS Comput. Biol. 9, e1003392 (2013). Primers were designed to measure transcript levels of PF3D7_1120200 (*P. falciparum* UCE). The assay was performed using cDNA in a 20 µl total reaction volume containing primers for each gene at a final concentration of 250 nM. Amplification was performed on a Viia7 qRT-PCR machine (Life Technologies) using SYBR Green Master Mix (Applied Biosystems) and the reaction conditions are as follows: 1 cycle×10 min at 95° C. and 40 cycles×1 s at 95° C. and 20 s at 60° C. Each cDNA sample was run in triplicate and the mean Ct value was used for the analysis. Ct values obtained above the cut-off (negative control) for each marker were considered negative for presence of specific transcripts. Blood samples from each mouse were also tested for background noise using the same primer sets before parasite inoculation. No amplification was detected from any samples.

Example 51: In Vivo C. parvum Assay

The NOD SCID gamma mouse model of chronic, asymptomatic C. parvum infection was used to test in vivo compound efficacy. NOD SCID gamma mice were infected with ~1×10$^5$ C. parvum oocysts by oral gavage 5-7 days after weaning. The infected animals begin shedding oocysts in the feces 1 week after infection, which is measured by quantitative PCR (qPCR). Based on experience with the positive control compound paromomycin, four mice are required per experimental group to achieve 80% power to detect an 80% percent reduction in parasite shedding after four days of drug compound. In additional to the experimental drug regimen groups, additional negative (gavage with DMSO/methylcellulose carrier) and positive (paromomycin 2000 mg/kg once daily) control groups are included in each experiment. Mice are infected 5-7 days after weaning (day −6), infection is confirmed 1 week later (day 0), and experimental compounds are dosed by oral gavage on days 1-4. The dosing frequency was as indicated. Treatment efficacy was assessed by measurement of fecal oocyst shedding by qPCR on day 5.

Example 52: C. parvum In Vitro EC$_{50}$ Assay

Human ileocecal adenocarcinoma (HCT-8) cells were obtained from ATCC and maintained in T-75 tissue culture flasks with RPMI 1640 medium with HEPES, sodium pyruvate (1 mM), and L-glutamine (ATCC) supplemented with 10% horse serum (ATCC) and 120 U/ml penicillin and 120 µg/ml streptomycin. Cells were plated into 384-well, tissue culture-treated, black-walled, clearbottom microwell plates (BD Falcon) at a density of 8,850 cells/well and allowed to grow to confluence. They were then inoculated with 5.5×10$^3$ primed C. parvum oocysts (Bunchgrass Farms, Deary, ID) suspended in inoculation medium (RPMI 1640 without horse serum). Oocysts were primed for excystation by following a previously described protocol (J. Eukaryot. Microbiol. 46:56S-57S). Briefly, oocysts were treated for 10 min with 10 mM HCl at 37° C., centrifuged, and treated with a 2 mM solution of sodium taurocholate (Sigma-Aldrich) in phosphate-buffered saline (PBS) with Ca$^{2+}$ and Mg$^{2+}$. The suspension was incubated for 10 min at 16° C. and then diluted in inoculation medium and added to each well. Infected cells were incubated at 37° C. for 3 h, at which point an equal volume of growth medium containing 20% horse serum (total serum concentration of 10%). Compounds were diluted and assayed at fixed doses of 0.12, 0.37, 1.1, 3.3, and 10 µM (each concentration, n=14) for the generation of EC$_{50}$ curves. In the case of final EC$_{50}$ curves, three wells were left uninfected but treated with each of the corresponding concentrations of the compound to assess for background staining. All curves were generated using the log[inhibitor] versus response_variable slope equation in GraphPad Prism (equation 3), with the bottom constraint set equal to 0.

By following the above-described protocol, the 50% effective concentration (EC$_{50}$) for several compounds having the structure of formula (I) was measured against C. parvum and the results are shown in Table 5 below.

TABLE 5

| Compound | EC$_{50}$ (nM) |
| --- | --- |
| E26 | 98 |
| E27 | 134 |
| E15 | 33 |
| E36 | 6 |
| E6 | 95 |
| E4 | 68 |

Other Embodiments

The disclosures of each and every patent, patent application, and publication cited herein are hereby incorporated herein by reference in their entirety. Also incorporated by reference is the disclosure of US Publication No. 2016/0289235. In particular embodiments, a compound of the invention is not a compound described in Table 1 of US Publication No. 2016/0289235.

While the disclosure provides specific embodiments, it will be understood that it is capable of further modifications and this application is intended to cover any variations, uses, or adaptations of the following, in general, the principles described herein and including such departures from the present disclosure come within known or customary practice within the art to which the disclosure pertains and may be applied to the essential features hereinbefore set forth.

What is claimed is:

1. A compound having the structure:

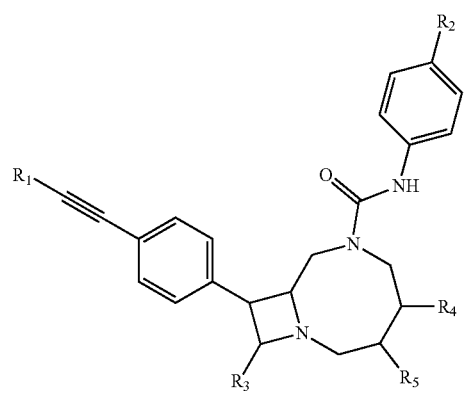

R$_1$ is optionally substituted aryl or heteroaryl;
R$_2$ is optionally substituted alkoxy, cycloalkoxy or heterocyclyl;
R$_3$ is hydrogen, or —CH$_2$—X;
R$_4$ and R$_5$ are independently hydrogen, —X, or —CH$_2$—X, and at least one of R$_4$ and R$_5$ is not hydrogen;
—X is independently selected at each occurrence from —OH, —OR, —S(O)R, —S(O)$_2$R, —N(R)—S(O)$_2$R, —S(O)$_2$—N(R)(R), —S(O)$_2$—NHR, —N(R)—C(O)—R, —NH$_2$, or —N(R)(R); and R is independently at each occurrence an optionally substituted $C_1$-$C_{12}$ alkyl;

or a pharmaceutically acceptable salt thereof.

2. The compound according to claim 1 having the structure:

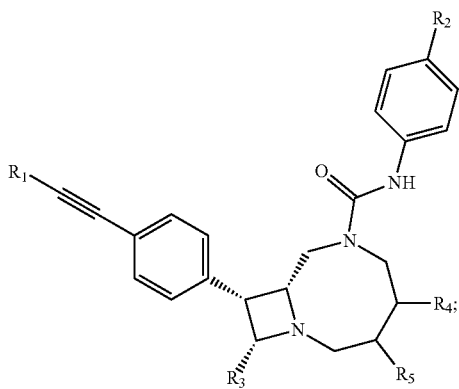

or pharmaceutically acceptable salts thereof.

3. The compound according to claim 1 having the structure:

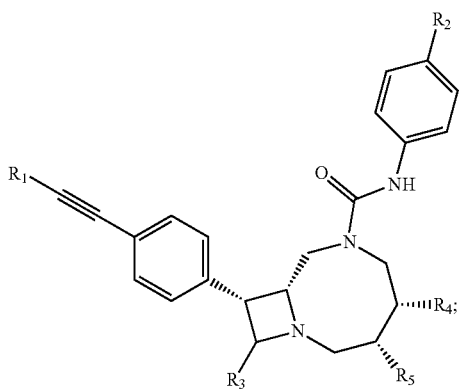

or pharmaceutically acceptable salts thereof.

4. The compound according to claim 1 having the structure:

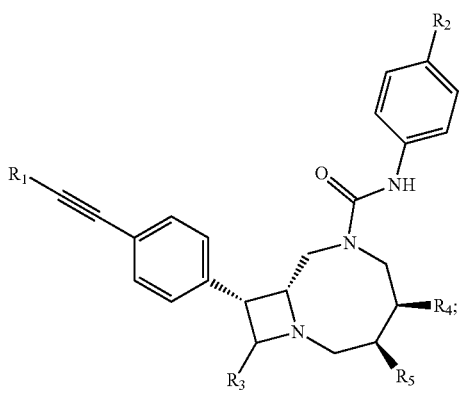

or pharmaceutically acceptable salts thereof.

5. The compound according to claim 1, wherein $R_4$ and $R_5$ are the same functional group selected from —X or —$CH_2$—X; or pharmaceutically acceptable salts thereof.

6. The compound according to claim 1, wherein $R_5$ is hydrogen and $R_4$ is —X, or —($CH_2$)—X; or pharmaceutically acceptable salts thereof.

7. The compound according to claim 1, wherein $R_4$ is hydrogen and $R_5$ is —X, or —($CH_2$)—X; or pharmaceutically acceptable salts thereof.

8. The compound according to claim 1, wherein —X in the group —X or —($CH_2$)—X of $R_4$ or $R_5$ is —OH, —$NH_2$, or —N(R)(R); or pharmaceutically acceptable salts thereof.

9. The compound according to claim 1, wherein $R_4$ and $R_5$ are —OH; or pharmaceutically acceptable salts thereof.

10. The compound according to claim 1, wherein $R_1$ is phenyl, fluorophenyl, difluorophenyl, or pyridyl; or pharmaceutically acceptable salts thereof.

11. The compound according to claim 1, wherein $R_2$ is $C_{1-4}$ linear or branched alkoxy; or pharmaceutically acceptable salts thereof.

12. The compound according to claim 1, wherein $R_2$ is methoxy; or pharmaceutically acceptable salts thereof.

13. The compound according to claim 1, wherein said compound is selected from the group consisting of

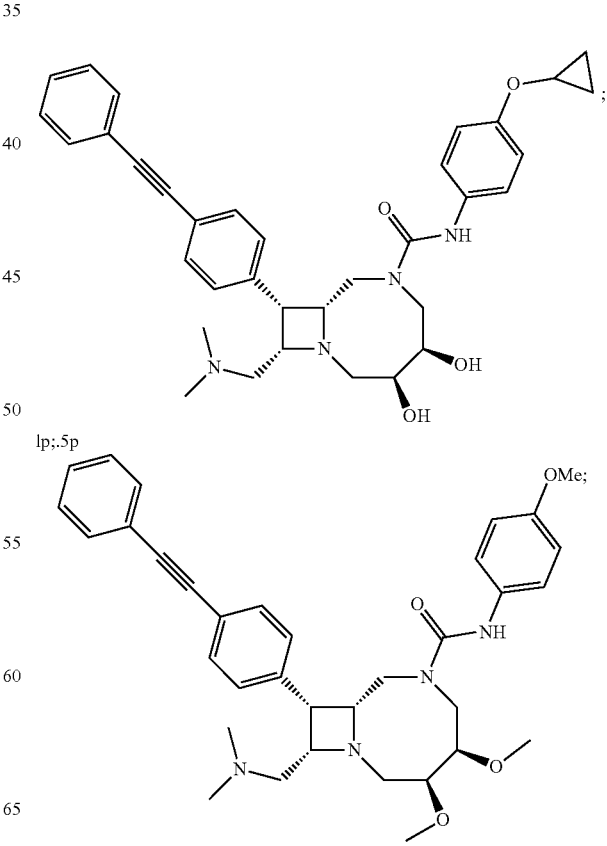

lp;.5p

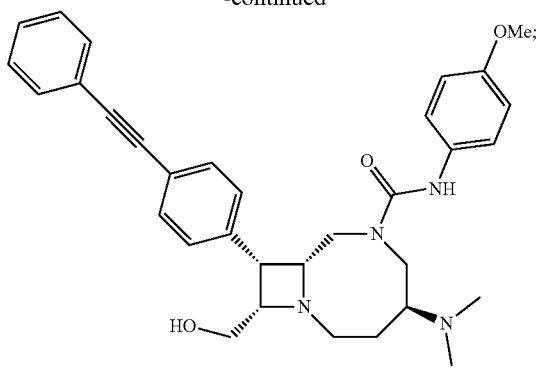
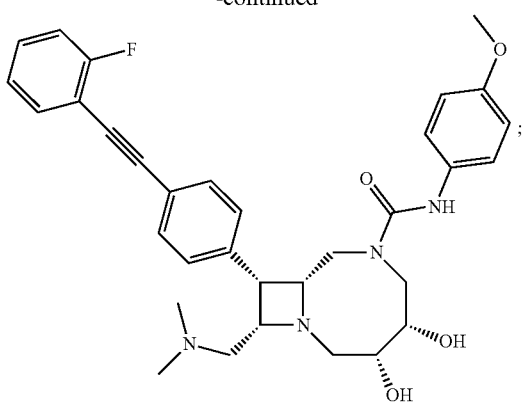
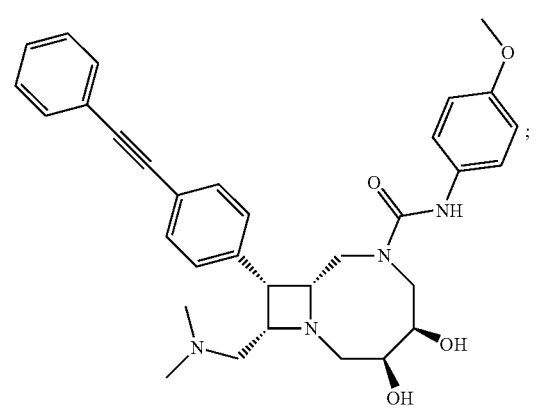
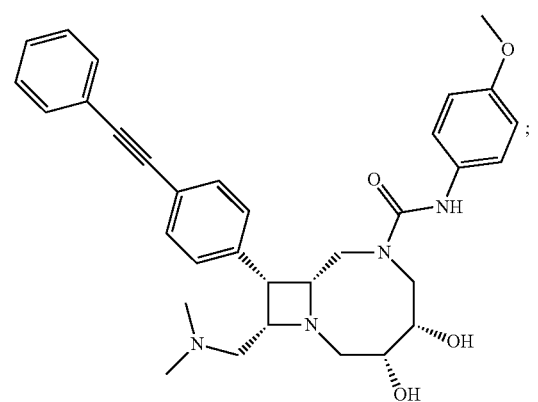
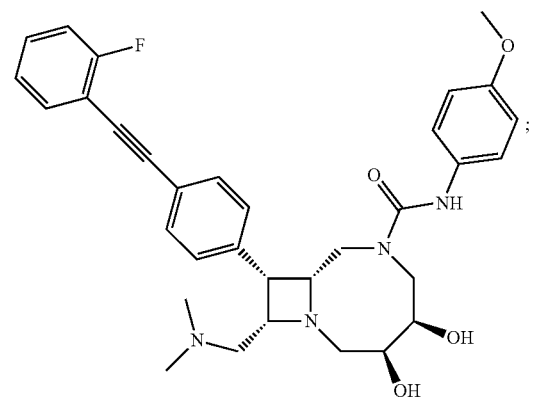
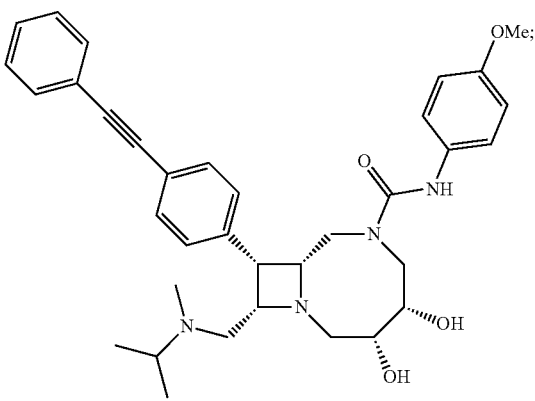

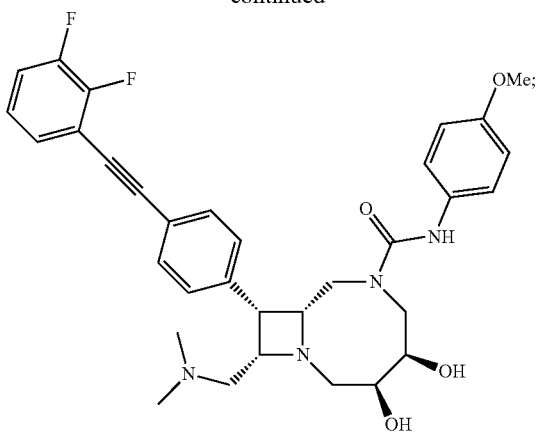
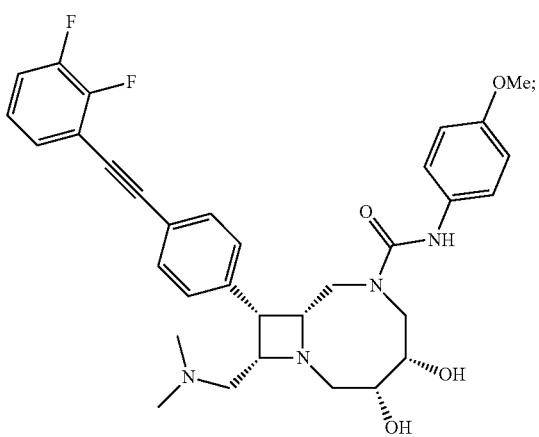
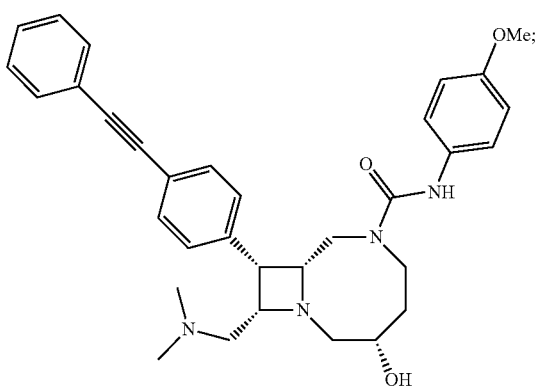
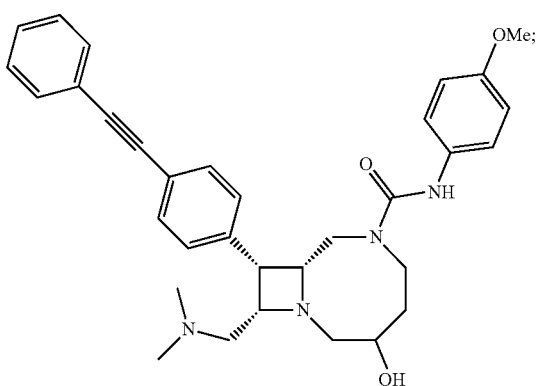
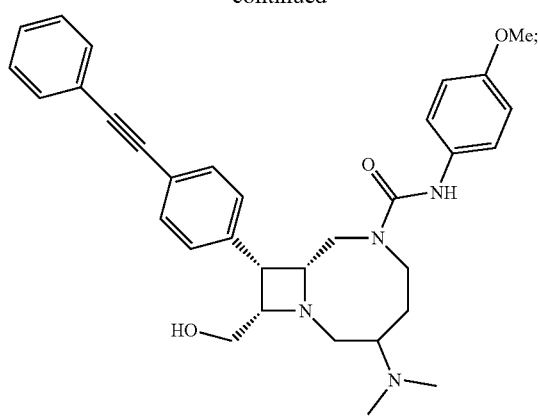
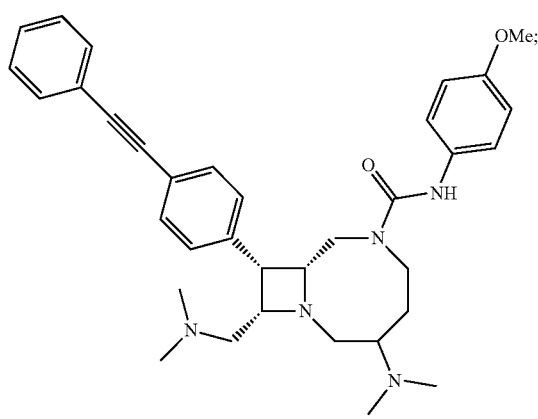
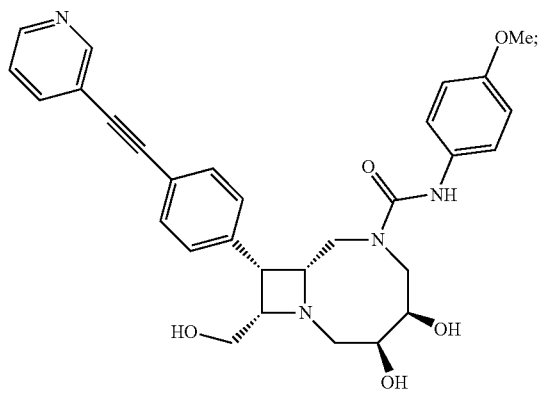
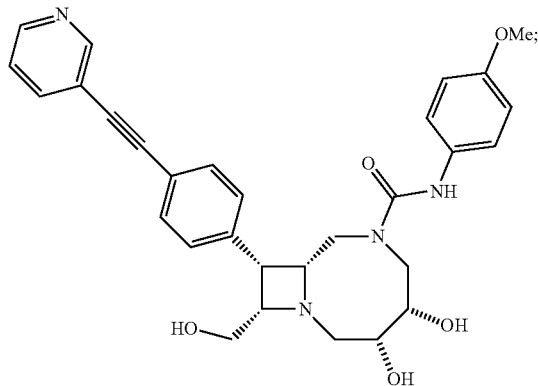

173
-continued
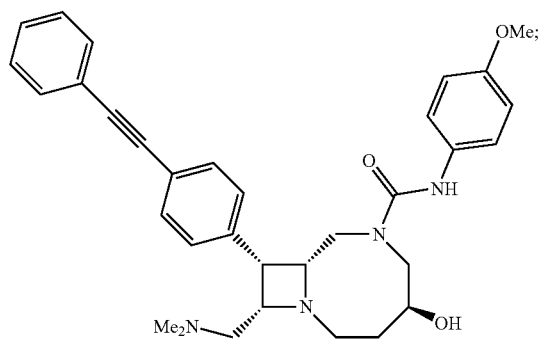
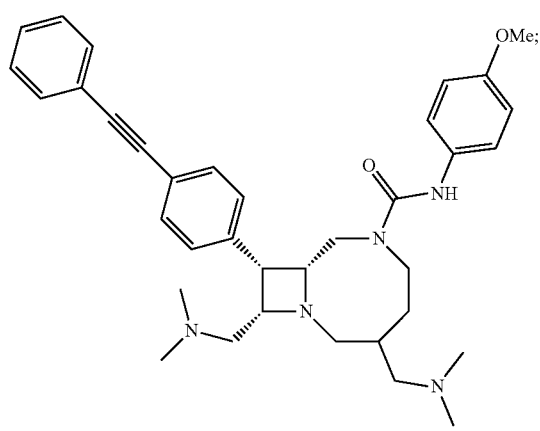
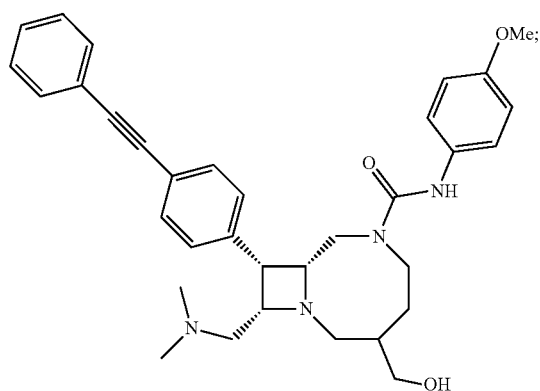
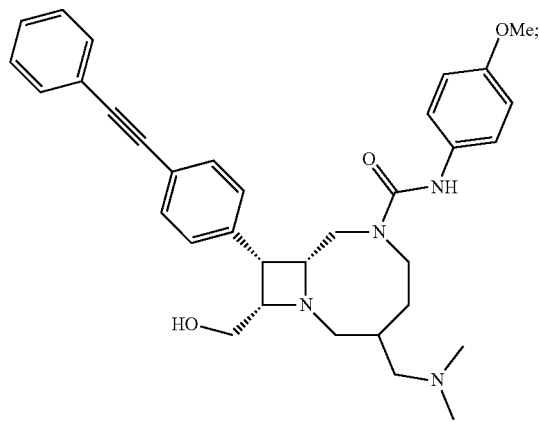
174
-continued
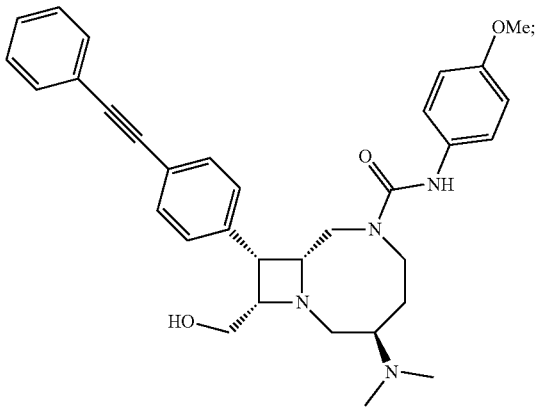
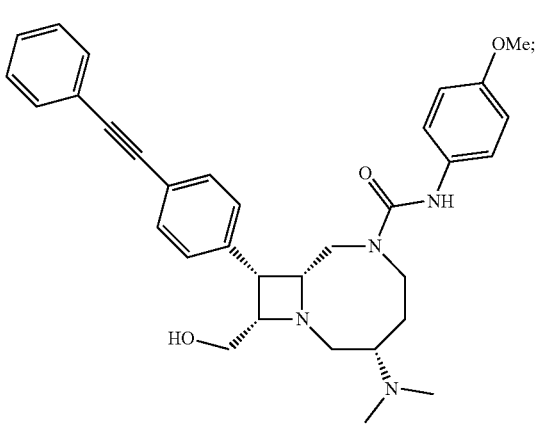
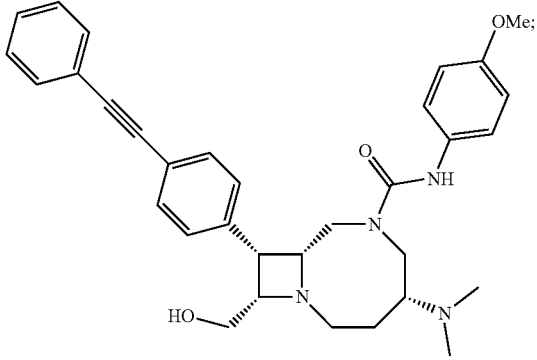
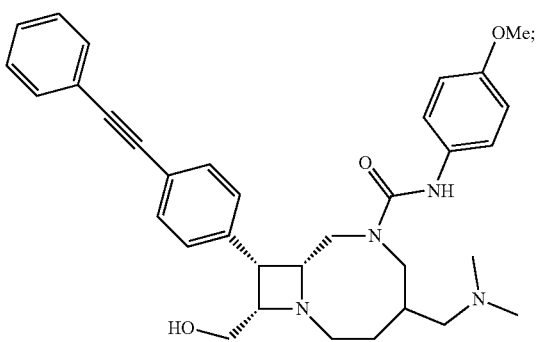

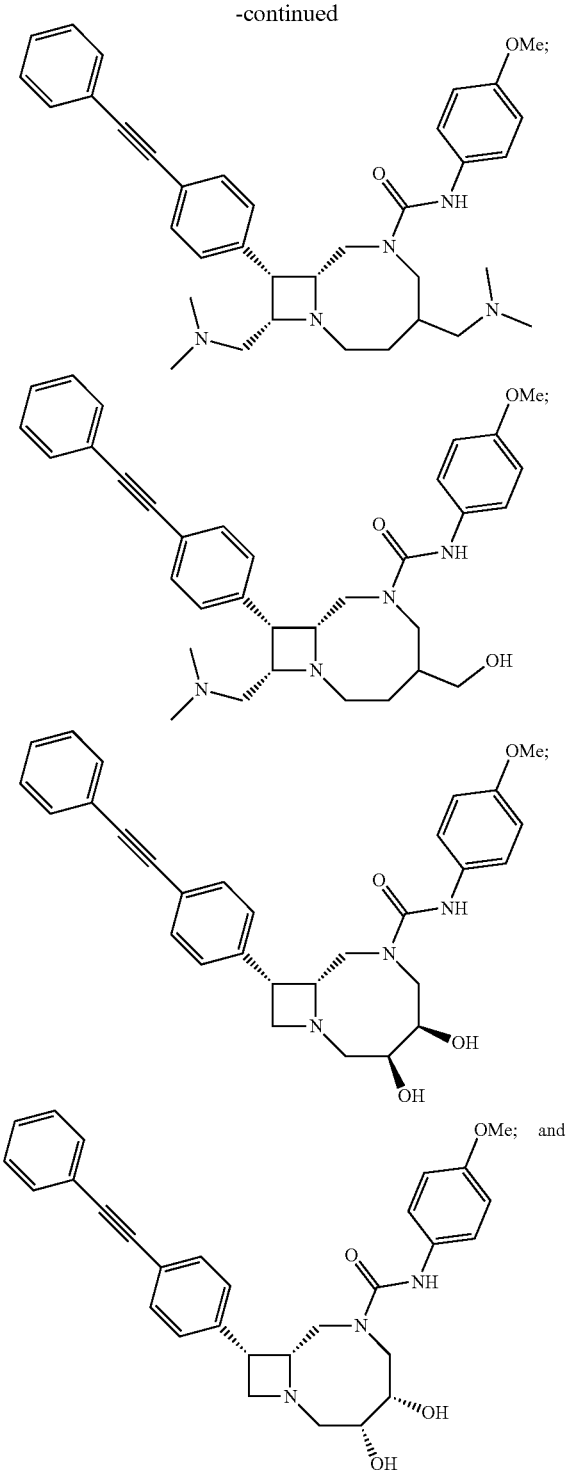

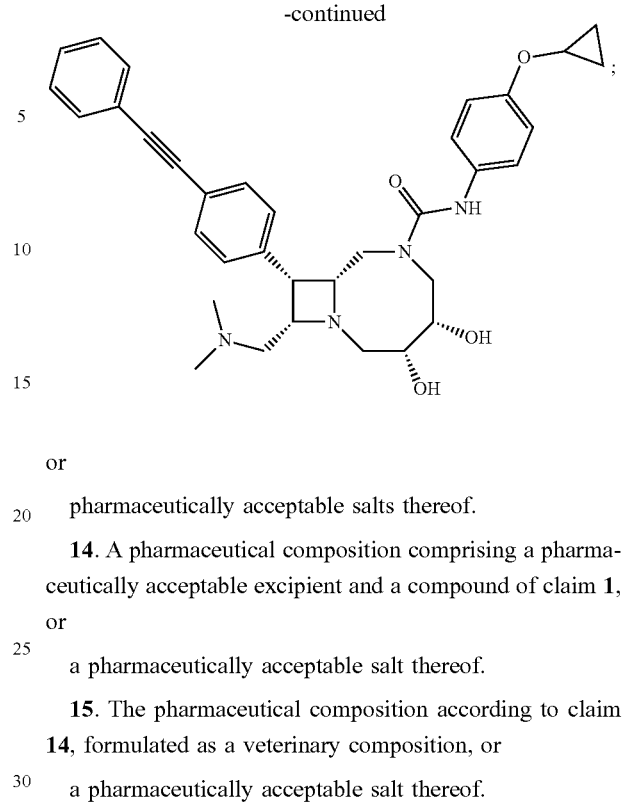

or pharmaceutically acceptable salts thereof.

14. A pharmaceutical composition comprising a pharmaceutically acceptable excipient and a compound of claim 1, or a pharmaceutically acceptable salt thereof.

15. The pharmaceutical composition according to claim 14, formulated as a veterinary composition, or a pharmaceutically acceptable salt thereof.

16. A method of treatment or prophylaxis of malaria, drug resistant malaria, or cryptosporidiosis in a subject, comprising the step of administering to the subject an effective amount of a compound of claim 1, or a pharmaceutically acceptable salt thereof.

17. The method of claim 16, wherein said parasitic disease is malaria or drug resistant malaria.

18. The method of claim 17, wherein the liver of said subject is infected with a malaria-causing parasite and administration prevents spread of said infection from their liver.

19. A method of preventing the spread of *Plasmodium* infection, preventing the symptomatic stage of malaria, or preventing establishment of *Plasmodium* infection in a subject, comprising administering to the subject an effective amount of a compound of claim 1, or a pharmaceutically acceptable salt thereof.

* * * * *